United States Patent
Jung et al.

(10) Patent No.: US 11,807,632 B2
(45) Date of Patent: Nov. 7, 2023

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 460 days.

(21) Appl. No.: 17/051,384

(22) PCT Filed: Oct. 21, 2019

(86) PCT No.: PCT/KR2019/013830
§ 371 (c)(1),
(2) Date: Oct. 28, 2020

(87) PCT Pub. No.: WO2020/085740
PCT Pub. Date: Apr. 30, 2020

(65) Prior Publication Data
US 2021/0139469 A1     May 13, 2021

(30) Foreign Application Priority Data

Oct. 22, 2018   (KR) .................. 10-2018-0125898
Oct. 21, 2019   (KR) .................. 10-2019-0130597

(51) Int. Cl.
*C07D 409/14*     (2006.01)
*H10K 85/60*      (2023.01)
(Continued)

(52) U.S. Cl.
CPC ......... *C07D 409/14* (2013.01); *H10K 85/654* (2023.02); *H10K 85/6574* (2023.02);
(Continued)

(58) Field of Classification Search
None
See application file for complete search history.

(56) References Cited

U.S. PATENT DOCUMENTS

2011/0309343 A1   12/2011   Langer et al.
2016/0248023 A1    8/2016   Parham et al.
(Continued)

FOREIGN PATENT DOCUMENTS

CN     107250132 A      10/2017
EP       3109231 A1     12/2016
(Continued)

*Primary Examiner* — Robert S Loewe
(74) *Attorney, Agent, or Firm* — Bryan Cave Leighton Paisner LLP

(57) ABSTRACT

A novel heterocyclic compound of Chemical Formula 1 and an organic light emitting device including the same.

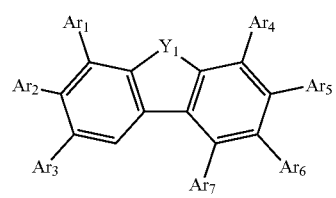

Chemical Formula 1 wherein one of $Ar_1$ to $Ar_3$ is of the following Chemical Formula 2, (Continued)

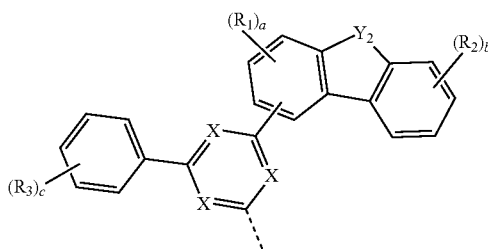

and one of $Ar_4$ to $Ar_7$ is a substituted or unsubstituted dibenzofuran; or a substituted or unsubstituted dibenzothiophene, the rest being hydrogen.

8 Claims, 1 Drawing Sheet

(51) Int. Cl.
*H10K 50/15* (2023.01)
*H10K 50/16* (2023.01)
*H10K 50/18* (2023.01)
*H10K 50/17* (2023.01)

(52) U.S. Cl.
CPC ......... *H10K 85/6576* (2023.02); *H10K 50/15* (2023.02); *H10K 50/16* (2023.02); *H10K 50/171* (2023.02); *H10K 50/18* (2023.02)

(56) References Cited

U.S. PATENT DOCUMENTS

| | | |
|---|---|---|
| 2016/0329506 A1 | 11/2016 | Lee et al. |
| 2017/0104163 A1 | 4/2017 | Lee et al. |
| 2017/0186965 A1 | 6/2017 | Parham et al. |
| 2018/0009776 A1 | 1/2018 | Cha et al. |
| 2018/0037546 A1 | 2/2018 | Sugino et al. |
| 2018/0162843 A1 | 6/2018 | Parham et al. |
| 2018/0212156 A1 | 7/2018 | Baba et al. |
| 2019/0047991 A1 | 2/2019 | Jung et al. |
| 2019/0198780 A1* | 6/2019 | Kim ............ H10K 85/654 |
| 2019/0214573 A1* | 7/2019 | Ryu ............ H10K 99/00 |
| 2020/0203623 A1* | 6/2020 | Lee ............ C07D 409/10 |
| 2020/0287140 A1* | 9/2020 | Chae ............ H10K 85/654 |
| 2021/0083198 A1* | 3/2021 | Han ............ H10K 99/00 |
| 2021/0320260 A1* | 10/2021 | Jung ............ H10K 85/6574 |
| 2022/0029104 A1* | 1/2022 | Lee ............ H10K 85/624 |

FOREIGN PATENT DOCUMENTS

| | | |
|---|---|---|
| JP | 2013245179 A | 12/2013 |
| KR | 10-2000-0051826 A | 8/2000 |
| KR | 10-2012-0116272 A | 10/2012 |
| KR | 10-2012-0116282 A | 10/2012 |
| KR | 10-2014-0099082 A | 8/2014 |
| KR | 10-2015-0042335 A | 4/2015 |
| KR | 10-2016-0011036 A | 1/2016 |
| KR | 10-2016-0028524 A | 3/2016 |
| KR | 10-2017-0094774 A | 8/2017 |
| KR | 10-2017-0113321 A | 10/2017 |
| KR | 10-1788094 B1 | 10/2017 |
| KR | 10-2018-0020578 A | 2/2018 |
| KR | 10-2018-0051355 A | 5/2018 |
| KR | 10-1856728 B1 | 5/2018 |
| KR | 10-2018-0061076 A | 6/2018 |
| WO | 2011157790 A1 | 12/2011 |
| WO | 2011158204 A1 | 12/2011 |
| WO | 2012093862 A2 | 7/2012 |
| WO | 2013068376 A1 | 5/2013 |
| WO | 2016079667 A1 | 5/2016 |
| WO | 2017014226 A1 | 1/2017 |
| WO | 2017126370 A1 | 7/2017 |
| WO | 2018084423 A2 | 5/2018 |

\* cited by examiner

【FIG. 1】
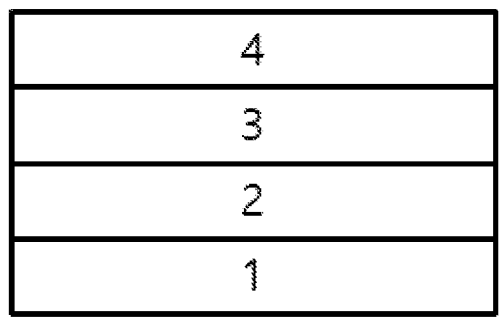
【FIG. 2】
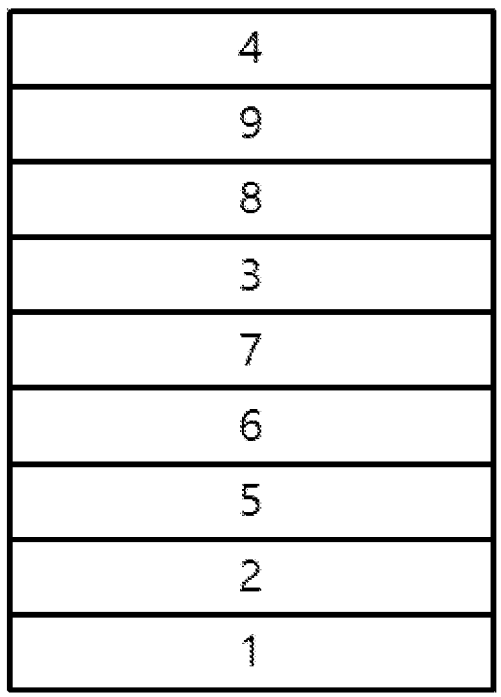

HETEROCYCLIC COMPOUND AND ORGANIC LIGHT EMITTING DEVICE COMPRISING THE SAME

CROSS-REFERENCE TO RELATED APPLICATION(S)

This application is a National Stage of International Application No. PCT/KR2019/013830, filed on Oct. 21, 2019, which claims priority to or the benefit of Korean Patent Application No. 10-2018-0125898 filed with the Korean Intellectual Property Office on Oct. 22, 2018 and Korean Patent Application No. 10-2019-0130597 filed with the Korean Intellectual Property Office on Oct. 21, 2019, the disclosures of which are incorporated herein by reference in their entirety.

FIELD OF THE INVENTION

The present invention relates to a novel heterocyclic compound and to an organic light emitting device including the same.

BACKGROUND OF THE INVENTION

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Unexamined Patent Publication No. 10-2000-0051826

SUMMARY OF THE INVENTION

It is an object of the present invention to provide a novel heterocyclic compound and an organic light emitting device including the same.

Technical Solution

In one aspect of the invention, there is provided a compound of the following Chemical Formula 1:

[Chemical Formula 1]

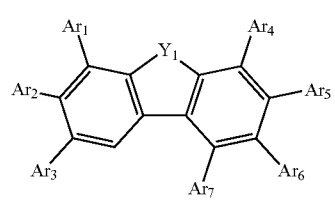

wherein, in Chemical Formula 1,
$Y_1$ is O or S,
one of $Ar_1$ to $Ar_3$ is of the following Chemical Formula 2, the rest being hydrogen;
one of $Ar_4$ to $Ar_7$ is a substituted or unsubstituted dibenzofuran; or a substituted or unsubstituted dibenzothiophene, the rest being hydrogen,
when $Ar_1$ is of the following Chemical Formula 2, $Ar_7$ is hydrogen,

[Chemical Formula 2]

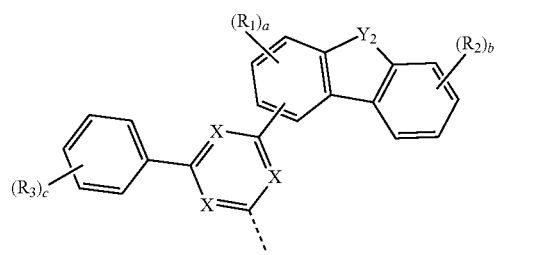

wherein, in Chemical Formula 2,
each X is independently N or CH, with the proviso that two or more of X is N,
$Y_2$ is O or S,
$R_1$ to $R_3$ are each independently hydrogen; deuterium; halogen; hydroxy; cyano; nitro; amino; a substituted or unsubstituted $C_{1-60}$ alkyl; a substituted or unsubstituted $C_{1-60}$ haloalkyl; a substituted or unsubstituted $C_{1-60}$ thioalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; or a substituted or unsubstituted $C_{2-60}$ alkenyl,
a is an integer from 1 to 3,
b is an integer from 1 to 4, and
c is an integer from 1 to 5.

In another aspect of the prevent invention, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula I.

Advantageous Effects

The compound of Chemical Formula 1 described above can be used as a material of an organic material layer of an organic light emitting device and may improve the efficiency, achieve low driving voltage and/or improve lifetime characteristics in the organic light emitting device. In particular, the compound of Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4.

DETAILED DESCRIPTION OF THE EMBODIMENTS

Hereinafter, embodiments of the present invention will be described in more detail to facilitate understanding of the invention.

The present invention provides the compound of Chemical Formula 1.

As used herein, the notation ┆ and

mean a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulae but is not limited thereto.

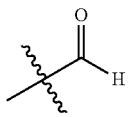 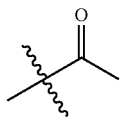 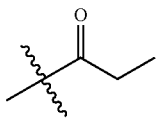

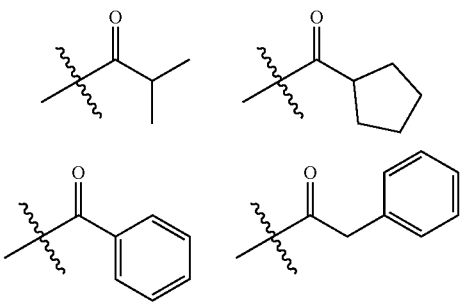

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

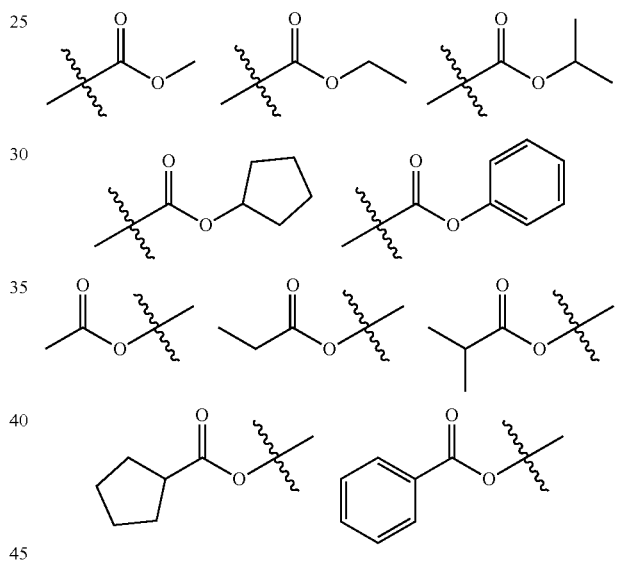

In the present specification, the number of carbon atoms of an imide group is not particularly limited, but is preferably 1 to 25. Specifically, the imide group may be a compound having the following structural formulae, but is not limited thereto.

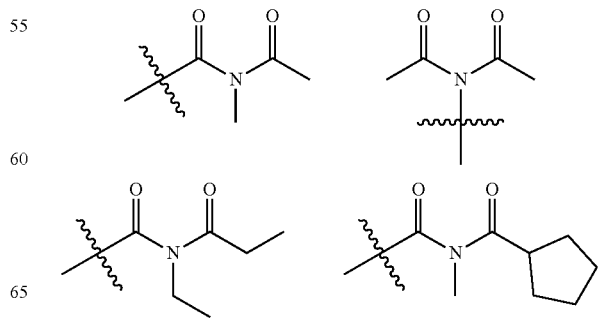

-continued

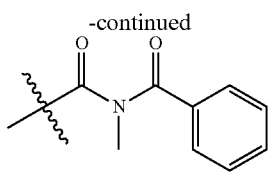

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be connected with each other to form a spiro structure. In the case where the fluorenyl group is substituted,

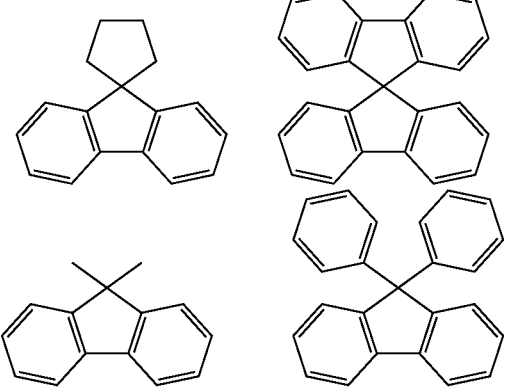

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, an thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heteroaryl can be applied, except that the heterocycle is not a monovalent group but formed by combining two substituent groups.

Preferably, the Chemical Formula 1 may be any one selected from compounds of the following Chemical Formulas 1-1 to 1-5.

[Chemical Formula 1-1]

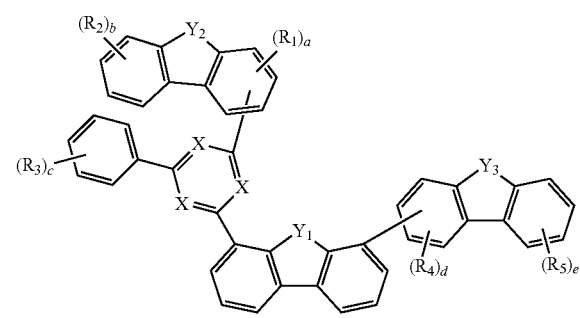

[Chemical Formula 1-2]

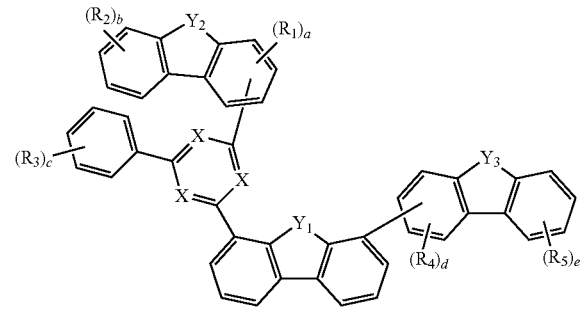

[Chemical Formula 1-3]

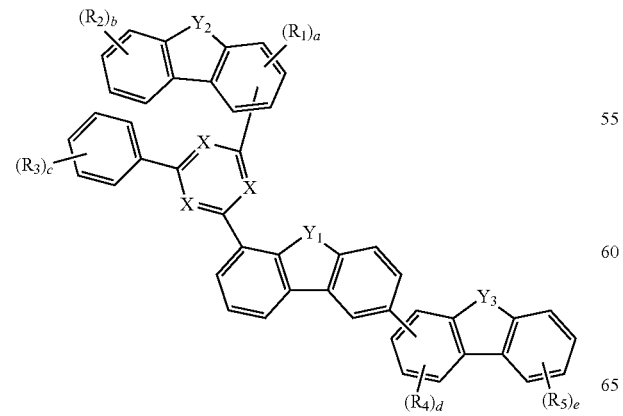

[Chemical Formula 1-4]

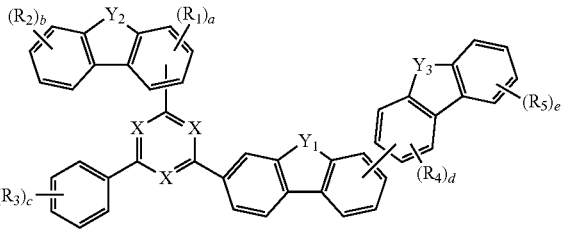

[Chemical Formula 1-5]

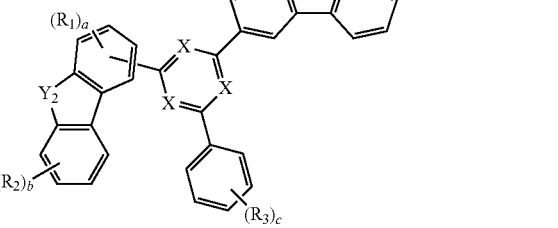

wherein, in Chemical Formulae 1-1 to 1-5,
$Y_1$, $Y_2$, X, $R_1$ to $R_3$, a, b and c are as defined above,
$Y_3$ is O or S,
$R_4$ and $R_5$ are each independently hydrogen; deuterium; halogen; hydroxy; cyano; nitro; amino; a substituted or unsubstituted $C_{1-60}$ alkyl; a substituted or unsubstituted $C_{1-60}$ haloalkyl; a substituted or unsubstituted $C_{1-60}$ thioalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; or a substituted or unsubstituted $C_{2-60}$ alkenyl, a substituted or unsubstituted $C_{6-60}$ aryl; a substituted or unsubstituted $C_{6-60}$ aryloxy; or a substituted or unsubstituted $C_{2-60}$ heteroaryl containing at least one of O, N, Si and S,
d is an integer from 1 to 3, and
e is an integer from 1 to 4.
Preferably, all of X is N.
Preferably, $R_1$ to $R_3$ may be each independently hydrogen or deuterium.
Preferably, the compound of Chemical Formula 1 may be selected from the group consisting of the following compounds.

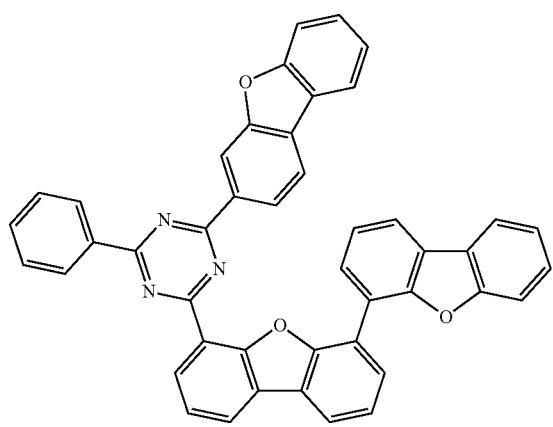
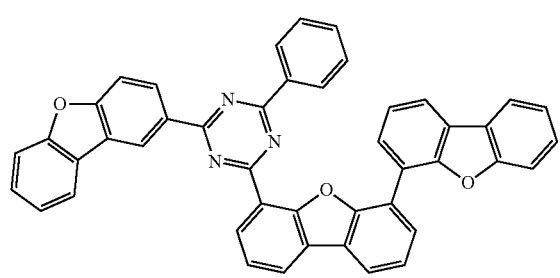
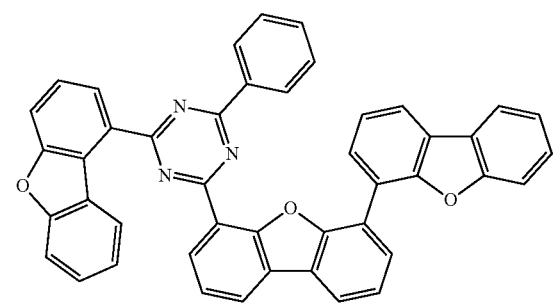
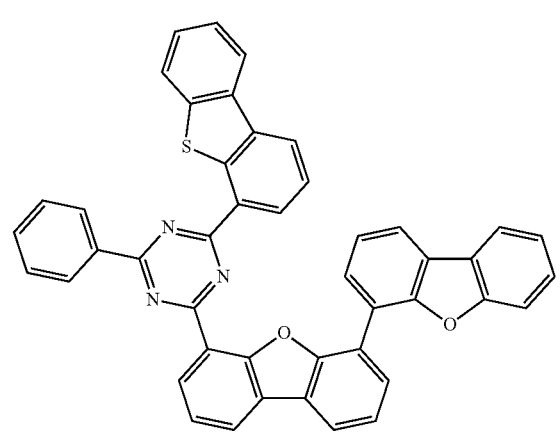
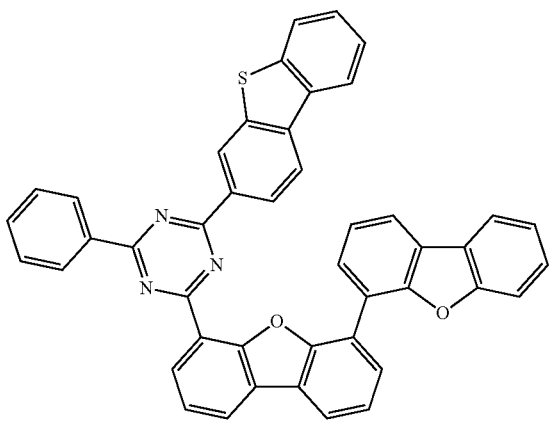
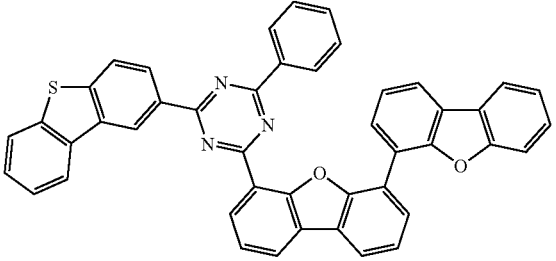
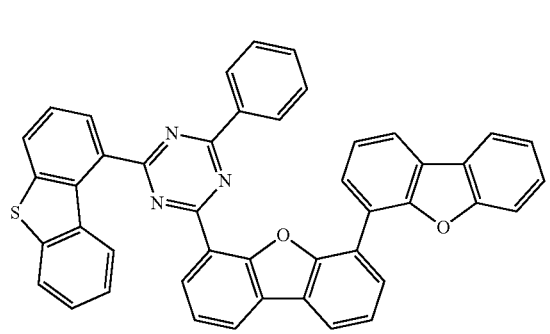
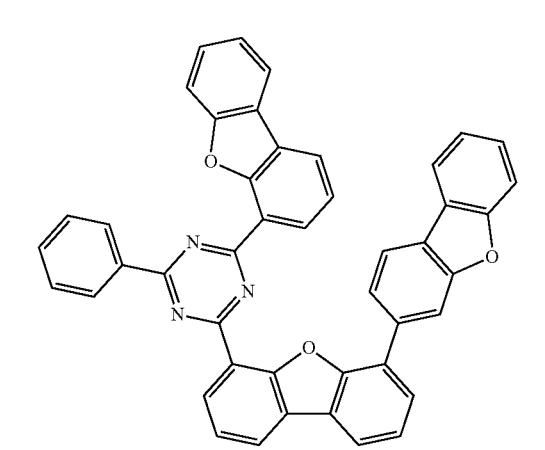

11
-continued
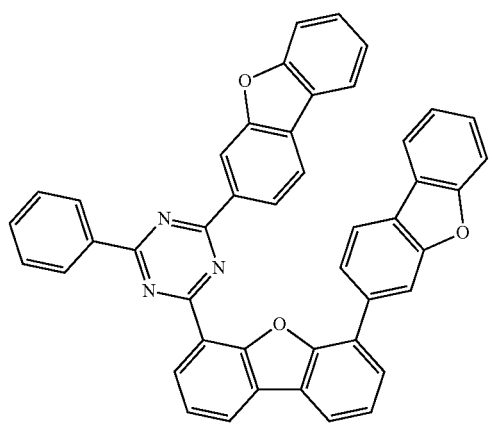
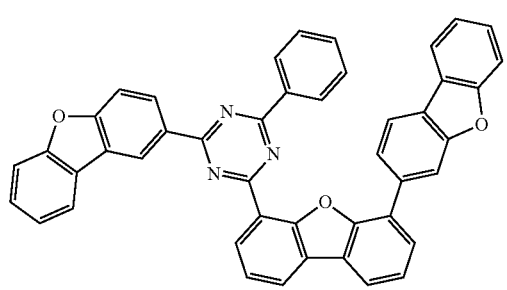
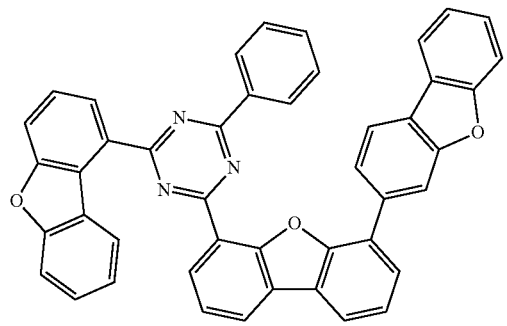
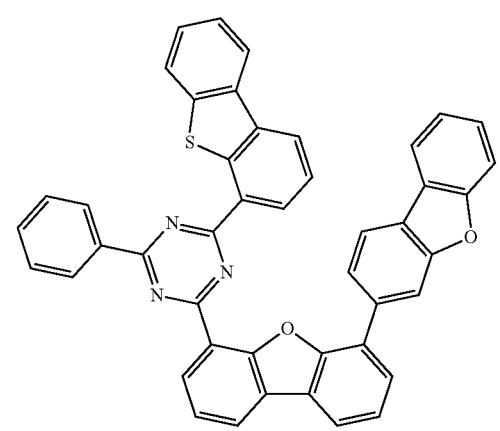
12
-continued
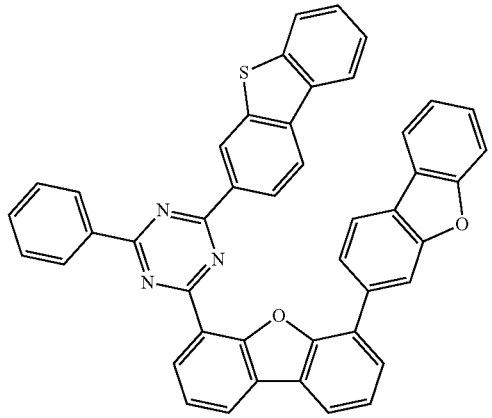
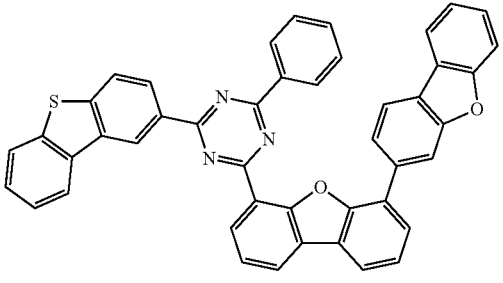
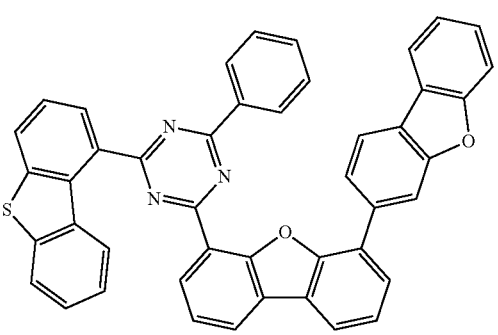
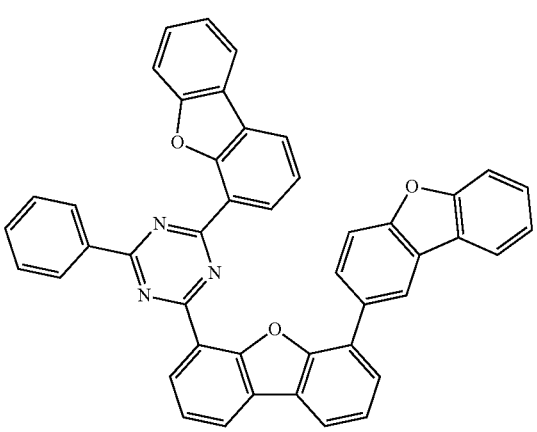

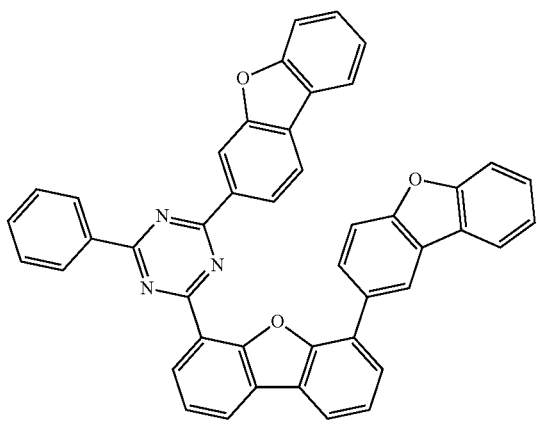
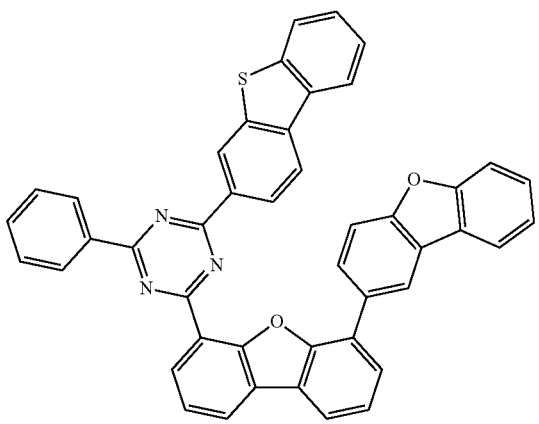
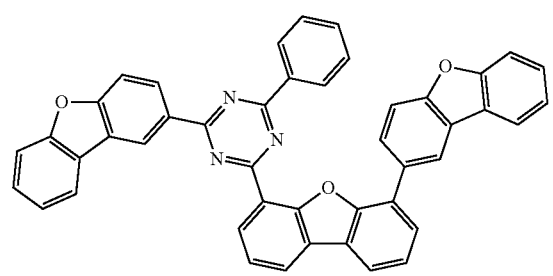
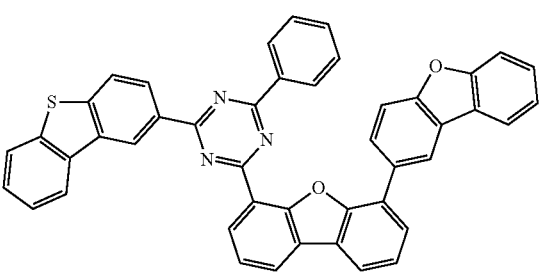
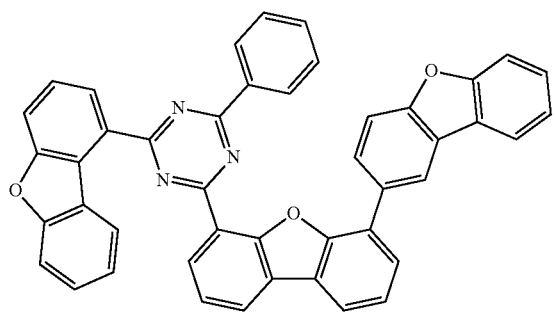
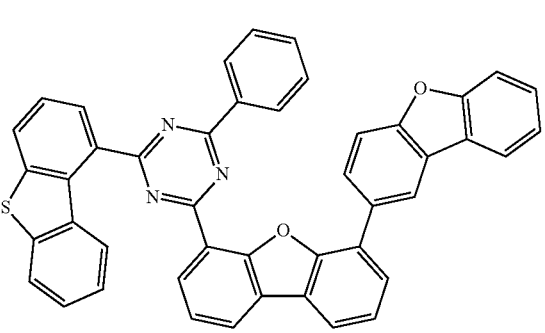
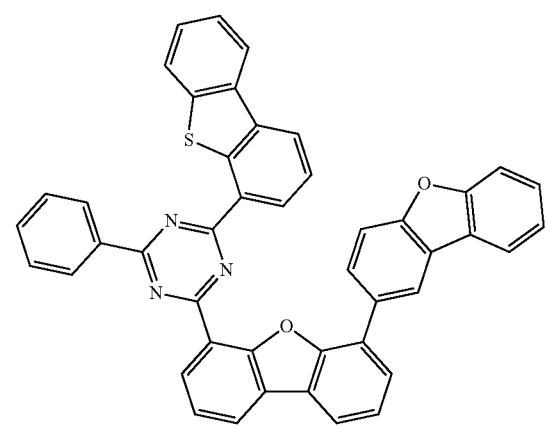
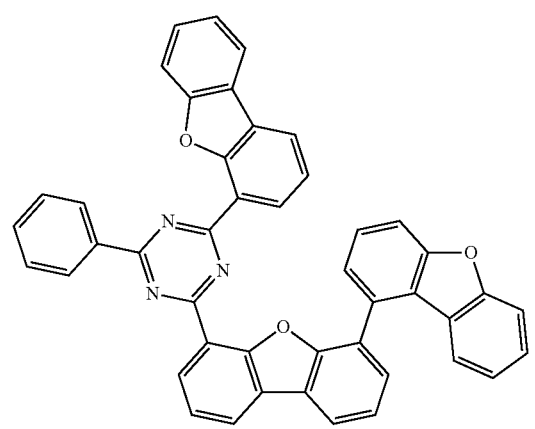

-continued
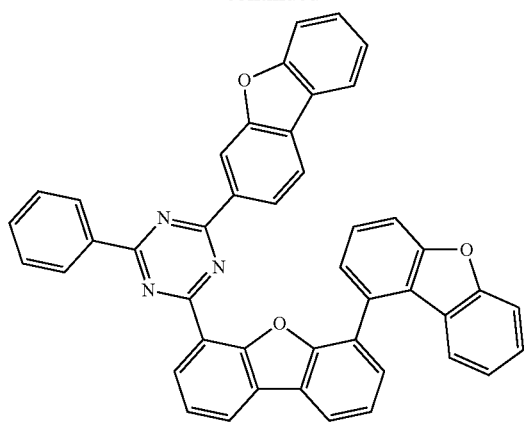
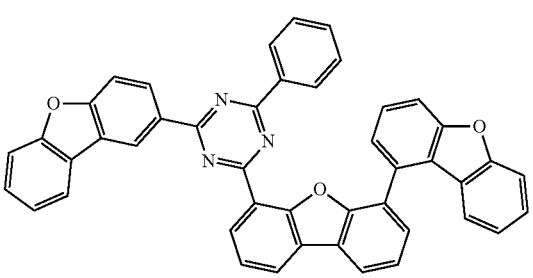
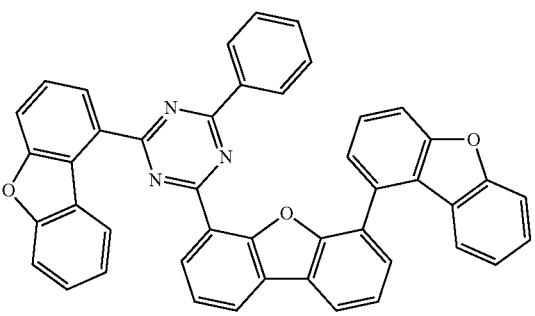
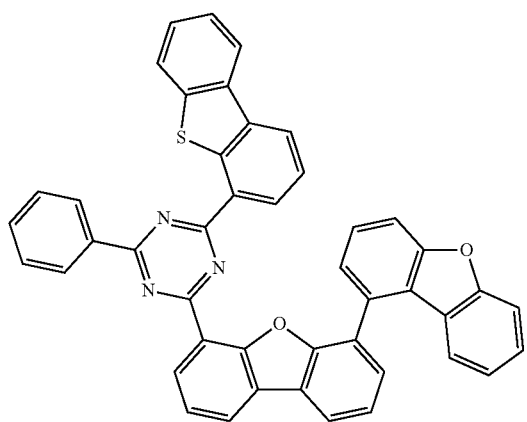
-continued
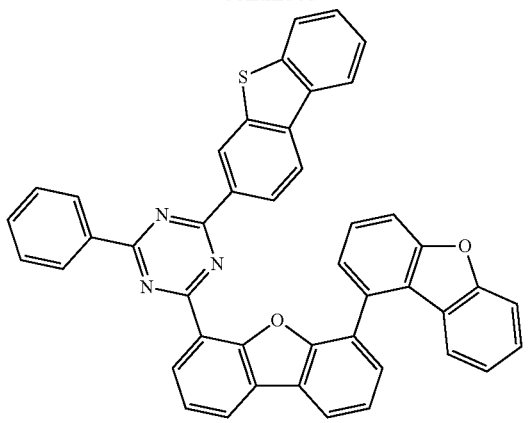
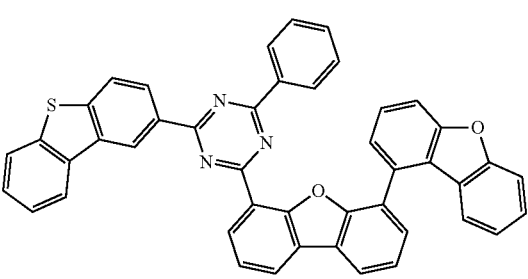
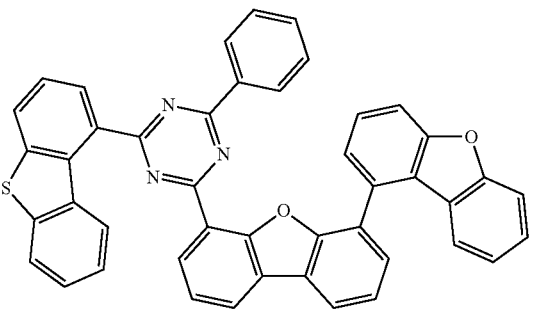
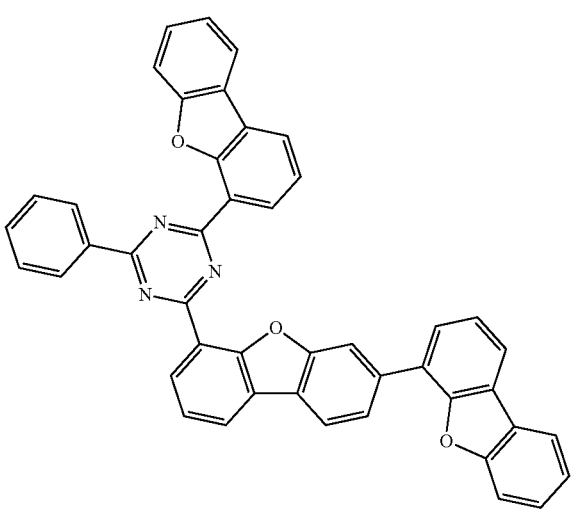

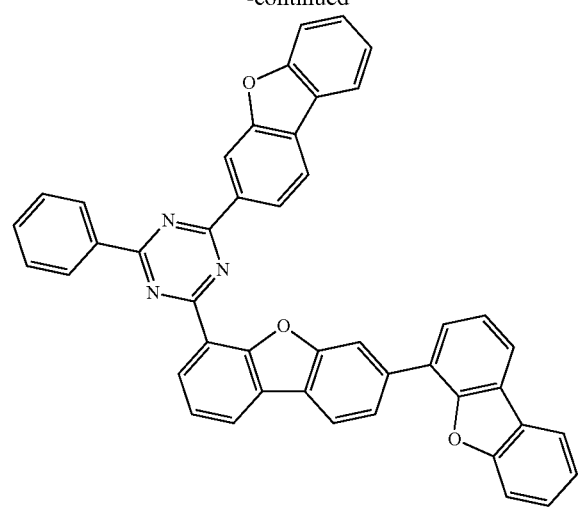
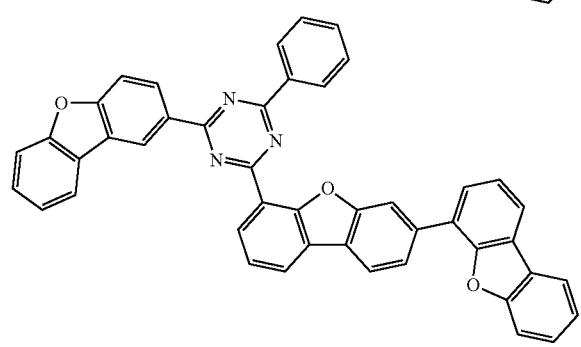
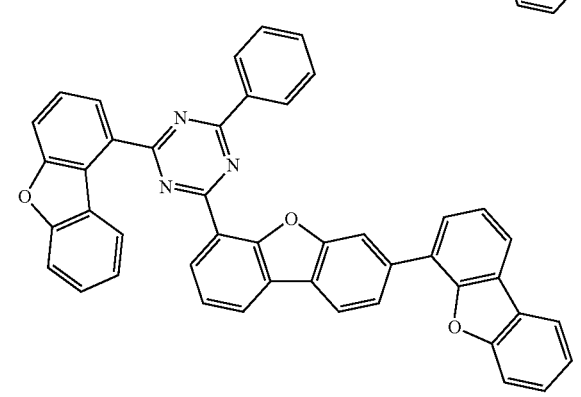
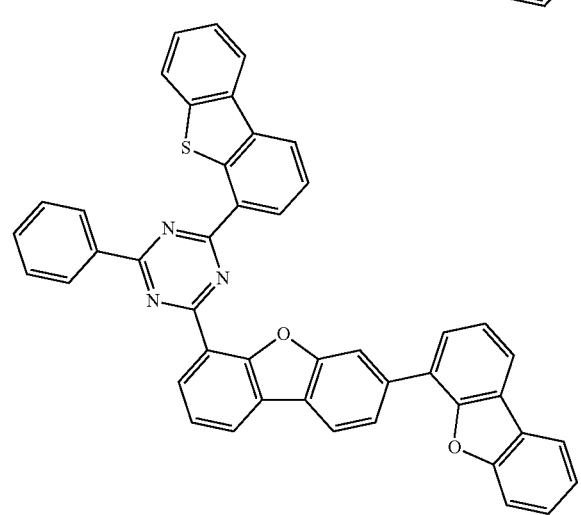
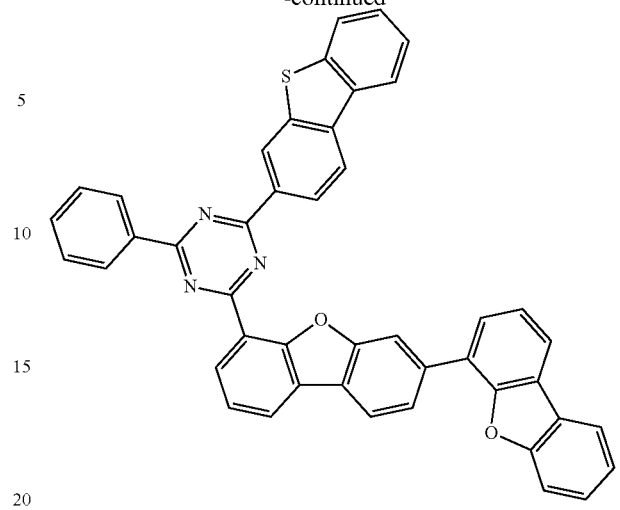
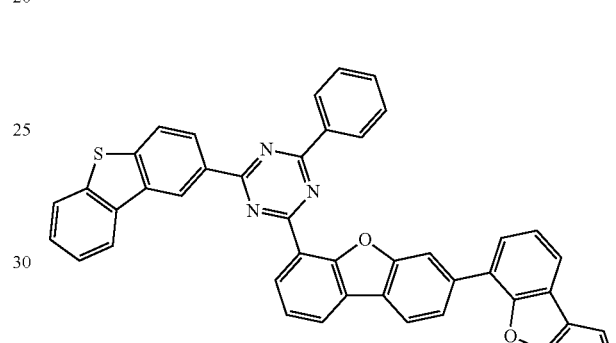
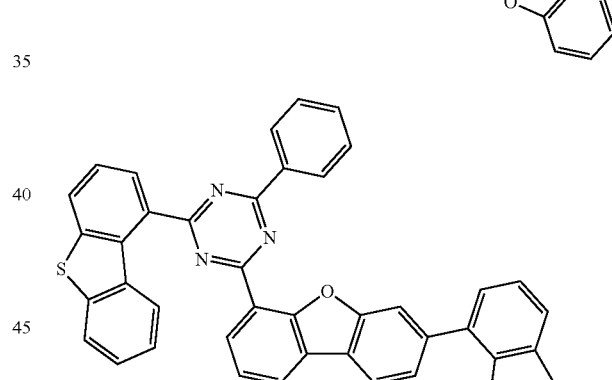
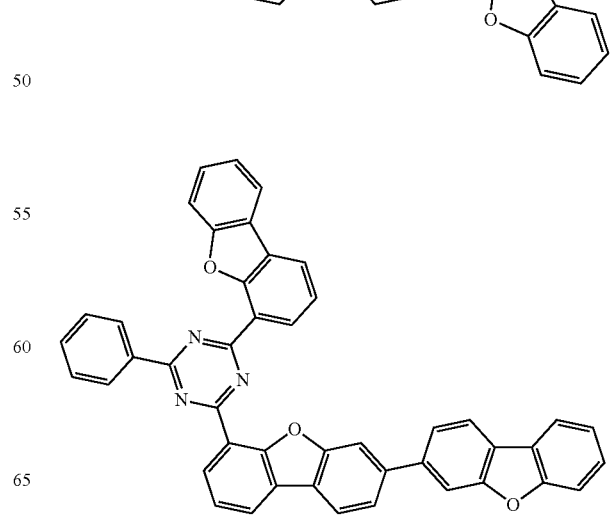

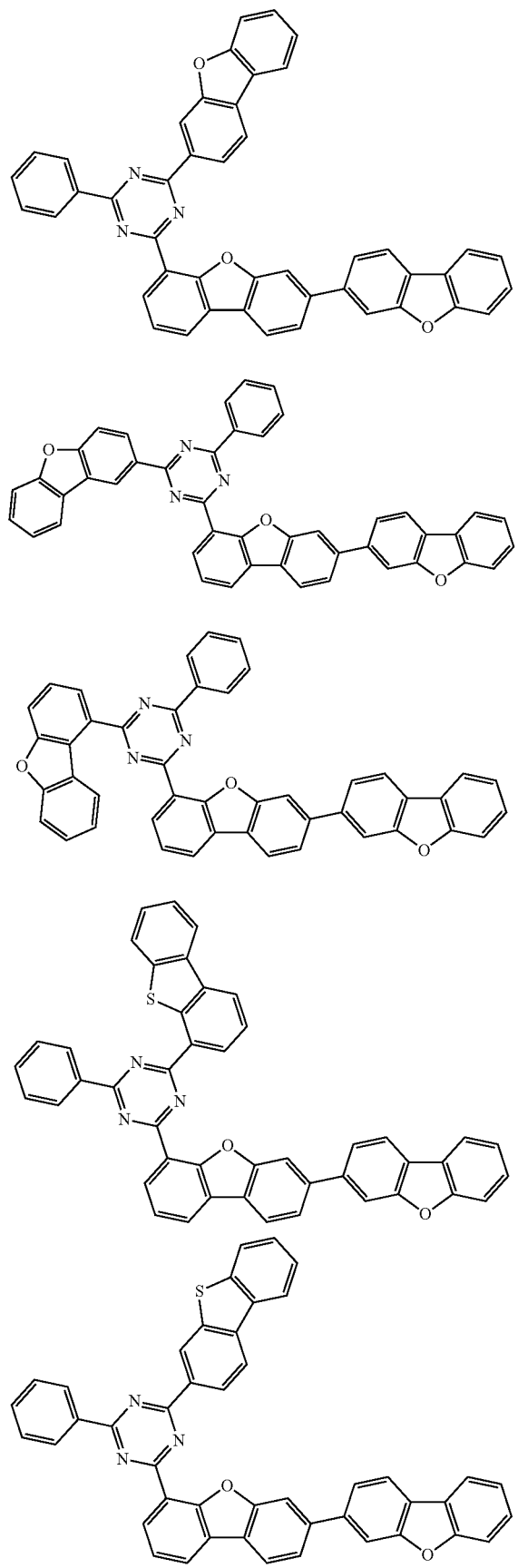
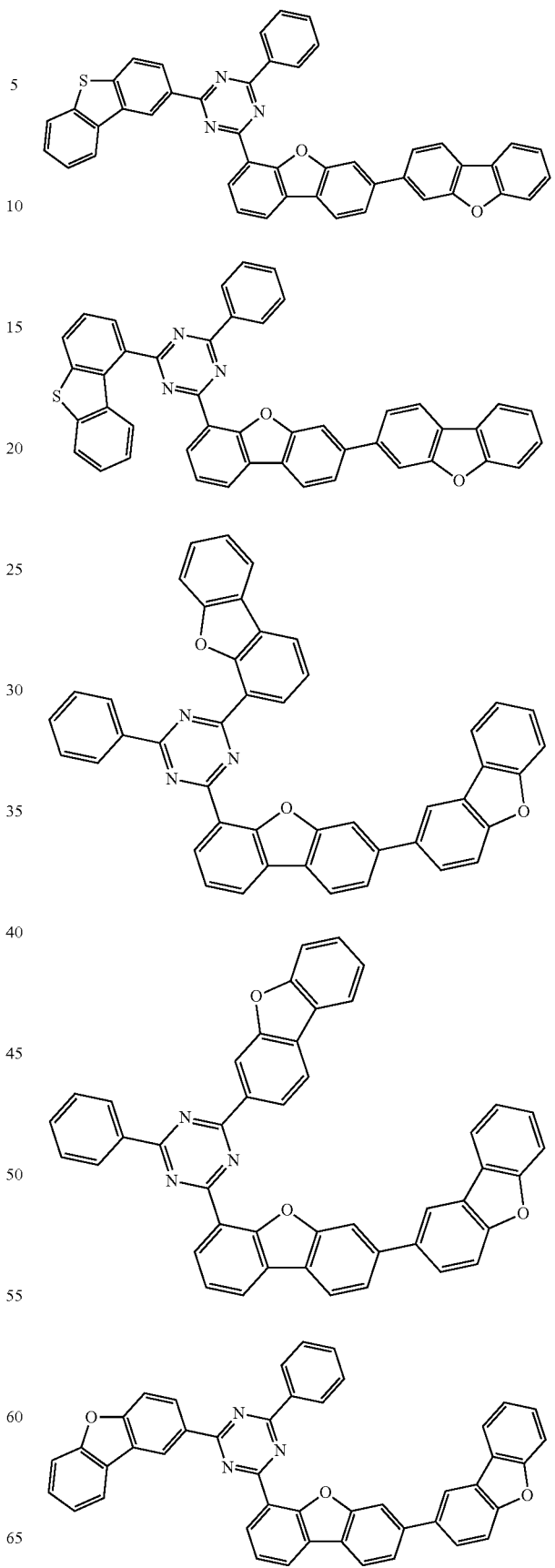

-continued
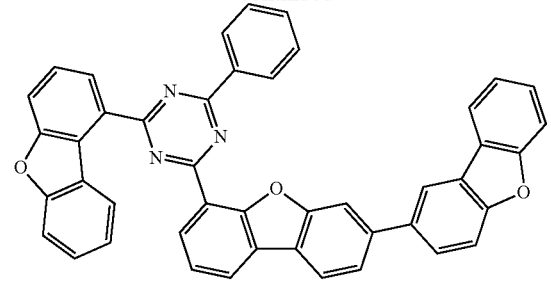
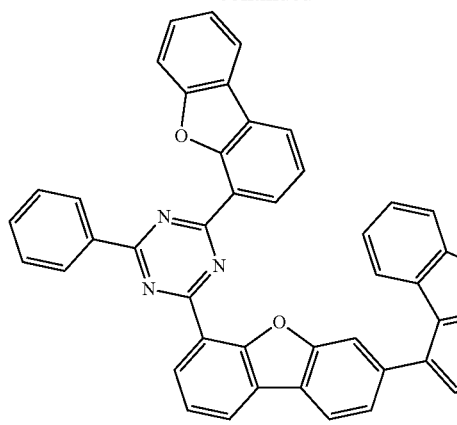
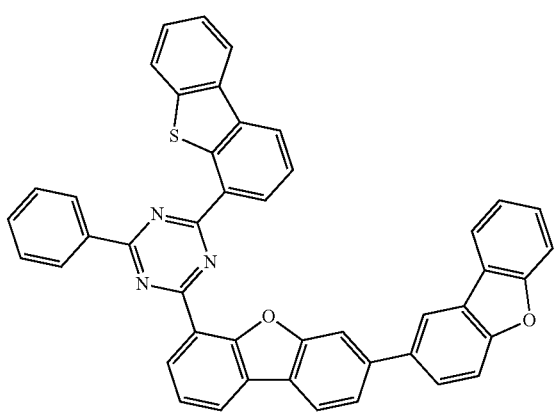
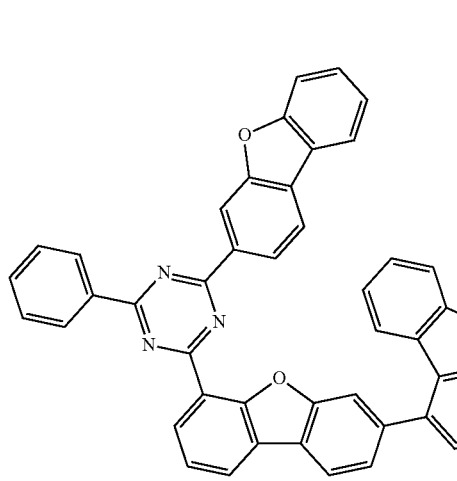
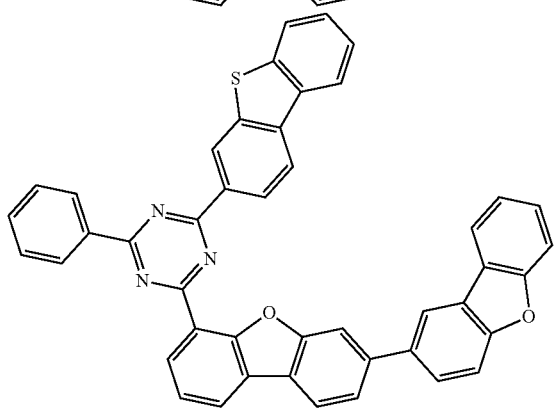
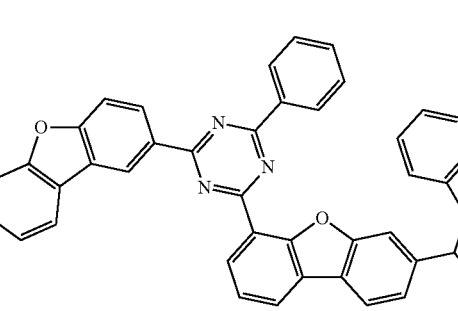
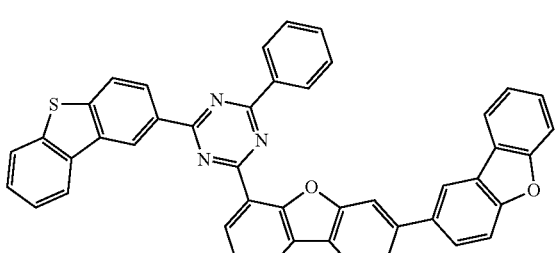
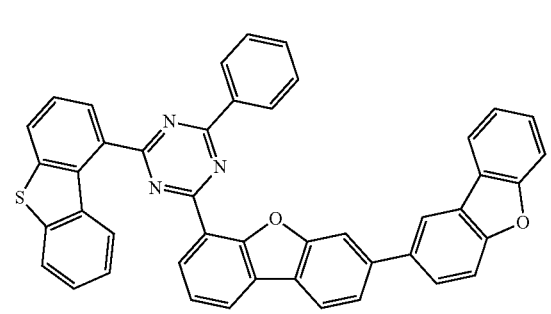
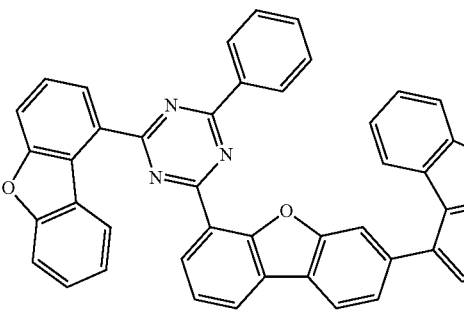

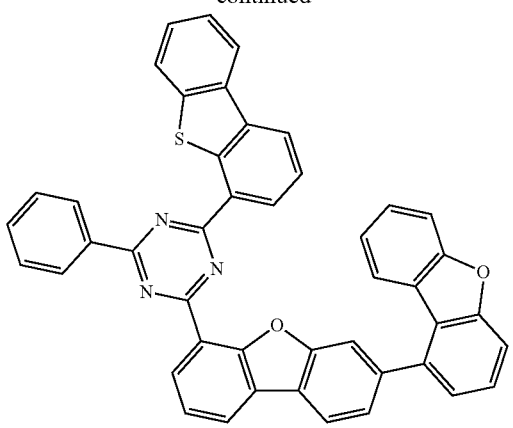
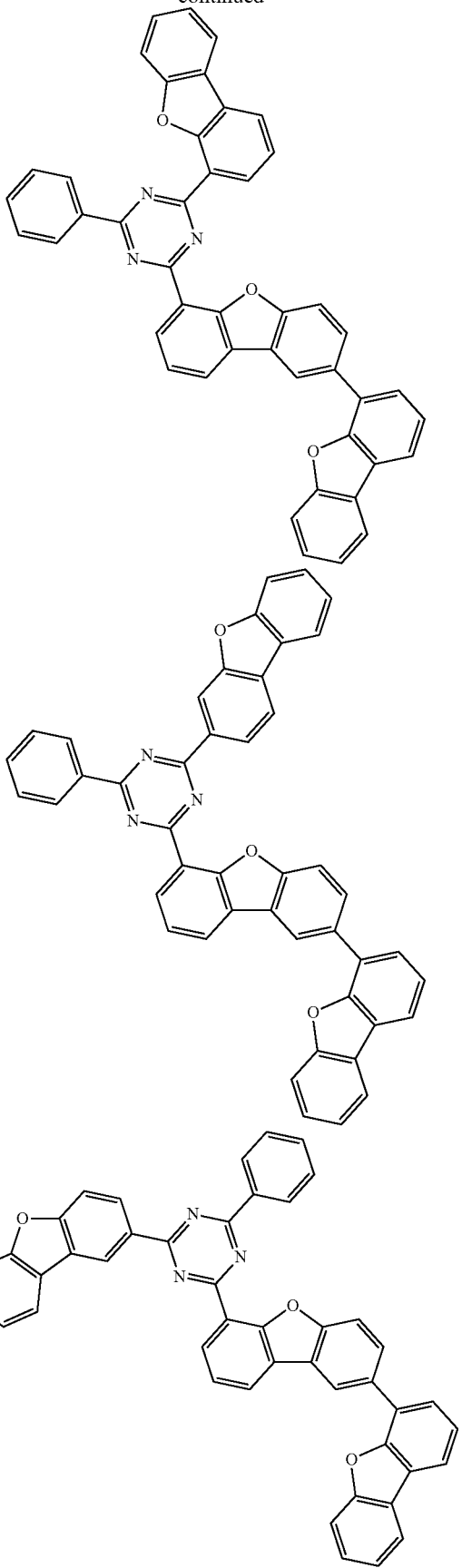

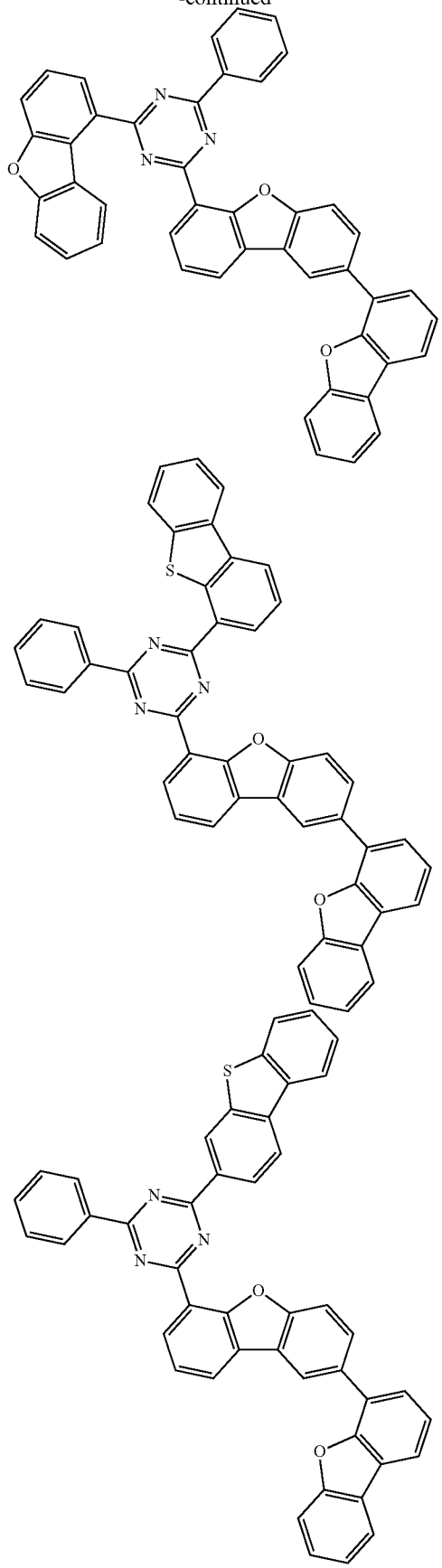
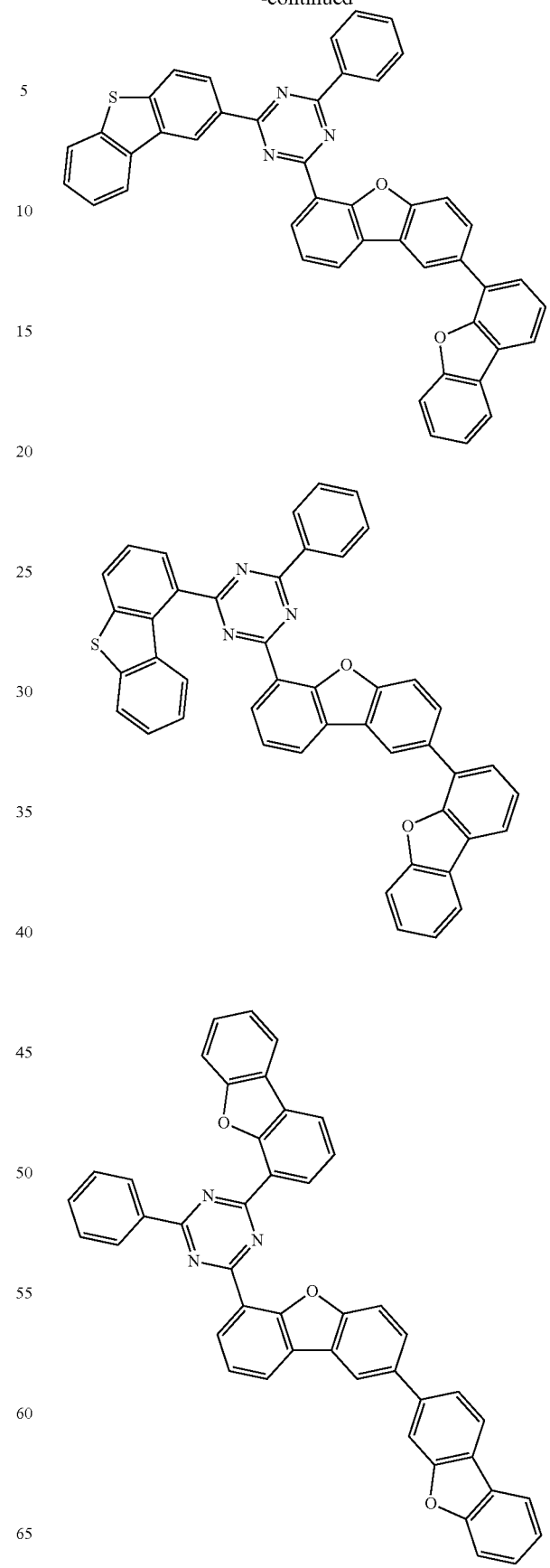

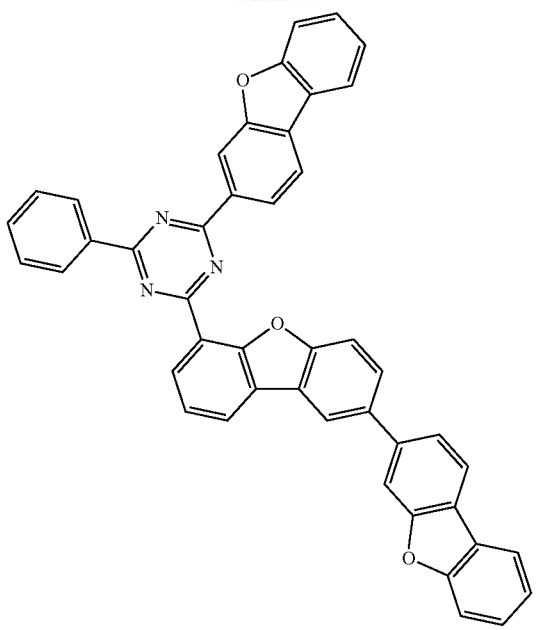
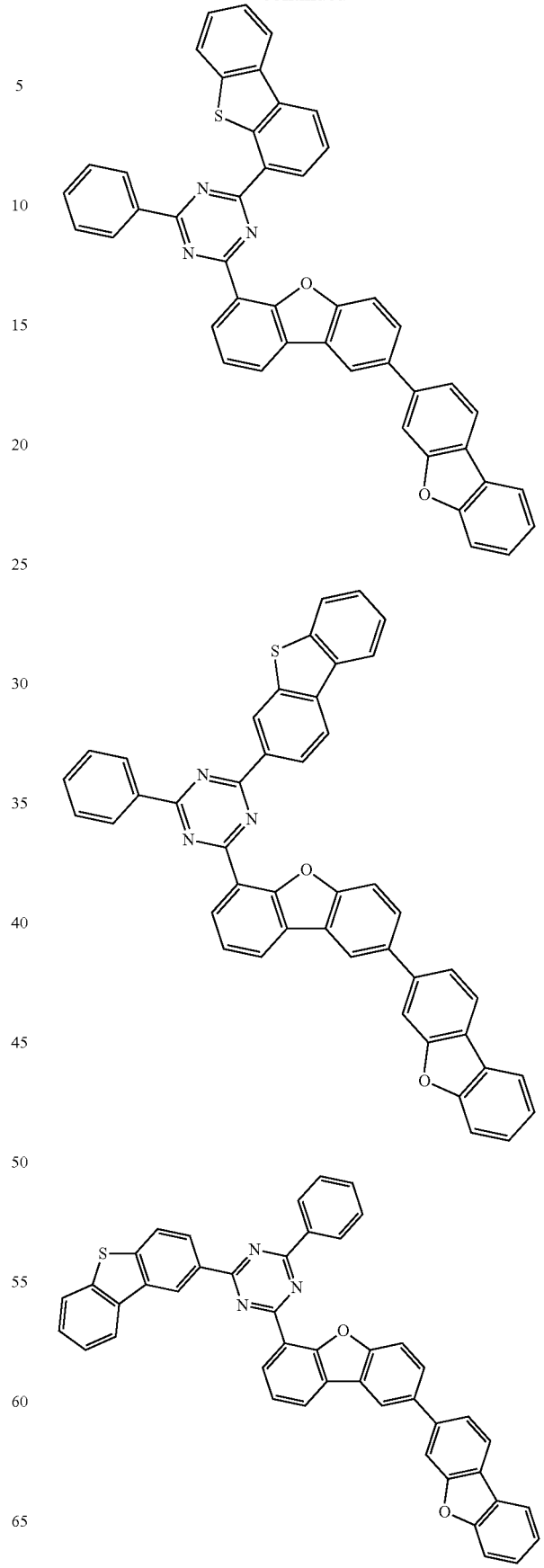

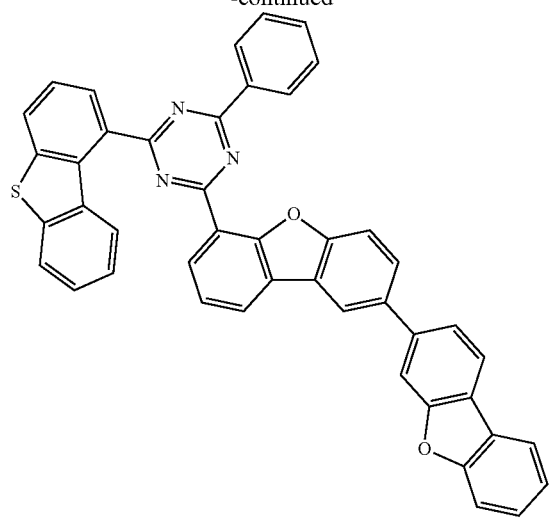
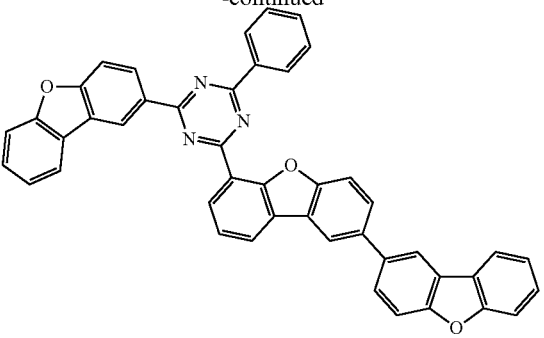
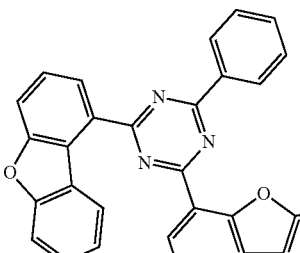
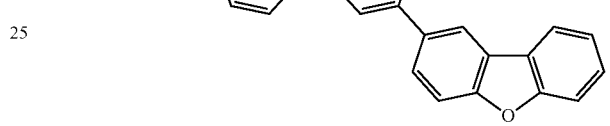
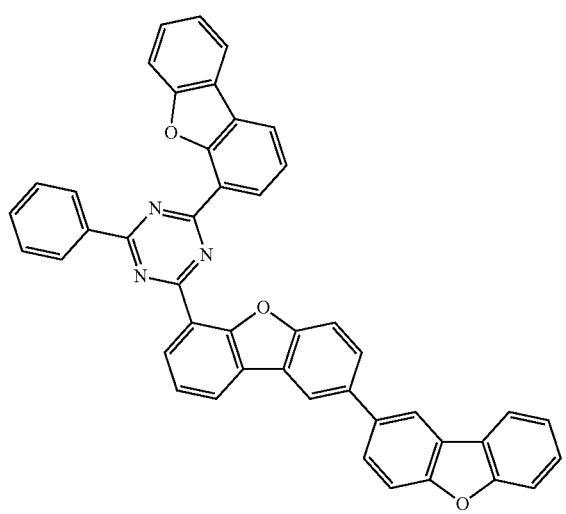
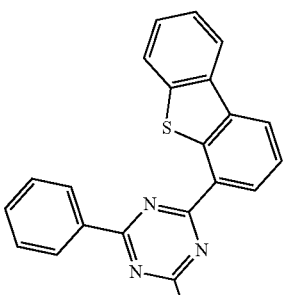
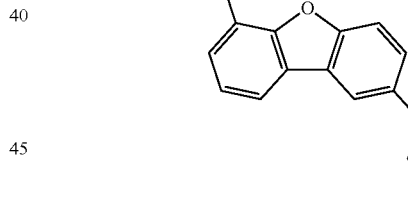
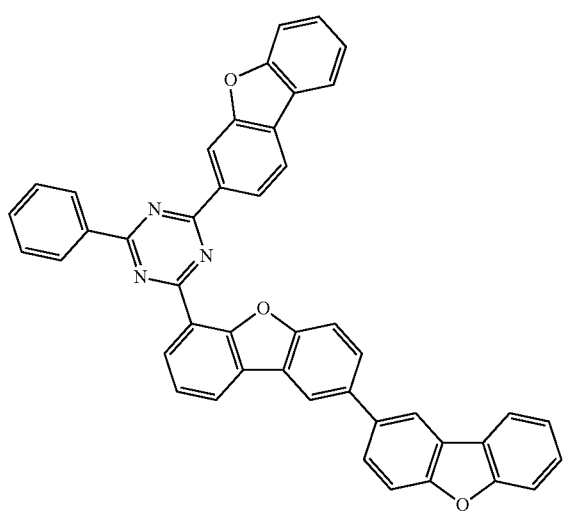
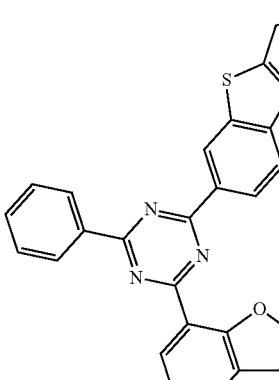
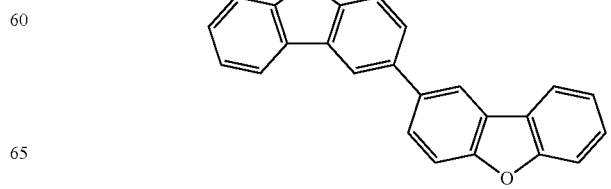

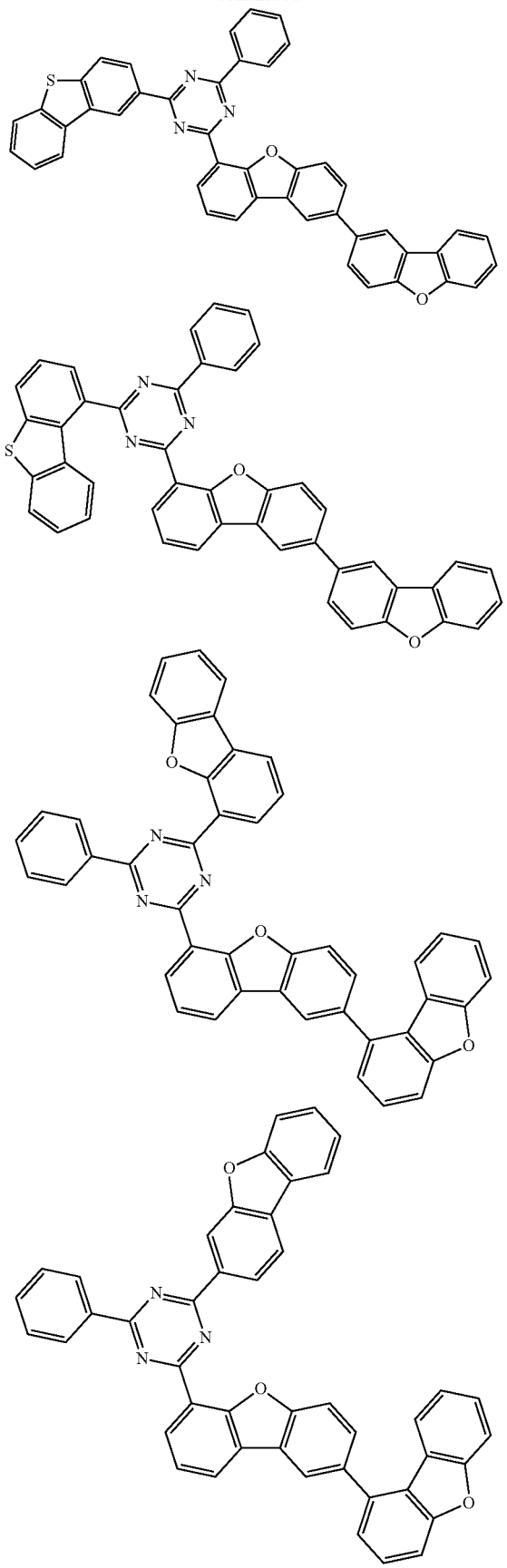
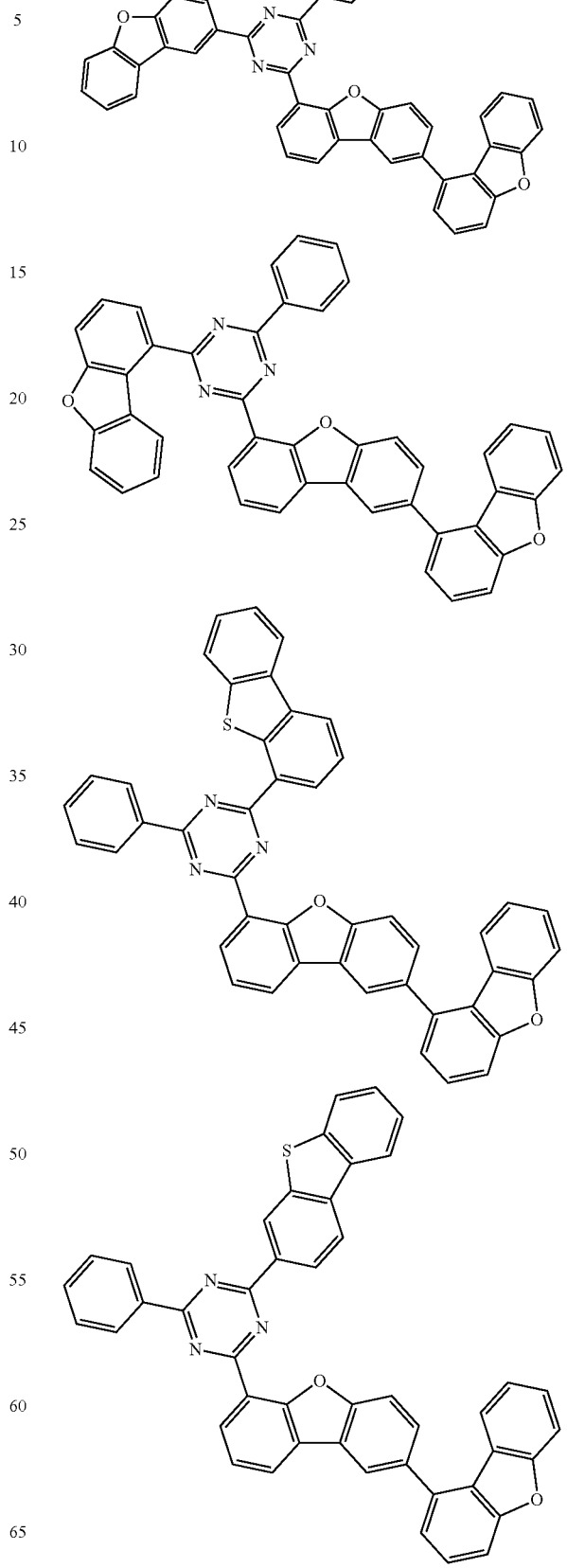

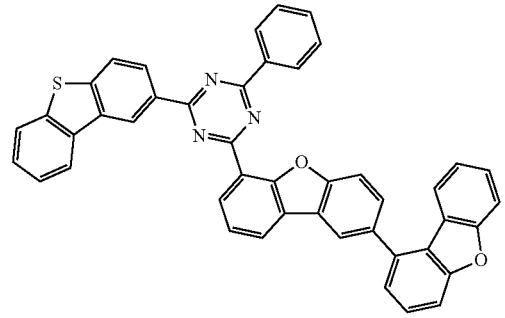
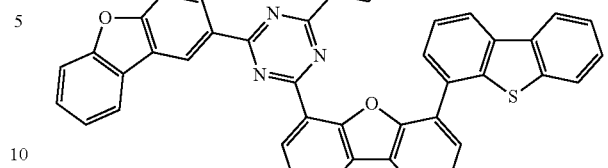
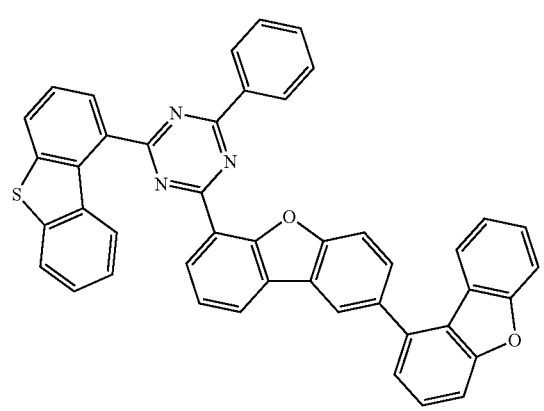
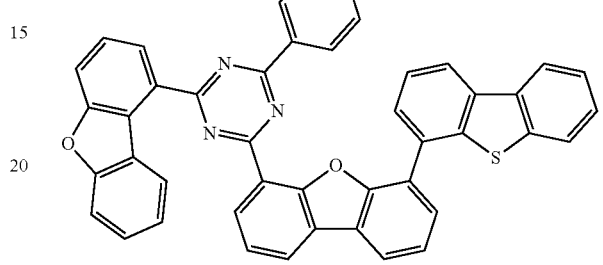
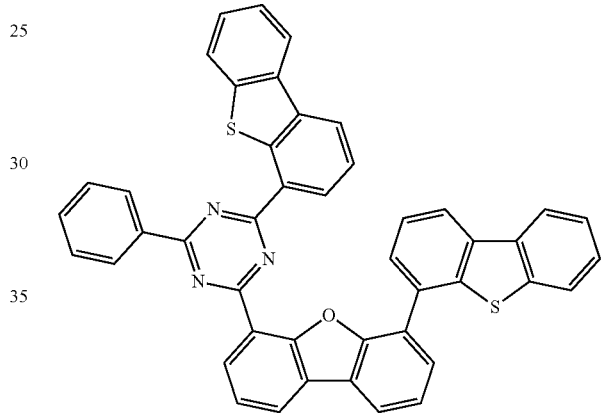
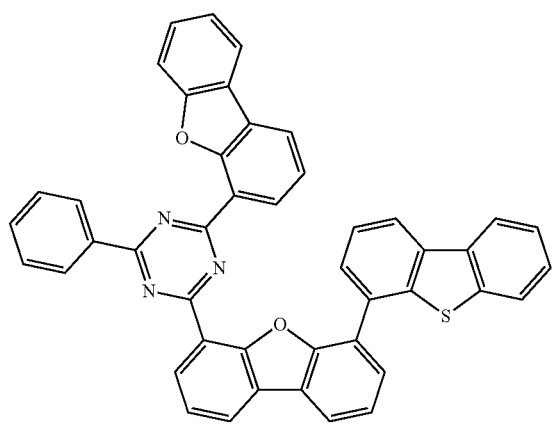
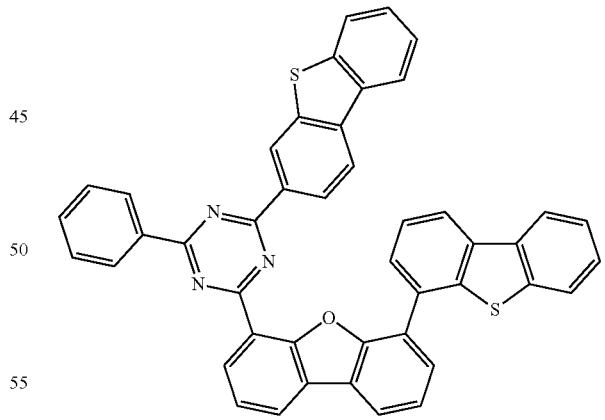
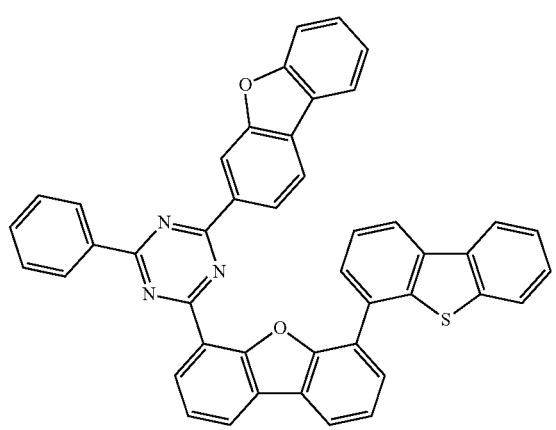
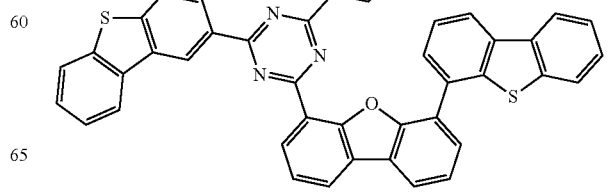

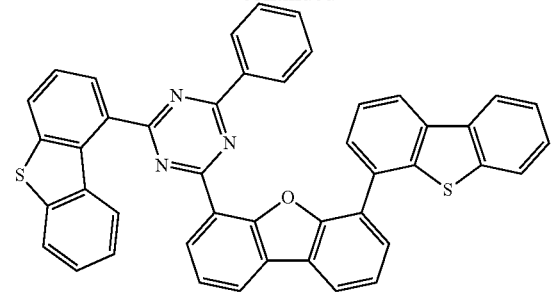
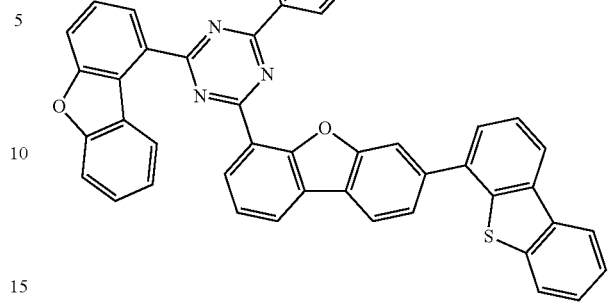
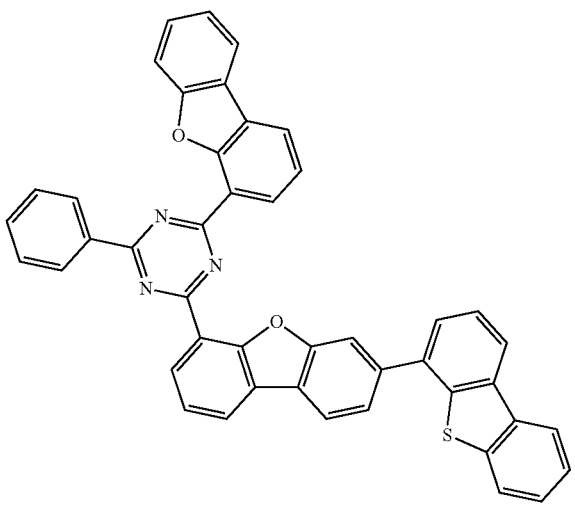
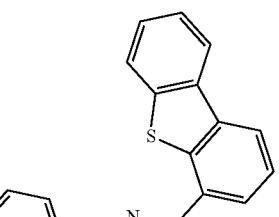
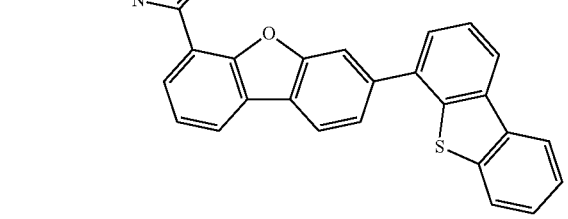
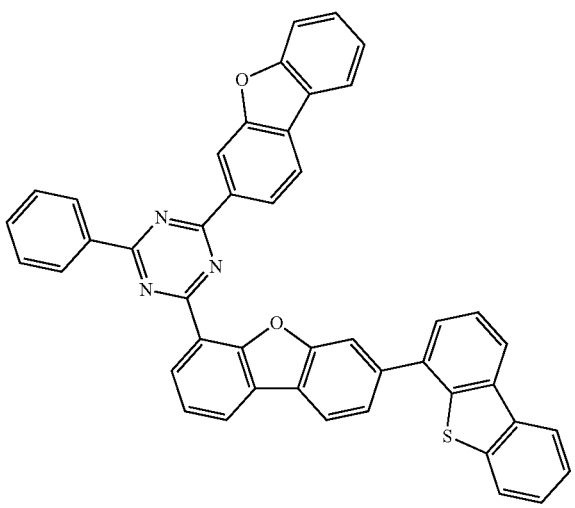
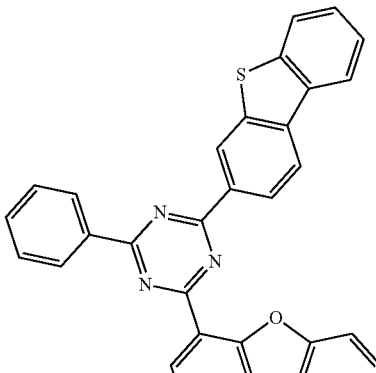
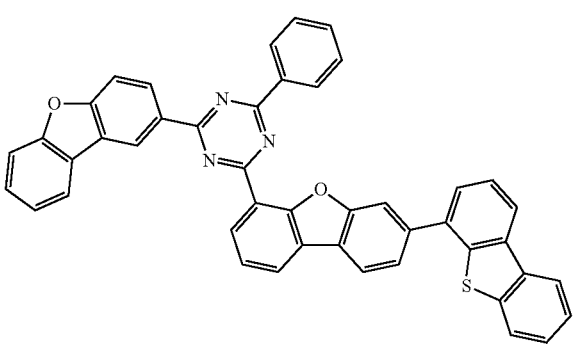
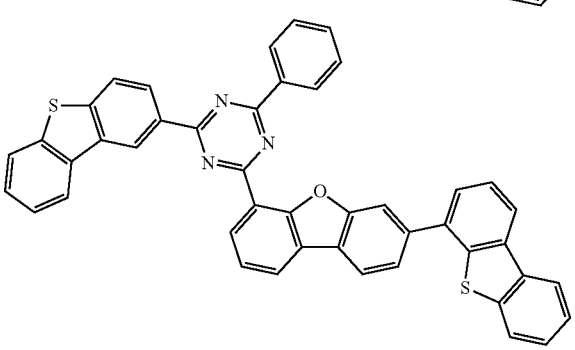

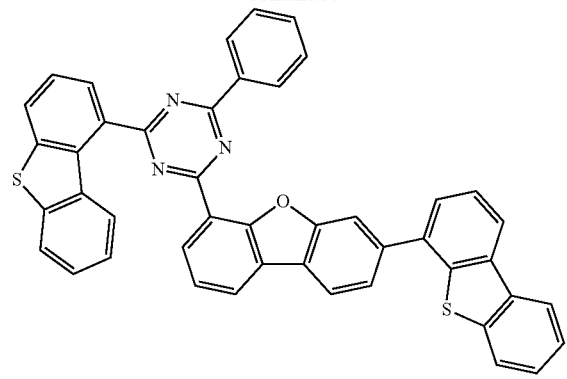
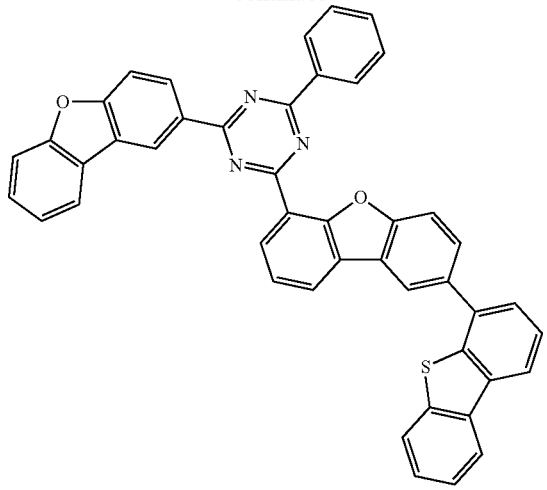
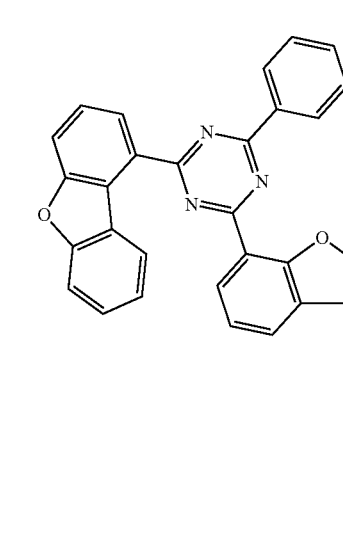
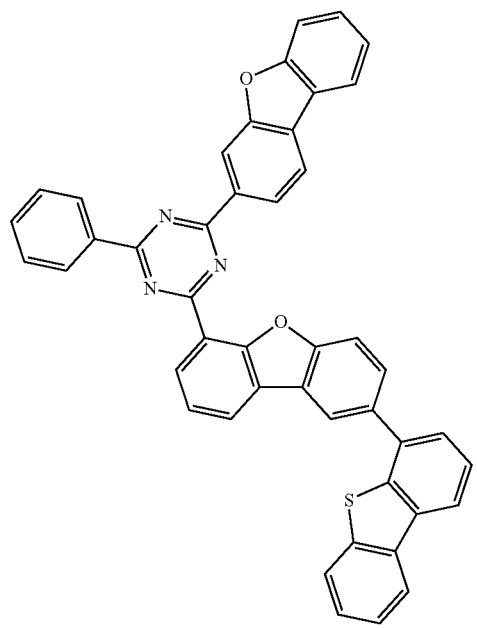
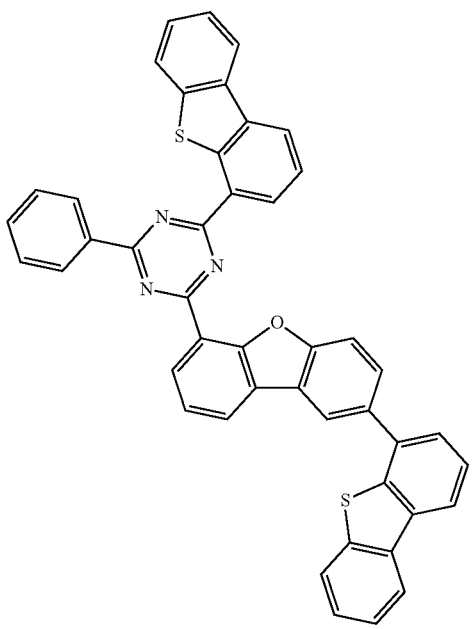

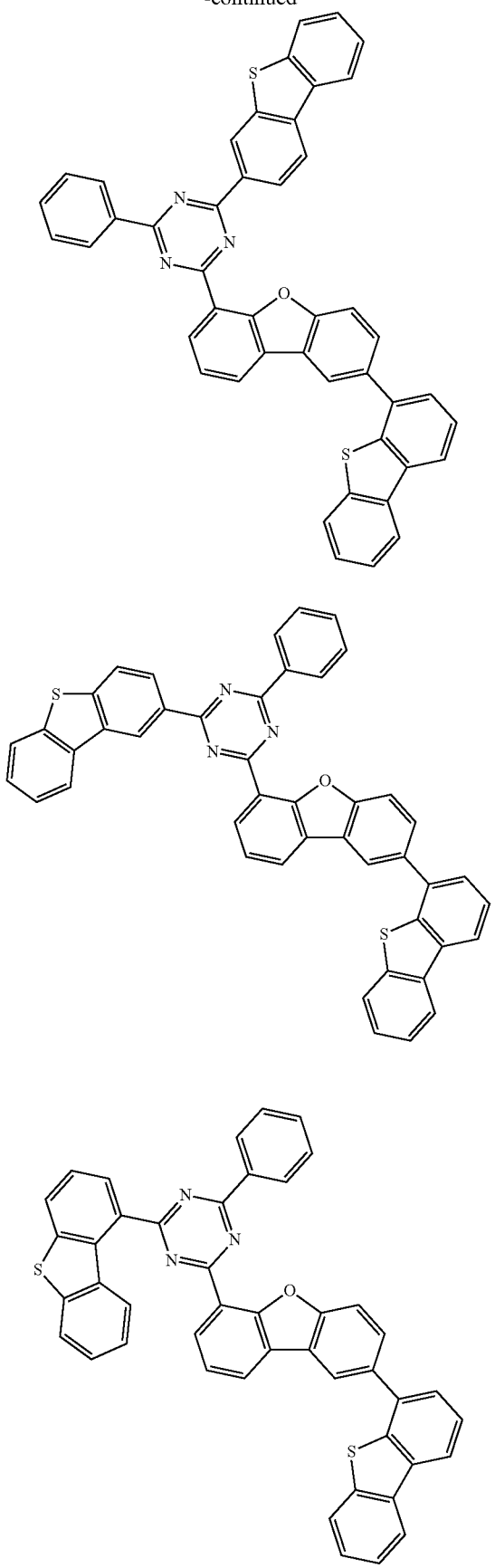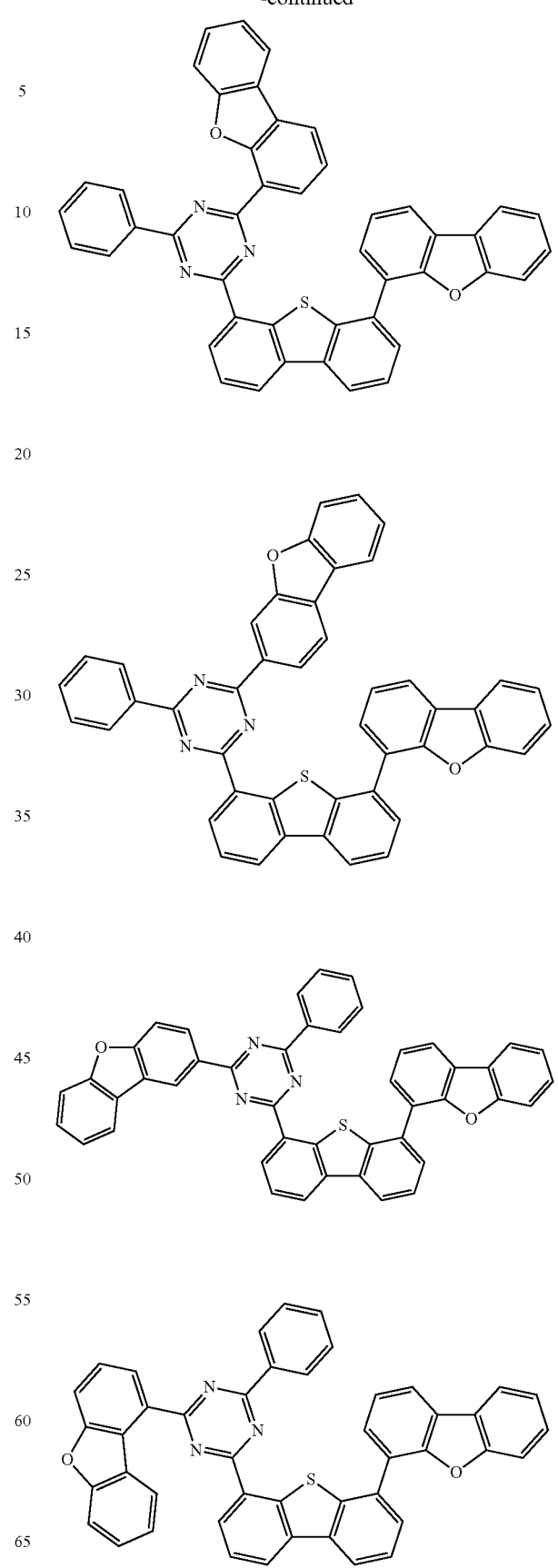

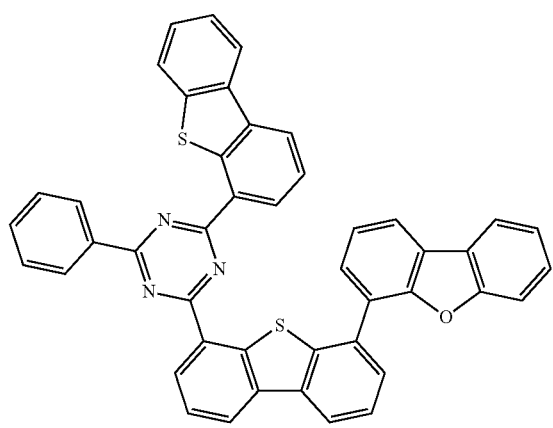
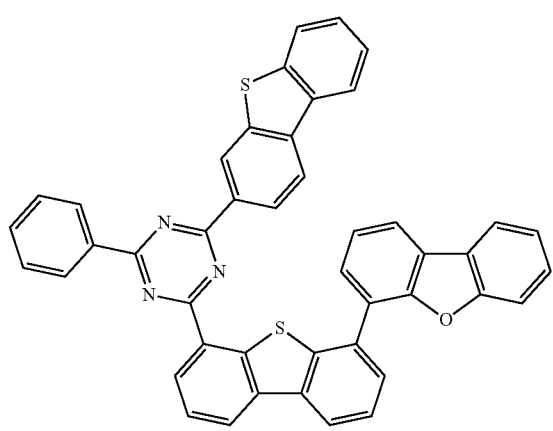
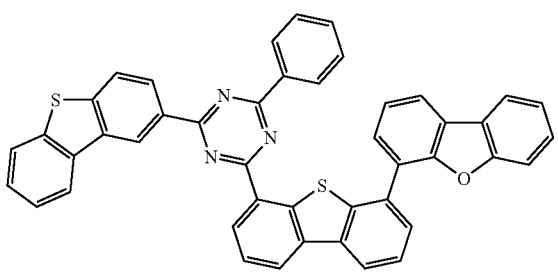
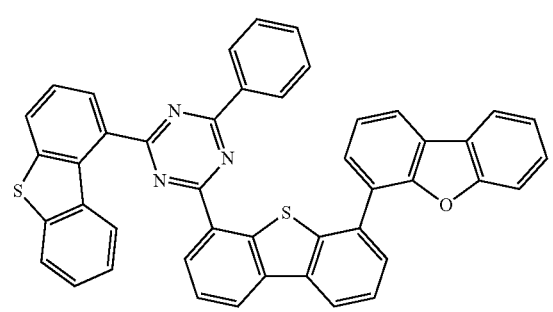
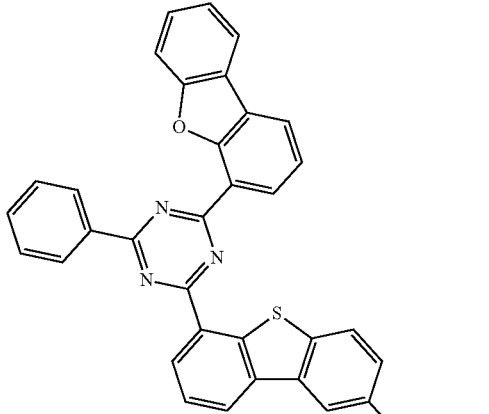
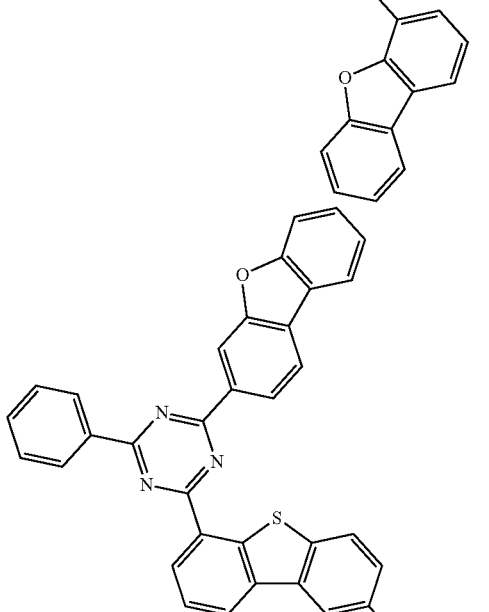
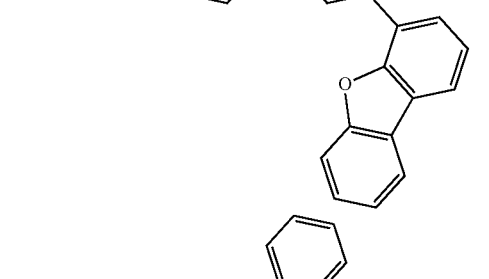
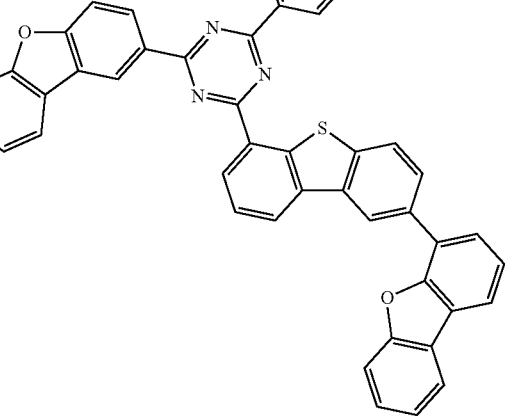

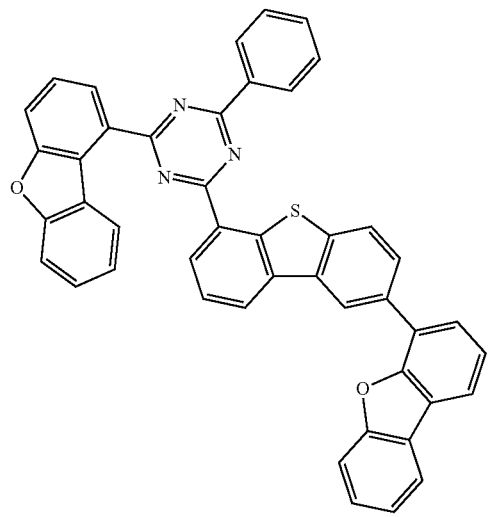
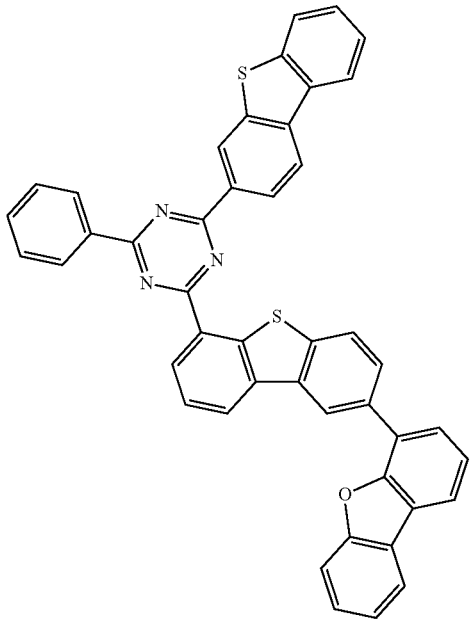
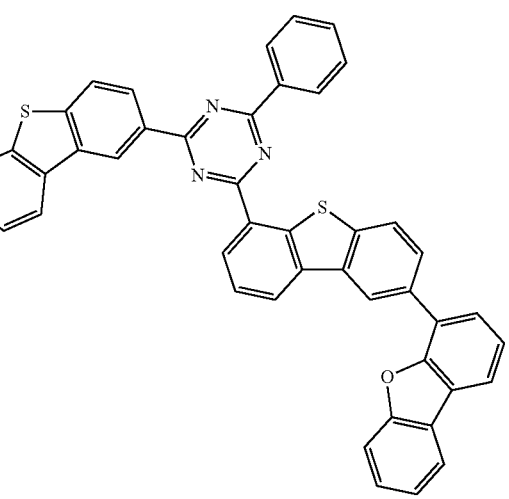
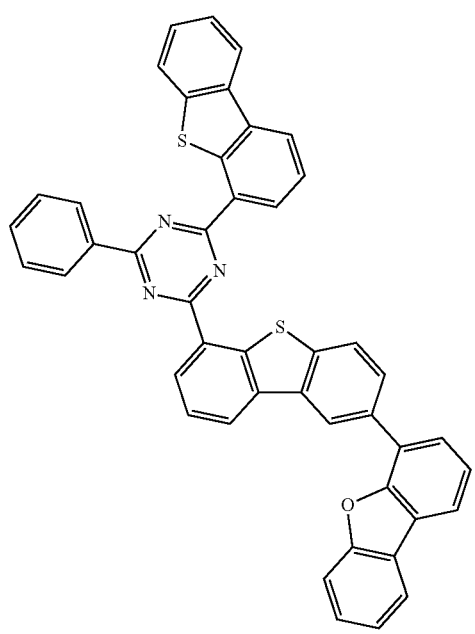
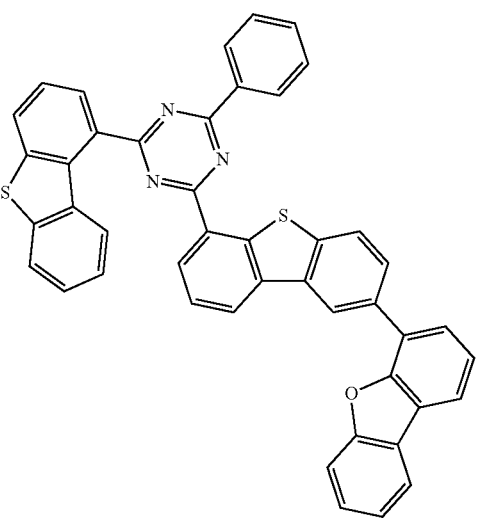

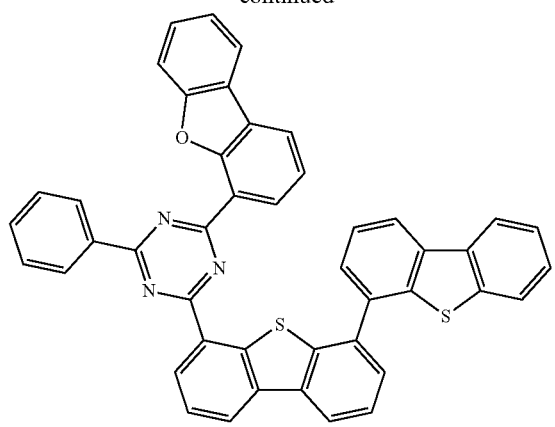
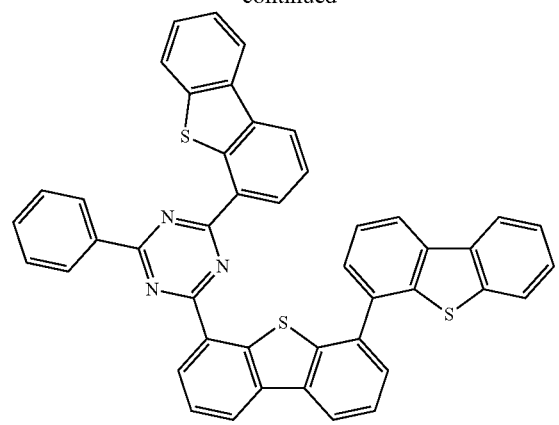
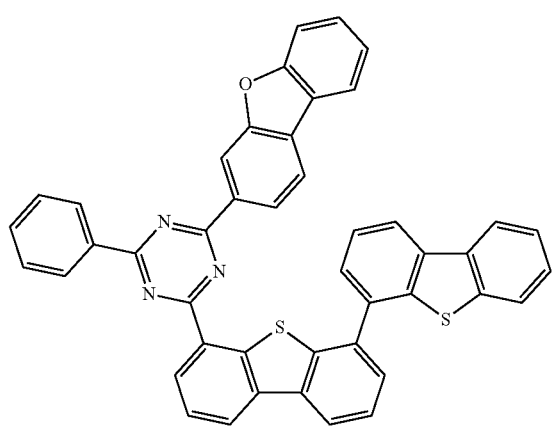
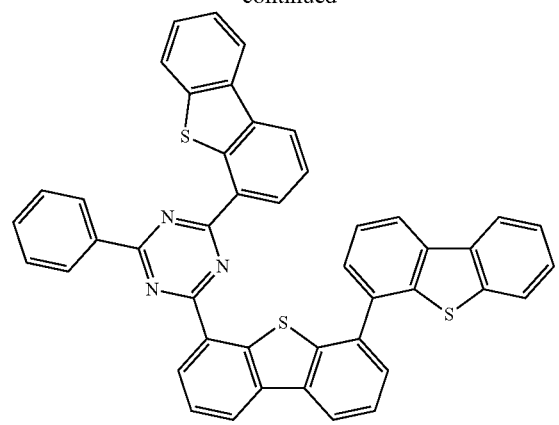
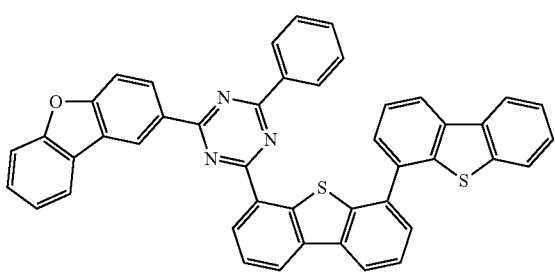
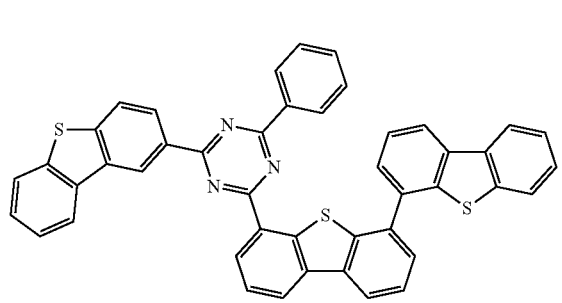
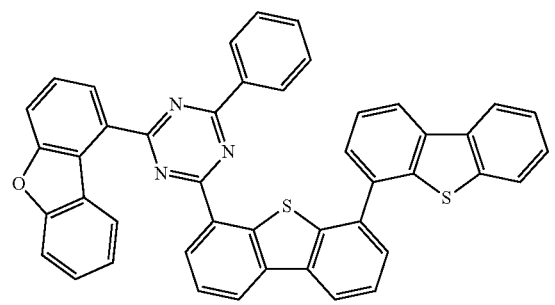
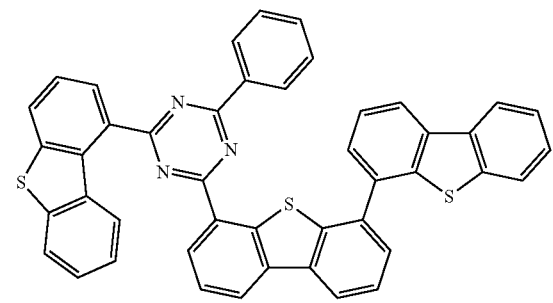

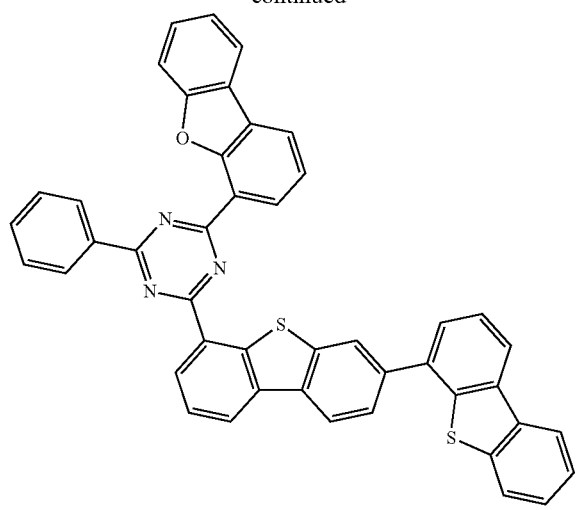
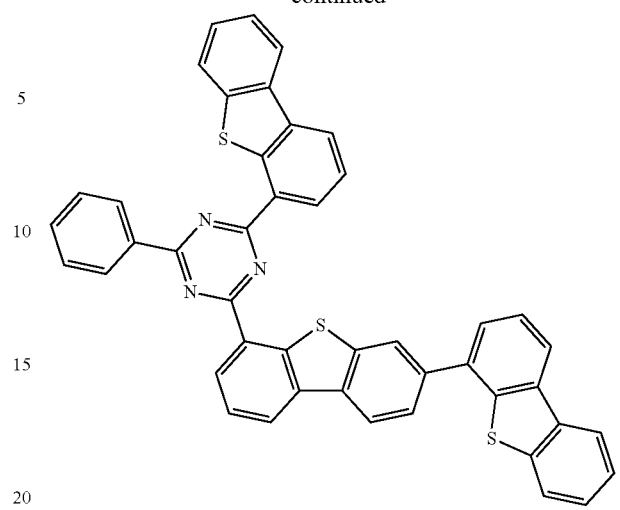
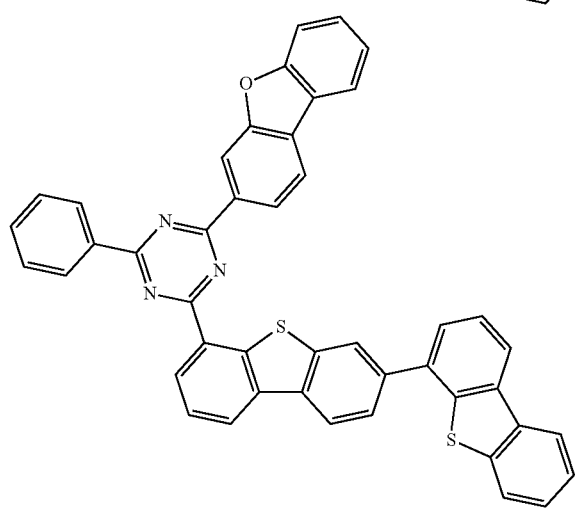
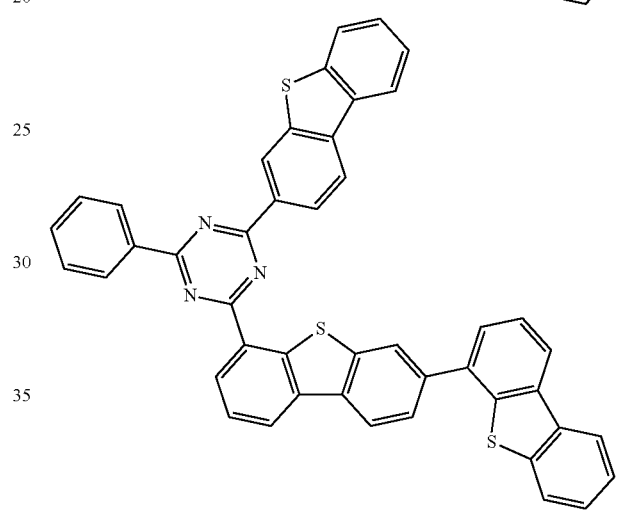
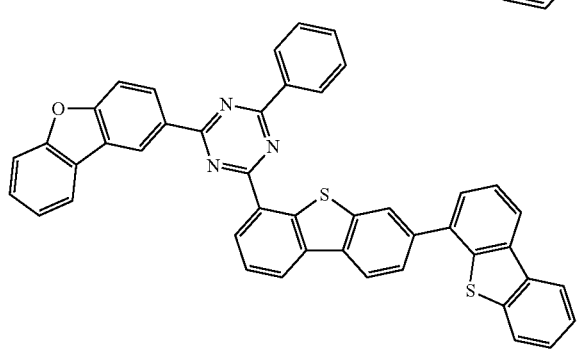
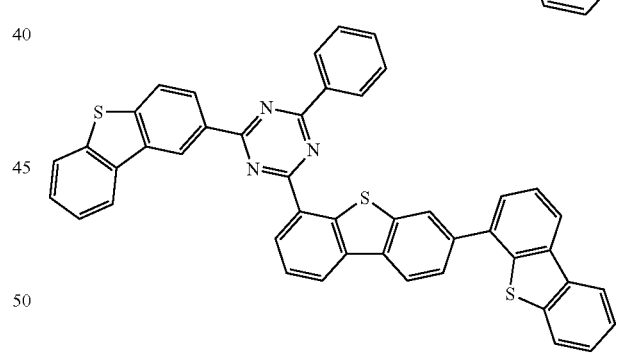
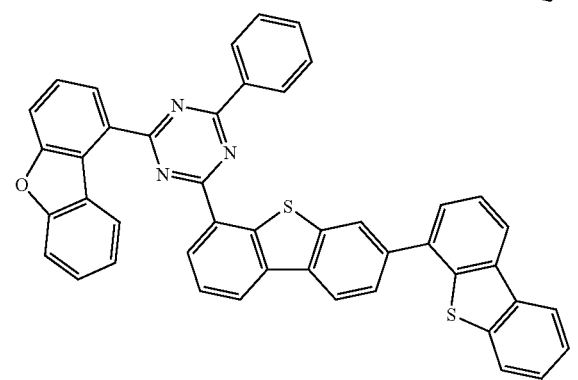
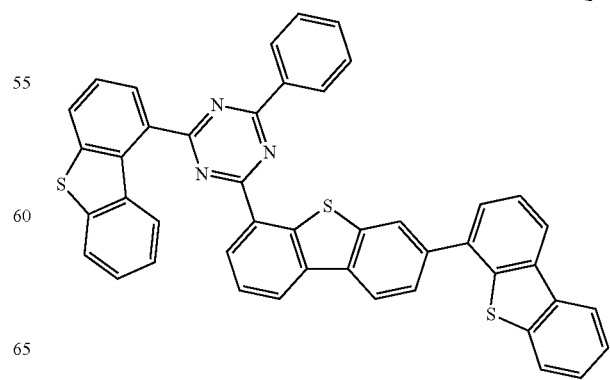

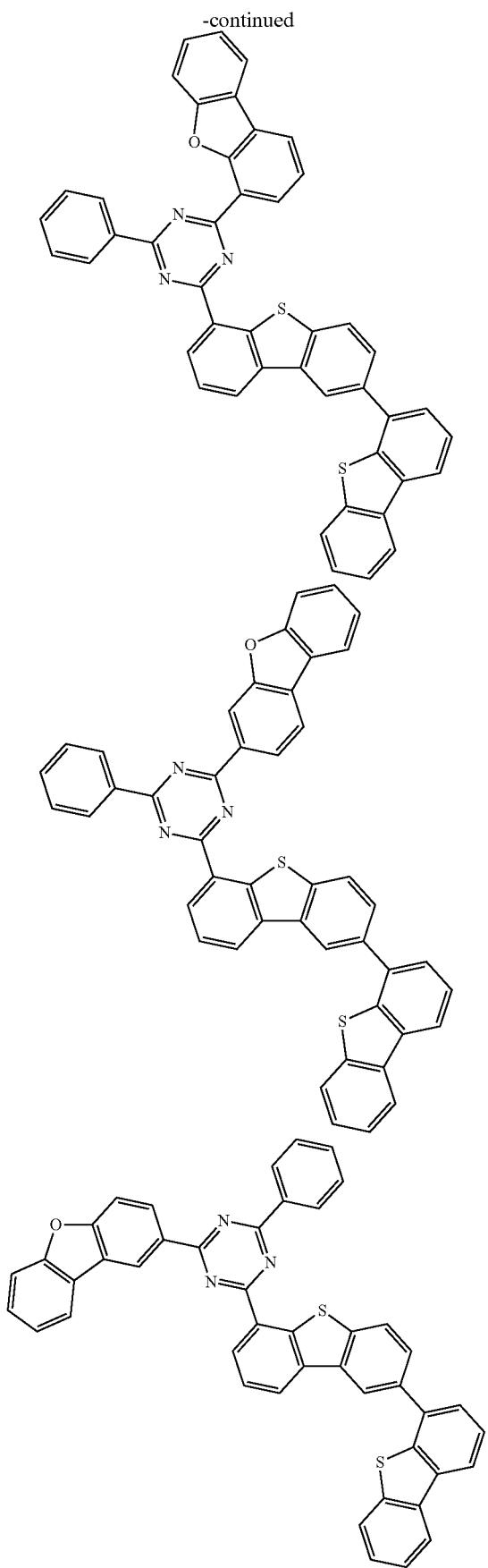
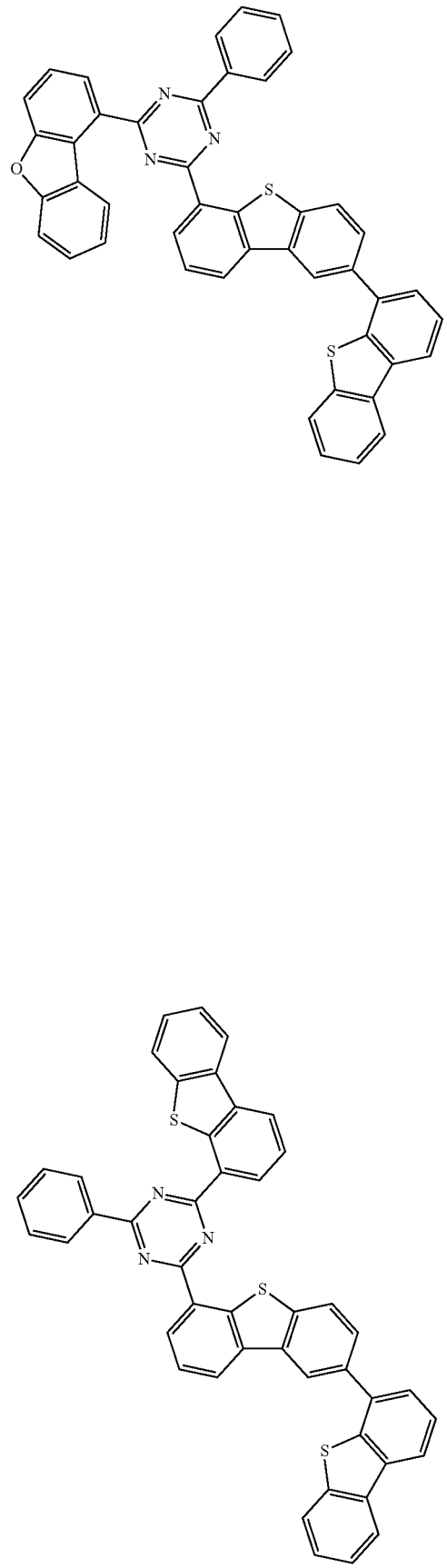

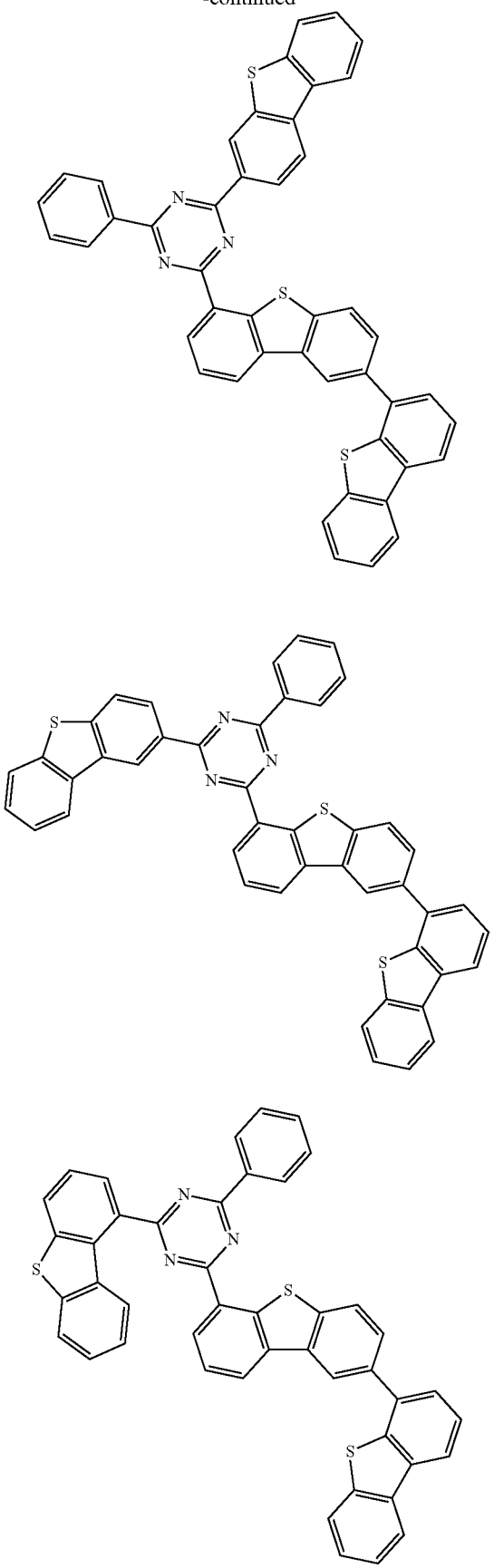
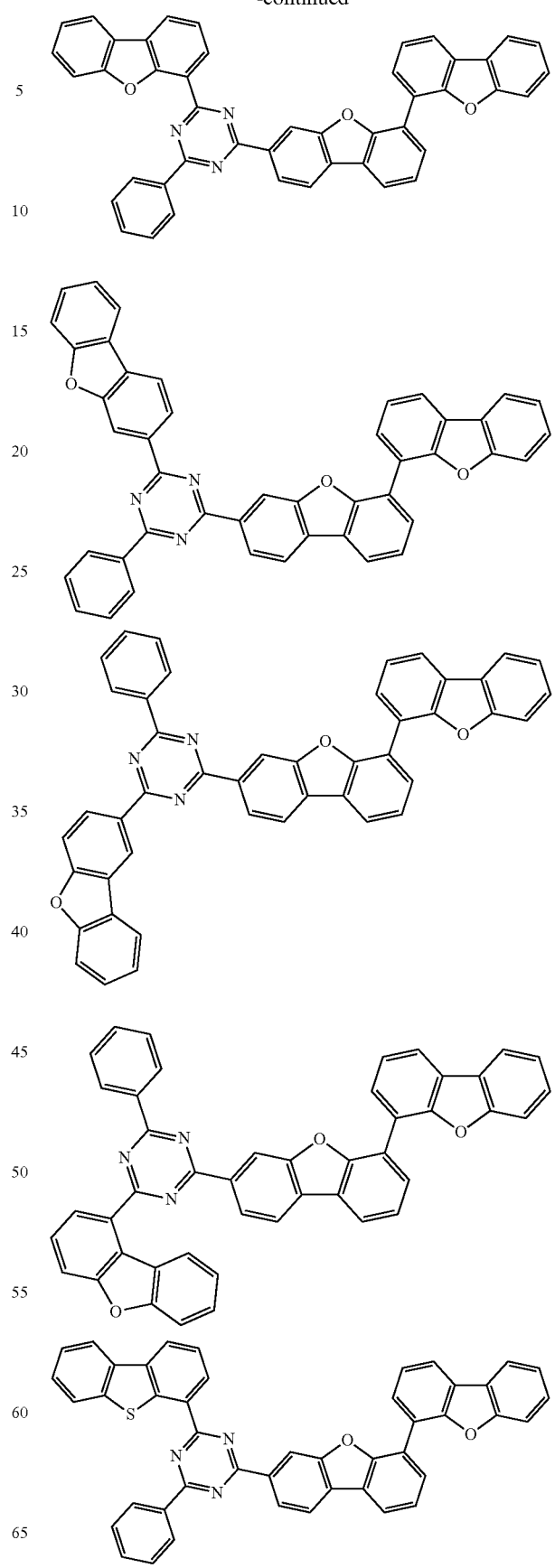

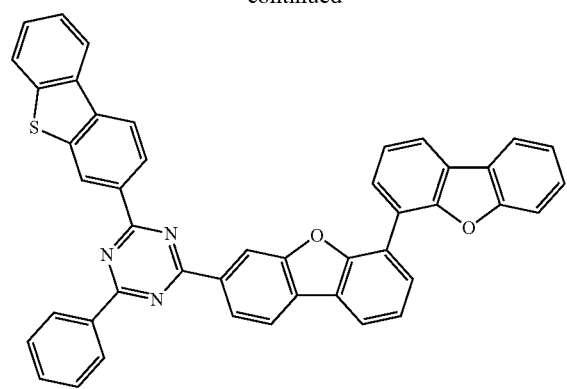
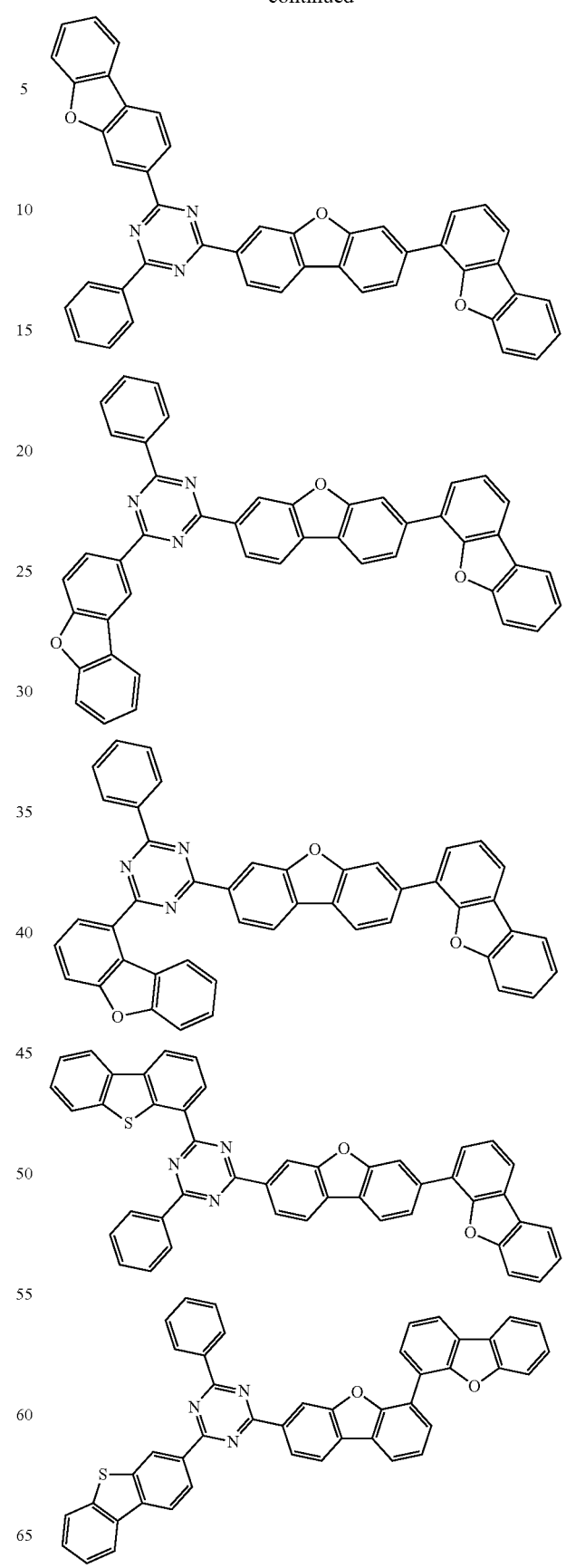

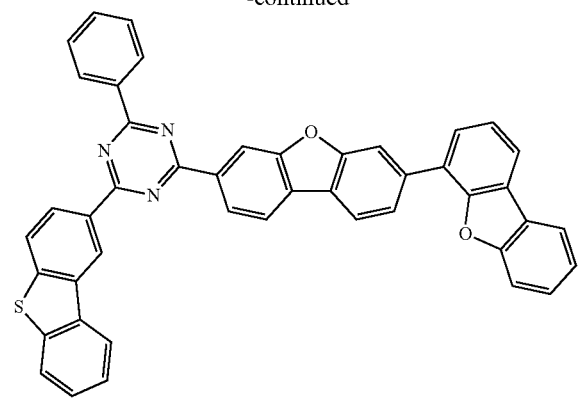
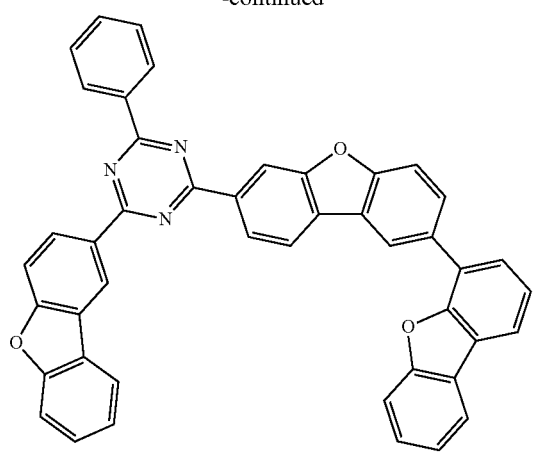
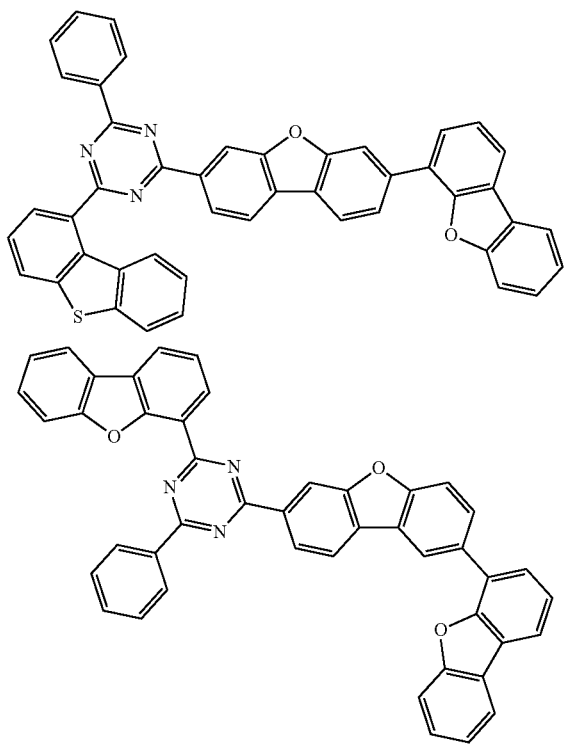
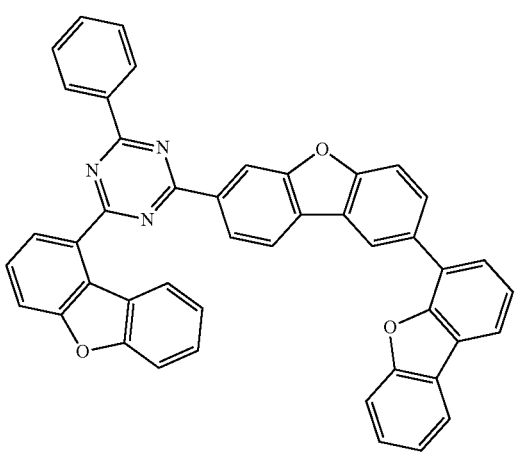
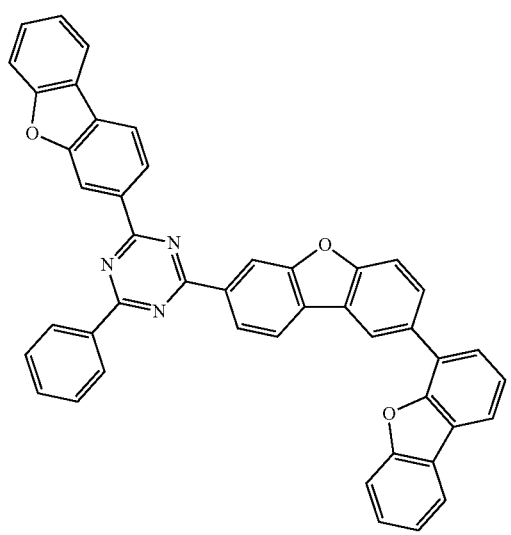
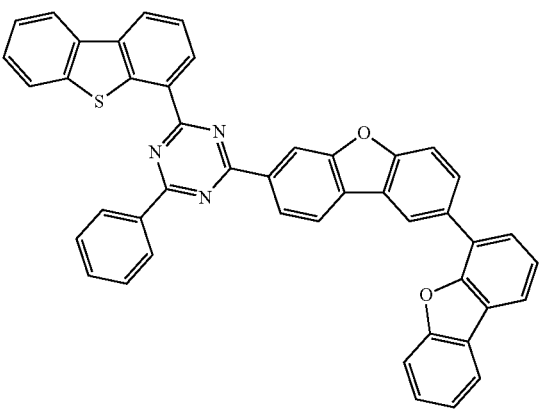

-continued
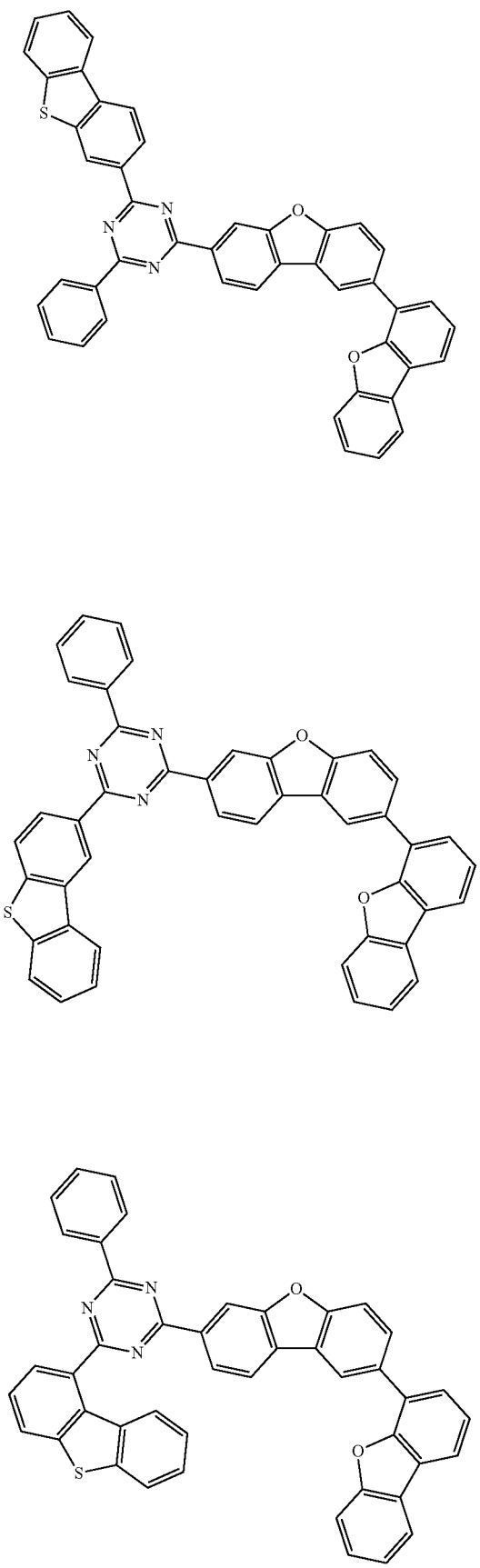
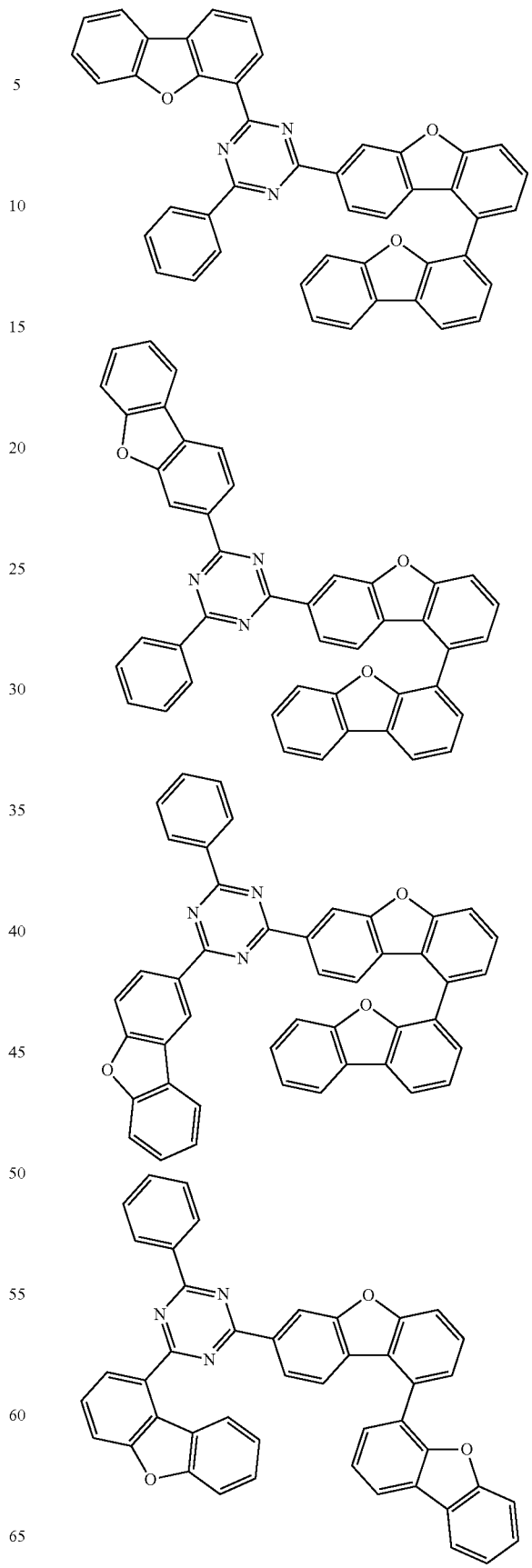

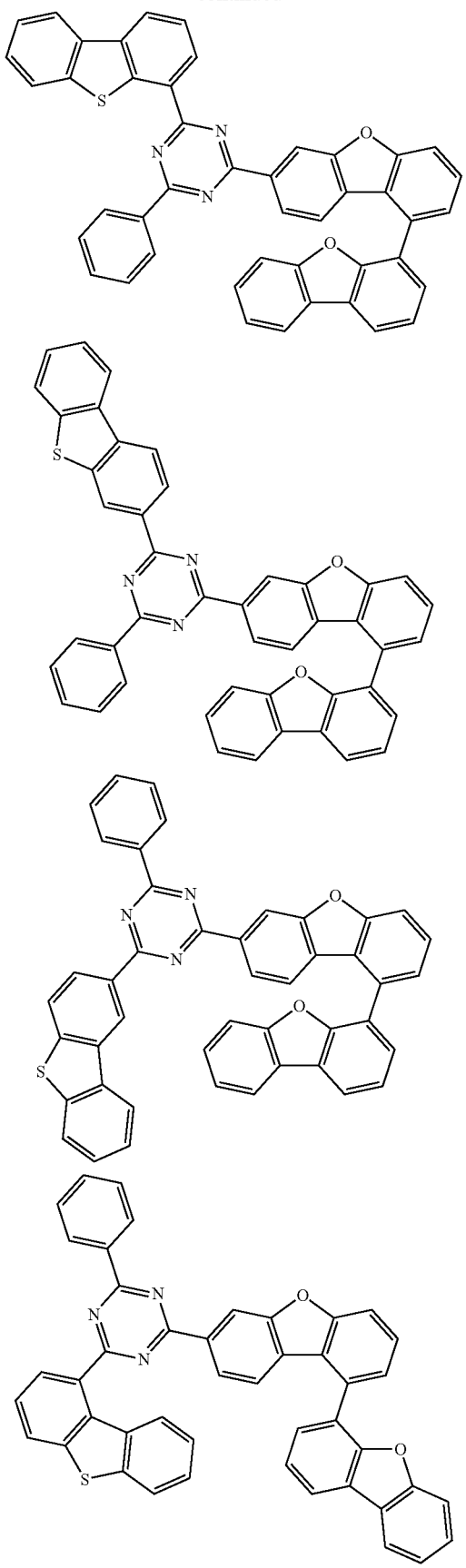
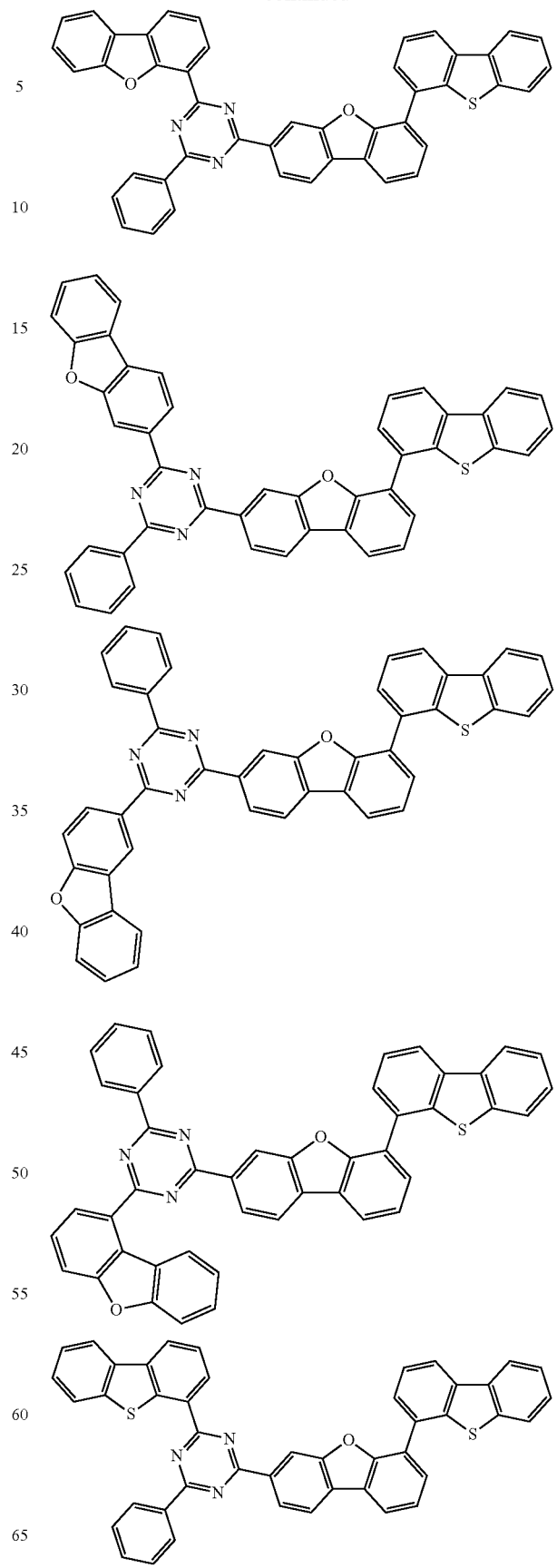

61
-continued
62
-continued
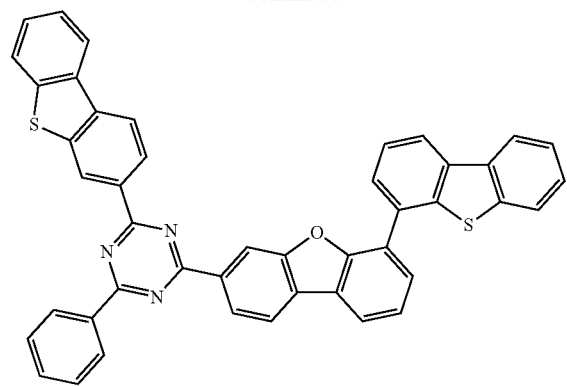
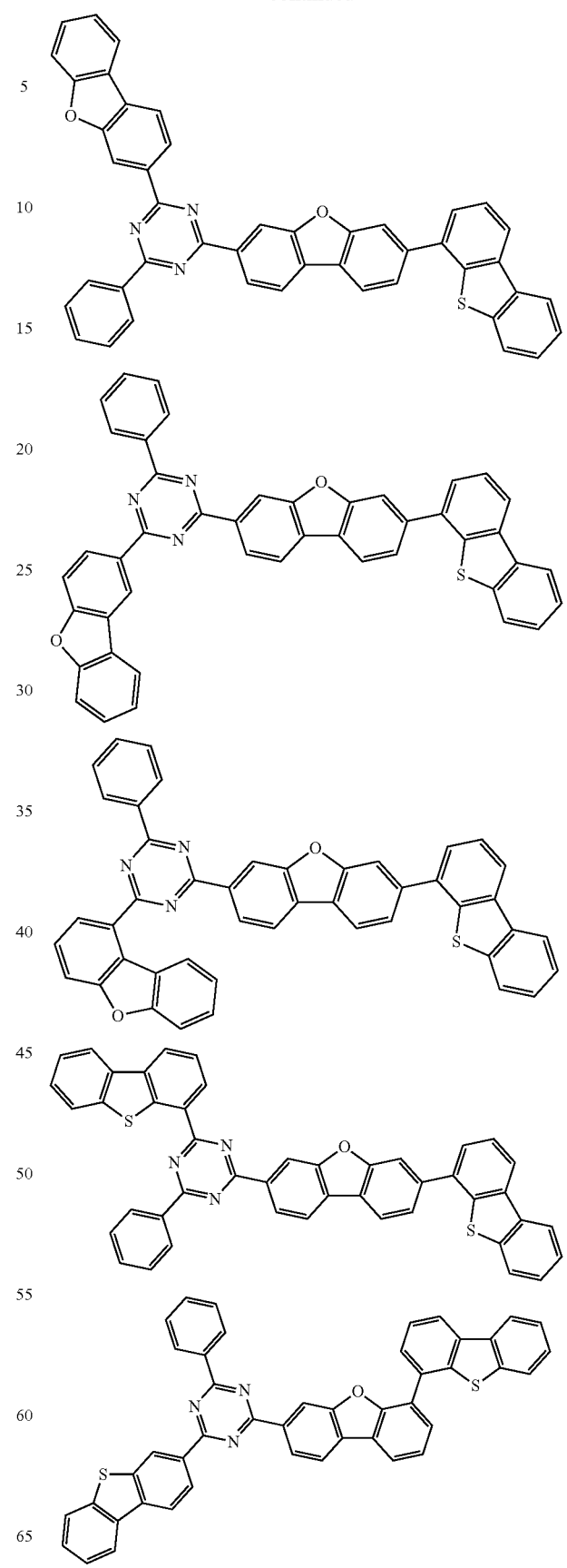

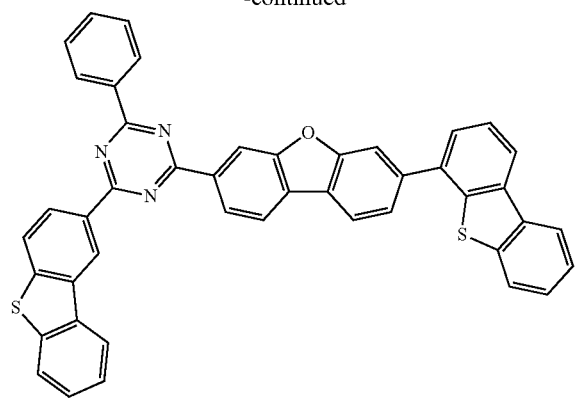
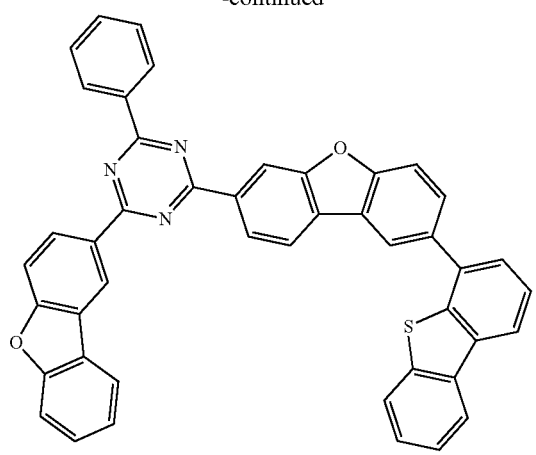
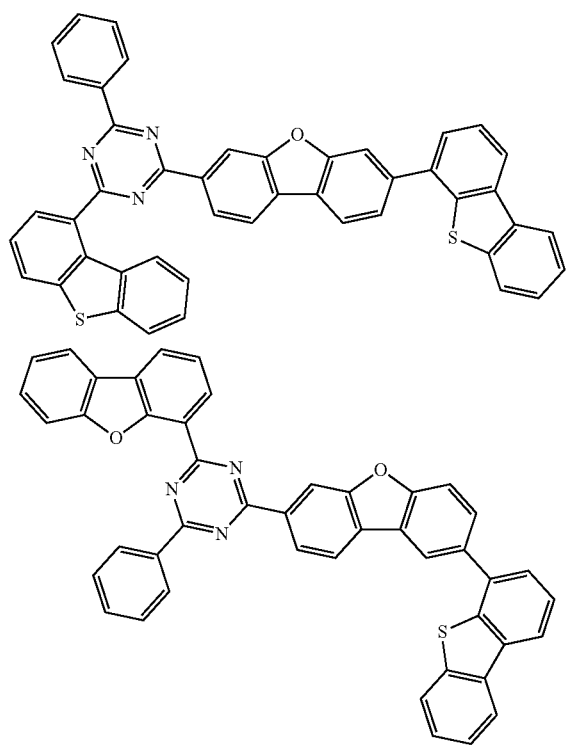
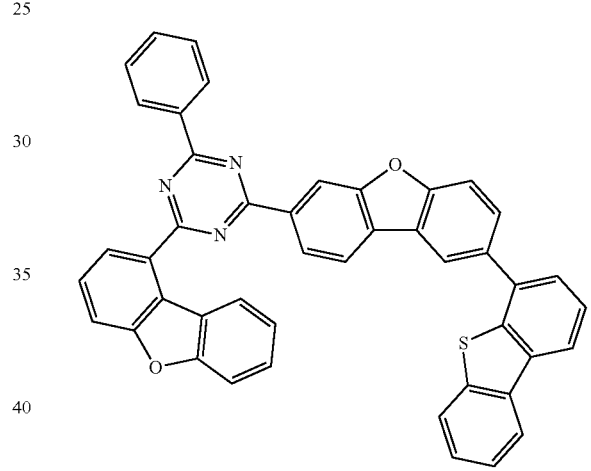
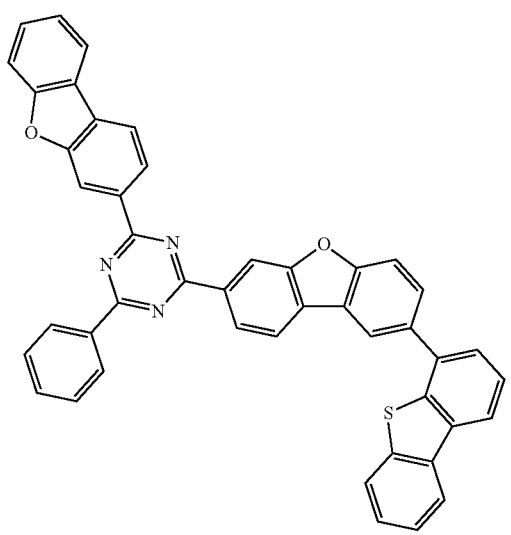
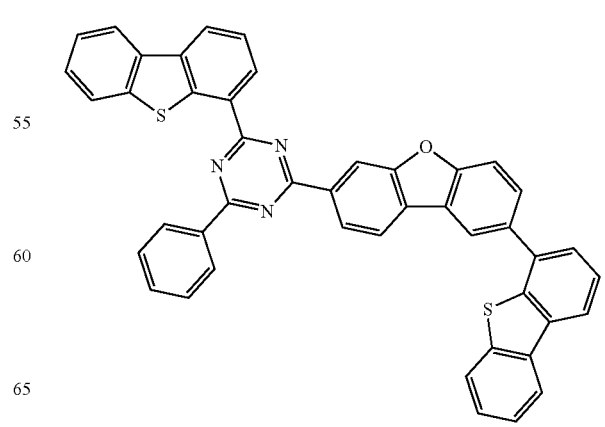

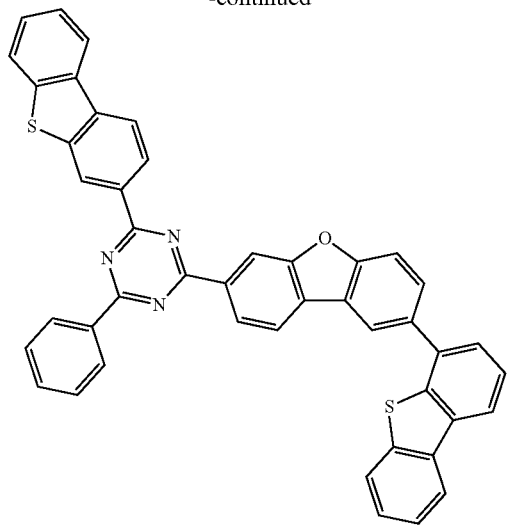
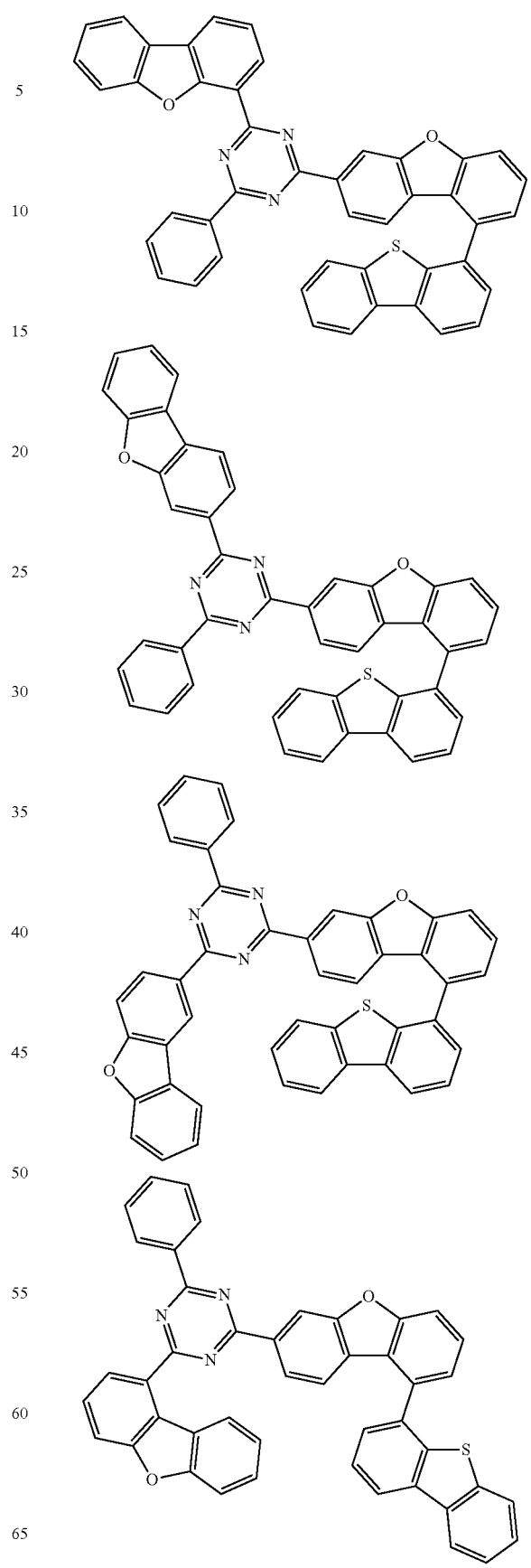

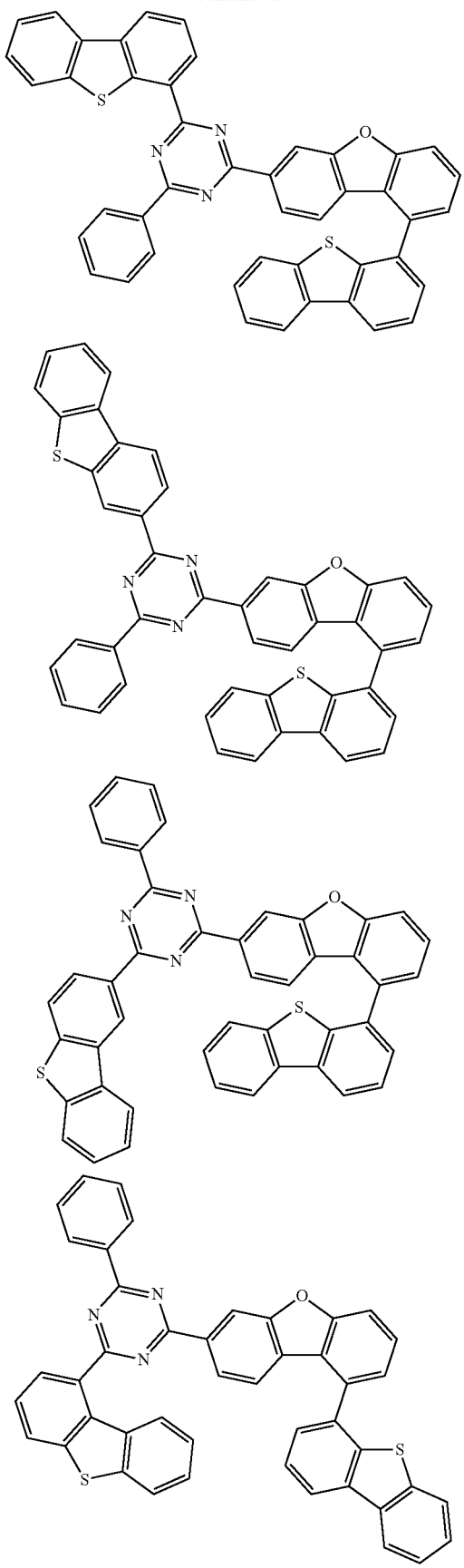
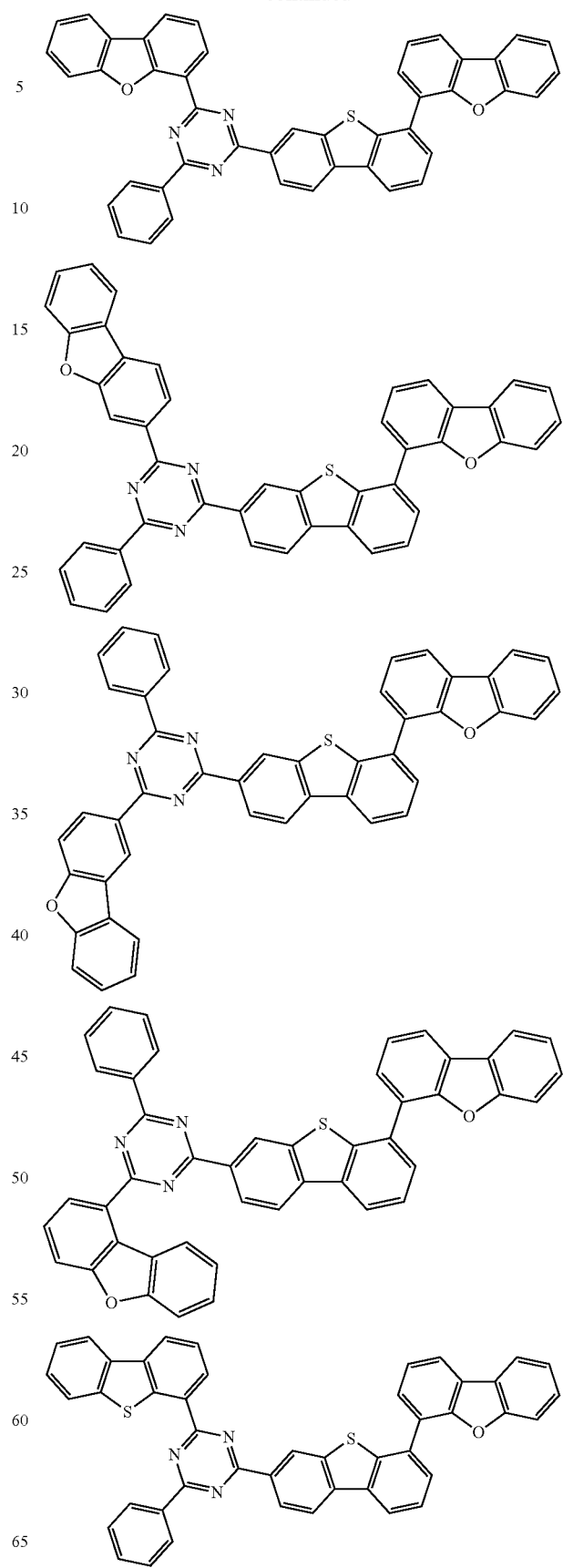

69
-continued
70
-continued
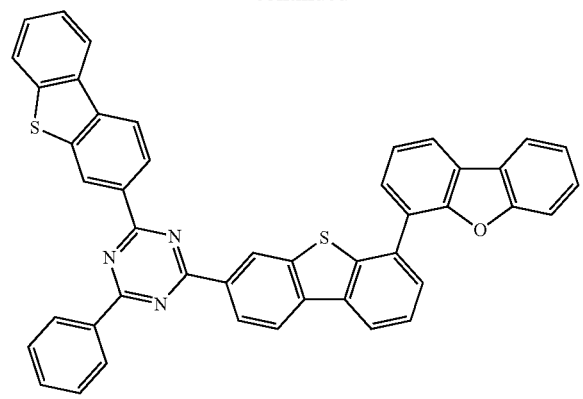
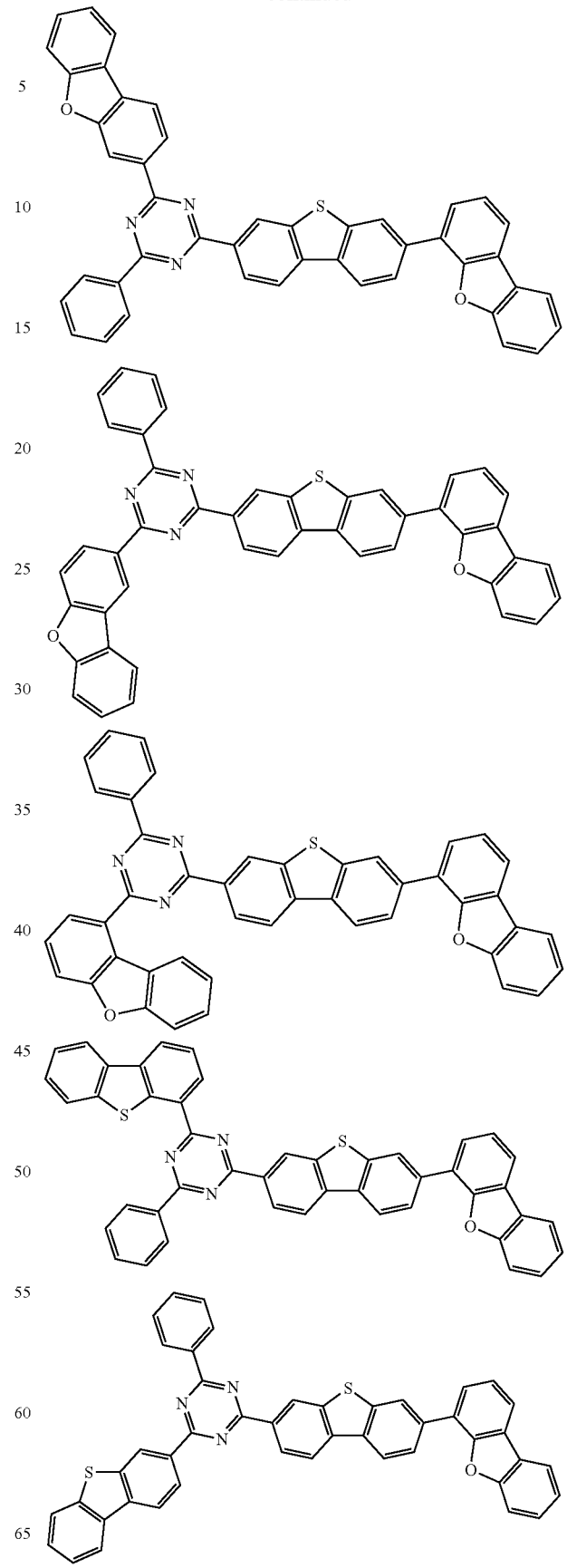

71
-continued
72
-continued
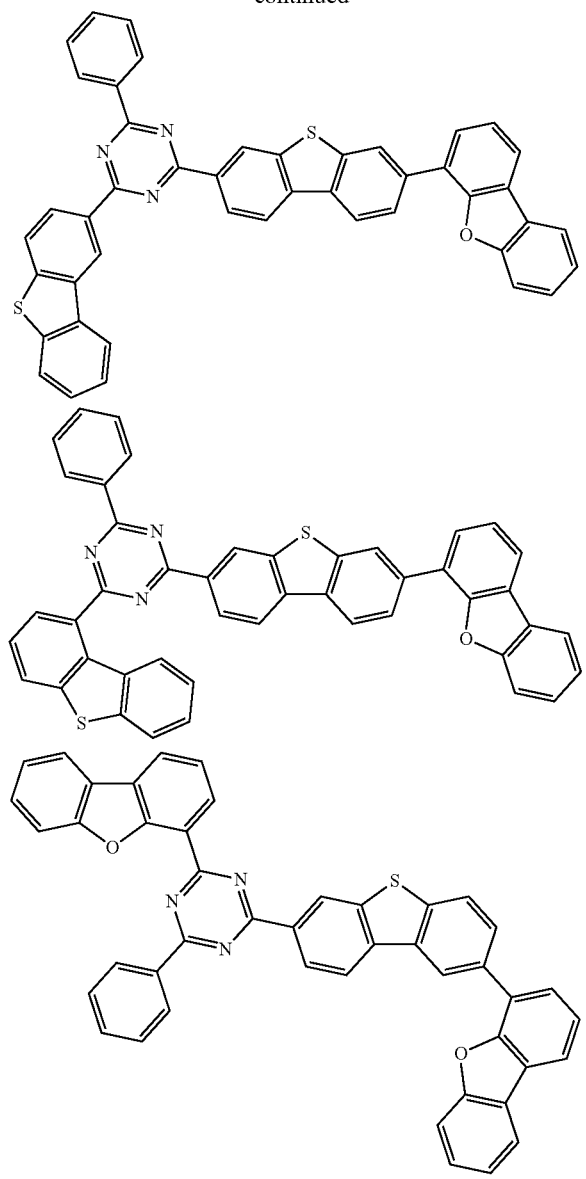
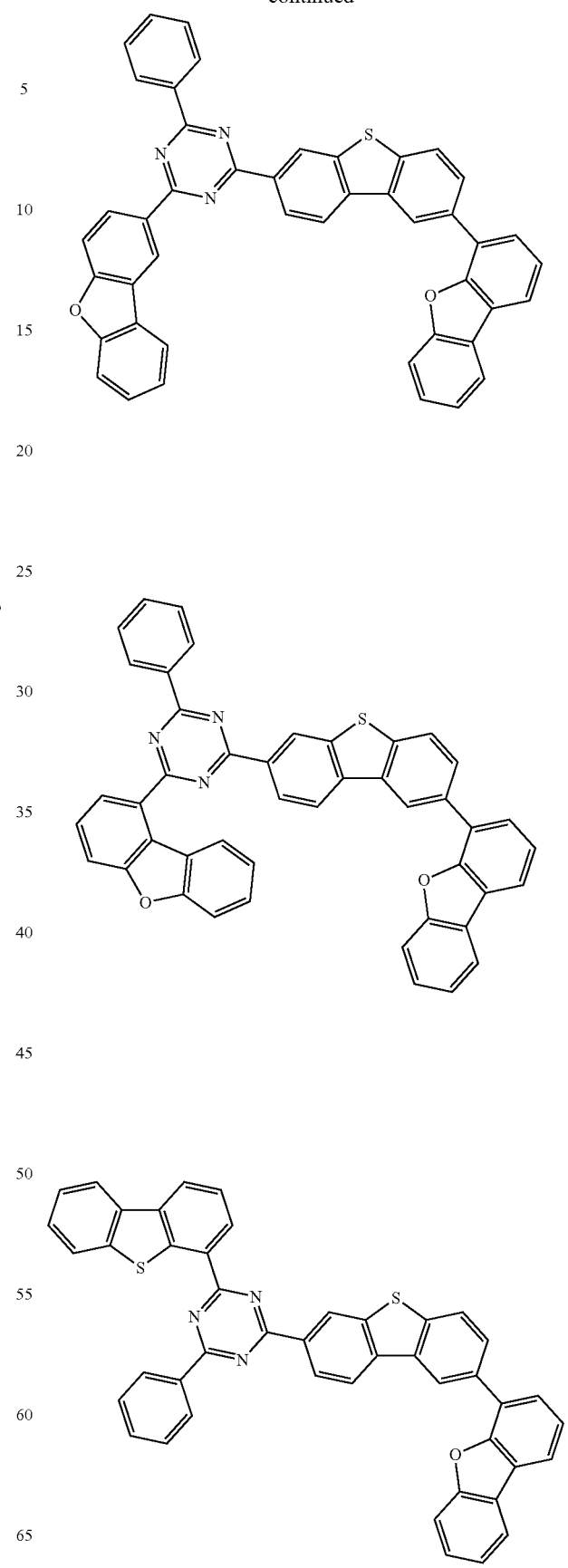

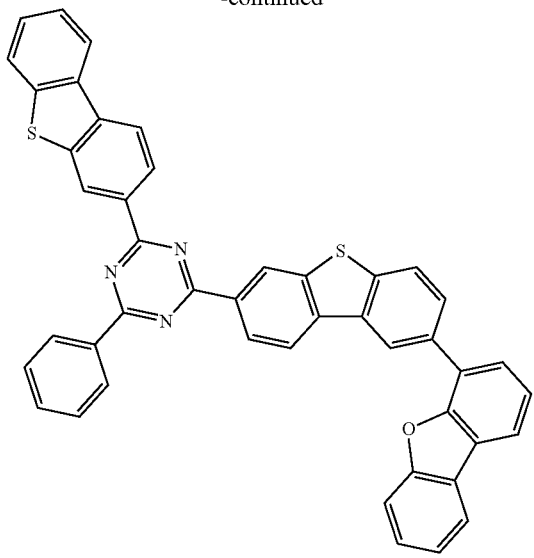
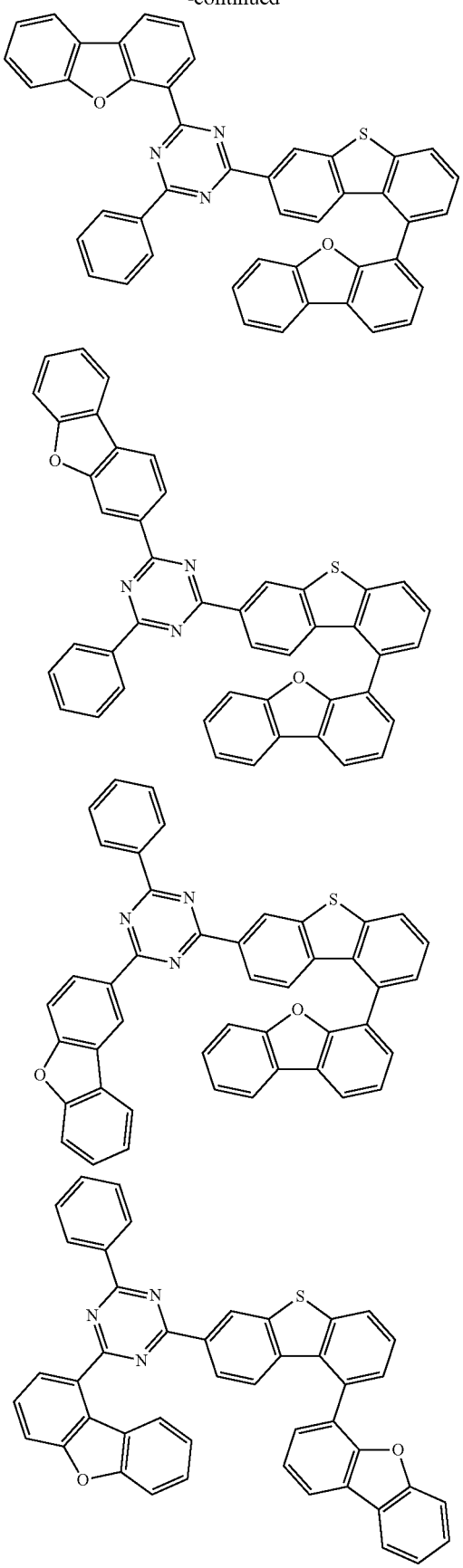

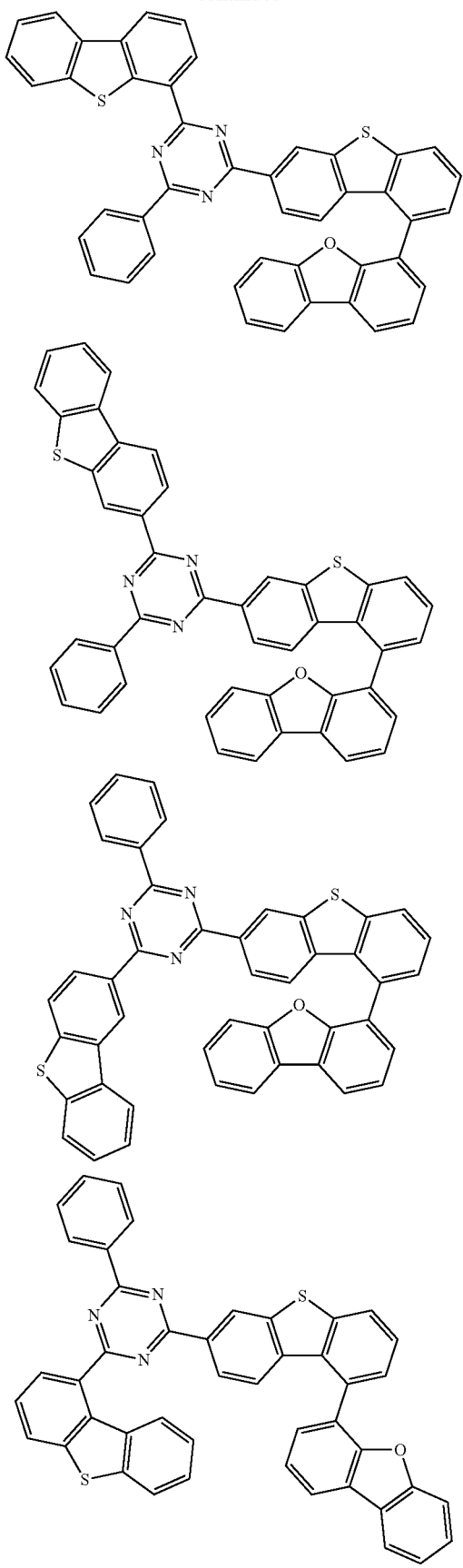
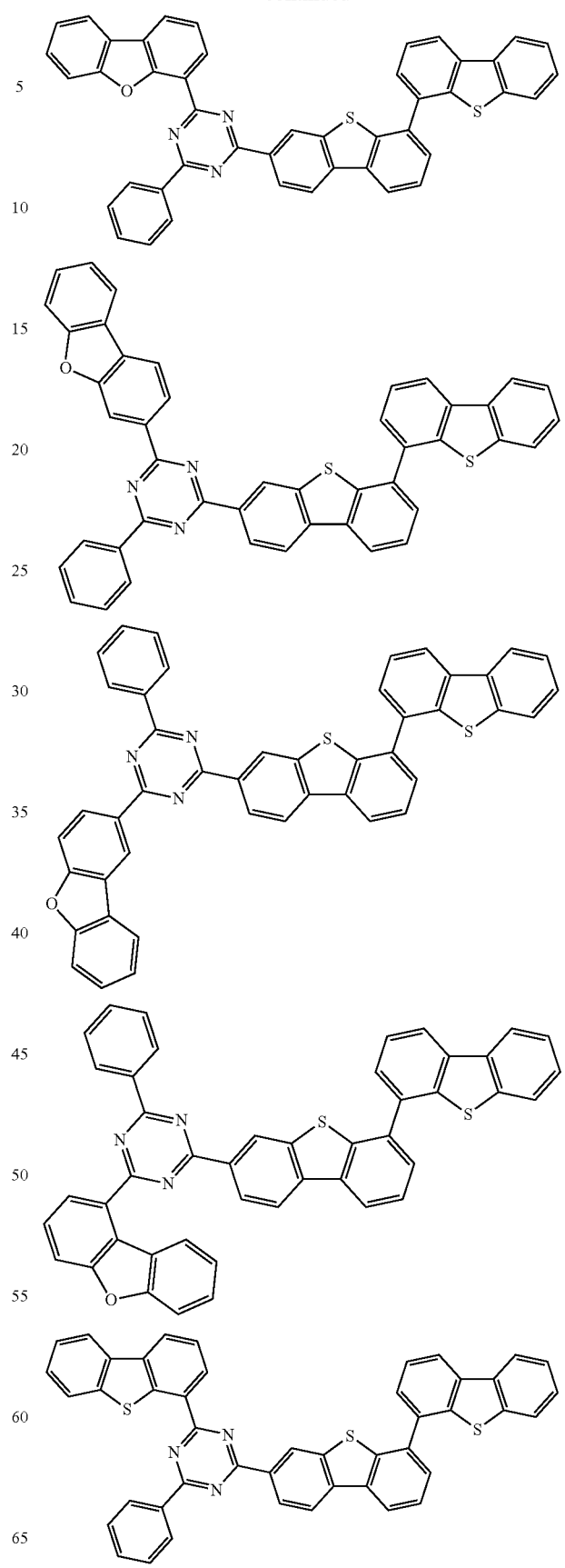

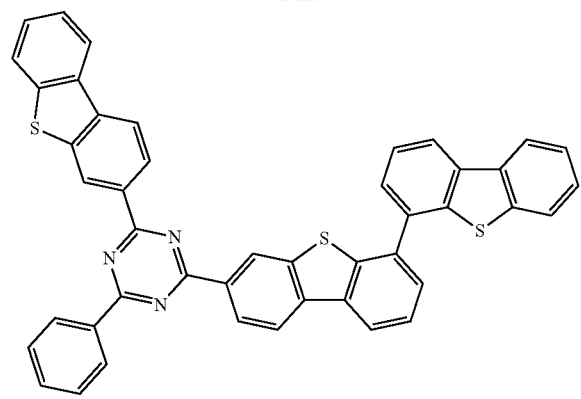
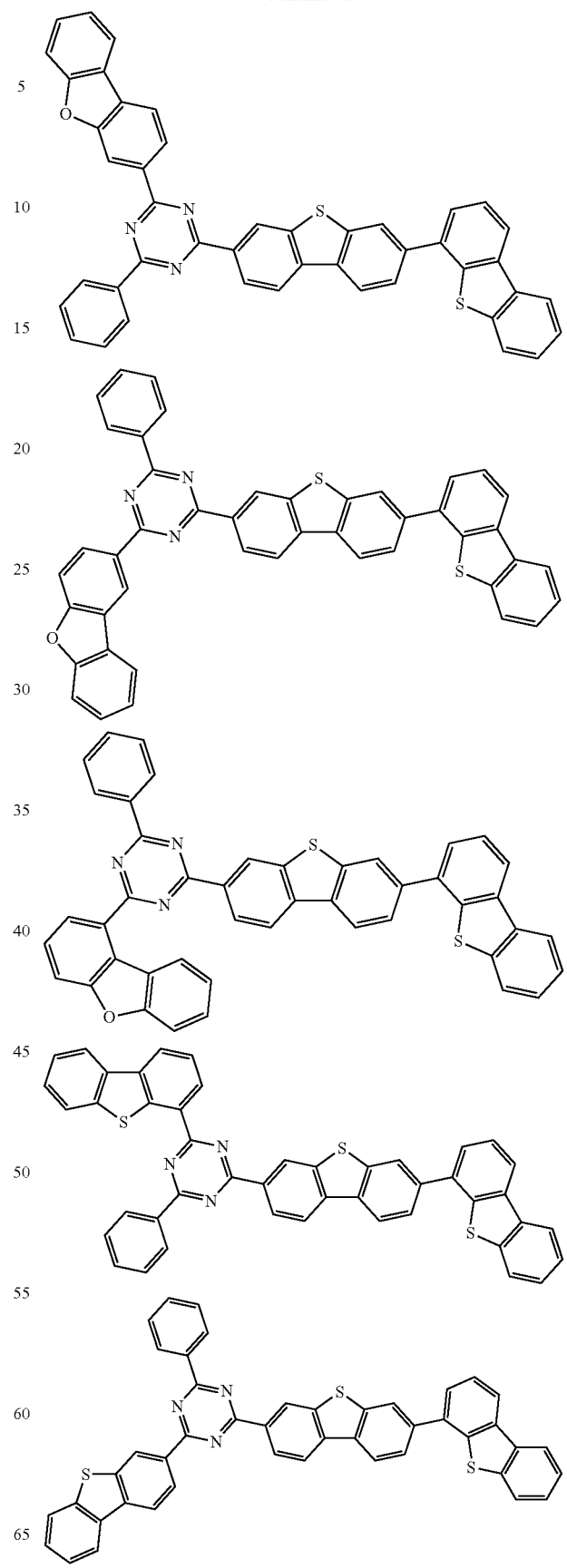

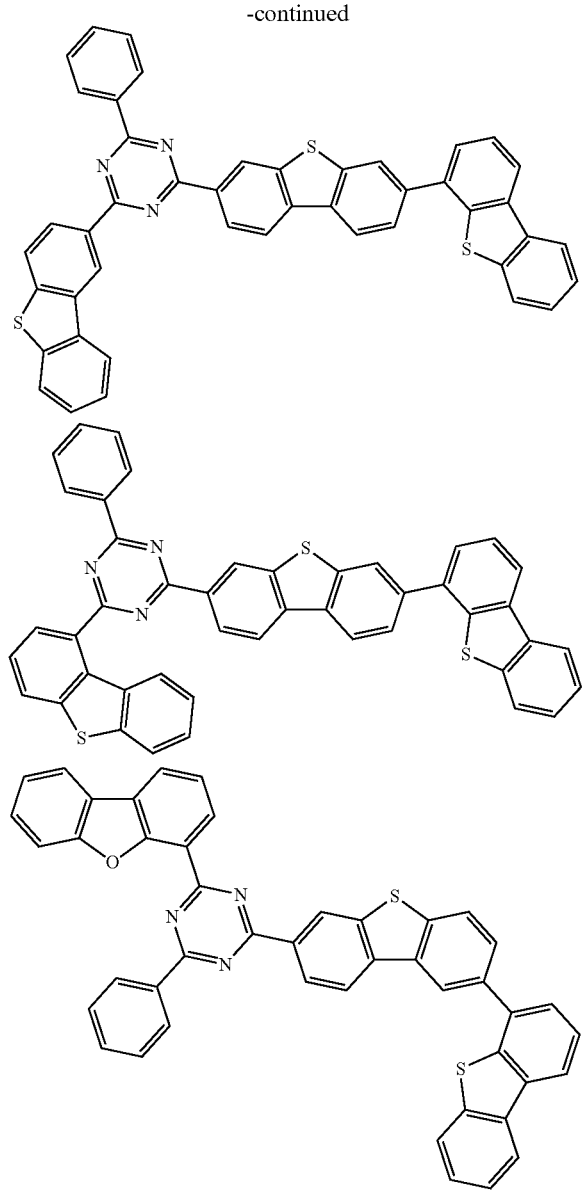
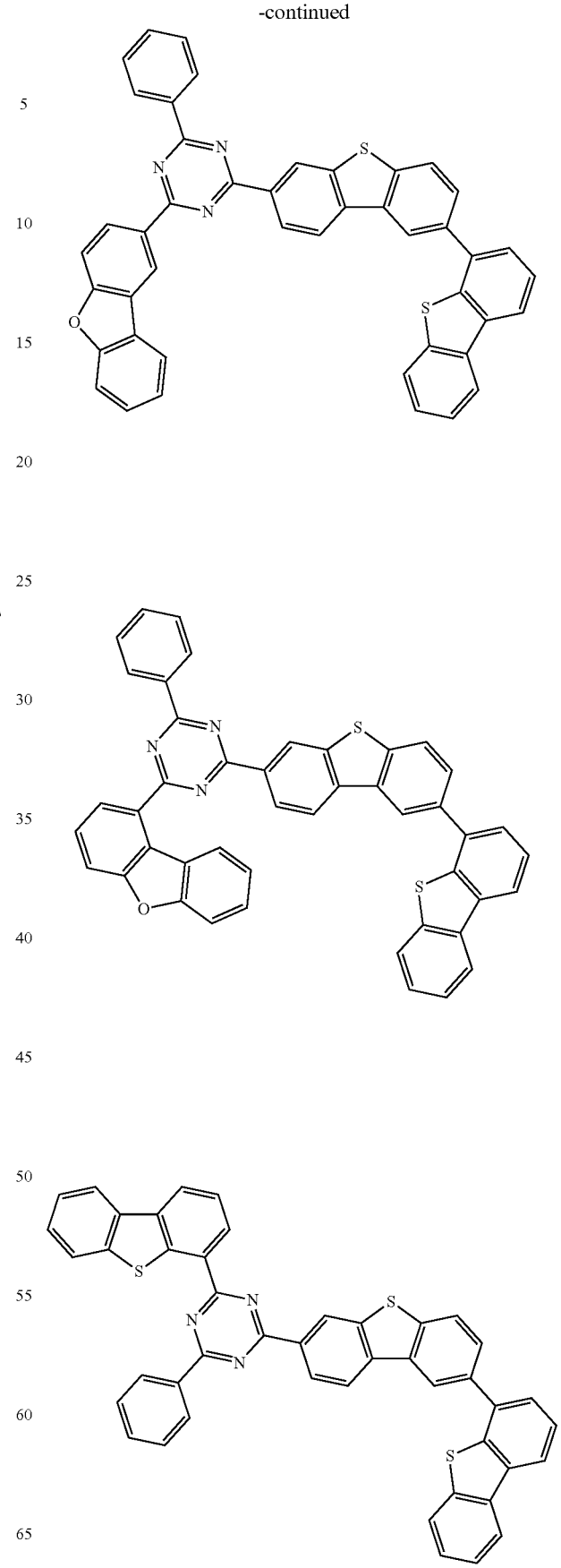

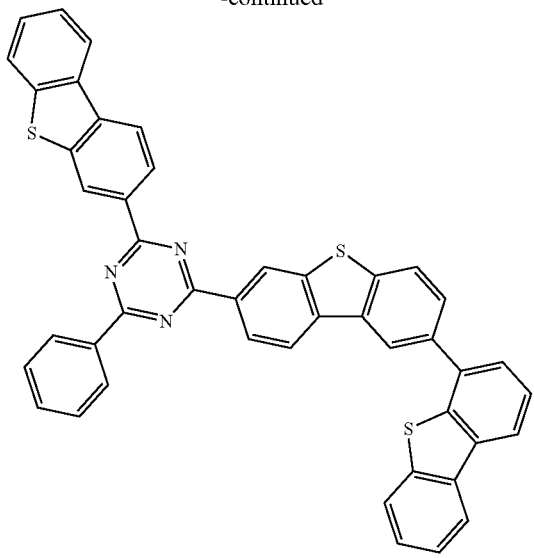
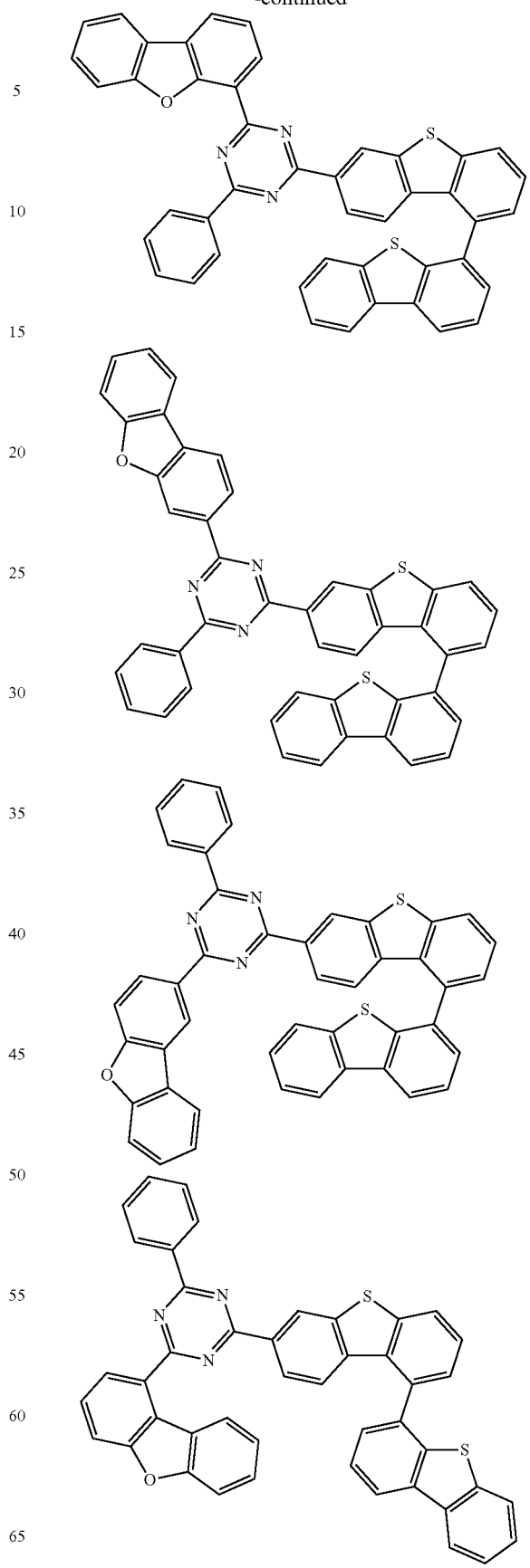

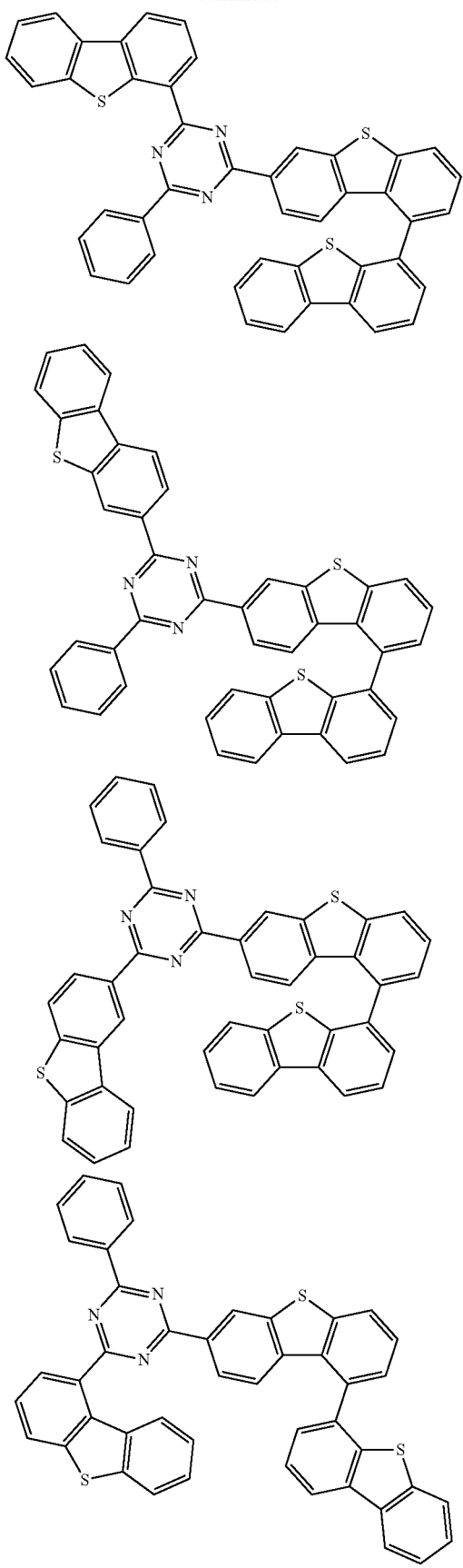
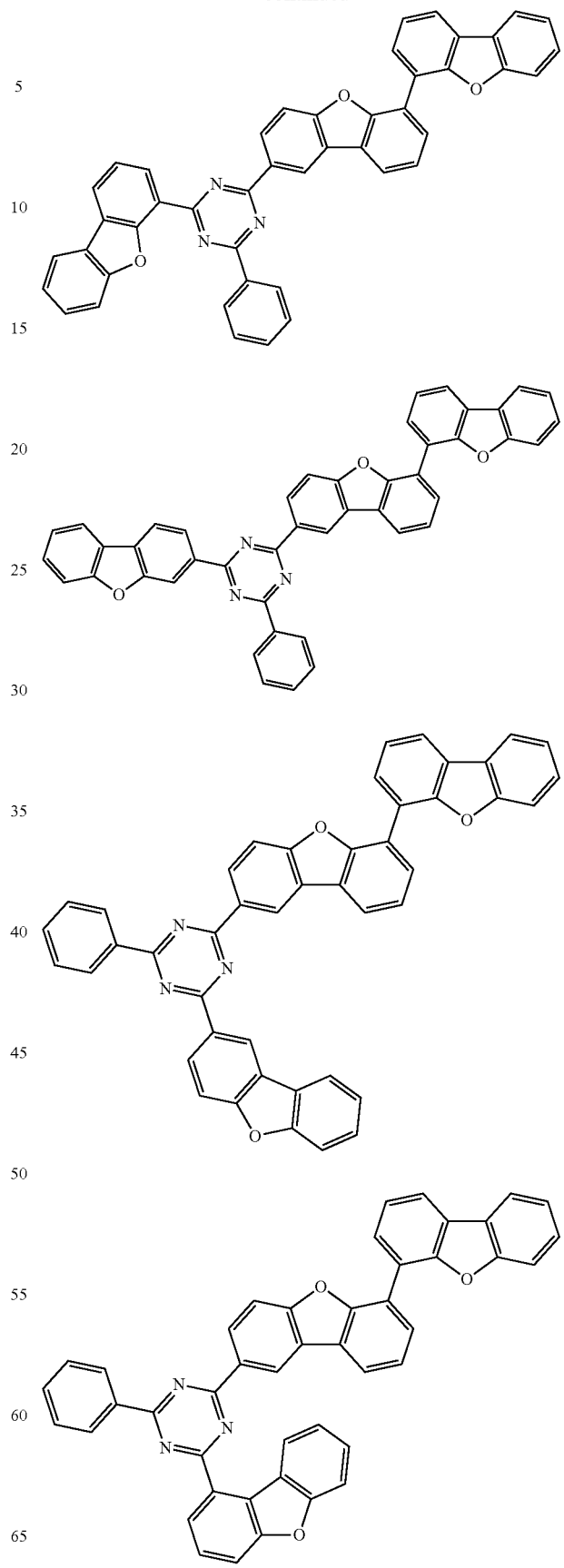

85
-continued
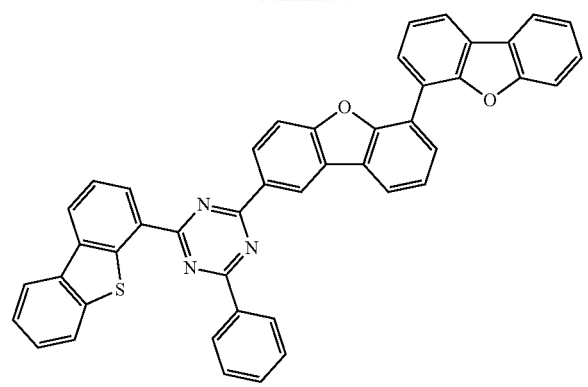
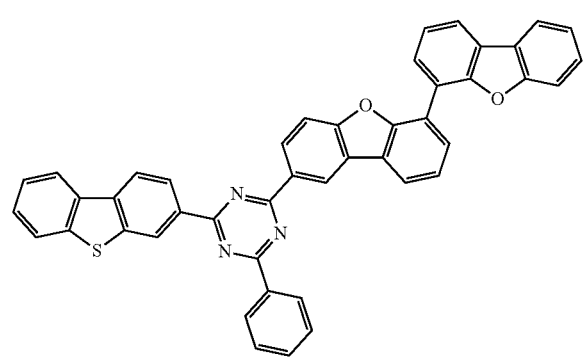
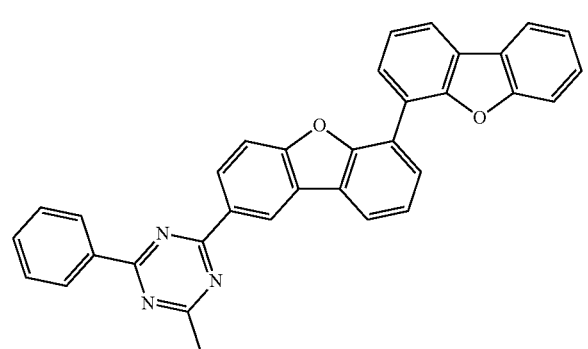
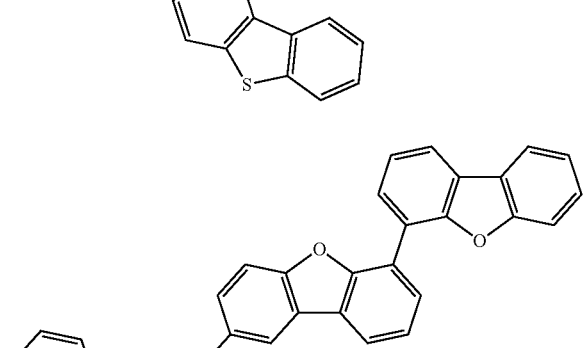
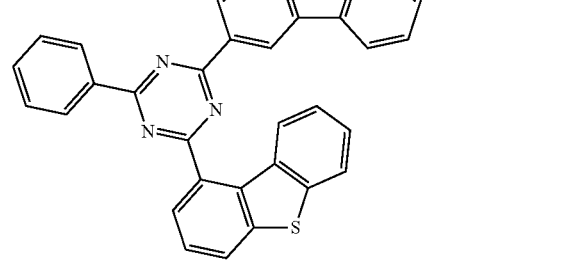
86
-continued
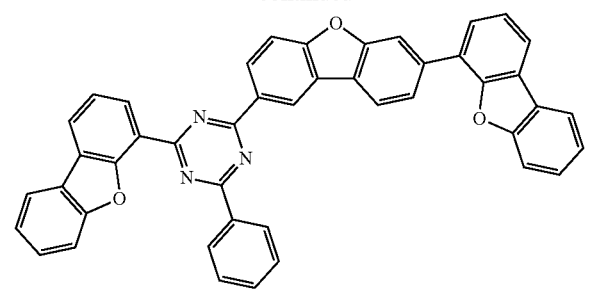
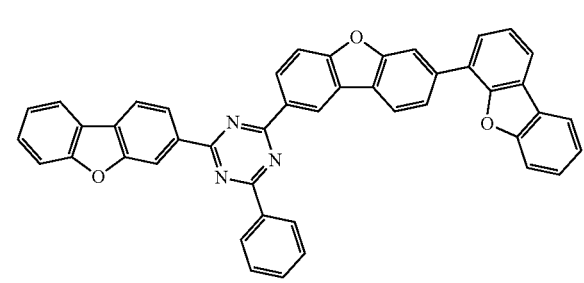
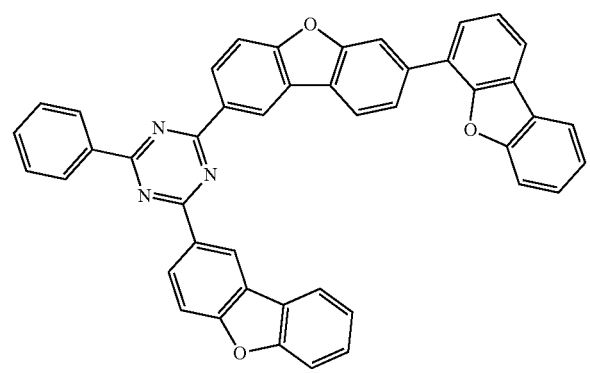
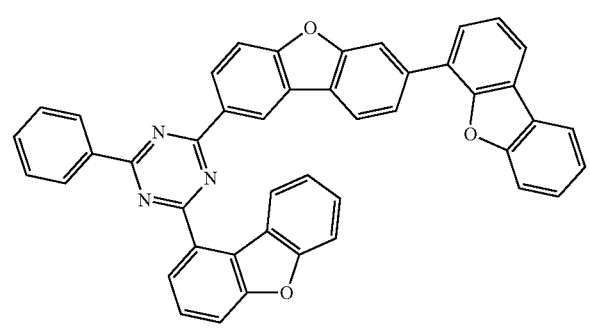
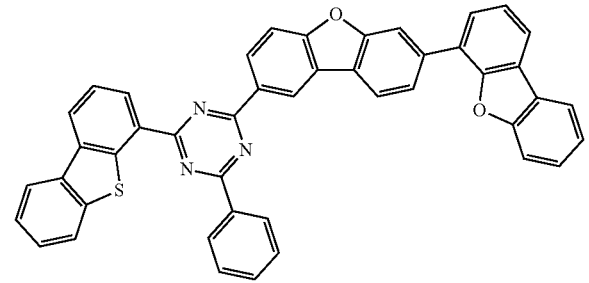

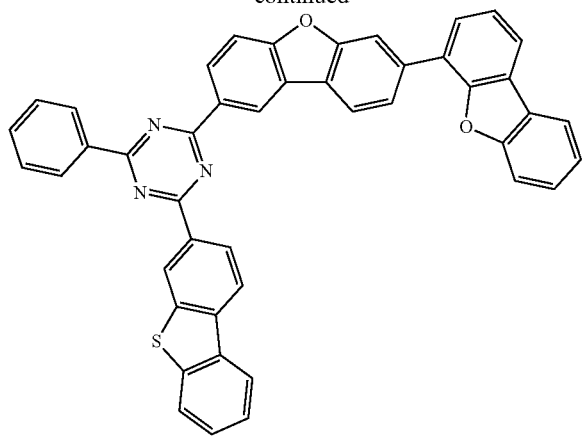
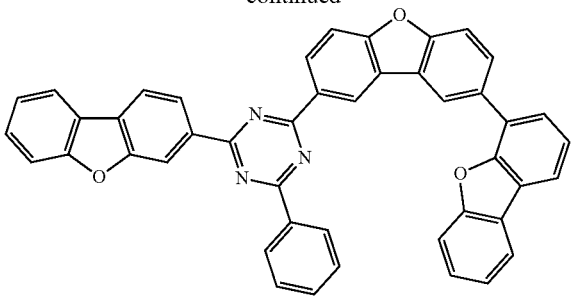
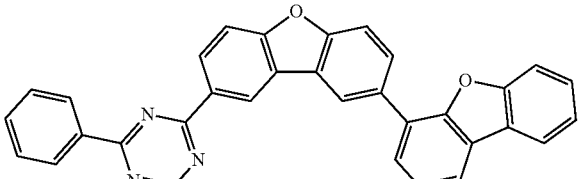
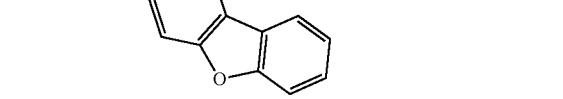
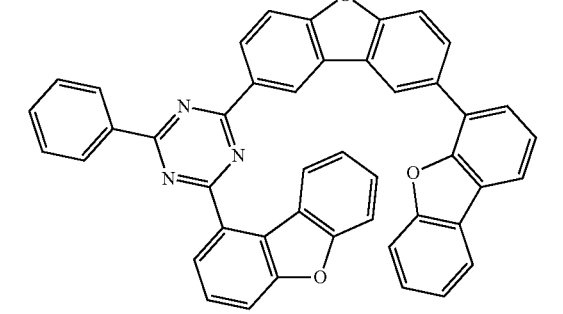
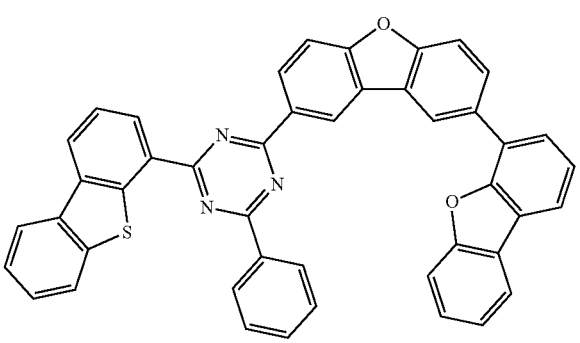
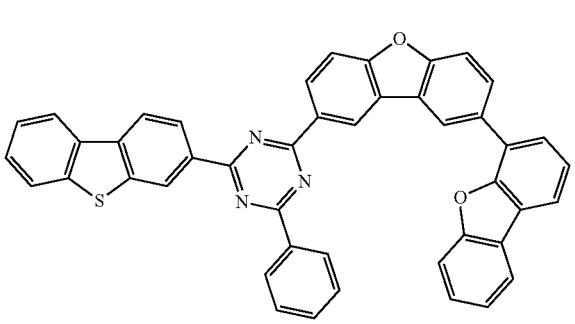

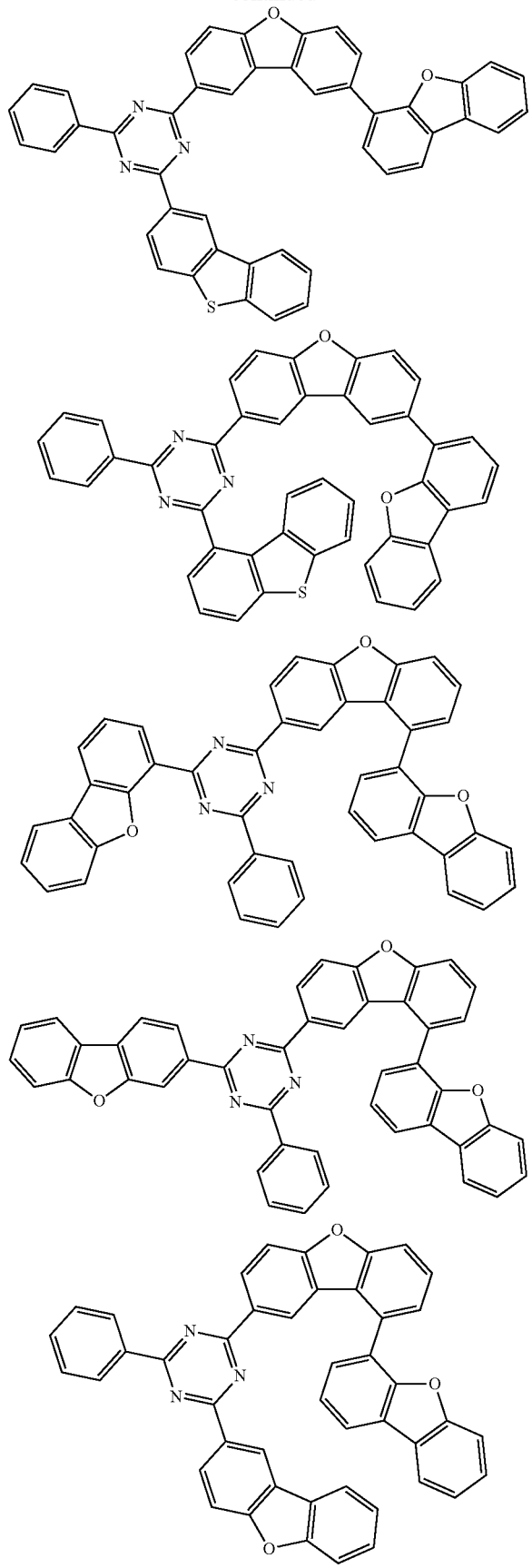
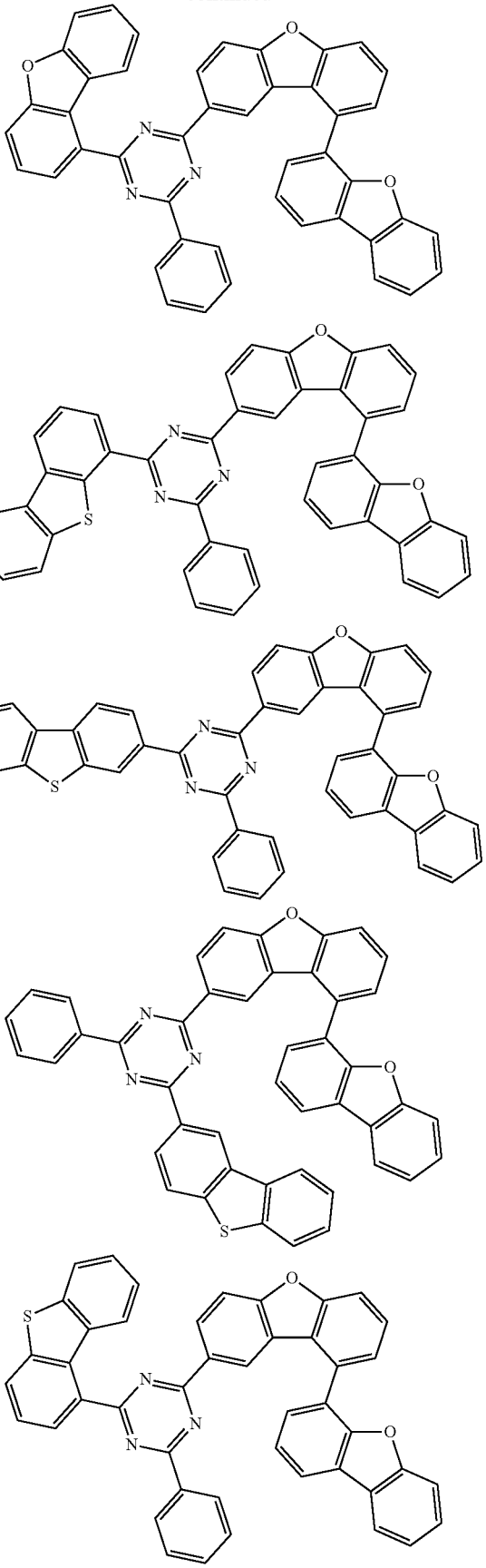

91
-continued
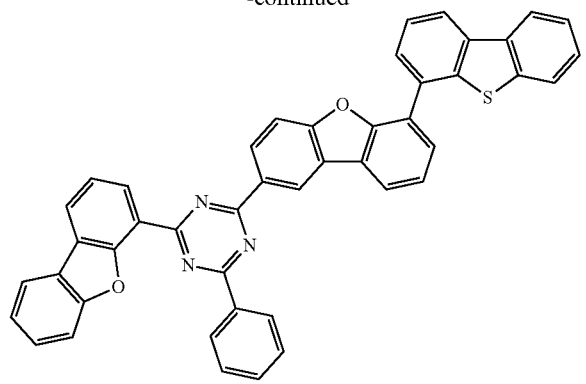
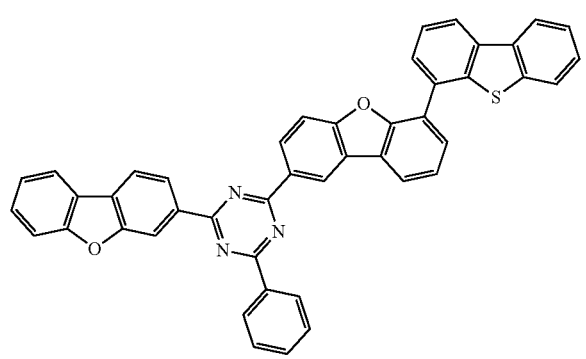
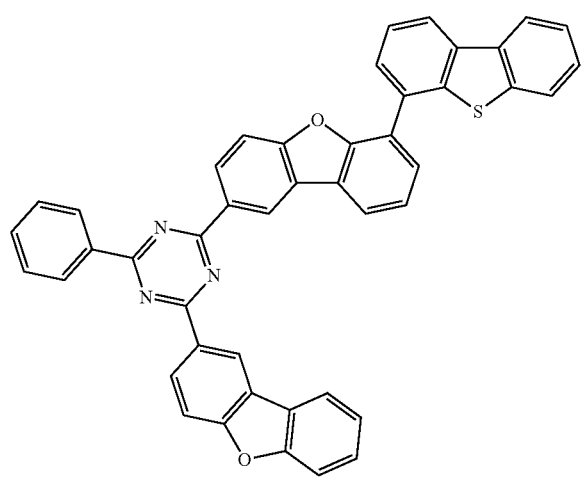
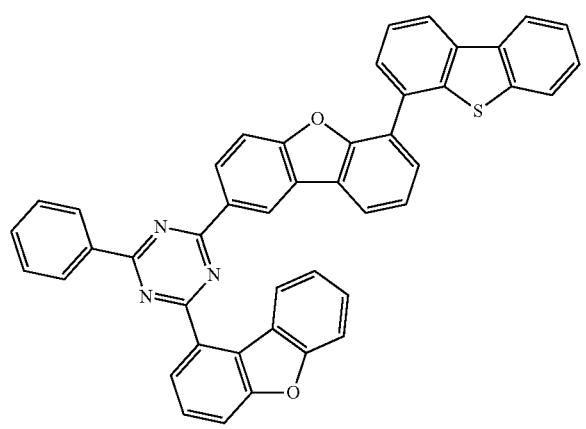
92
-continued
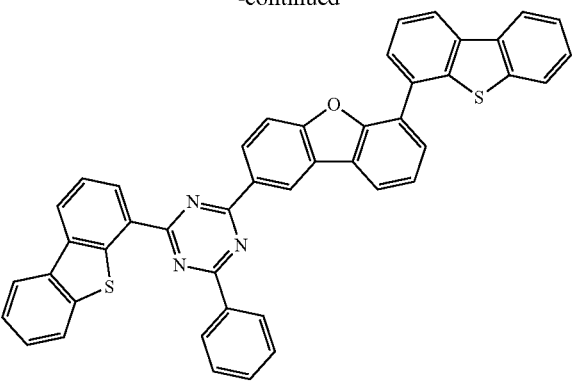
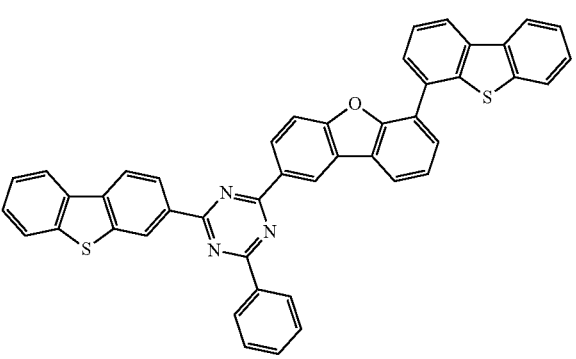
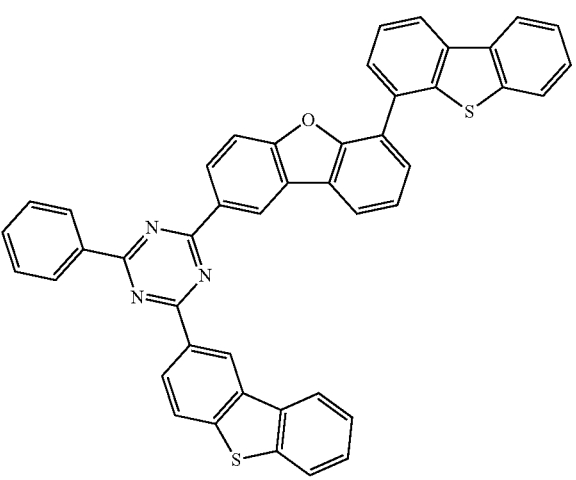
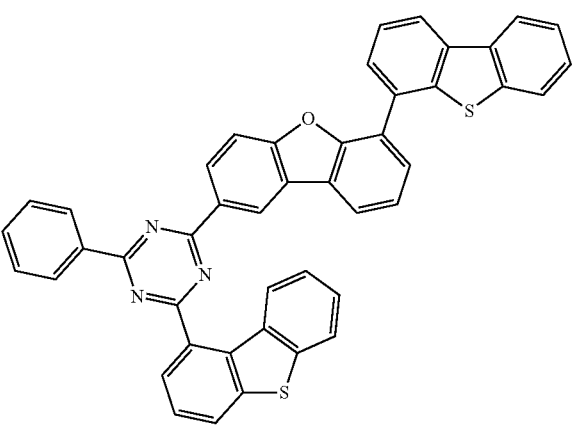

93
-continued
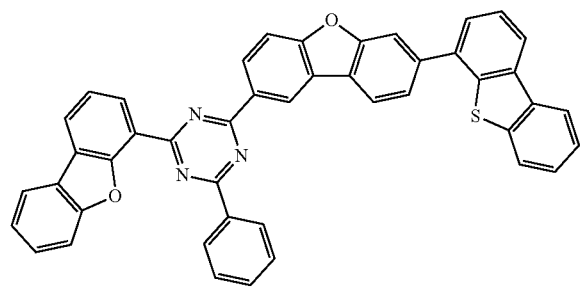
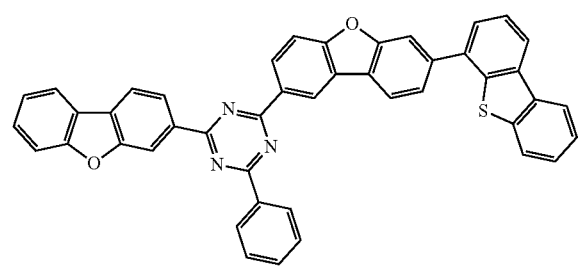
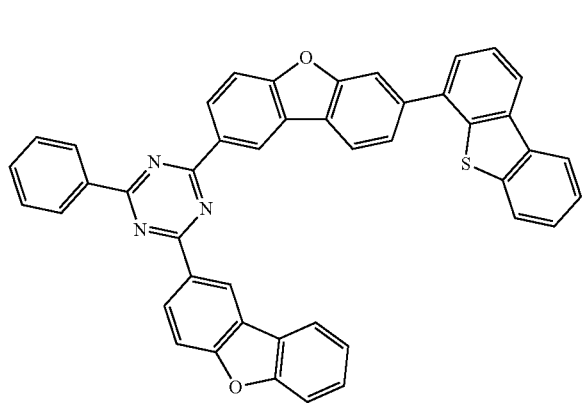
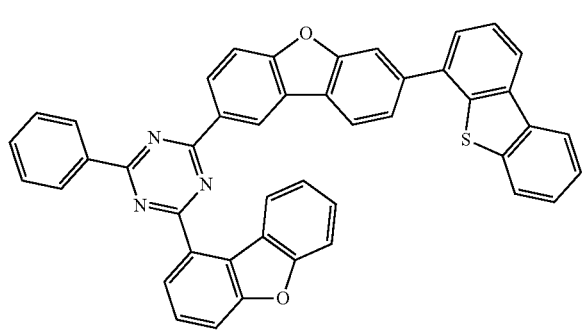
94
-continued
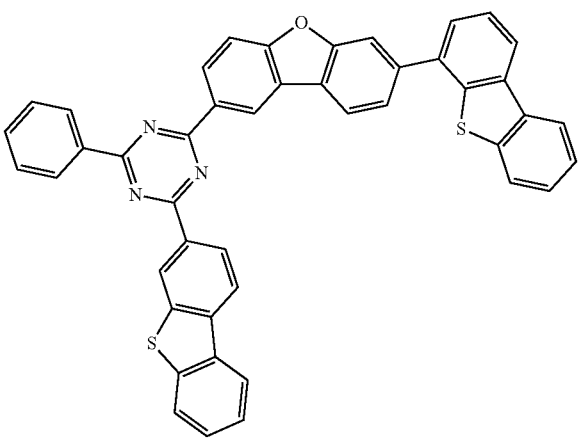
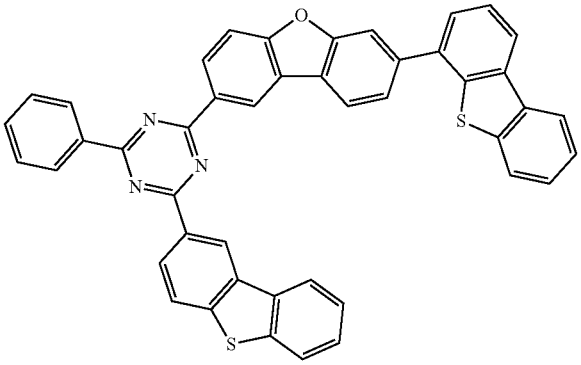
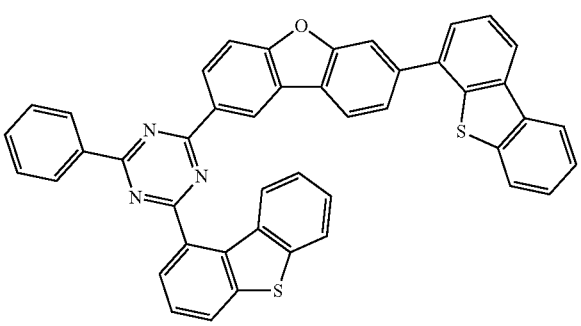
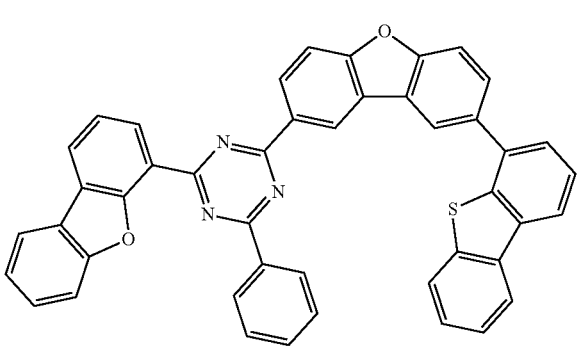

95
-continued
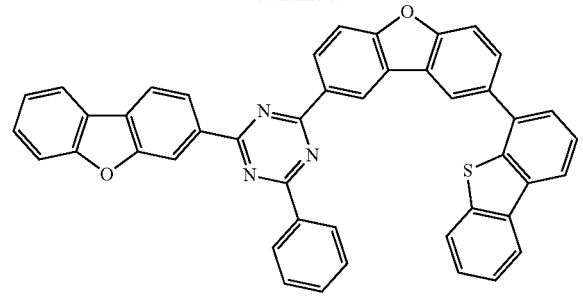
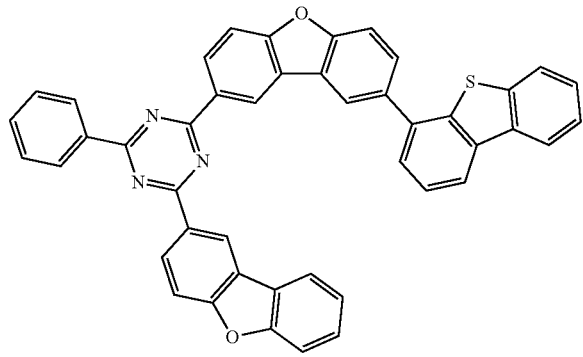
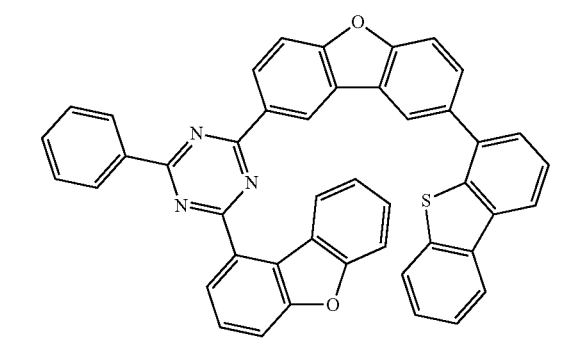
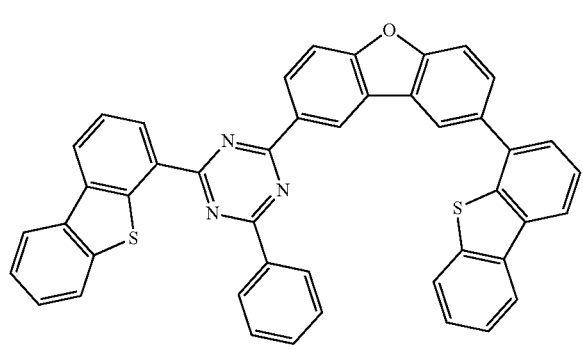
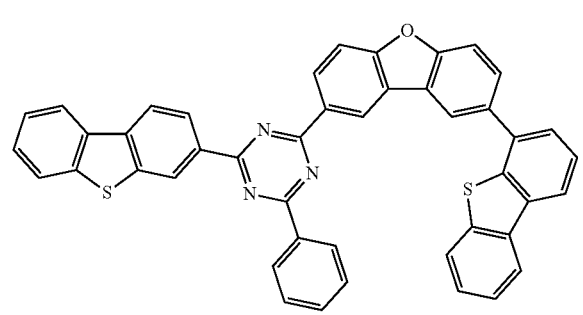
96
-continued
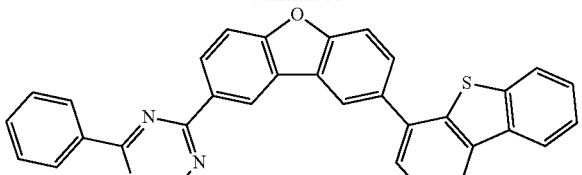
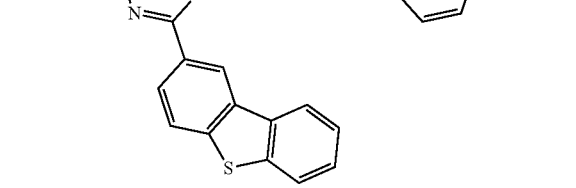
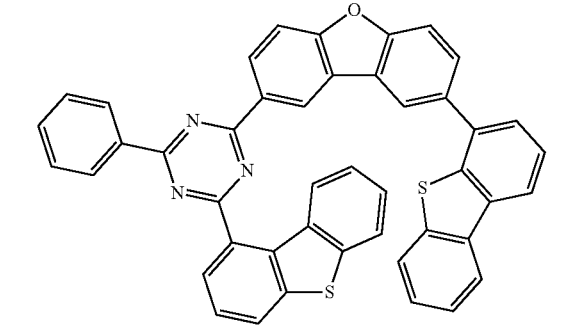
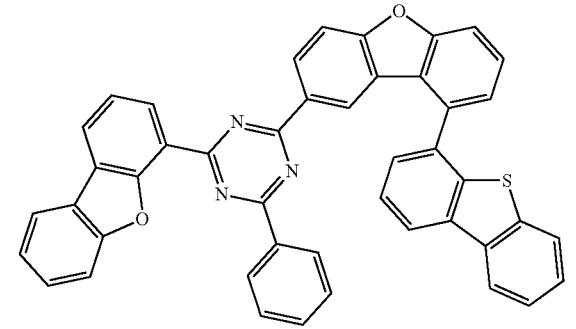
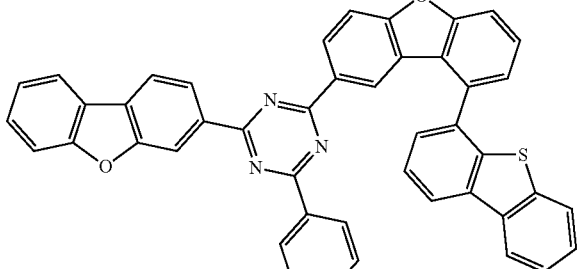
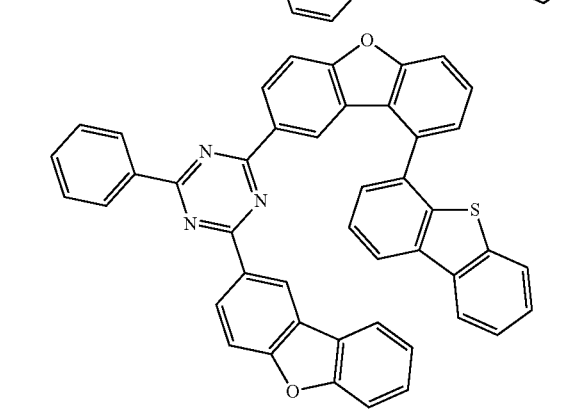

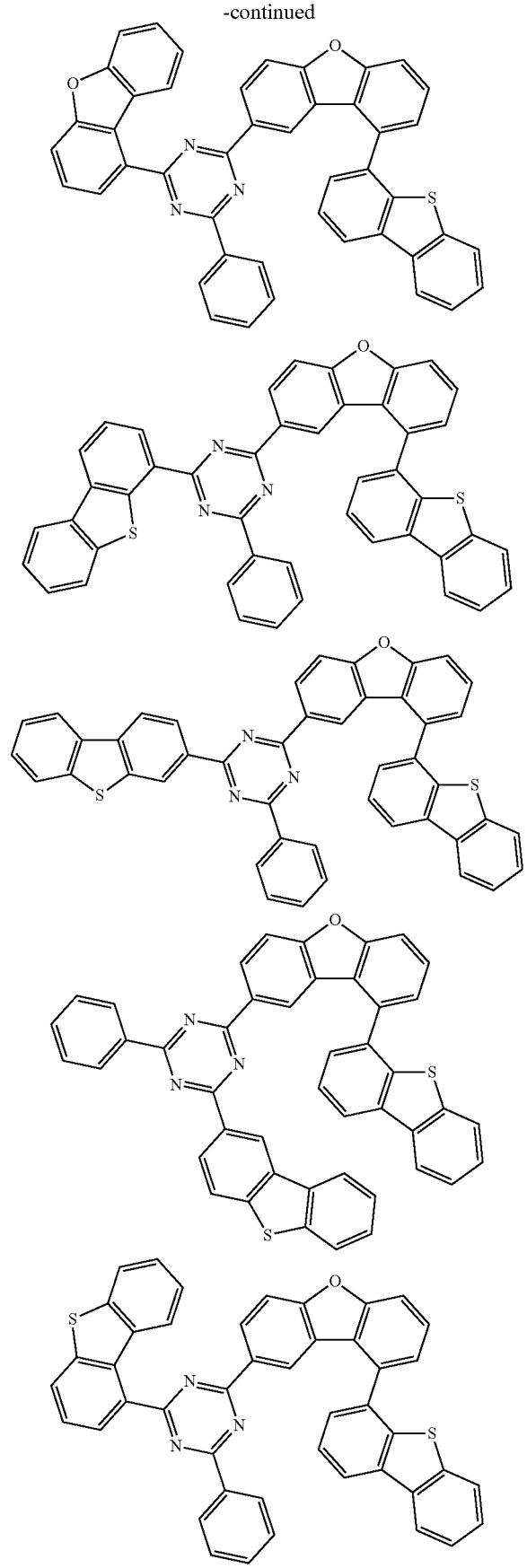
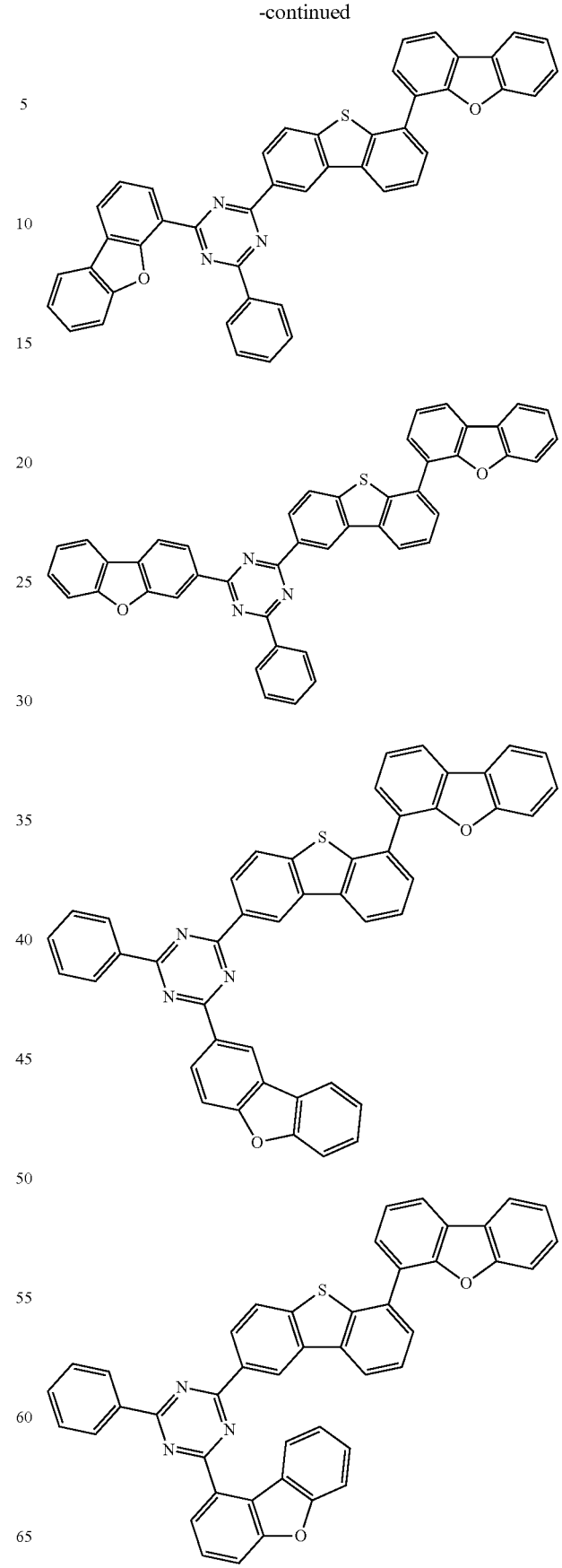

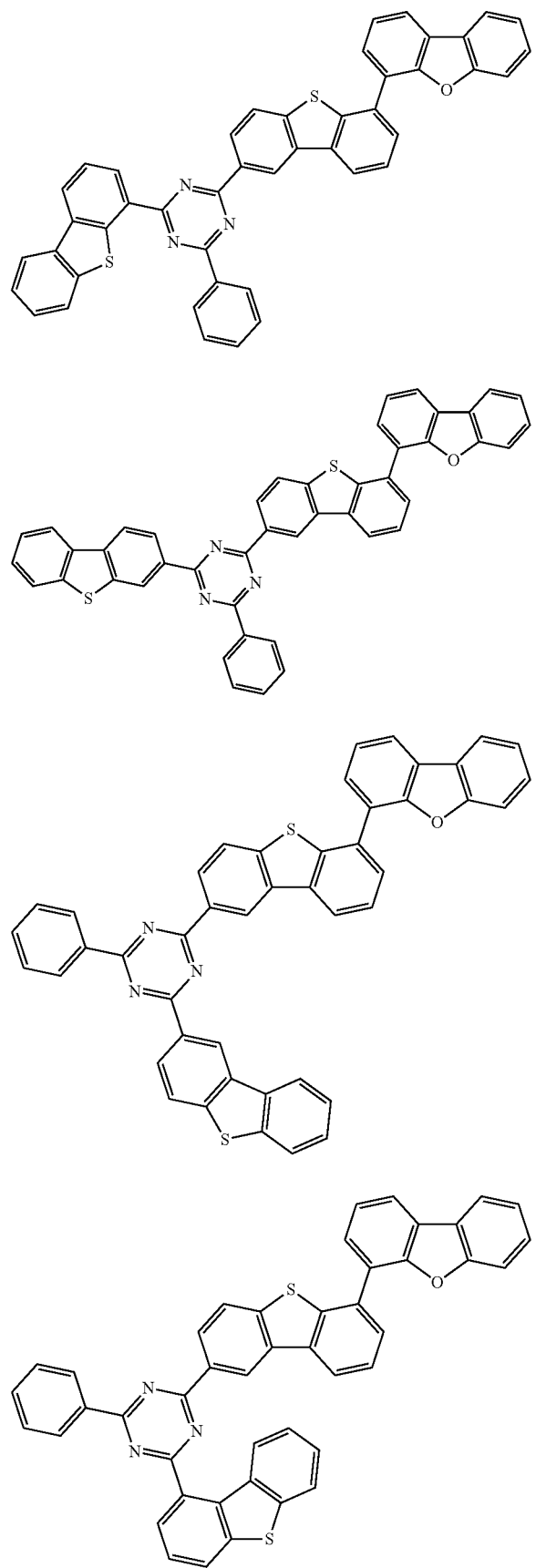
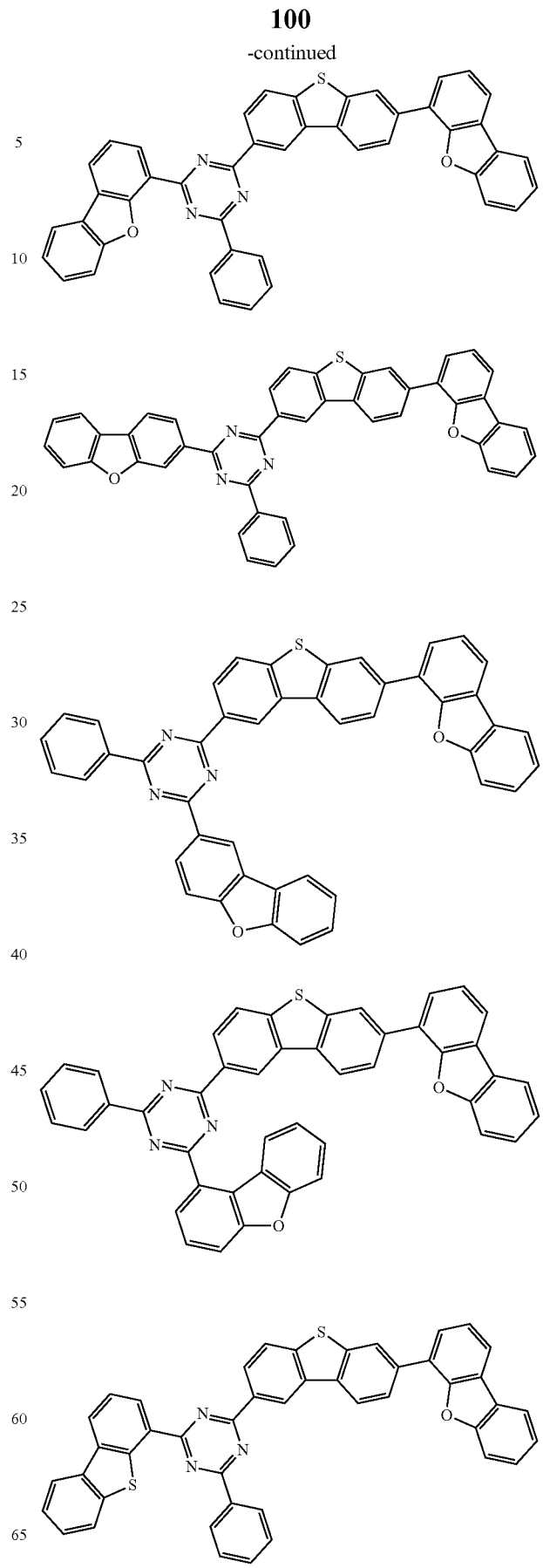

101
-continued
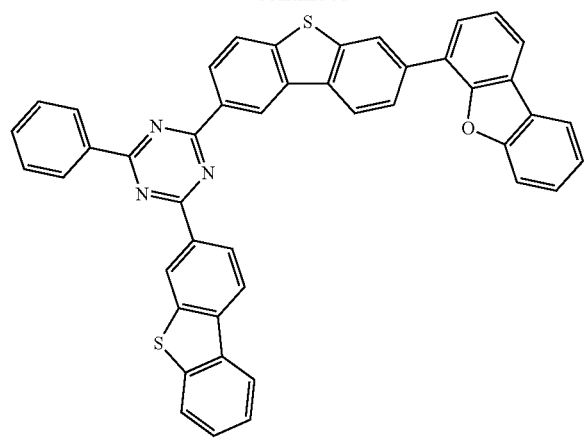
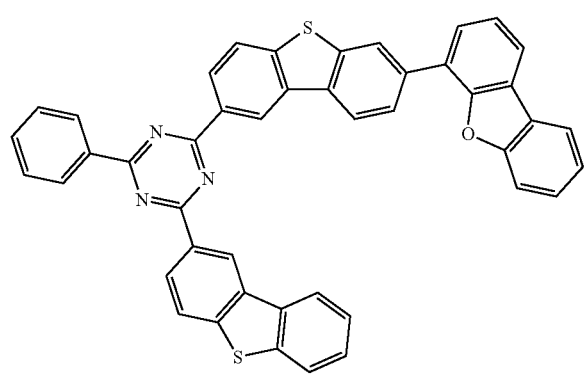
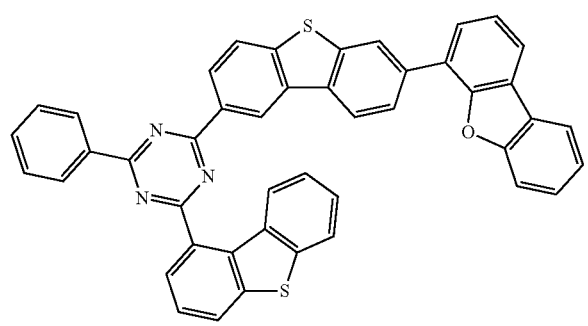
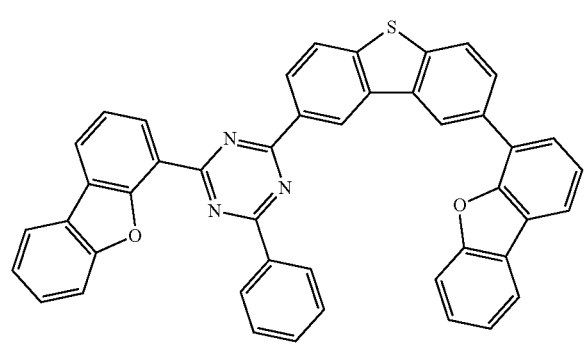
102
-continued
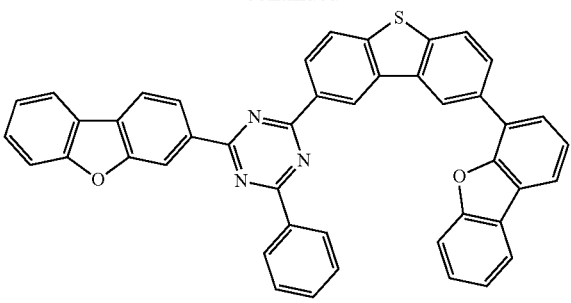
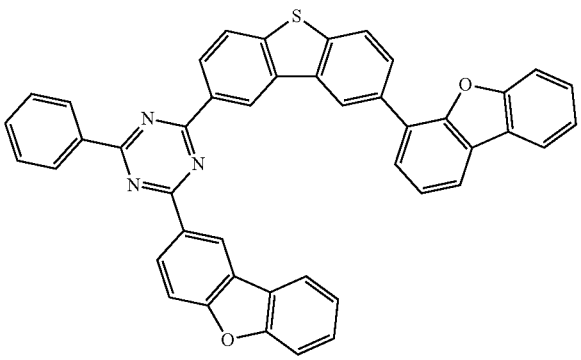
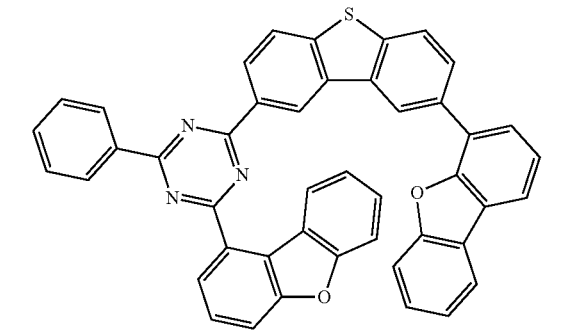
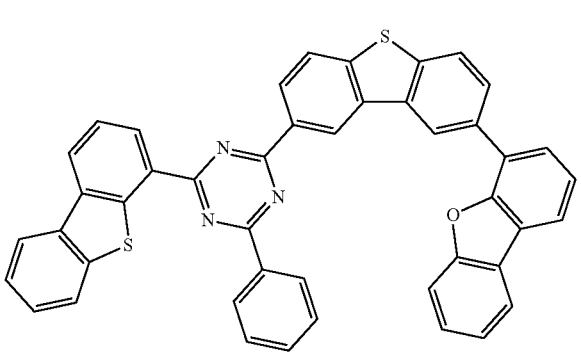
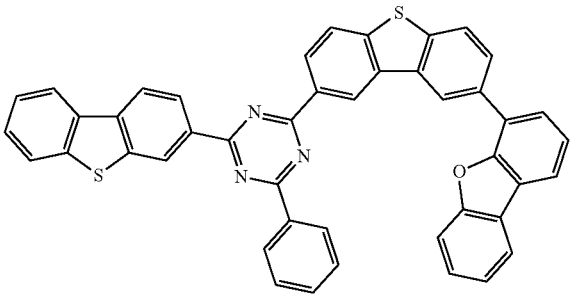

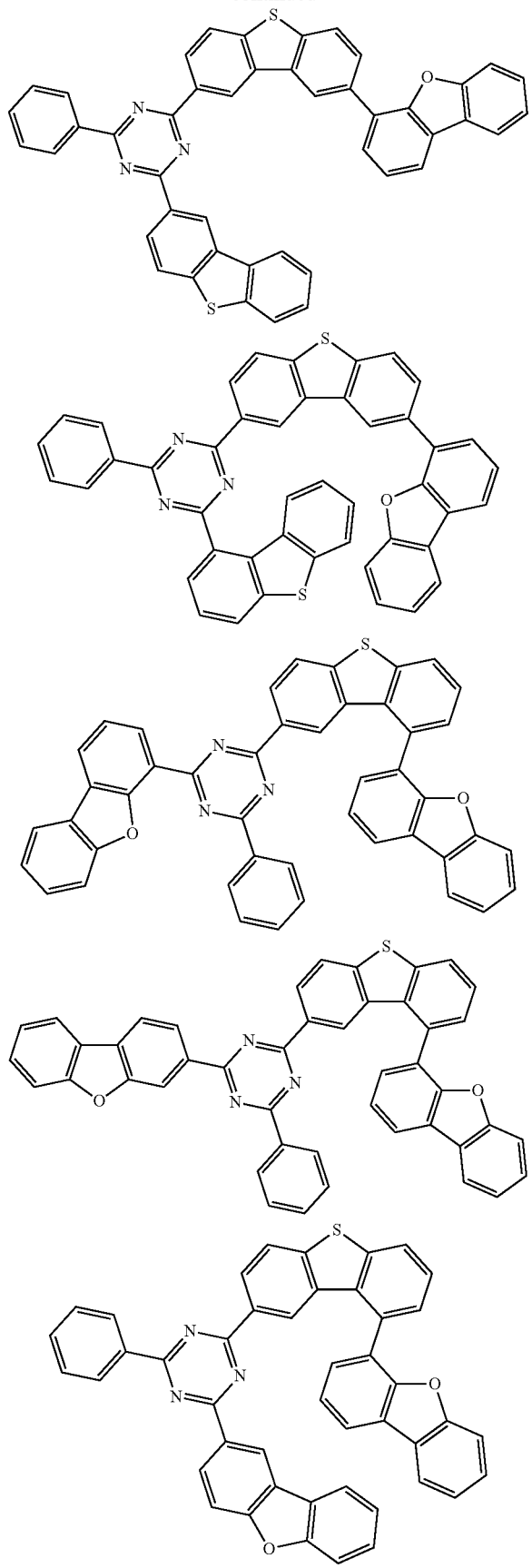
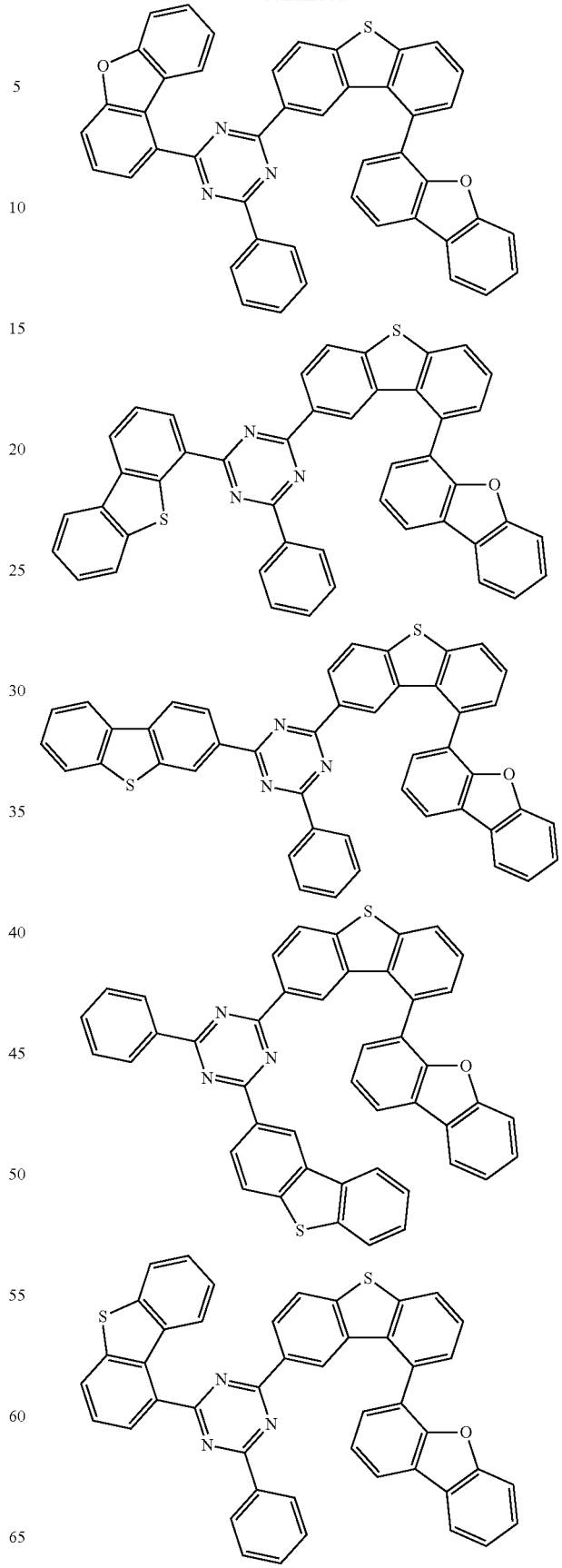

105
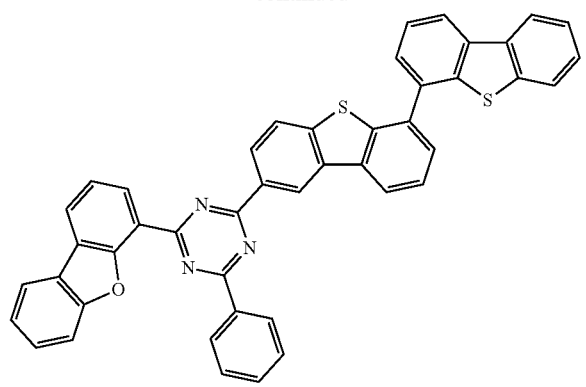
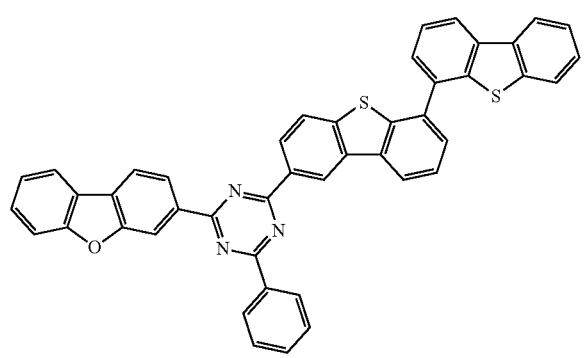
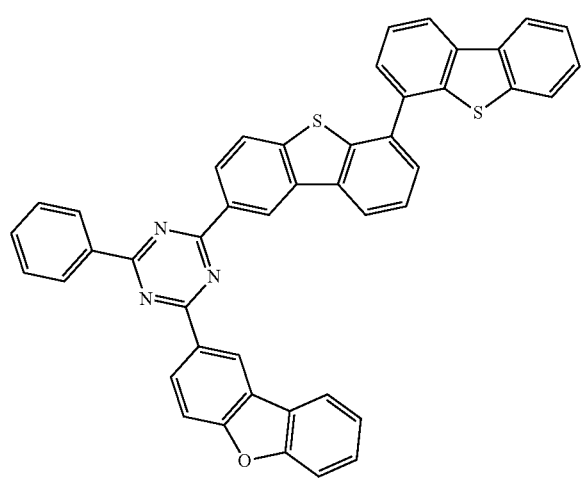
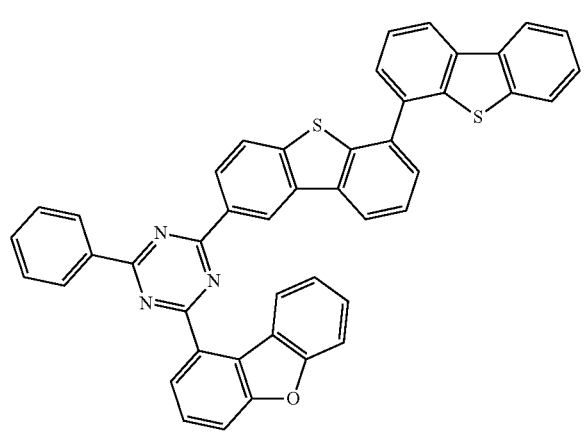
106
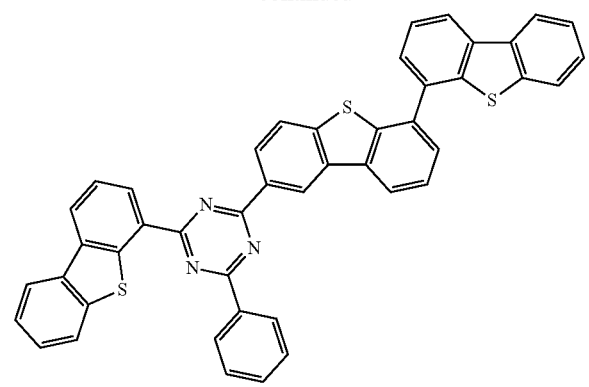
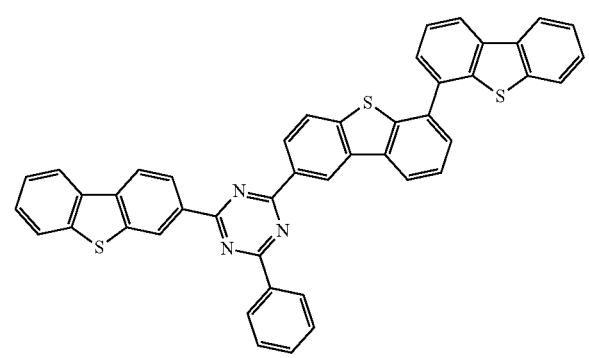
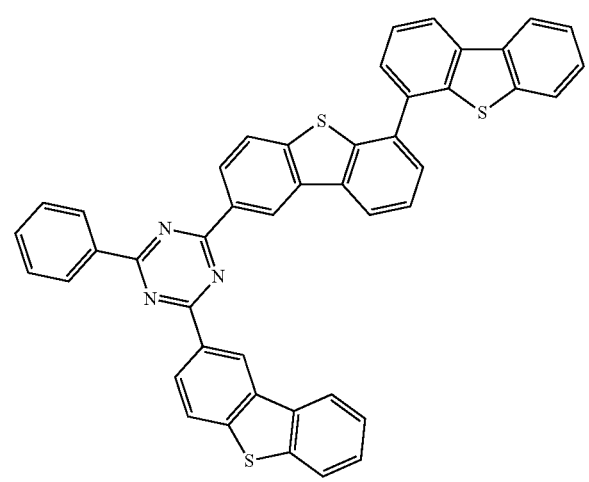
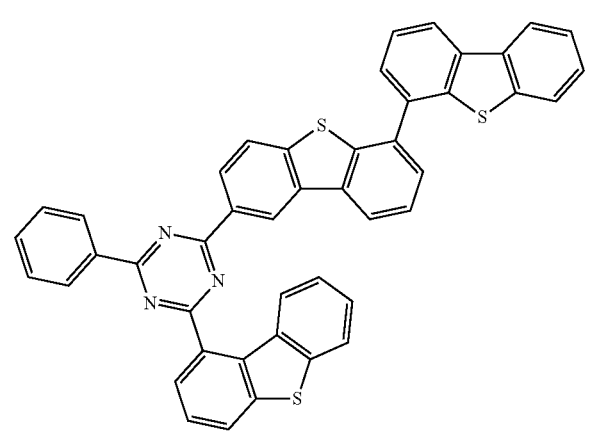

107
-continued
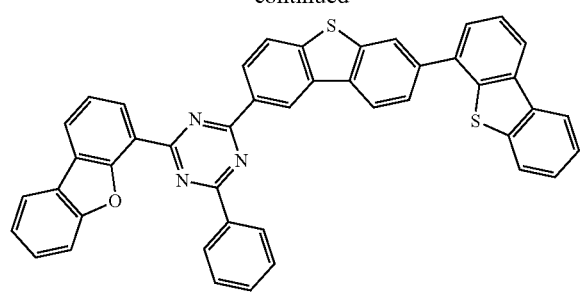
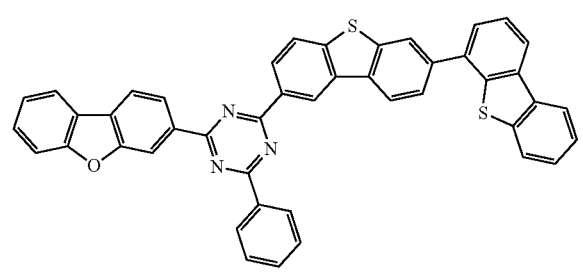
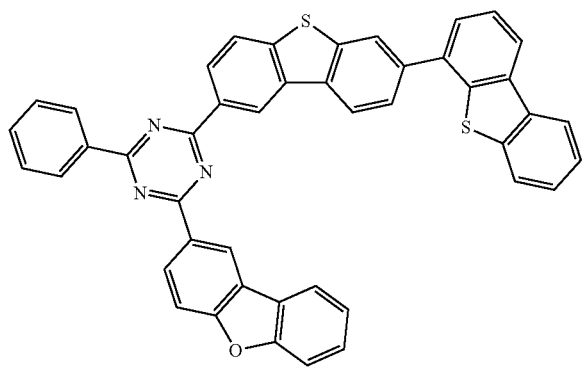
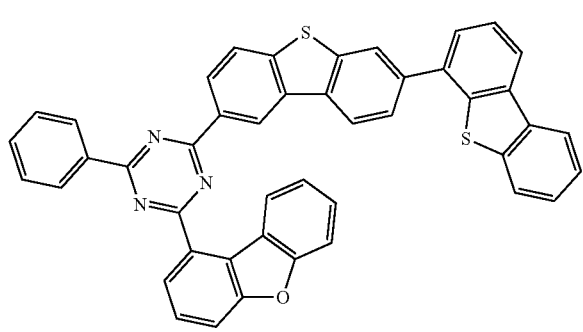
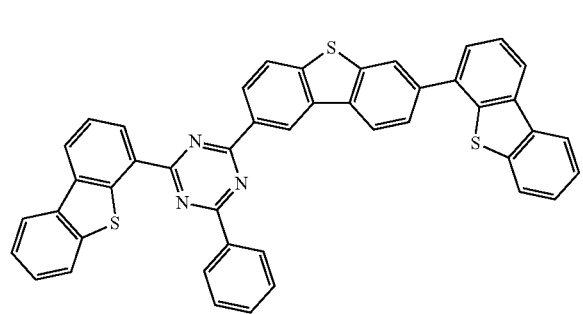
108
-continued
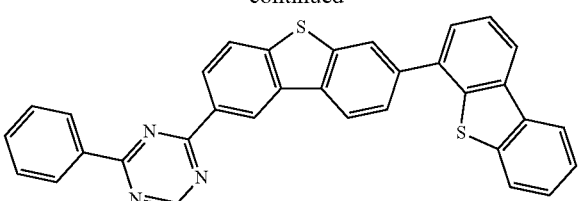
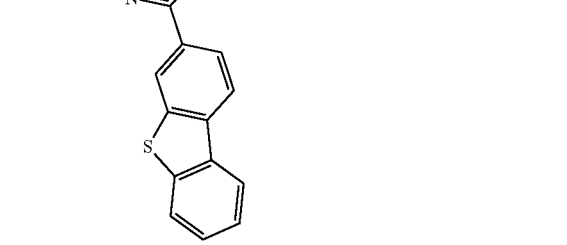
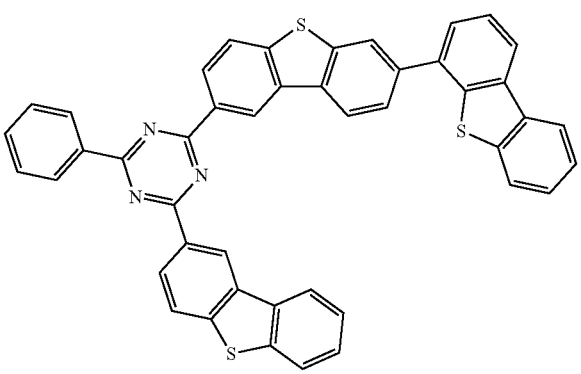
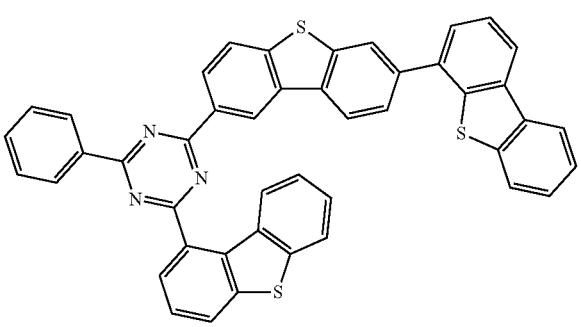
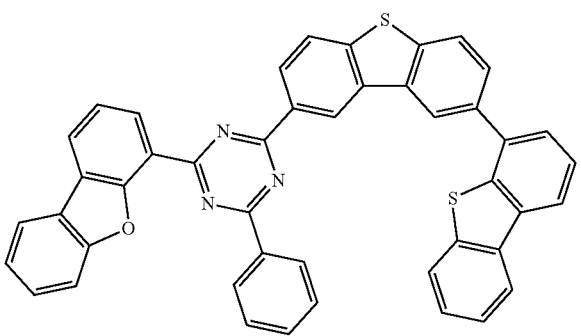

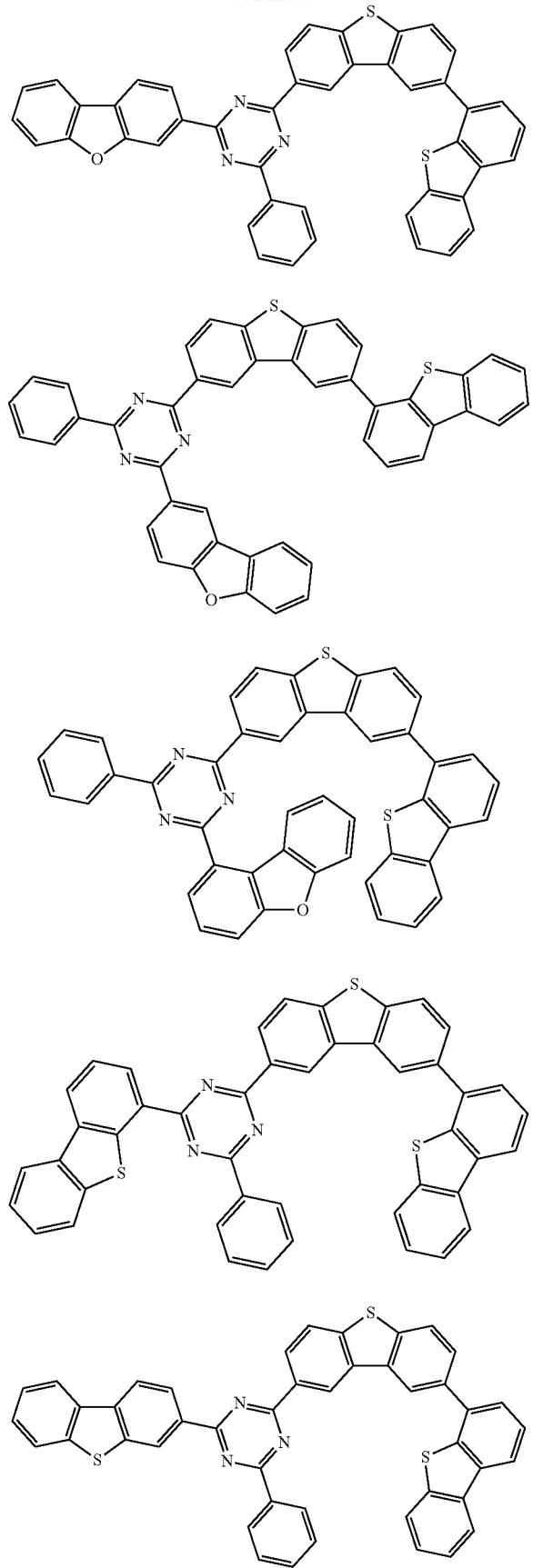
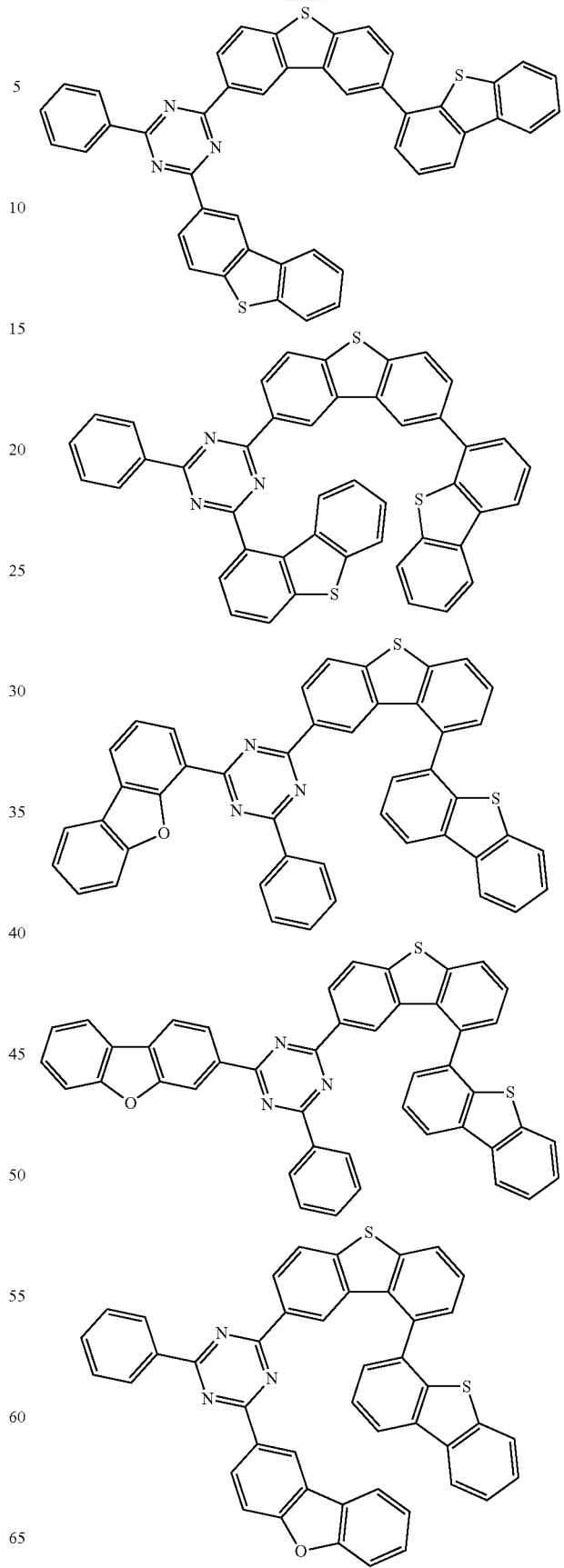

111
-continued
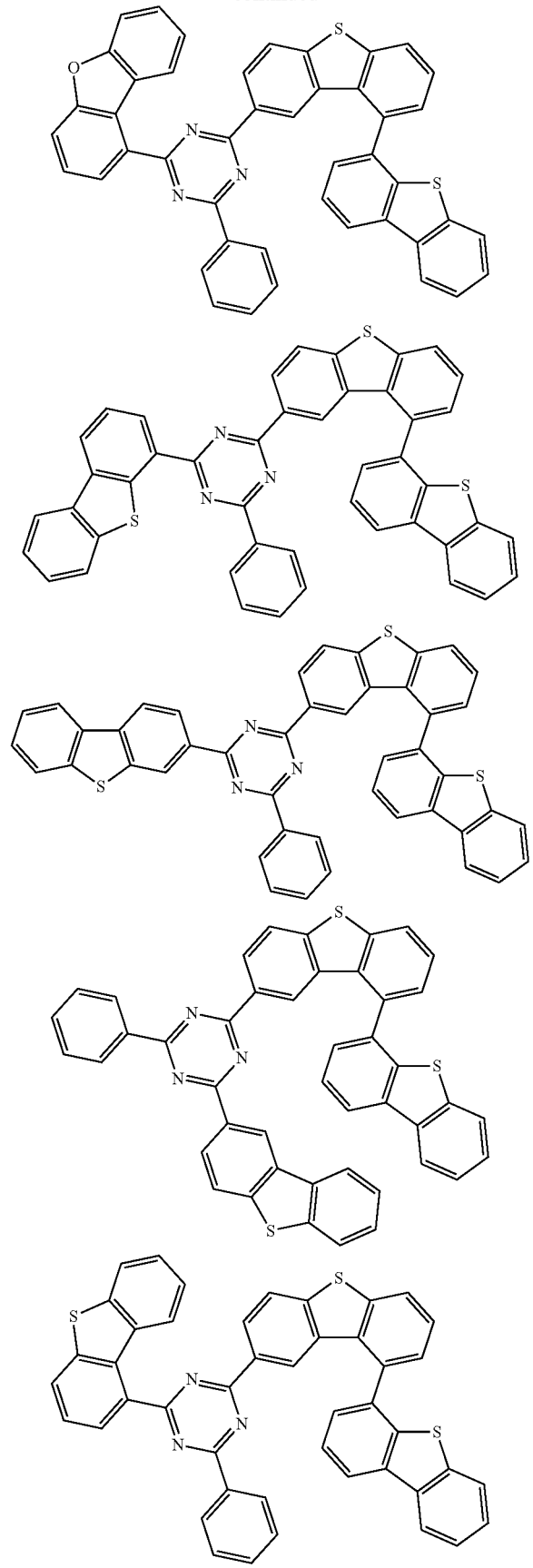
112
-continued
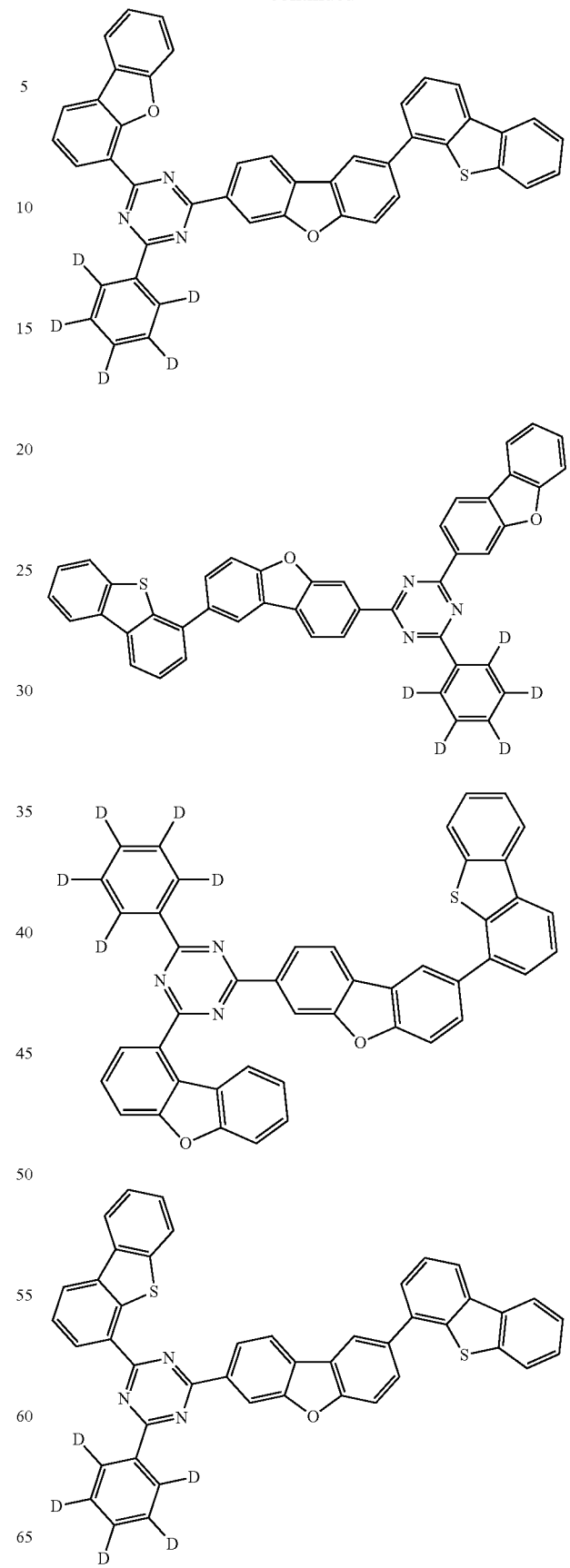

-continued

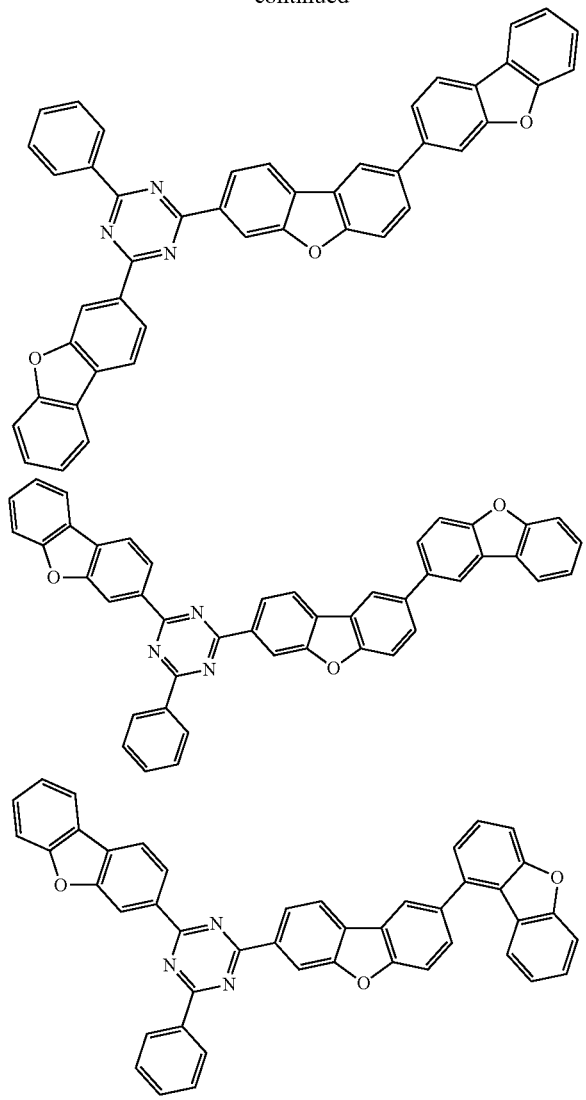

The compound of Chemical Formula 1 may be prepared by a preparation method as shown in Reaction Scheme 1 below. The above preparation method may be further specified in the Preparation Examples described hereinafter.

[Reaction Scheme 1]

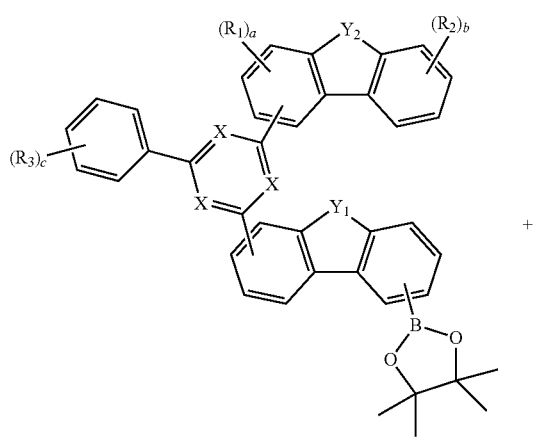

+

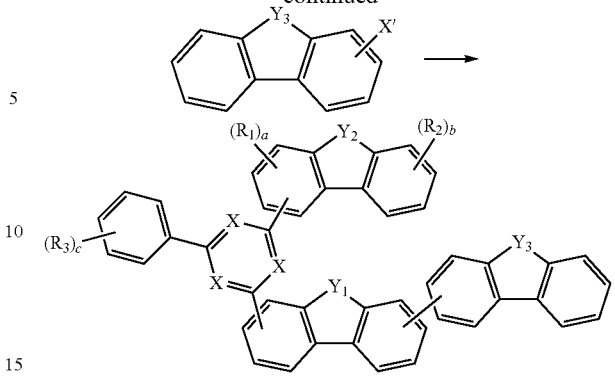

In Reaction Scheme 1, the remaining definitions excluding X' are the same as defined above, and X' is halogen and more preferably bromo or chloro. The above-mentioned reaction is a Suzuki coupling reaction, which is preferably carried out in the presence of a palladium catalyst and a base, and a reactive group for the Suzuki coupling reaction can be modified as known in the art. The above preparation method may be further specified in the Preparation Examples described hereinafter.

In another embodiment of the invention, there is provided an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula I.

The organic material layer of the organic light emitting device of the present invention may have a single-layer structure, or it may have a multilayered structure in which two or more organic material layers are stacked. For example, the organic light emitting device of the present invention may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer for simultaneously performing hole injection and transport, wherein the hole injection layer, the hole transport layer, or the layer for simultaneously performing hole injection and transport include the compound of Chemical Formula 1.

Further, the organic material layer may include a light emitting layer, wherein the light emitting layer includes the compound of Chemical Formula 1.

Further, the organic material layer may include an electron transport layer or an electron injection layer, wherein the electron transport layer or the electron injection layer includes the compound of Chemical Formula 1.

Further, the electron transport layer, the electron injection layer, or the layer for simultaneously performing electron transport and electron injection include the compound of Chemical Formula 1.

In addition, the organic material layer includes a light emitting layer and an electron transport layer, wherein the electron transport layer may include a compound of Chemical Formula 1.

Further, the organic light emitting device according to the present invention may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 may be included in the light emitting layer.

FIG. 2 shows an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound of Chemical Formula 1 may be included in one or more layers of the hole injection layer, the hole transport layer, the electron blocking layer, the light emitting layer and the electron transport layer. and the electron injection layer.

Specifically, the organic material layer may include a light emitting layer, wherein the light emitting layer may include two or more host materials.

In this case, the two or more host materials may include a compound of Chemical Formula 1.

The organic light emitting device according to the present invention may be manufactured by materials and methods known in the art, except that one or more layers of the organic material layers include the compound of Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound of Chemical Formula 1 may be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb, conductive polymers such as poly(3-methylthiophene), poly[3,4-(ethylene-1,2-dioxy)thiophene](PEDOT) polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a Spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport material is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the used material.

In addition, the compound of Chemical Formula 1 may be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present invention.

Preparation Example 1: Preparation of Intermediate Compound Q-4

(a) Preparation of Compound Q-1

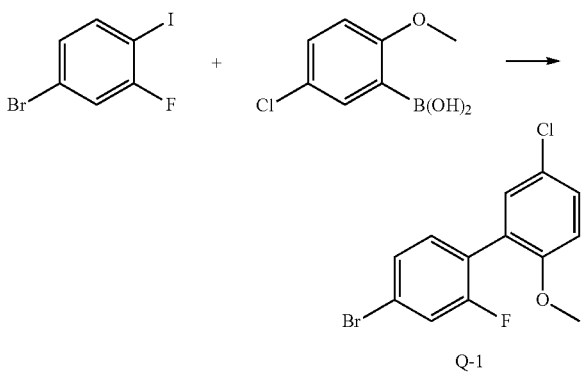

Bromo-3-fluoro-4-iodobenzene (50 g, 166.6 mmol) and 5-chloro-2-methoxyphenylboronic acid (31.1 g, 166.6 mmol) were dissolved in tetrahydrofuran (THF) (800 mL). 2 M sodium carbonate ($Na_2CO_3$) solution (250 mL) and tetrakis(triphenylphosphine)palladium (0) [$Pd(PPh_3)_4$] (3.8 g, 3 mol %) were added and the mixture was refluxed for 12 hours. After completion of the reaction, the reaction mixture was cooled to room temperature and extracted three times with water and toluene. The toluene layer was separated, then dried over magnesium sulfate, filtered, and the filtrate was distilled under reduced pressure. The resulting mixture was recrystallized three times with chloroform and ethanol to give Compound Q-1 (27.5 g, yield: 51%, MS: [M+H]$^+$=314).

(b) Preparation of Compound Q-2

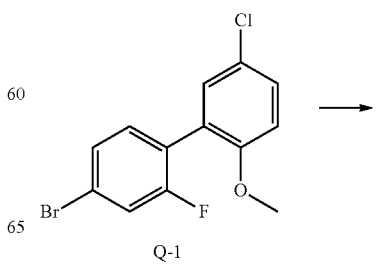

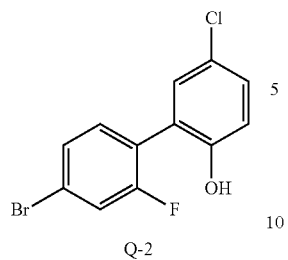

Q-2

Compound Q-1 (25.0 g, 150 mmol) was dissolved in dichloromethane (300 ml) and then cooled to 0° C. Boron tribromide (7.9 ml, 83.2 mmol) was slowly added dropwise thereto and then stirred for 12 hours. After completion of the reaction, the reaction mixture was washed three times with water, dried over magnesium sulfate and filtered. The filtrate was distilled under reduced pressure and purified by column chromatography to give Compound Q-2 (23.7 g, yield: 99%; MS: [M+H]$^+$=300).

c) Preparation of Compound Q-3

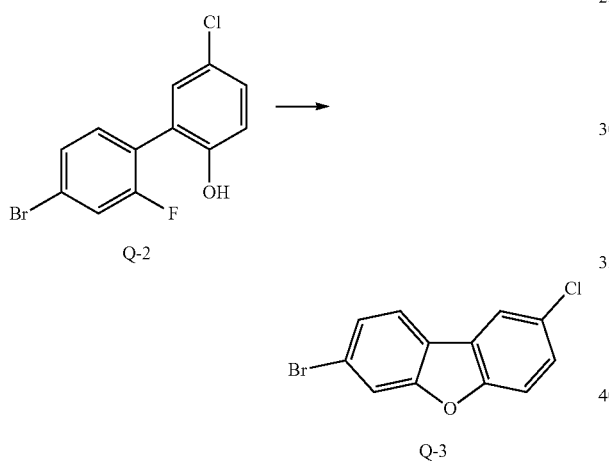

Q-2

Q-3

Compound Q-2 (20.0 g, 66.4 mmol) was dissolved in distilled dimethylformamide (DMF) (200 ml). It was cooled to 0° C. and sodium hydride (1.8 g, 72.9 mmol) was slowly added dropwise thereto. After stirring for 20 minutes, the mixture was stirred at 100° C. for 1 hour. After completion of the reaction, the reaction mixture was cooled to room temperature, and 100 ml of ethanol was slowly added thereto. The above mixture was distilled under reduced pressure, and the resulting mixture was recrystallized from chloroform and ethyl acetate to give Compound Q-3 (15.2 g, yield: 81%; MS: [M+H]$^+$=280).

d) Preparation of Compound Q-4

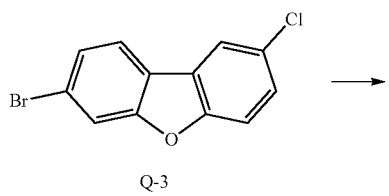

Q-3

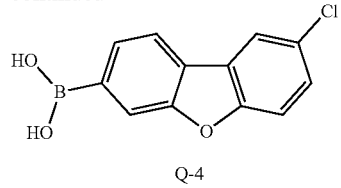

Q-4

After Compound Q-3 (15.0 g, 53.3 mmol) was dissolved in tetrahydrofuran (150 ml), the temperature was lowered to −78° C., and 1.7M tert-butyllithium (t-BuLi) (31.8 ml, 53.3 mmol) was slowly added thereto. After stirring for 1 hour at the same temperature, triisopropylborate (B(OiPr)$_3$) (14.2 ml, 107.0 mmol) was added thereto and then stirred for 3 hours while gradually raising the temperature to room temperature. 2 N aqueous hydrochloric acid solution (100 ml) was added to the reaction mixture and then stirred for 1.5 hours at room temperature. The produced precipitate was filtered, washed sequentially with water and ethyl ether, and then dried under vacuum. After drying, it was dispersed in ethyl ether, stirred for 2 hours, then filtered and dried to prepare Compound Q-4 (12.2 g, yield: 93%; MS: [M+H]$^+$=247).

Preparation Example 2: Preparation of Intermediate Compound R-4

(a) Preparation of Compound R-1

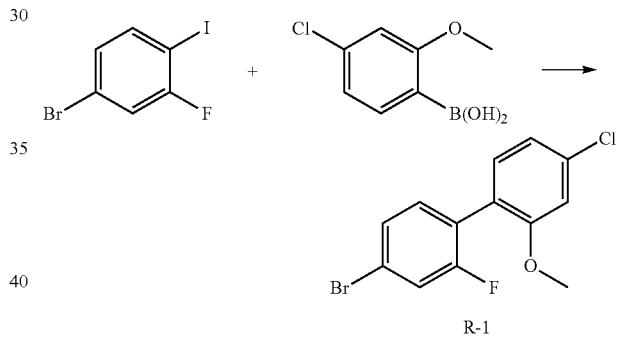

R-1

Compound R-1 (27.5 g, yield: 51%, MS: [M+H]$^+$=314) was prepared in the same manner as in the preparation method of Compound Q-1 of Preparation Example 1, except that 4-chloro-2-methoxyphenylboronic acid was used instead of 5-chloro-2-methoxyphenylboronic acid.

(b) Preparation of Compound R-2

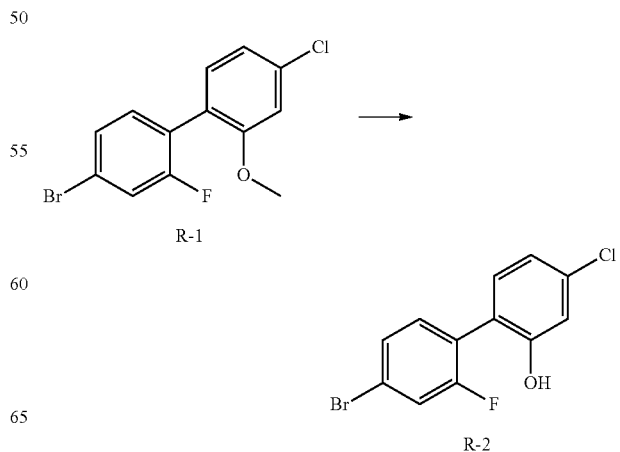

R-1

R-2

Compound R-2 (23.7 g, yield: 99%, MS: [M+H]⁺=300) was prepared in the same manner as in the preparation method of Compound Q-2 of Preparation Example 1, except that Compound R-1 was used instead of Compound Q-1.

(c) Preparation of Compound R-3

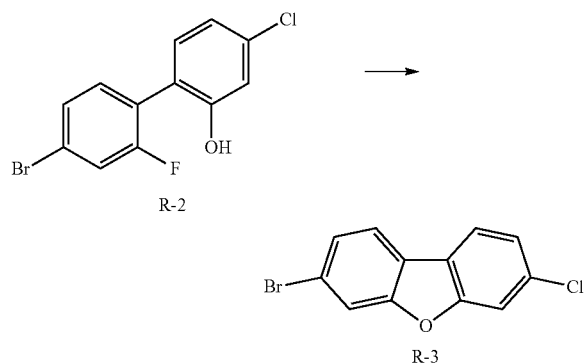

Compound R-3 (15.2 g, yield: 81%, MS: [M+H]⁺=280) was prepared in the same manner as in the preparation method of Compound Q-3 of Preparation Example 1, except that Compound R-2 was used instead of Compound Q-2.

(d) Preparation of Compound R-4

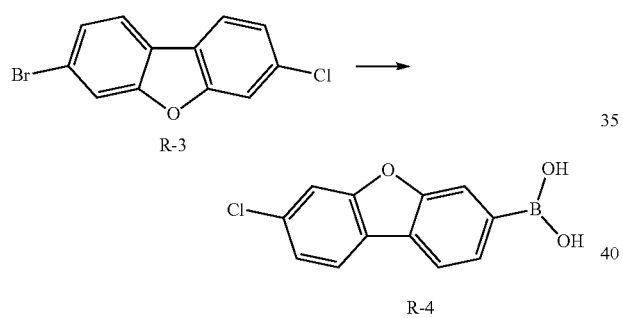

Compound R-4 (12.2 g, yield: 93%, MS: [M+H]⁺=247) was prepared in the same manner as in the preparation method of Compound Q-4 of Preparation Example 1, except that Compound R-3 was used instead of Compound Q-3.

Preparation Example 3: Preparation of Intermediate Compound P-4

(a) Preparation of Compound P-1

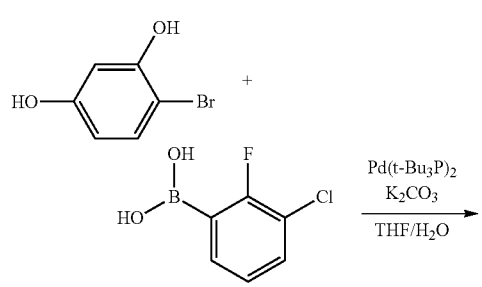

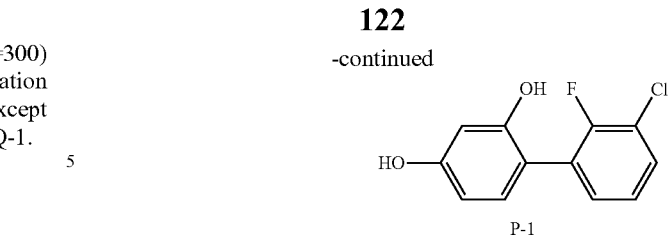

After 4-bromoresorcinol (50 g, 0.26 mol) and 3-chloro-2-fluorophenylboronic acid (46.1 g, 0.21 mol) were dissolved in tetrahydrofuran (500 mL) in a 2000 mL round bottom flask under a nitrogen atmosphere, 1.5 M aqueous potassium carbonate solution (400 mL) was added and bis(tri-tert-butylphosphine)palladium (0) (1.35 g, 2.36 mmol) was added. The mixture was heated and stirred for 1 hour. The temperature was lowered to room temperature and the aqueous layer was separated and removed, dried over anhydrous magnesium sulfate, then concentrated under reduced pressure, recrystallized with hexane, and then dried to give Compound P-1 (49.8 g, yield: 79%, MS: [M+H]+=239).

(b) Preparation of Compound P-2

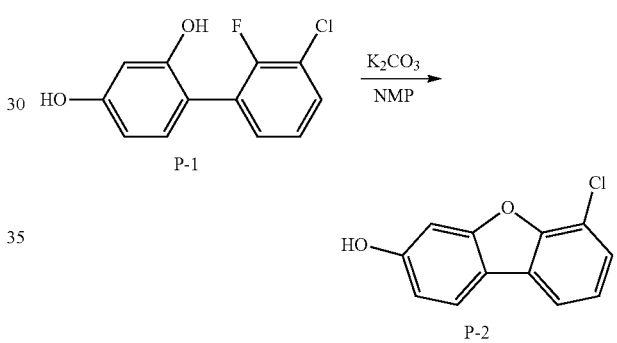

Compound P-1 (49.8 g, 0.21 mol) and calcium carbonate (57.7 g, 0.42 mol) were dissolved in N-methyl-2-pyrrolidone (200 mL) in a 500 mL round bottom flask, and the mixture was heated and stirred for 2 hours. The temperature was lowered to room temperature, subjected to reverse precipitation in water, and filtered. The product was completely dissolved in dichloromentane, then washed with water, dried over anhydrous magnesium sulfate, concentrated under reduced pressure, recrystallized with ethanol, and dried to give Compound P-2 (31.8 g, yield: 70%, MS: [M+H]+=219).

(c) Preparation of Compound P-3

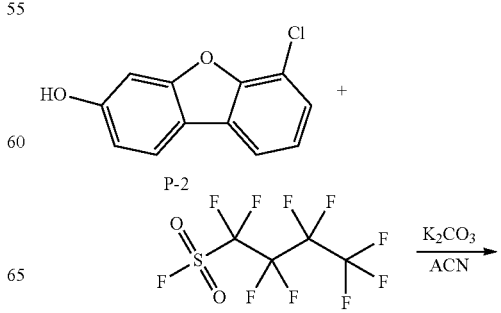

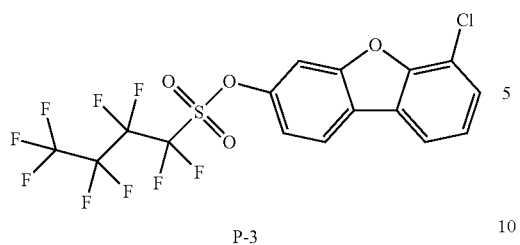

P-3

Compound P-2 (31.8 g, 0.15 mol) was dissolved in acetonitrile (150 mL) in a 500 mL round bottom flask, and calcium carbonate (33.1 g, 0.24 mol) was dissolved in water (150 mL), added thereto and then nonafluorobutanesulfonyl fluoride (28.7 mL, 0.16 mol) was slowly added dropwise at 30 minutes. Then, the mixture was stirred at room temperature for 3 hours. Upon completion of the reaction, the reaction mixture was filtered, completely dissolved in dichloromentane, then washed with water, dried over anhydrous magnesium sulfate, concentrated under reduced pressure, recrystallized with ethanol, and then dried to give Compound P-3 (53.3 g, yield: 73%, MS: [M+H]+=501).

(d) Preparation of Compound P-4

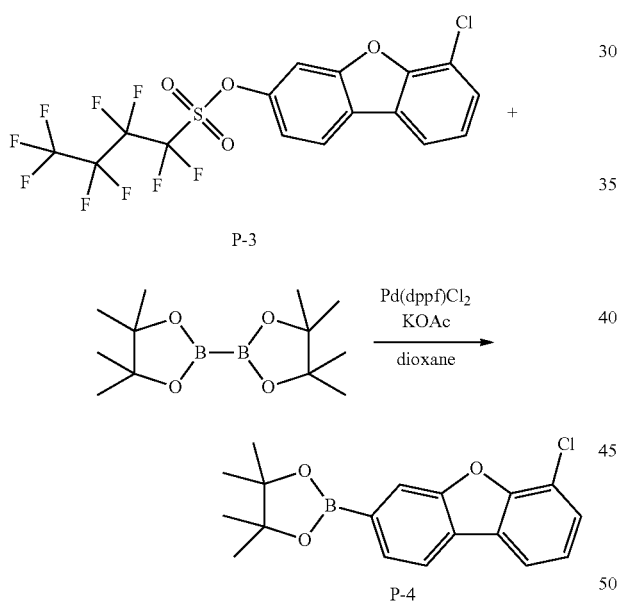

P-4

Compound P-3 (53.3 g, 0.11 mol), 4,4,5,5-tetramethyl-[1,3,2]-dioxaborolane (28.4 g, 17.85 mol), [1,1'-bis(diphenylphosphino)ferrocene]palladium(II) dichloride (Pd(dppf)Cl₂) (0.78 g, 1.06 mmol), and potassium acetate (KOAc) (31.3 g, 0.32 mol) were added to dioxane (650 mL) and stirred under reflux for 8 hours. The temperature was lowered to room temperature and the solvent was concentrated under reduced pressure. The concentrated solution was completely dissolved in chloroform (CHCl₃) and washed with water. The solution in which the product was dissolved was concentrated under reduced pressure and purified by column chromatography to obtain Compound P-4 (30.1 g, yield: 86%, MS: [M+H]⁺=329).

Preparation Example 4: Preparation of Intermediate Compound S2

(a) Preparation of Compound S1

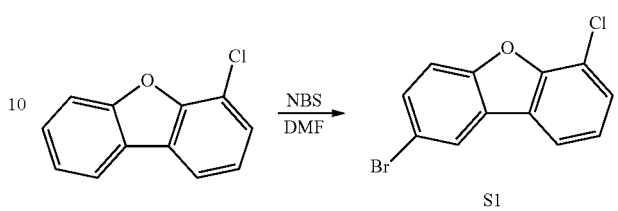

S1

After 4-chlorodibenzofuran (75 g, 0.37 mol) was dissolved in dimethylformamide (DMF) (700 mL) in a 1000 mL round bottom flask under a nitrogen atmosphere, N-bromosuccinimide (NBS) (69.2 g, 0.39 mol) was added while dividing into five times at 0° C. and then stirred at room temperature for 3 hours. Then, the solution was subjected to pressure reduction, dissolved in ethyl acetate, washed with water, the organic layer was separated, and the solvent was removed under reduced pressure. This was subjected to column chromatography to give Compound 51 (92.5 g, yield: 89%, MS: [M+H]+=280).

(b) Preparation of Compound S2

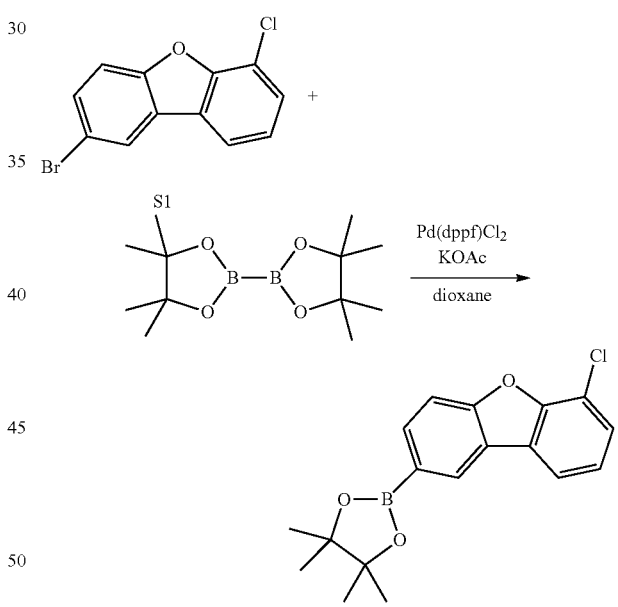

S2

Compound 51 (92.5 g, 0.33 mol), 4,4,5,5-tetramethyl-[1,3,2]-dioxaborolane (87.9 g, 0.35 mol), [1,1'-bis(diphenylphosphino)ferrocene]palladium(II) dichloride (Pd(dppf)Cl₂) (2.41 g, 3.30 mmol) and potassium acetate (KOAc) (97.1 g, 0.99 mol) were added to dioxane (1000 mL) and stirred under reflux for 9 hours. The temperature was lowered to room temperature and the solvent was concentrated under reduced pressure. The concentrated solution was completely dissolved in chloroform (CHCl₃), washed with water, and the solution in which the product was dissolved was concentrated under reduced pressure, recrystallized with ethanol, dried and purified to give Compound S2 (115 g, yield: 67%, MS: [M+H]+=329).

Preparation Example 5: Preparation of Intermediate Compound U-4

(a) Preparation of 3-bromo-2-methoxyphenylboronic Acid

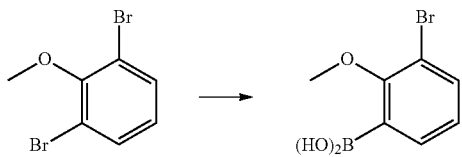

After 1,3-dibromo-2-methoxybenzene (113.2 g, 426.4 mmol) was dissolved in tetrahydrofuran (1000 ml), the temperature was lowered to −78° C., and 1.7M tert-butyllithium (t-BuLi) (251.7 ml, 426.4 mmol) was slowly added thereto. After stirring for 1 hour at the same temperature, triisopropylborate (B(OiPr)$_3$) (113.2 ml, 852.4 mmol) was added thereto and then stirred for 3 hours while gradually raising the temperature to room temperature. 2 N aqueous hydrochloric acid solution (800 ml) was added to the reaction mixture and then stirred for 1.5 hours at room temperature. The produced precipitate was filtered, washed sequentially with water and ethyl ether, and then dried under vacuum. After drying, it was recrystallized with chloroform and ethyl acetate and dried to prepare 3-bromo-2-methoxyphenylboronic acid (89.6 g, yield: 91%, MS: [M+H]$^+$=230).

(b) Preparation of Compound U-1

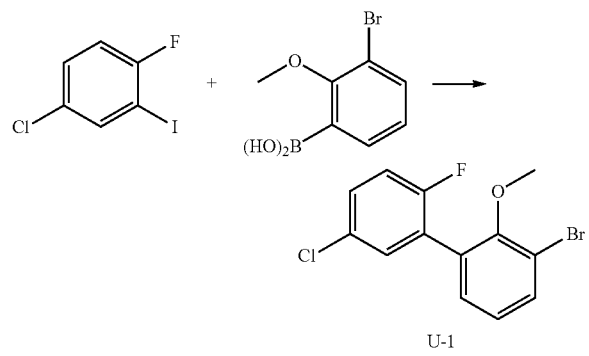

Compound U-1 (55.8 g, yield: 53%, MS: [M+H]$^+$=314) was prepared in the same manner as in the preparation method of Compound Q-1 of Preparation Example 1, except that 4-chloro-1-fluoro-2-iodinebenzene was used instead of bromo-3-fluoro-4-iodobenzene and 3-bromo-2-methoxyphenylboronic acid was used instead of 5-chloro-2-methoxyphenylboronic acid.

(c) Preparation of Compound U-2

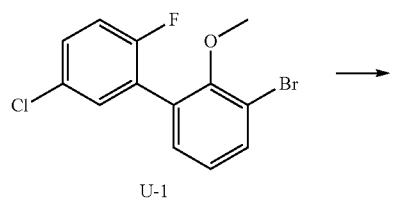

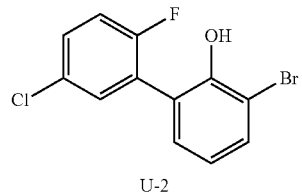

Compound U-2 (39.7 g, yield: 83%, MS: [M+H]$^+$=300) was prepared in the same manner as in the preparation method of Compound Q-2 of Preparation Example 1, except that Compound U-1 was used instead of Compound Q-1.

(d) Preparation of Compound U-3

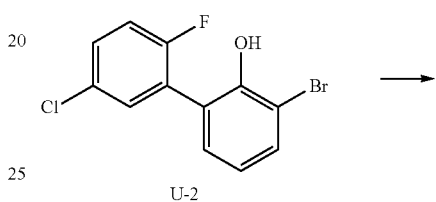

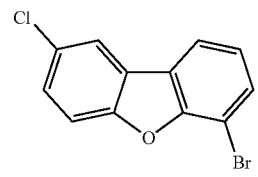

Compound U-3 (31.4 g, yield: 84%, MS: [M+H]$^+$=280) was prepared in the same manner as in the preparation method of Compound Q-3 of Preparation Example 1, except that Compound U-2 was used instead of Compound Q-2.

(e) Preparation of Compound U-4

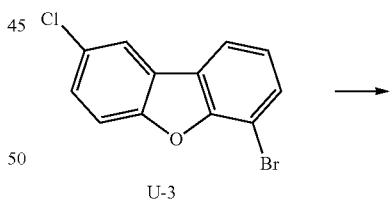

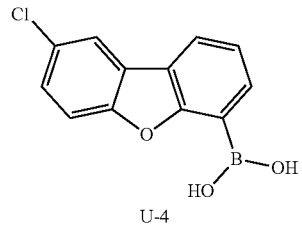

Compound U-4 (25.5 g, yield: 97%, MS: [M+H]$^+$=247) was prepared in the same manner as in the preparation method of Compound Q-4 of Preparation Example 1, except that Compound U-3 was used instead of Compound Q-3.

Preparation Example 6: Preparation of Intermediate Compound A1

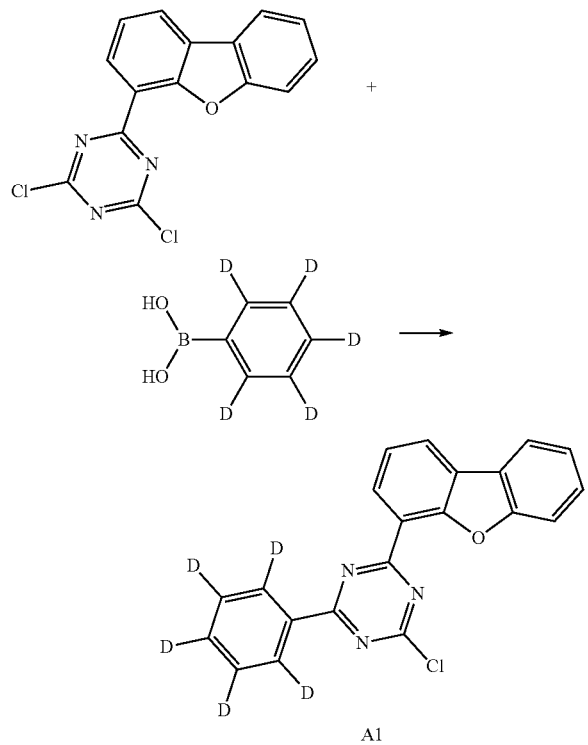

A1

After 2,4-dichloro-6-(dibenzo[b,d]furan-4-yl)-1,3,5-triazine (50.0 g, 158.7 mmol) and phenyl-d5-boronic acid (20.2 g, 158.7 mmol) were dispersed in tetrahydrofuran (500 mL), 2M aqueous potassium carbonate solution (aq. K$_2$CO$_3$) (238 mL, 476.2 mmol) was added and tetrakistriphenylphosphinopalladium [Pd(PPh$_3$)$_4$] (5.5 g, 3 mol %) was added. The mixture was stirred and refluxed for 5 hours. The temperature was lowered to room temperature and the resulting solid was filtered. The filtered solid was recrystallized with chloroform and ethyl acetate, filtered and then dried to give Compound A1 (39.1 g, yield: 68%, MS: [M+H]$^+$=363).

Preparation Example 7: Preparation of Intermediate Compound A2

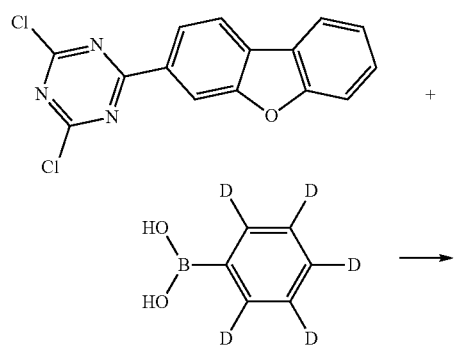

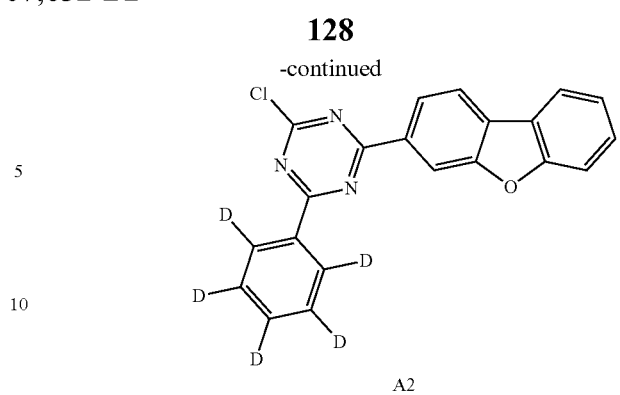

A2

Compound A2 (42.5 g, yield: 74%, MS: [M+H]$^+$=363) was prepared in the same manner as in the preparation method of Compound A1 of Preparation Example 6, except that 2,4-dichloro-6-(dibenzo[b,d]furan-3-yl)-1,3,5-triazine was used instead of 2,4-dichloro-6-(dibenzo[b,d]furan-4-yl)-1,3,5-triazine.

Preparation Example 8: Preparation of Intermediate Compound A4

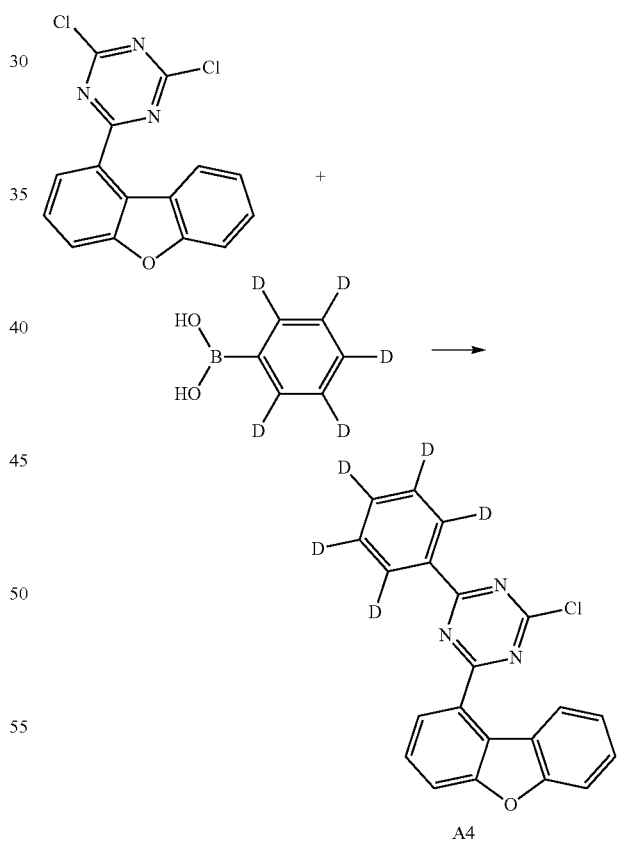

A4

Compound A4 (33.9 g, yield: 59%, MS: [M+H]$^+$=363) was prepared in the same manner as in the preparation method of Compound A1 of Preparation Example 6, except that 2,4-dichloro-6-(dibenzo[b,d]furan-3-yl)-1,3,5-triazine was used instead of 2,4-dichloro-6-(dibenzo[b,d]furan-4-yl)-1,3,5-triazine.

Preparation Example 9: Preparation of Intermediate Compound A5

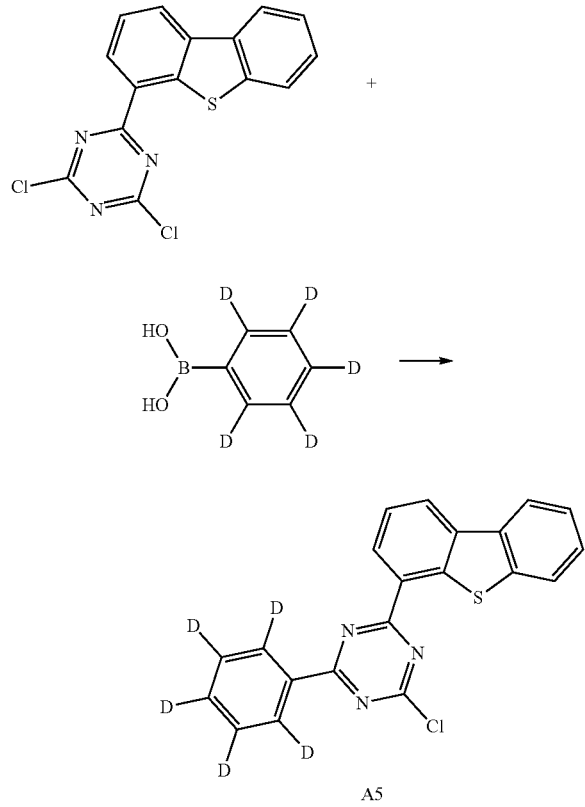

Compound A5 (42.8 g, yield: 75%, MS: [M+H]$^+$=379) was prepared in the same manner as in the preparation method of Compound A1 of Preparation Example 6, except that 2,4-dichloro-6-(dibenzo[b,d]thiophen-4-yl)-1,3,5-triazine was used instead of 2,4-dichloro-6-(dibenzo[b,d]furan-4-yl)-1,3,5-triazine.

Preparation Example 10: Preparation of Intermediate Compound B1

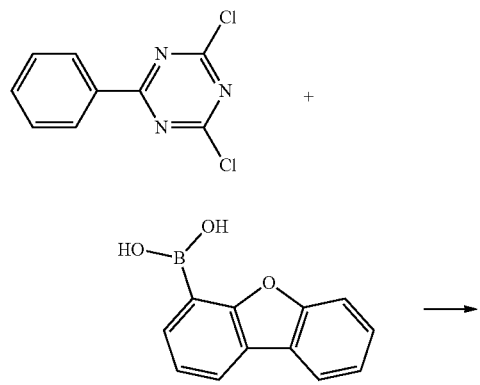

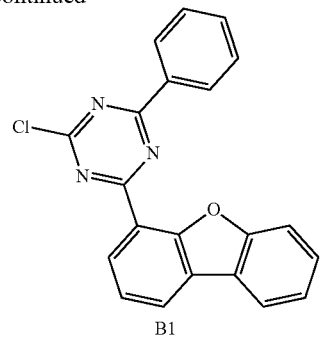

Under a nitrogen atmosphere, 2,4-dichloro-6-phenyl-1,3,5-triazine (20 g, 88.9 mmol) and dibenzo[b,d]furan-4-ylboronic acid (18.9 g, 88.9 mmol) were added to tetrahydrofuran (400 mL) and the mixture was stirred and refluxed. Then, potassium carbonate (36.9 g, 266.7 mmol) was dissolved in water (37 mL), added thereto, sufficiently stirred, and then tetrakistriphenylphosphinopalladium (3.1 g, 2.7 mmol) was added. After the reaction for 2 hours, the reaction mixture was cooled to room temperature, the organic layer and the aqueous layer were separated, and the organic layer was distilled. This was again added to and dissolved in chloroform (635 mL) by 20 times the theoretical yield of Compound B1 and washed twice with water. The organic layer was then separated, anhydrous magnesium sulfate was added thereto, stirred and filtered, and the filtrate was distilled under reduced pressure. The concentrated compound was recrystallized from chloroform and ethyl acetate to give Compound B1 (20.6 g, yield: 65%, MS: [M+H]$^+$=358.1) as a white solid.

Preparation Example 11: Preparation of Intermediate Compound B2

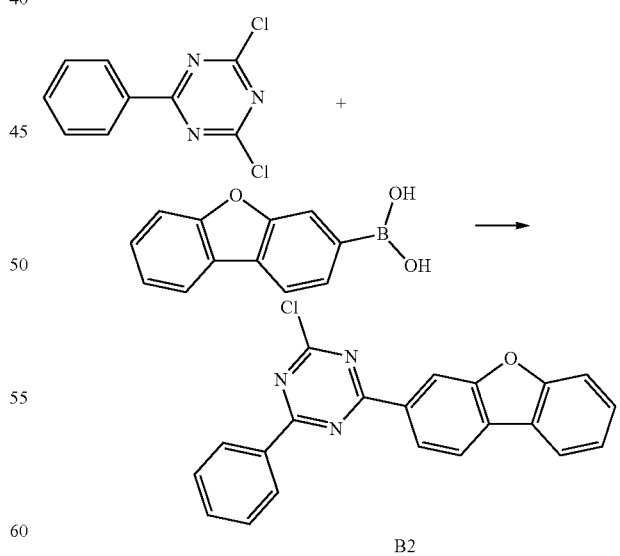

Compound B2 (18.4 g, yield: 58%, MS: [M+H]$^+$=358.1) was prepared in the same manner as in the preparation method of Compound B1 of Preparation Example 10, except that dibenzo[b,d]furan-3-ylboronic acid was used instead of dibenzo[b,d]furan-4-ylboronic acid.

Preparation Example 12: Preparation of Intermediate Compound B3

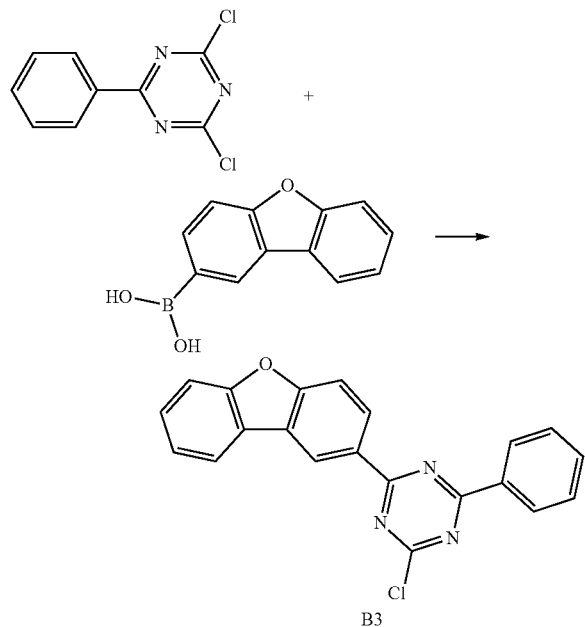

Compound B3 (24.4 g, yield: 77%, MS: [M+H]$^+$=358.1) was prepared in the same manner as in the preparation method of Compound B1 of Preparation Example 10, except that dibenzo[b,d]furan-2-ylboronic acid was used instead of dibenzo[b,d]furan-4-ylboronic acid.

Preparation Example 13: Preparation of Intermediate Compound B4

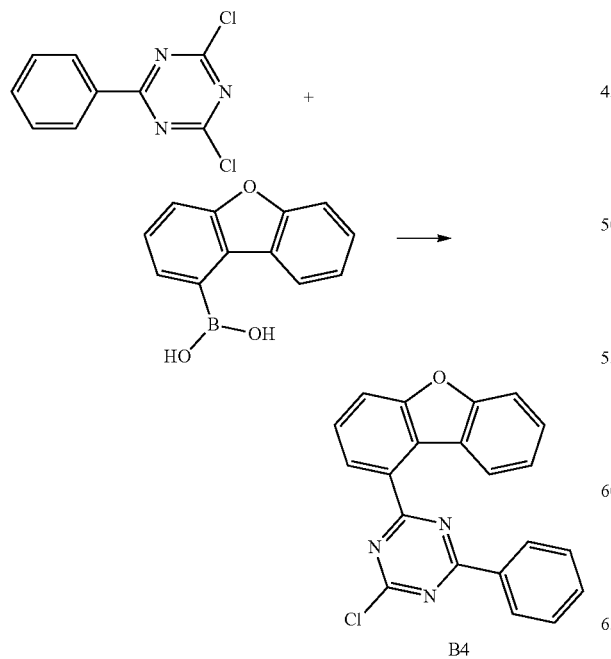

Compound B4 (21.9 g, yield: 69%, MS: [M+H]$^+$=358.1) was prepared in the same manner as in the preparation method of Compound B1 of Preparation Example 10, except that dibenzo[b,d]furan-1-ylboronic acid was used instead of dibenzo[b,d]furan-4-ylboronic acid.

Preparation Example 14: Preparation of Intermediate Compound B5

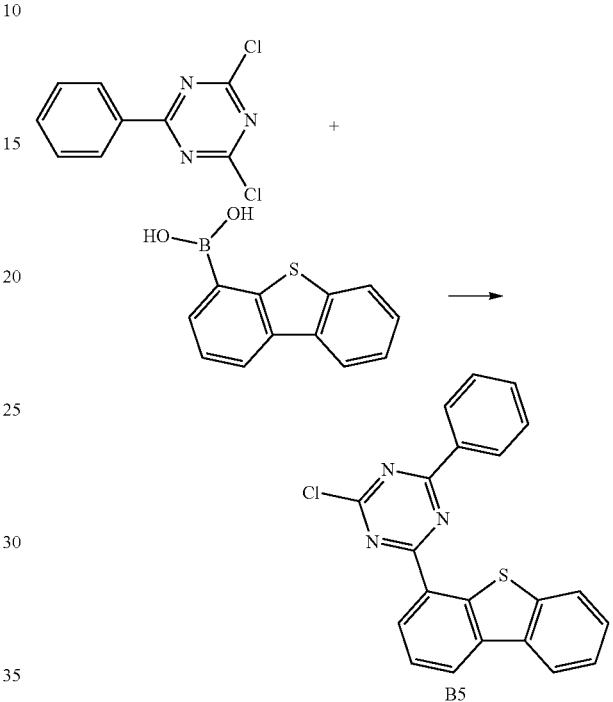

Compound B5 (21.6 g, yield: 65%, MS: [M+H]$^+$=374) was prepared in the same manner as in the preparation method of Compound B1 of Preparation Example 10, except that dibenzo[b,d]thiophen-4-ylboronic acid was used instead of dibenzo[b,d]furan-4-ylboronic acid.

Example 1: Preparation of Compound 1

(a) Preparation of Intermediate 1-1

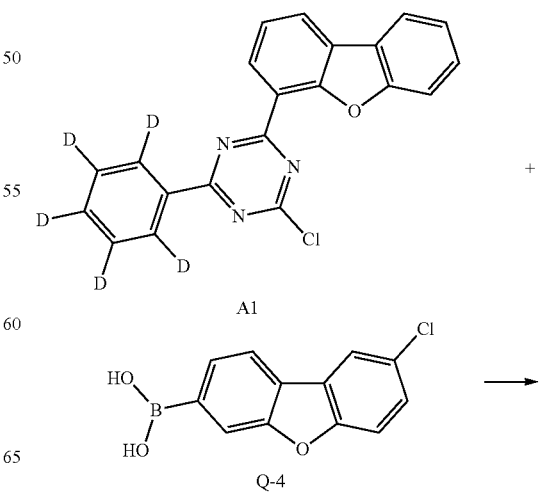

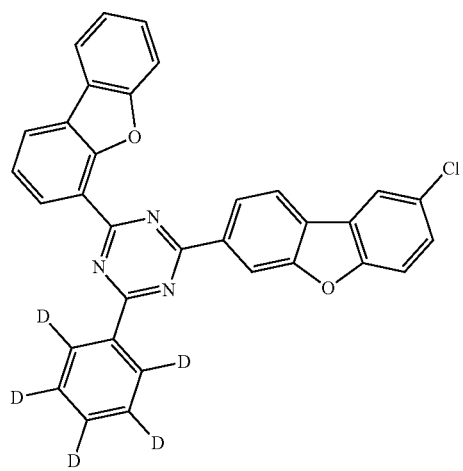

1-1

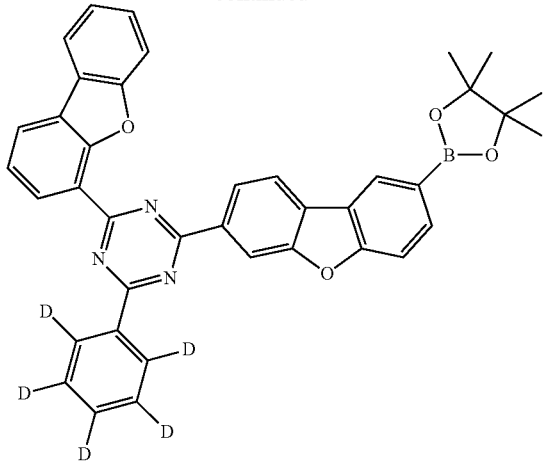

1-2

Compound A1 (20 g, 55.2 mmol) and Compound Q-4 (13.6 g, 55.2 mmol) were added to tetrahydrofuran (400 mL) under a nitrogen atmosphere, and the mixture was stirred and refluxed. Then, potassium carbonate (22.9 g, 165.7 mmol) was dissolved in water (23 mL), added thereto, sufficiently stirred, and then tetrakistriphenylphosphinopalladium (1.9 g, 1.7 mmol) was added. After the reaction for 1 hour, the reaction mixture was cooled to room temperature, the organic layer and the water layer was separated, and then the organic layer was distilled. This was again added to and dissolved in 20 times more chloroform (583 mL) relative to the theoretical yield of Intermediate 1-1, and washed twice with water. The organic layer was then separated, anhydrous magnesium sulfate was added thereto, stirred, and filtered, and the filtrate was distilled under reduced pressure. The concentrated compound was recrystallized from chloroform and ethyl acetate to give Intermediate 1-1 (18.4 g, yield: 63%, MS: $[M+H]^+=529.1$) as a white solid compound.

(b) Preparation of Intermediate 1-2

Intermediate 1-1 (15 g, 28.4 mmol) and bis(pinacolato)diboron (11.2 g, 28.4 mmol) were added to dioxane (300 mL) under a nitrogen atmosphere, and the mixture was stirred and refluxed. Then, potassium phosphate tribasic (18.1 g, 85.2 mmol) was added thereto, sufficiently stirred, and then palladium dibenzylidene acetone palladium (0.5 g, 0.9 mmol) and tricyclohexylphosphine (0.5 g, 1.7 mmol) were added. After the reaction for 5 hours, the mixture was cooled to room temperature, the organic layer was filtered to remove salt, and then the filtered organic layer was distilled. This was again added to and dissolved chloroform (176 mL) by 10 times the theoretical yield of Intermediate 1-2, washed twice with water, the organic layer was separated, anhydrous magnesium sulfate was added thereto, stirred, and filtered. The filtrate was distilled under reduced pressure. The concentrated compound was recrystallized from chloroform and ethanol to give Intermediate 1-2 (12.7 g, yield: 72%, MS: $[M+1-1]+=621.2$) as a white solid compound.

(c) Preparation of Compound 1

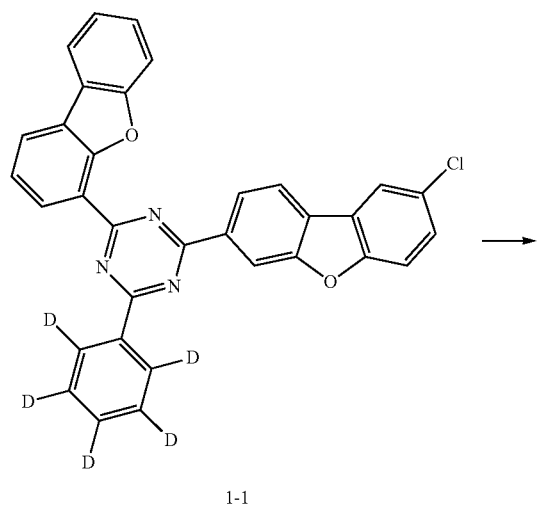

1-1

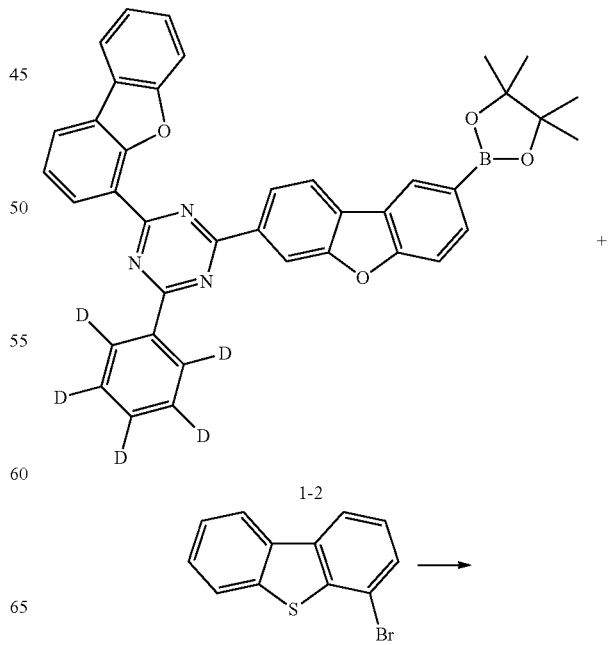

1-2

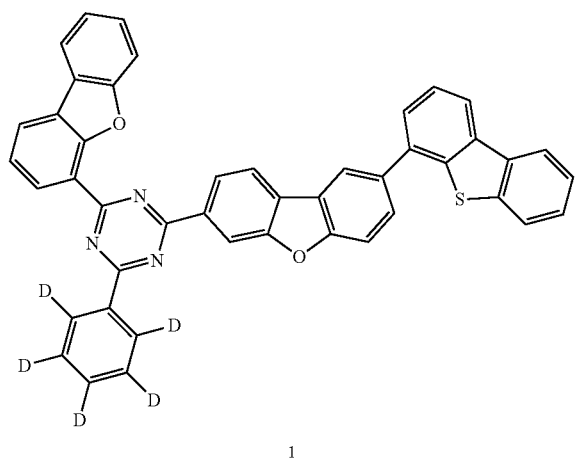

1

Under a nitrogen atmosphere, Intermediate 1-2 (10 g, 16.1 mmol) and 4-bromodibenzo[b,d]thiophene (4.2 g, 16.1 mmol) were added to tetrahydrofuran (200 mL), and the mixture was stirred and refluxed. Then, potassium carbonate (6.7 g, 48.4 mmol) was dissolved in water (7 mL), added thereto, sufficiently stirred, and then tetrakistriphenylphosphinopalladium (0.6 g, 0.5 mmol) was added. After the reaction for 1 hour, the reaction mixture was cooled to room temperature, the organic layer and the aqueous layer were separated, and the organic layer was distilled. This was again added to and dissolved in chloroform (218 mL) by 20 times the theoretical yield of Compound 1, and washed twice with water. The organic layer was separated, and anhydrous magnesium sulfate was added, stirred, and filtered, and the filtrate was distilled under reduced pressure. The concentrated compound was recrystallized from chloroform and ethyl acetate to give Compound 1 (7.2 g, yield: 66%, MS: [M+H]$^+$=677.2) as a white solid.

Example 2: Preparation of Compound 2

(a) Preparation of Intermediate 2-1

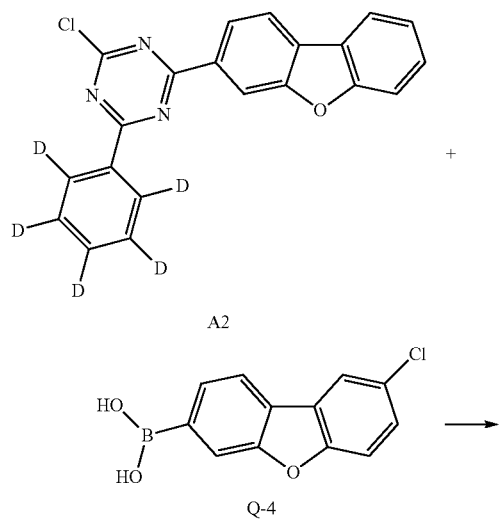

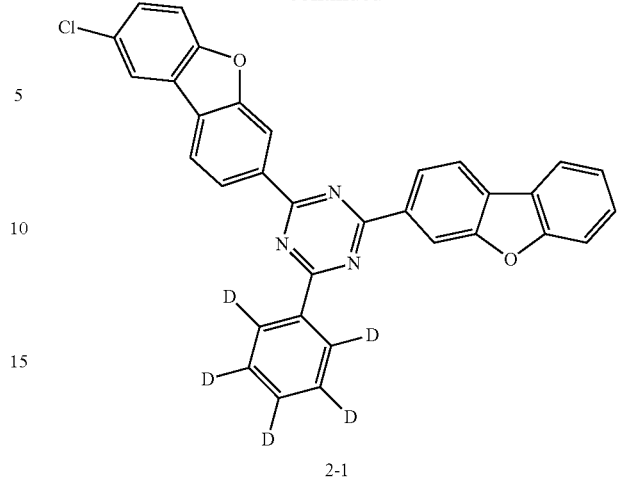

2-1

Intermediate 2-1 (21.6 g, yield: 74%, MS: [M+H]$^+$=529.1) was prepared in the same manner as in the preparation method of Intermediate 1-1 of Example 1, except that Compound A2 was used instead of Compound A1.

(b) Preparation of Intermediate 2-2

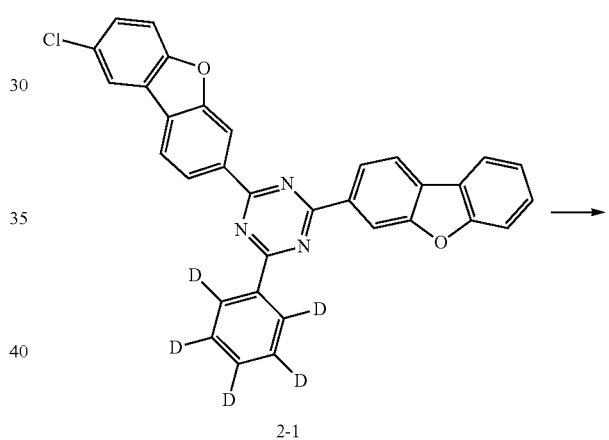

2-1

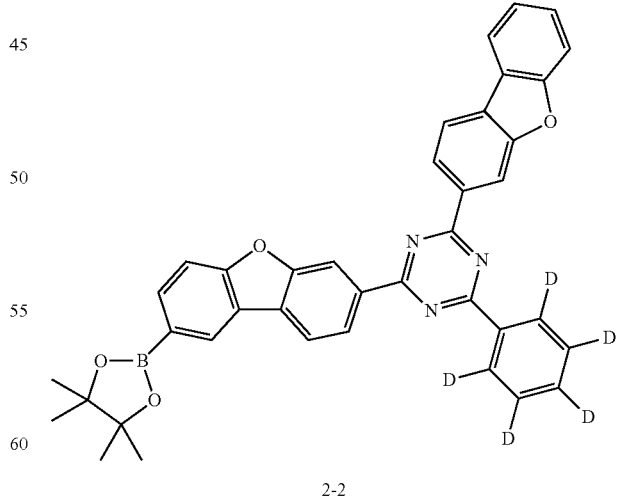

2-2

Intermediate 2-2 (13.6 g, yield: 77%, MS: [M+H]$^+$=621.2) was prepared in the same manner as in the preparation method of Intermediate 1-2 of Example 1, except that Intermediate 2-1 was used instead of Intermediate 1-1.

(c) Preparation of Compound 2

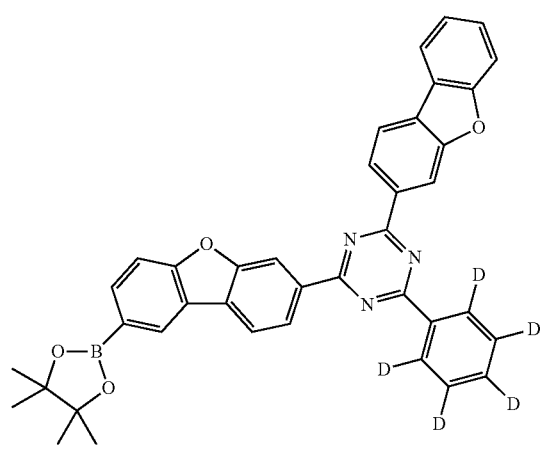

2-2

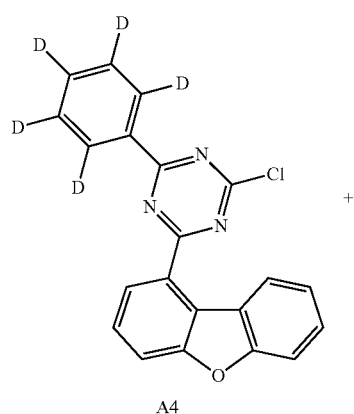

A4

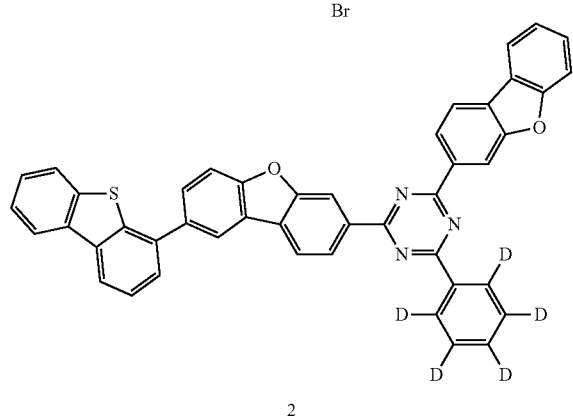

2

Compound 2 (8.7 g, yield: 80%, MS: [M+H]⁺=677.2) was prepared in the same manner as in the preparation method of Compound 1 of Example 1, except that Intermediate 2-2 was used instead of Intermediate 1-2.

Example 3: Preparation of Compound 3

(a) Preparation of Intermediate 3-1

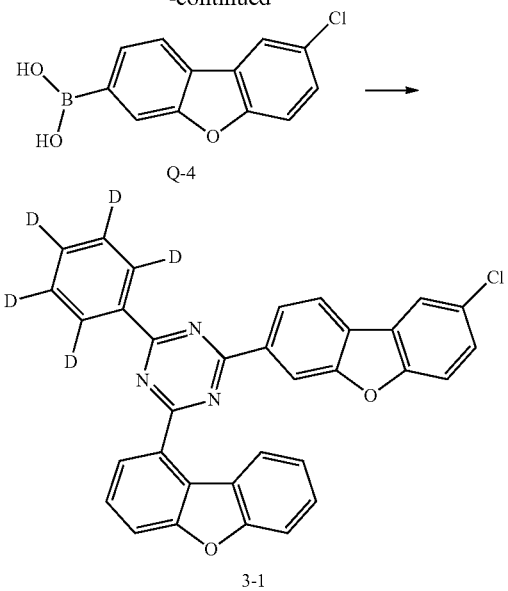

3-1

Intermediate 3-1 (20.4 g, yield: 70%, MS: [M+H]⁺=529.1) was prepared in the same manner as in the preparation method of Intermediate 1-1 of Example 1, except that Compound A4 was used instead of Compound A1.

(b) Preparation of Intermediate 3-2

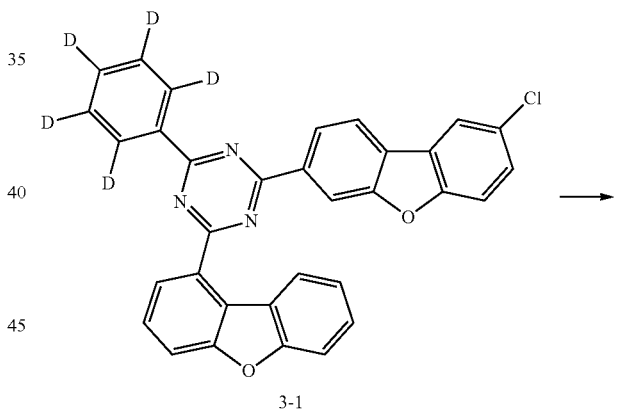

3-1

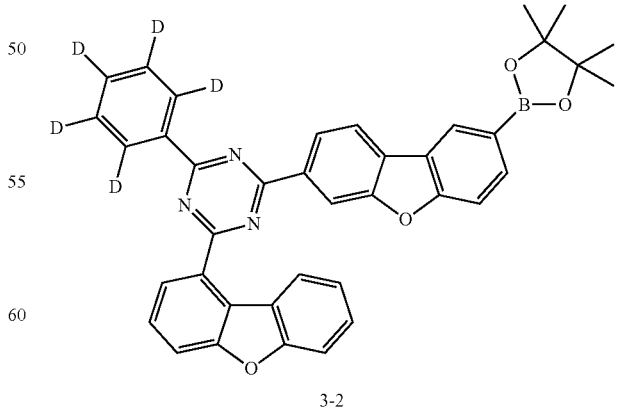

3-2

Intermediate 3-2 (10.6 g, yield: 60%, MS: [M+H]⁺=621.2) was prepared in the same manner as in the preparation method of Intermediate 1-2 of Example 1, except that Intermediate 3-1 was used instead of Intermediate 1-1.

(c) Preparation of Compound 3

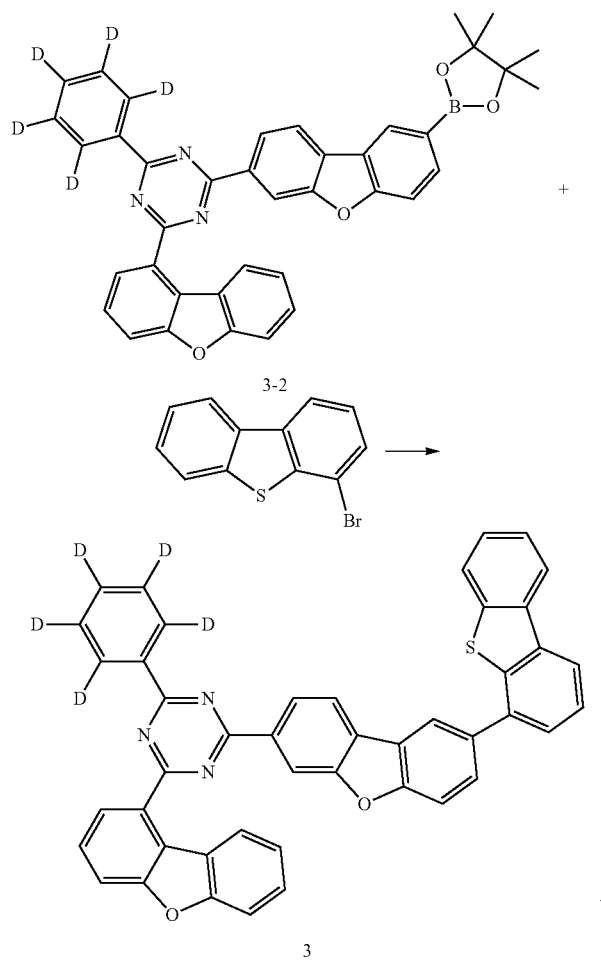

Compound 3 (5.7 g, yield: 52%, MS: [M+H]⁺=677.2) was prepared in the same manner as in the preparation method of Compound 1 of Example 1, except that Intermediate 3-2 was used instead of Intermediate 1-2.

Example 4: Preparation of Compound 4

(a) Preparation of Intermediate 4-1

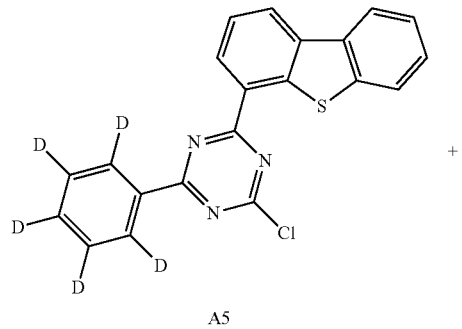

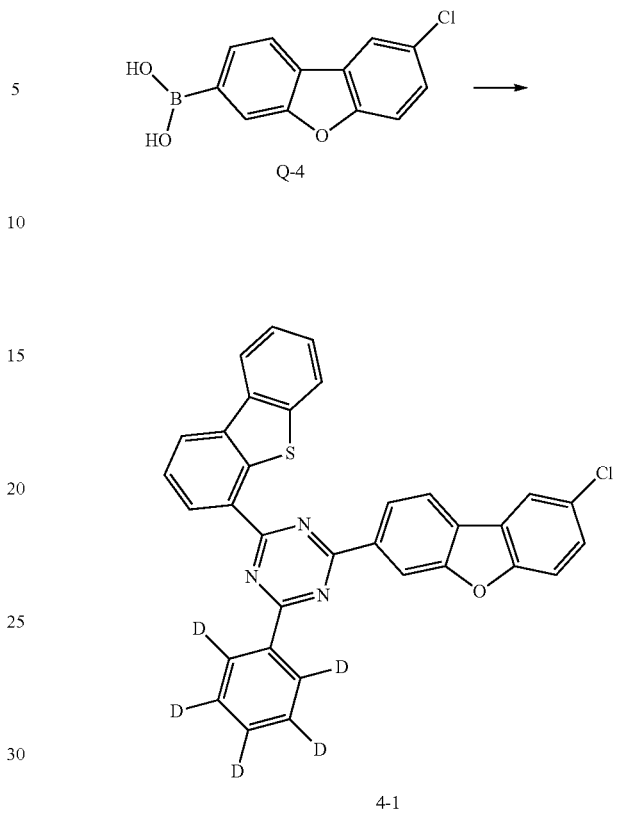

Intermediate 4-1 (19.8 g, yield: 68%, MS: [M+H]⁺=529.1) was prepared in the same manner as in the preparation method of Intermediate 1-1 of Example 1, except that Compound A5 was used instead of Compound A1.

(b) Preparation of Intermediate 4-2

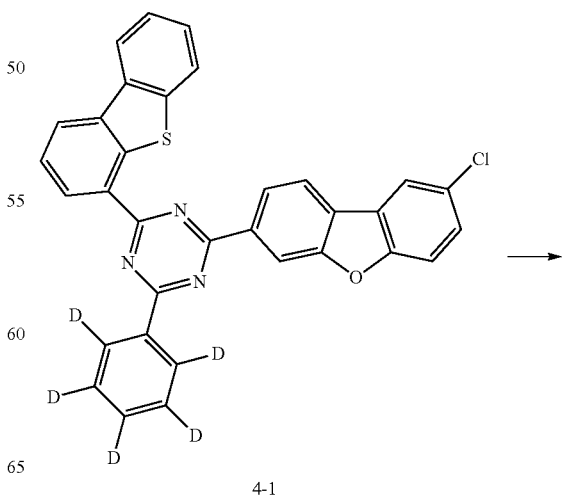

-continued

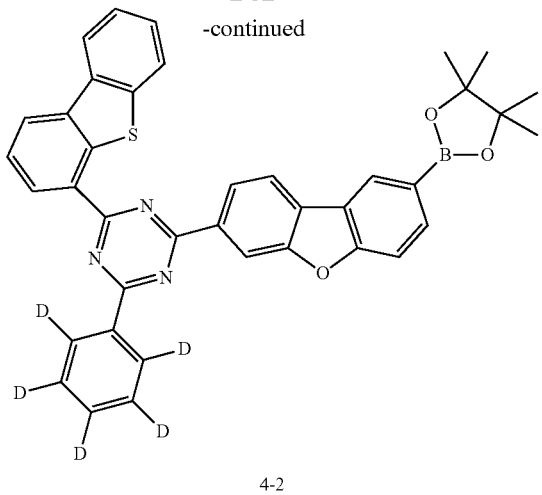

4-2

Intermediate 4-2 (10.2 g, yield: 58%, MS: [M+H]⁺=621.2) was prepared in the same manner as in the preparation method of Intermediate 1-2 of Example 1, except that Intermediate 4-1 was used instead of Intermediate 1-1.

(c) Preparation of Intermediate 4

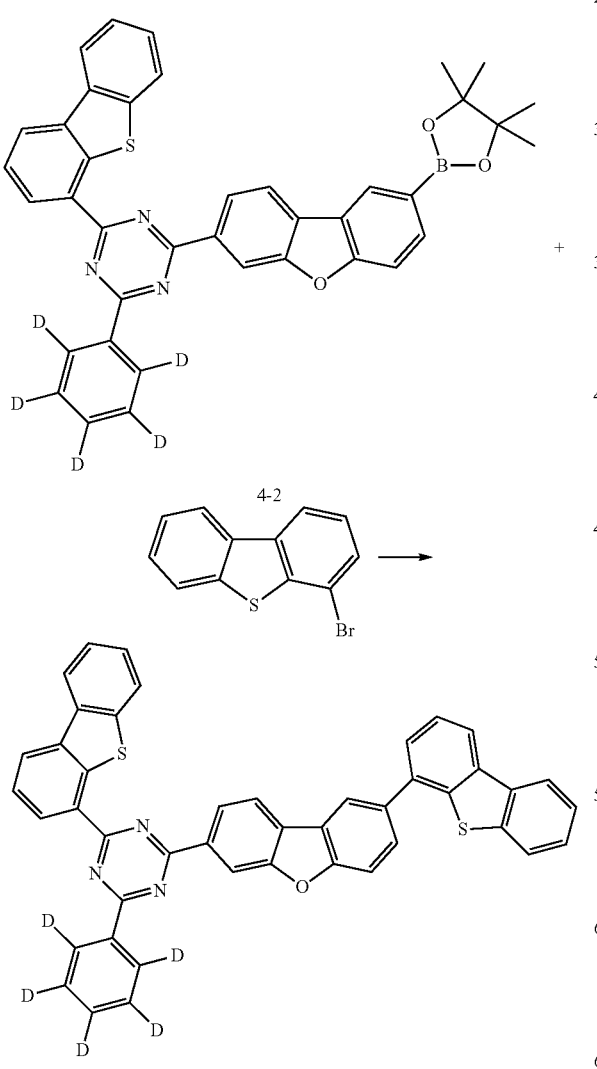

Compound 4 (6.5 g, yield: 60%, MS: [M+H]⁺=693.2) was prepared in the same manner as in the preparation method of Compound 1 of Example 1, except that Intermediate 4-2 was used instead of Intermediate 1-2.

Example 5: Preparation of Compound 5

(a) Preparation of Intermediate 5-1

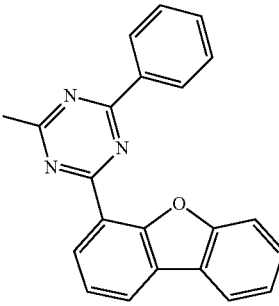

B1

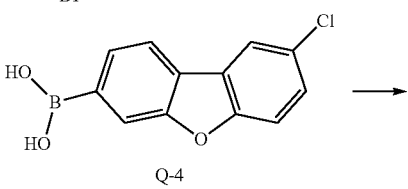

Q-4

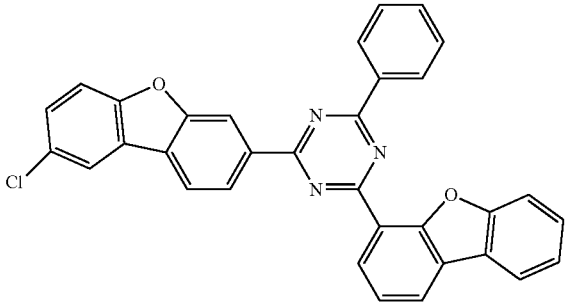

5-1

Intermediate 5-1 (17.2 g, yield: 59%, MS: [M+H]⁺=529.1) was prepared in the same manner as in the preparation method of Intermediate 1-1 of Example 1, except that Compound B1 was used instead of Compound A1.

(b) Preparation of Intermediate 5-2

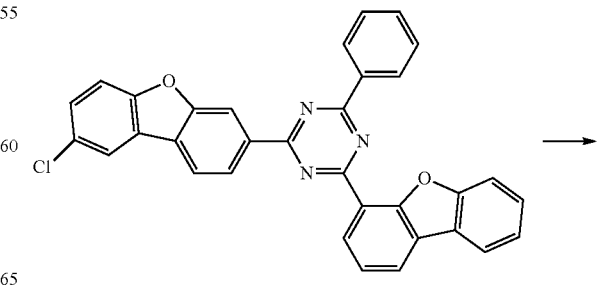

5-1

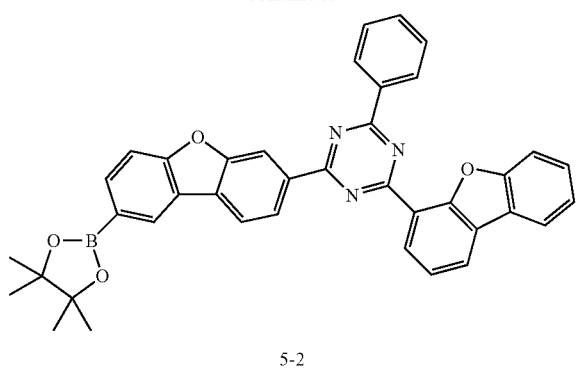

5-2

Intermediate 5-2 (11.3 g, yield: 64%, MS: [M+H]$^+$=616.2) was prepared in the same manner as in the preparation method of Intermediate 1-2 of Example 1, except that Intermediate 5-1 was used instead of Intermediate 1-1.

(c) Preparation of Compound 5

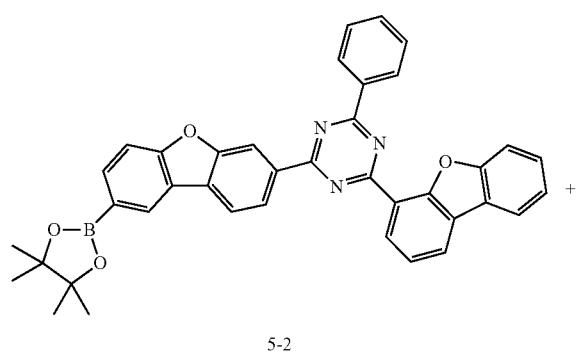

5-2

+

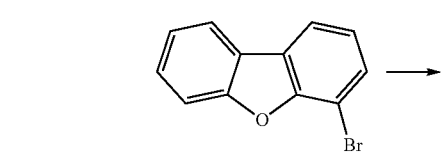

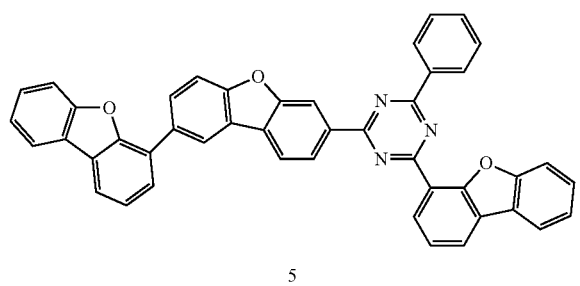

5

Compound 5 (6.4 g, yield: 60%, MS: [M+H]$^+$=656.2) was prepared in the same manner as in the preparation method of Compound 1 of Example 1, except that Intermediate 5-2 was used instead of Intermediate 1-2.

Example 6: Preparation of Compound 6

(a) Preparation of Intermediate 6-1

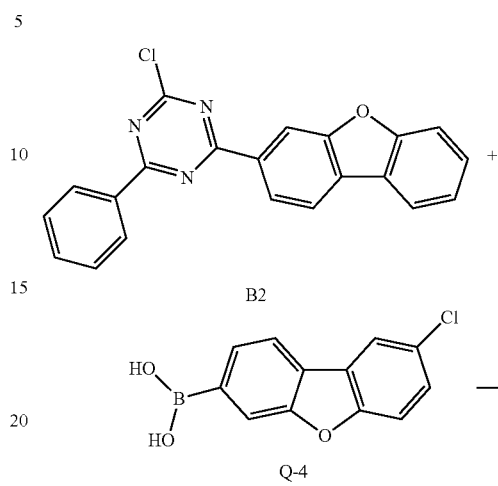

B2

+

Q-4

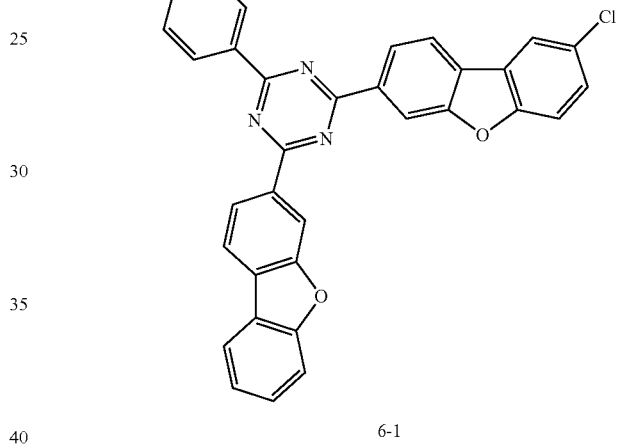

6-1

Intermediate 6-1 (22.5 g, yield: 77%, MS: [M+H]$^+$=529.1) was prepared in the same manner as in the preparation method of Intermediate 1-1 of Example 1, except that Compound B2 was used instead of Compound A1.

(b) Preparation of Intermediate 6-2

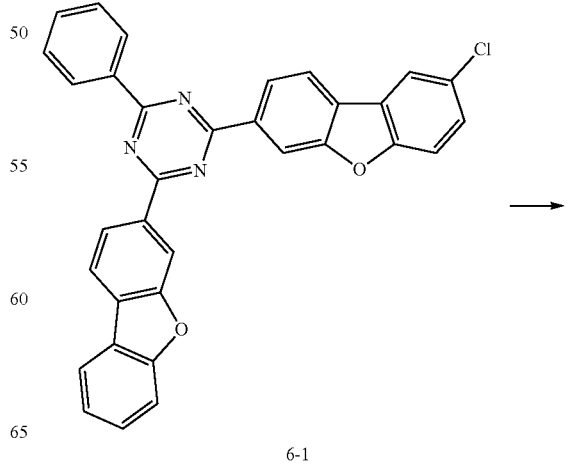

6-1

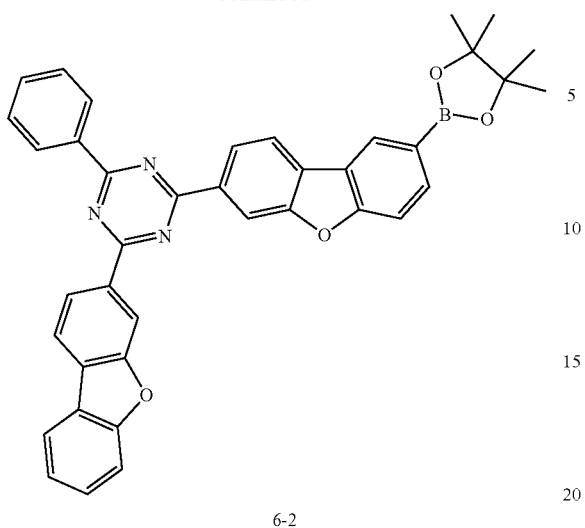

6-2

Intermediate 6-2 (11.8 g, yield: 67%, MS: [M+H]⁺=616.2) was prepared in the same manner as in the preparation method of Intermediate 1-2 of Example 1, except that Intermediate 6-1 was used instead of Intermediate 1-1.

(c) Preparation of Compound 6

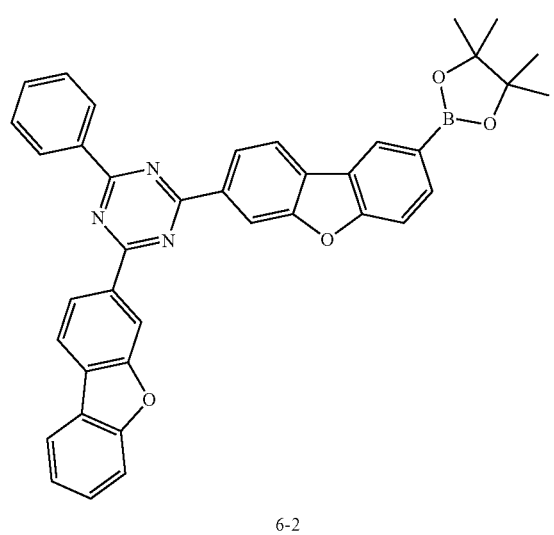

6-2

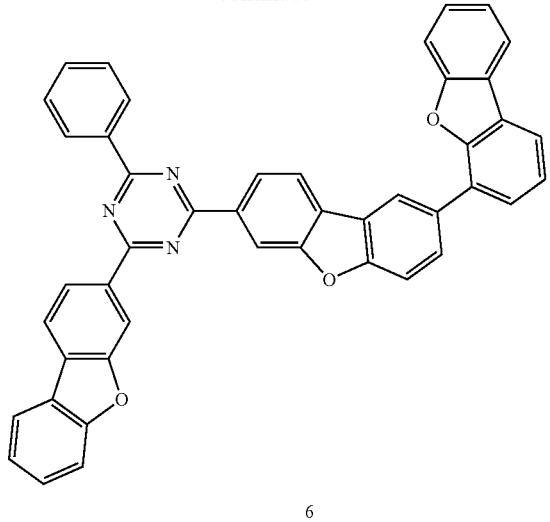

6

Compound 6 (5.9 g, yield: 55%, MS: [M+H]⁺=656.2) was prepared in the same manner as in the preparation method of Compound 1 of Example 1, except that Intermediate 6-2 was used instead of Intermediate 1-2.

Example 7: Preparation of Compound 7

(a) Preparation of Intermediate 7-1

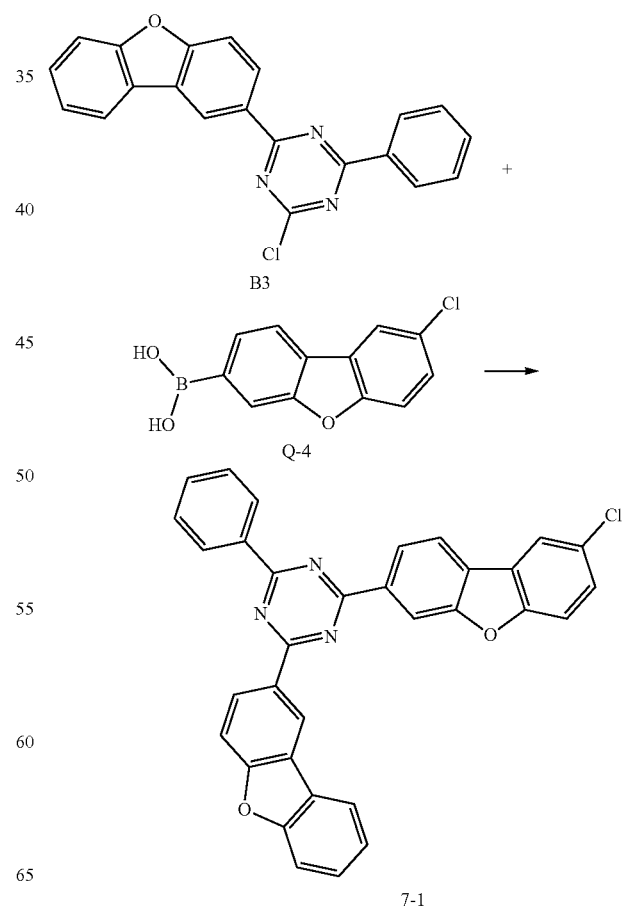

7-1

Intermediate 7-1 (20.4 g, yield: 70%, MS: [M+H]⁺=529.1) was prepared in the same manner as in the preparation method of Intermediate 1-1 of Example 1, except that Compound B3 was used instead of Compound A1.

(b) Preparation of Intermediate 7-2

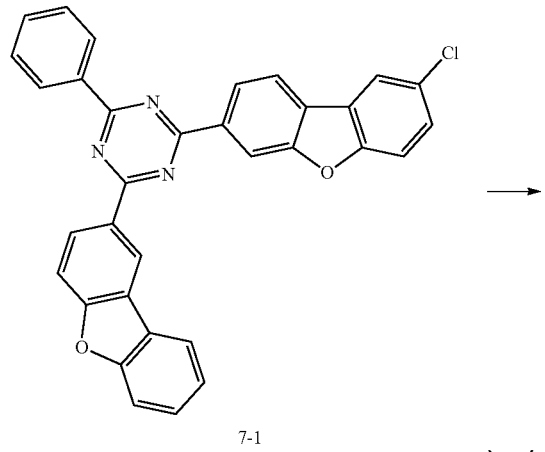

7-1

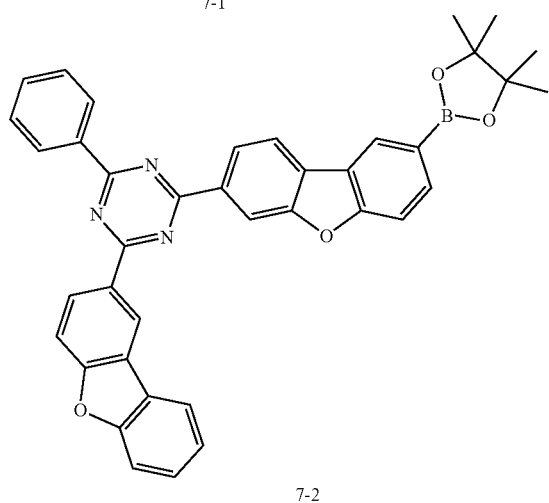

7-2

Intermediate 7-2 (10.4 g, yield: 59%, MS: [M+H]⁺=616.2) was prepared in the same manner as in the preparation method of Intermediate 1-2 of Example 1, except that Intermediate 7-1 was used instead of Intermediate 1-1.

(c) Preparation of Compound 7

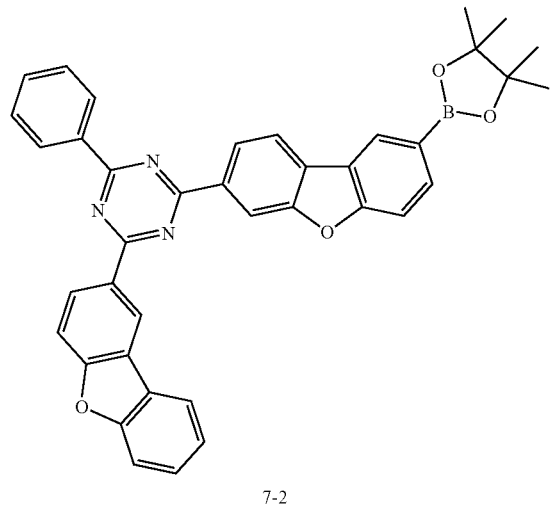

7-2

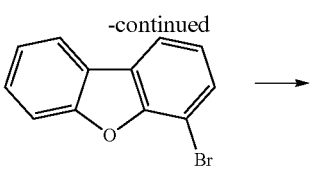

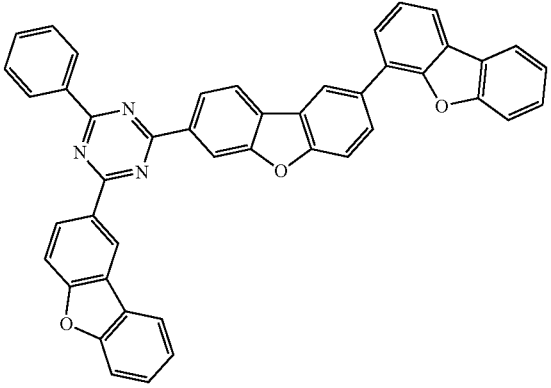

7

Compound 7 (6.5 g, yield: 61%, MS: [M+H]⁺=656.2) was prepared in the same manner as in the preparation method of Compound 1 of Example 1, except that Intermediate 7-2 was used instead of Intermediate 1-2.

Example 8: Preparation of Compound 8

(a) Preparation of Intermediate 8-1

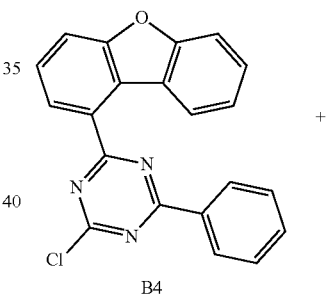

B4

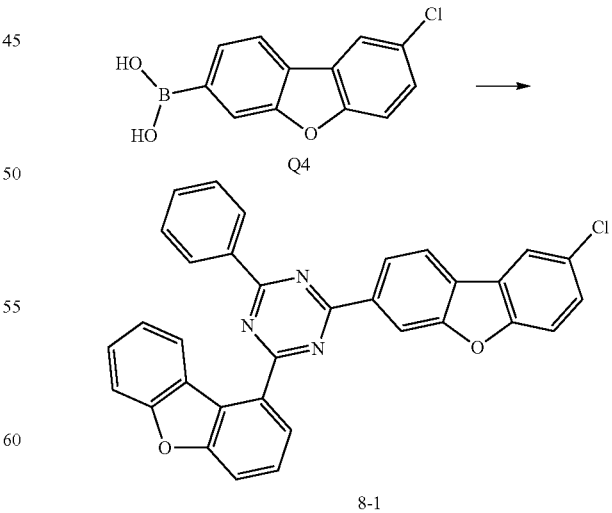

8-1

Intermediate 8-1 (19 g, yield: 65%, MS: [M+H]⁺=529.1) was prepared in the same manner as in the preparation method of Intermediate 1-1 of Example 1, except that Compound B4 was used instead of Compound A1.

(b) Preparation of Intermediate 8-2

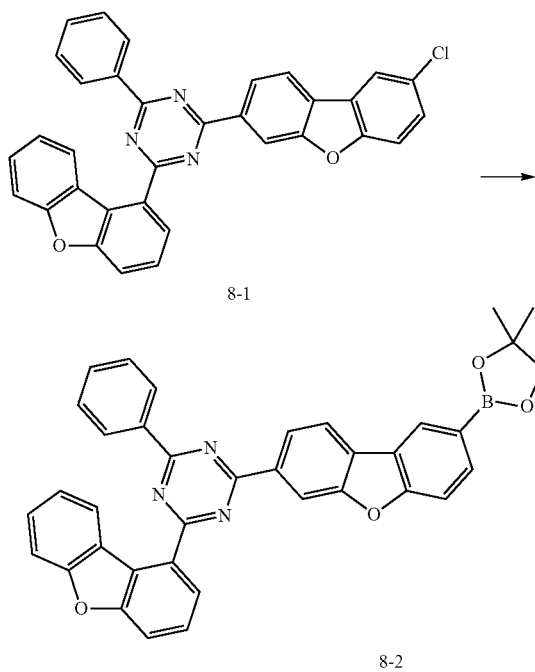

Intermediate 8-2 (9.7 g, yield: 55%, MS: [M+H]⁺=616.2) was prepared in the same manner as in the preparation method of Intermediate 1-2 of Example 1, except that Intermediate 8-1 was used instead of Intermediate 1-1.

(c) Preparation of Compound 8

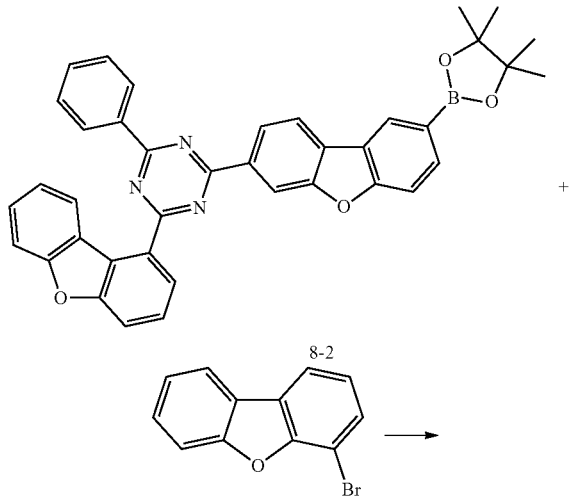

Compound 8 (5.4 g, yield: 51%, MS: [M+H]⁺=656.2) was prepared in the same manner as in the preparation method of Compound 1 of Example 1, except that Intermediate 8-2 was used instead of Intermediate 1-2.

Example 9: Preparation of Compound 9

(a) Preparation of Intermediate 9-1

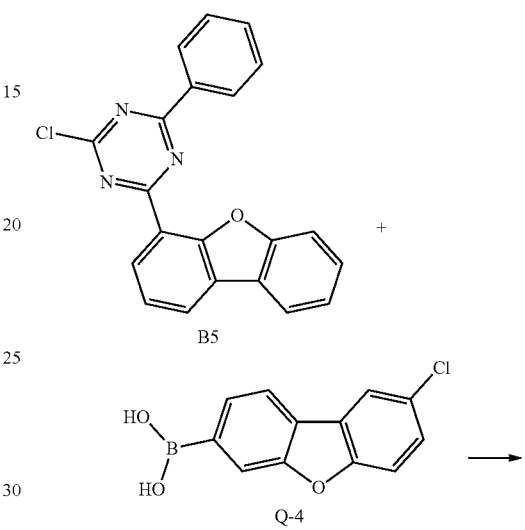

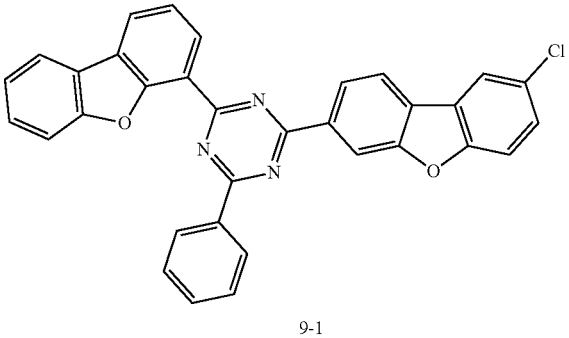

Intermediate 9-1 (14.6 g, yield: 52%, MS: [M+H]⁺=545.1) was prepared in the same manner as in the preparation method of Intermediate 1-1 of Example 1, except that Compound B5 was used instead of Compound A1.

(b) Preparation of Intermediate 9-2

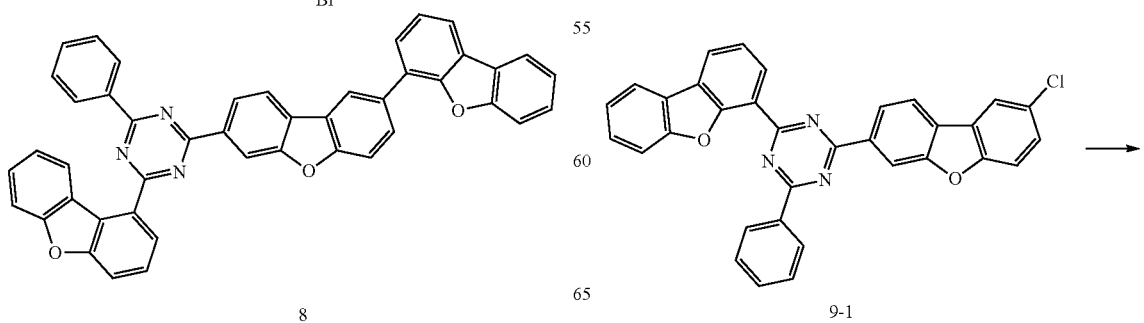

151
-continued

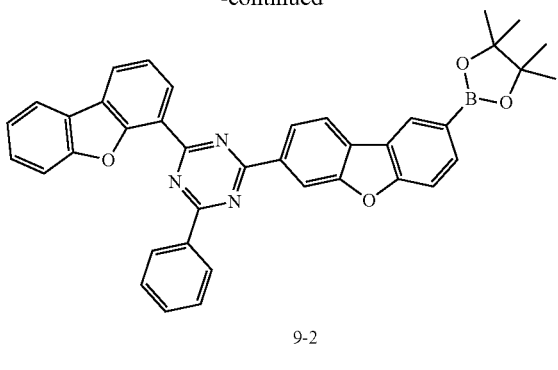

9-2

Intermediate 9-2 (12.1 g, yield: 69%, MS: [M+H]$^+$=632.2) was prepared in the same manner as in the preparation method of Intermediate 1-2 of Example 1, except that Intermediate 9-1 was used instead of Intermediate 1-1.

(c) Preparation of Compound 9

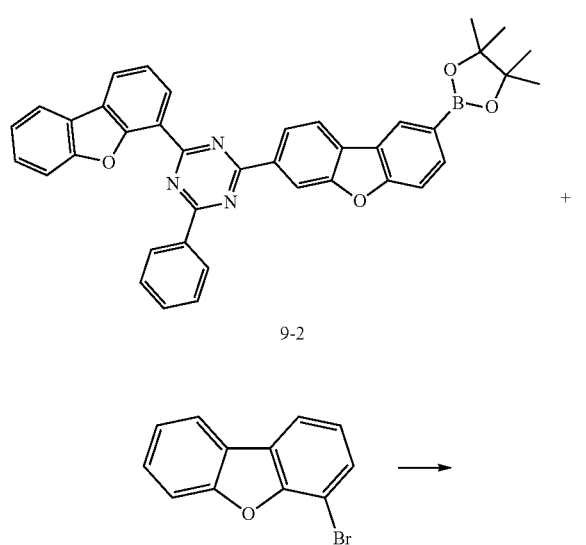

9

Compound 9 (7.3 g, yield: 69%, MS: [M+H]$^+$=672.2) was prepared in the same manner as in the preparation method of Compound 1 of Example 1, except that Intermediate 9-2 was used instead of Intermediate 1-2.

152

Example 10: Preparation of Compound 10

(a) Preparation of Intermediate 10-1

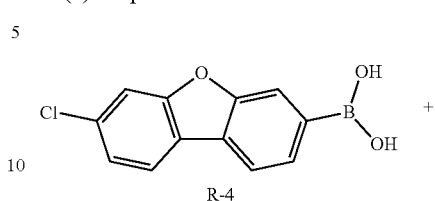

R-4

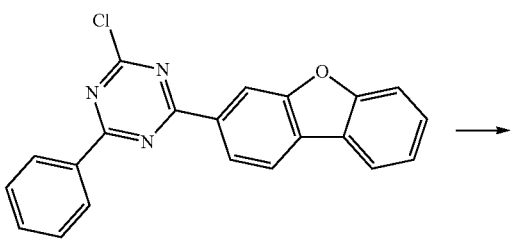

B2

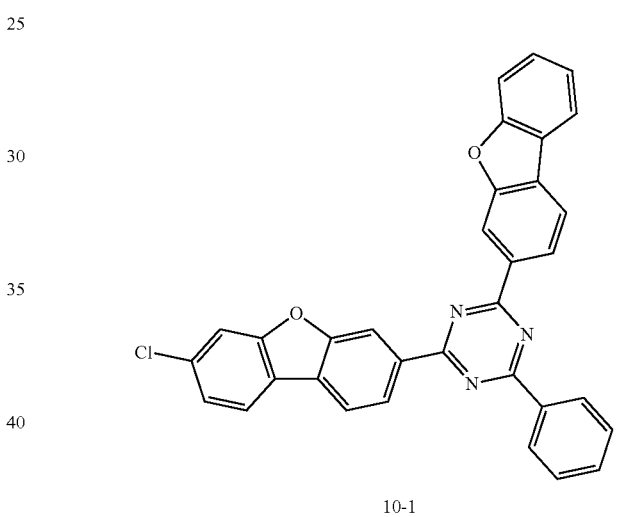

10-1

Compound R-4 (20 g, 81.3 mmol) and Compound B2 (29 g, 81.3 mmol) were added to tetrahydrofuran (400 mL) under a nitrogen atmosphere, and the mixture was stirred and refluxed. Potassium carbonate (33.7 g, 243.9 mmol) was dissolved in water (34 mL), added thereto, sufficiently stirred, and then tetrakistriphenylphosphinopalladium (2.8 g, 2.4 mmol) was added. After the reaction for 1 hour, the mixture was cooled to room temperature, the organic layer and the aqueous layer were separated, and the organic layer was distilled. This was again added to and dissolved in chloroform (850 mL) by 20 times the theoretical yield of Intermediate 10-1 and washed twice with water. The organic layer was separated, anhydrous magnesium sulfate was added, stirred, and filtered, and the filtrate was distilled under reduced pressure. The concentrated compound was recrystallized from chloroform and ethyl acetate to give Intermediate 10-1 (28.1 g, yield: 66%, MS: [M+H]+=524.1) as a white solid compound.

153
(b) Preparation of Intermediate 10-2

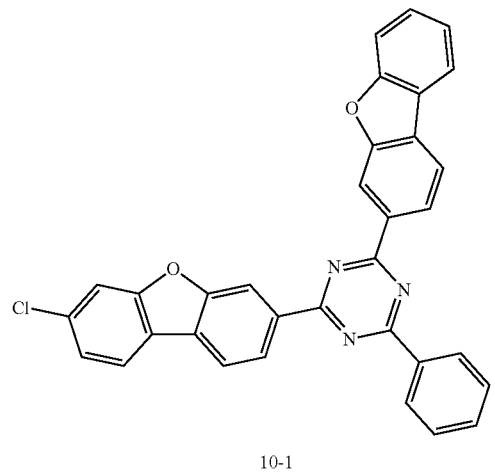

10-1

10-2

Intermediate 10-1 (15 g, 28.4 mmol) and bis(pinacolato) diboron (7.2 g, 28.4 mmol) were added to dioxane (300 mL) under a nitrogen atmosphere, and the mixture was stirred and refluxed. Then, potassium phosphate tribasic (18.1 g, 85.2 mmol) was added thereto, sufficiently stirred, and then palladium dibenzylidene acetone palladium (0.5 g, 0.9 mmol) and tricyclohexylphosphine (0.5 g, 1.7 mmol) were added. After the reaction for 5 hours, the mixture was cooled to room temperature, the organic layer was filtered to remove salt, and then the filtered organic layer was distilled. This was again added to and dissolved in chloroform (175 mL) by 10 times the theoretical yield of Intermediate 10-2, washed twice with water, the organic layer was separated, anhydrous magnesium sulfate was added thereto, stirred, and filtered, and the filtrate was distilled under reduced pressure. The concentrated compound was recrystallized from chloroform and ethanol to give Intermediate 10-2 (11.7 g, yield: 67%, MS: [M+H]+=616.2) as a white solid compound.

154
(c) Preparation of Compound 10

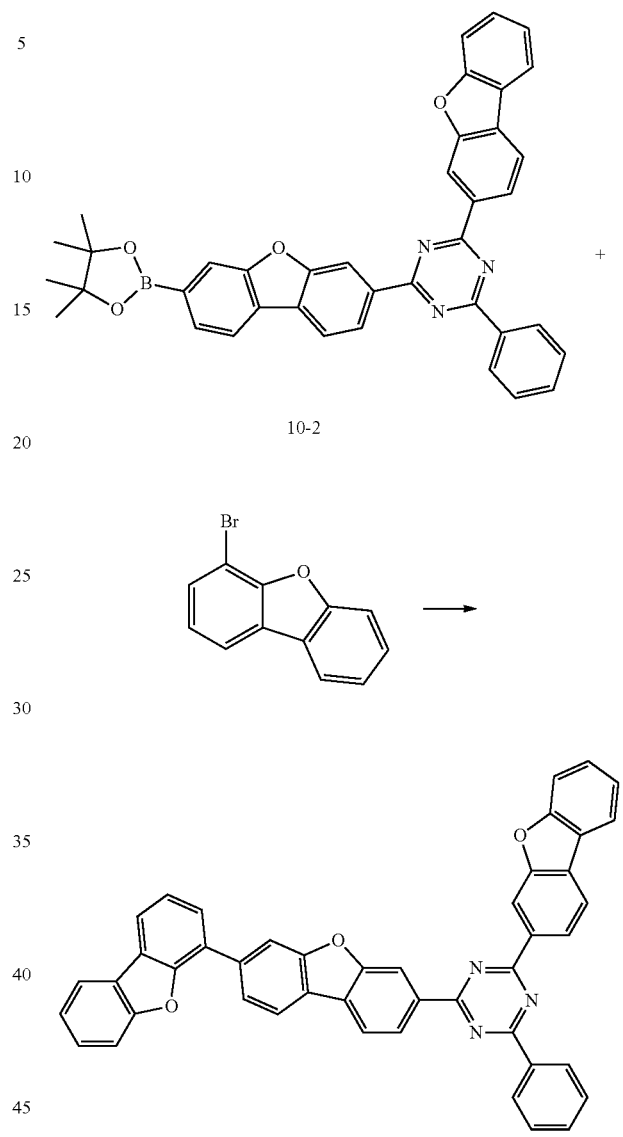

10

Under a nitrogen atmosphere, Intermediate 10-2 (20 g, 32.7 mmol) and 4-bromodibenzo[b,d]thiophene (8 g, 32.7 mmol) were added to tetrahydrofuran (400 mL), and the mixture was stirred and refluxed. Then, potassium carbonate (13.5 g, 98 mmol) was dissolved in water (14 mL), added thereto, sufficiently stirred, and then tetrakistriphenylphosphinopalladium (1.1 g, 1 mmol) was added. After the reaction for 1 hour, the reaction mixture was cooled to room temperature, the organic layer and the aqueous layer were separated, and then the organic layer was distilled. This was again added to and dissolved in chloroform (428 mL) by 20 times the theoretical yield of Compound 10, and washed twice with water. The organic layer was separated, and anhydrous magnesium sulfate was added, stirred and filtered, and the filtrate was distilled under reduced pressure. The concentrated compound was recrystallized from chloroform and ethyl acetate to give Compound 10 (16.7 g, yield: 78%, MS: [M+H]$^+$=656.2) as a white solid.

Example 11: Preparation of Compound 11

(a) Preparation of Intermediate 11-1

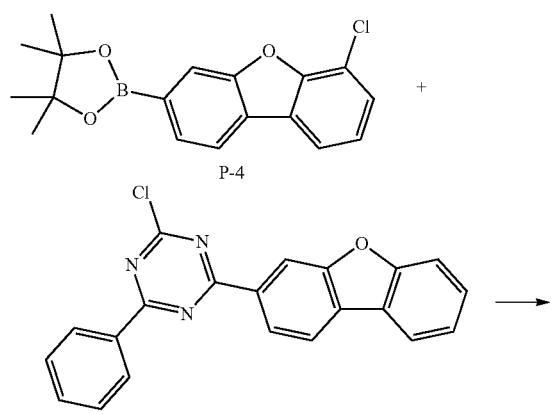

Compound 11-1 (21.7 g, yield: 51%, MS: [M+H]$^+$=524.1) was prepared in the same manner as in the preparation method of Intermediate 10-1 of Example 10, except that Compound P-4 was used instead of Compound R-4.

(b) Preparation of Intermediate 11-2

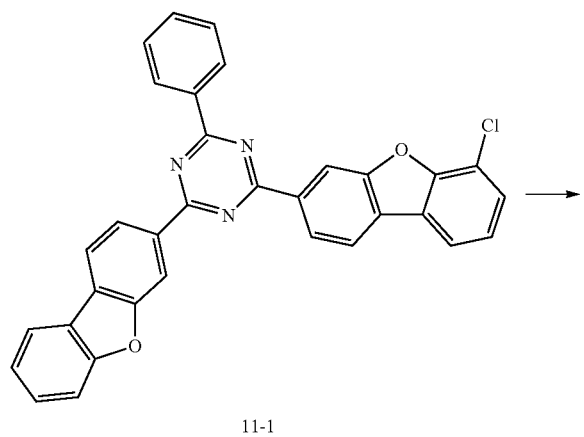

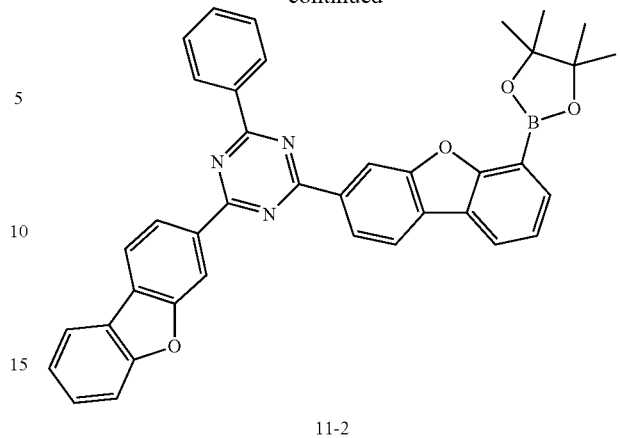

Compound 11-2 (8.7 g, yield: 50%, MS: [M+H]$^+$=616.2) was prepared in the same manner as in the preparation method of Intermediate 10-2 of Example 10, except that Intermediate 11-1 was used instead of Intermediate 10-1.

(c) Preparation of Compound 11

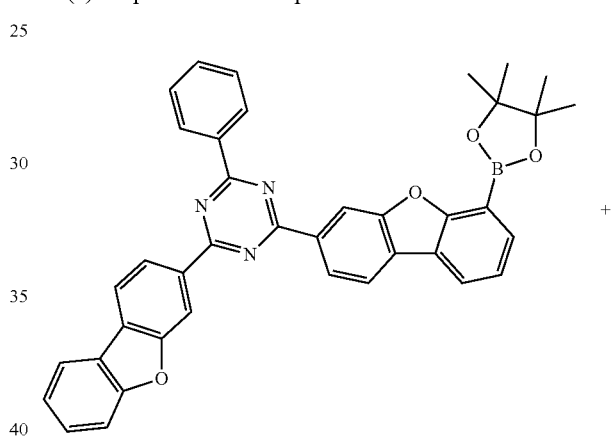

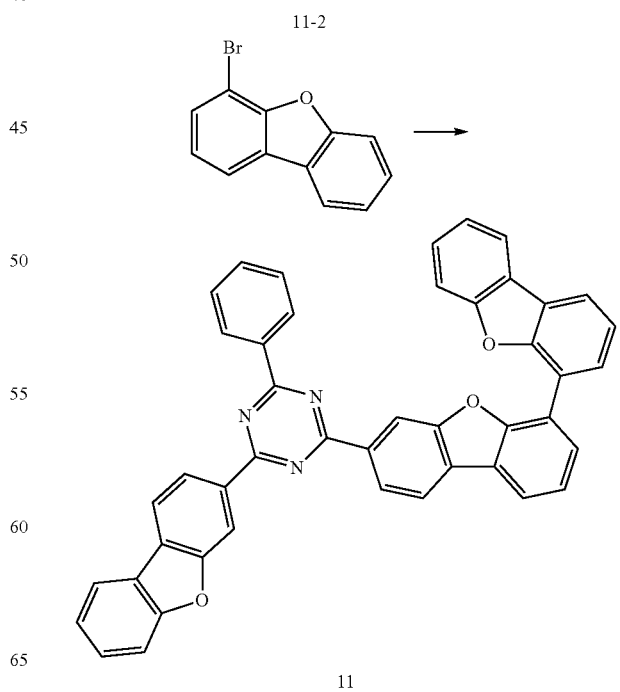

Compound 11 (27.6 g, yield: 65%, MS: [M+H]$^+$=524.1) was prepared in the same manner as in the preparation method of Intermediate 10 of Example 10, except that Intermediate 11-2 was used instead of Intermediate 10-2.

Example 12: Preparation of Compound 12

(a) Preparation of Intermediate 12-1

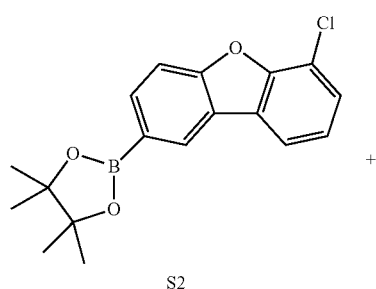

S2

+

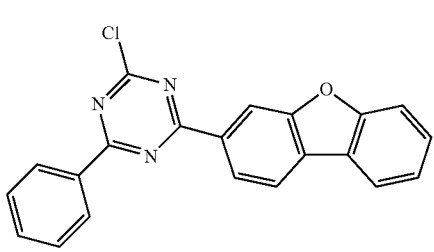

B2

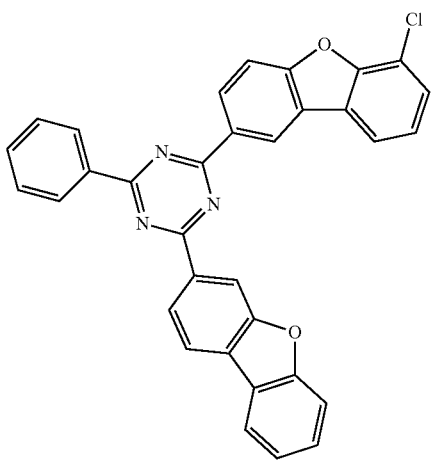

12-1

(b) Preparation of Intermediate 12-2

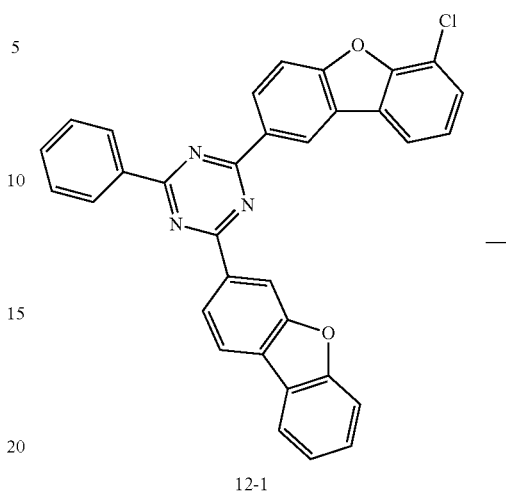

12-1

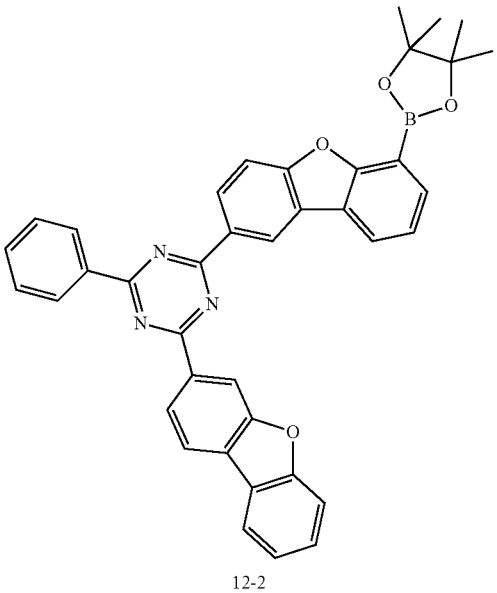

12-2

Intermediate 12-1 (34 g, yield: 80%, MS: [M+H]$^+$=524.1) was prepared in the same manner as in the preparation method of Intermediate 10-1 of Example 10, except that Compound S2 was used instead of Compound R-4.

Compound 12-2 (11 g, yield: 63%, MS: [M+H]$^+$=616.2) was prepared in the same manner as in the preparation method of Intermediate 10-2 of Example 10, except that Intermediate 12-1 was used instead of Intermediate 10-1.

(c) Preparation of Compound 12

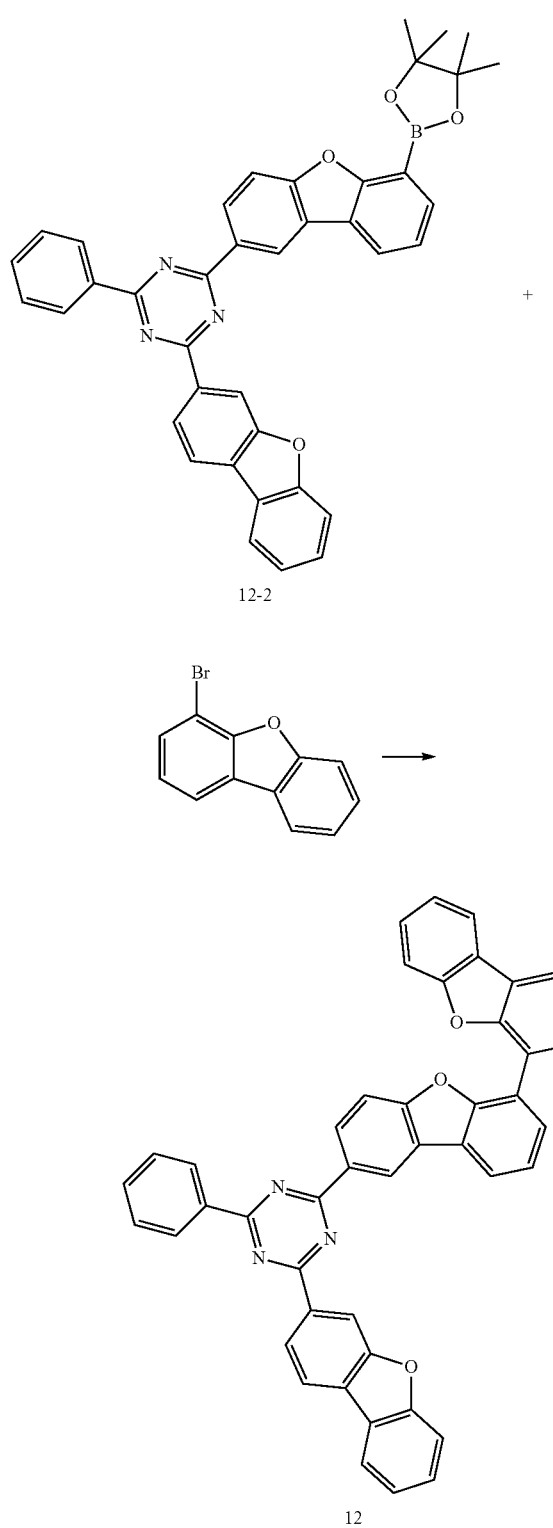

Compound 12 (30.2 g, yield: 71%, MS: [M+H]$^+$=524.1) was prepared in the same manner as in the preparation method of Compound 10 of Example 10, except that Intermediate 12-2 was used instead of Intermediate 10-2.

Example 13: Preparation of Compound 13

(a) Preparation of Intermediate 13-1

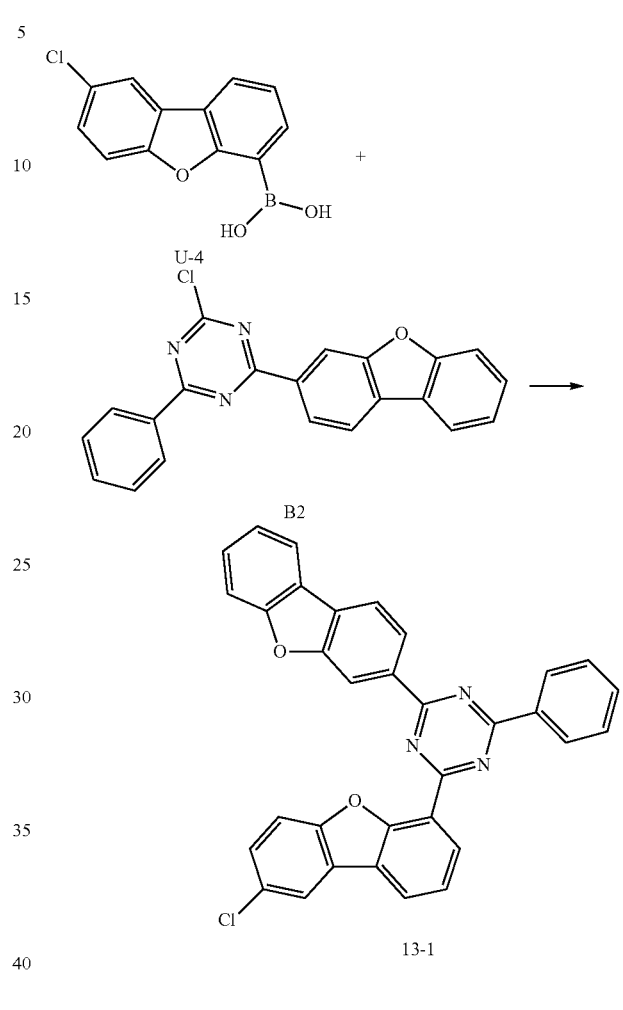

Intermediate 13-1 (29.8 g, yield: 70%, MS: [M+H]$^+$=524.1) was prepared in the same manner as in the preparation method of Intermediate 10-1 of Example 10, except that Compound U-4 was used instead of Compound R-4.

(b) Preparation of Intermediate 13-2

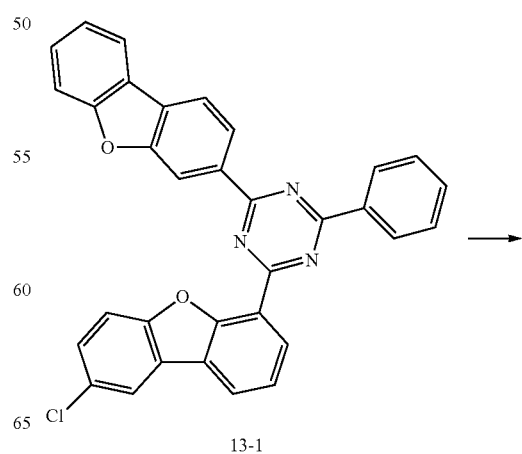

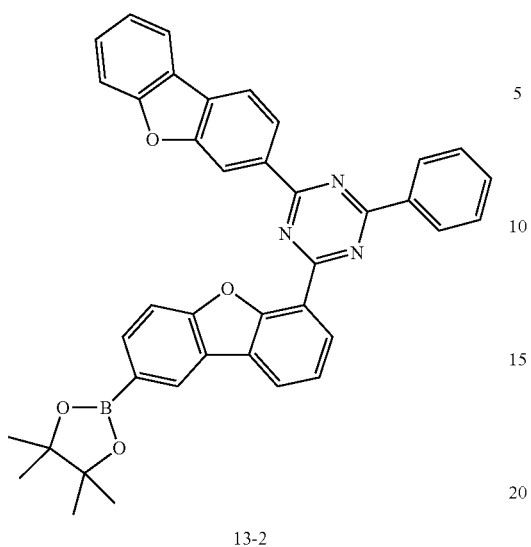

13-2

Intermediate 13-2 (9.1 g, yield: 53%, MS: [M+H]⁺=616.2) was prepared in the same manner as in the preparation method of Intermediate 10-2 of Example 10, except that Intermediate 13-1 was used instead of Intermediate 10-1

(c) Preparation of Compound 13

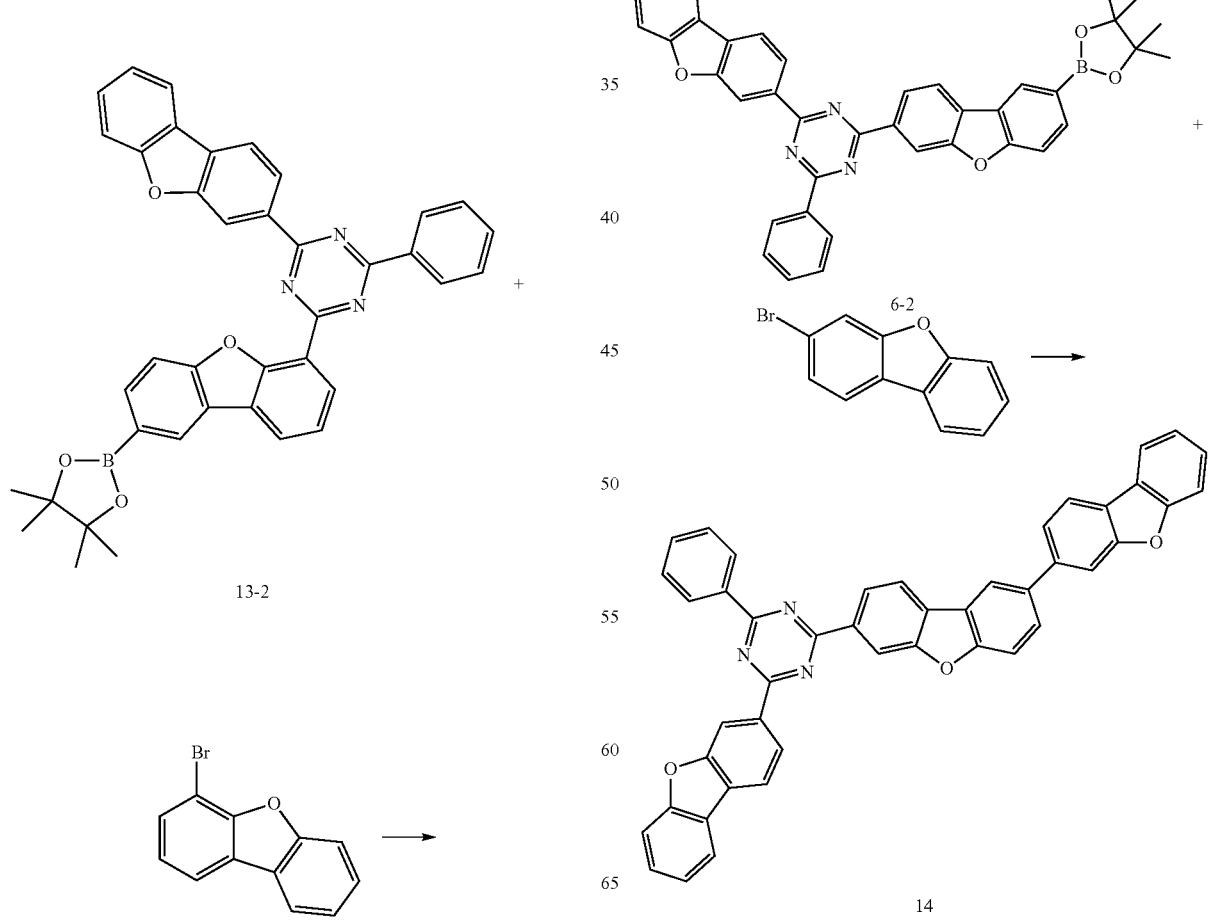

13

Compound 13 (31.5 g, yield: 74%, MS: [M+H]⁺=524.1) was prepared in the same manner as in the preparation method of Compound 10 of Example 10, except that Intermediate 13-2 was used instead of Intermediate 10-2.

Example 14: Preparation of Compound 14

Under a nitrogen atmosphere, Intermediate 6-2 (20 g, 32.7 mmol) and 3-bromodibenzo[b,d]furan (8 g, 32.7 mmol) were added to tetrahydrofuran (400 mL) and the mixture was stirred and refluxed. Then, potassium carbonate (13.5 g, 98 mmol) was dissolved in water (14 mL), added thereto, sufficiently stirred, and then tetrakistriphenylphosphinopalladium (1.1 g, 1 mmol) was added. After the reaction for 2 hours, the reaction mixture was cooled to room temperature, the organic layer and the aqueous layer were separated and then the organic layer was distilled. This was again added to and dissolved in chloroform (428 mL) by 20 times the theoretical yield of Compound 14, and washed twice with water. The organic layer was separated, anhydrous magnesium sulfate was added thereto, stirred, and filtered, and the filtrate was distilled under reduced pressure. The concentrated compound was recrystallized from chloroform and ethyl acetate to give Compound 14 (15 g, yield: 70%, MS: [M+H]+=656.2) as a white solid.

Example 15: Preparation of Compound 15

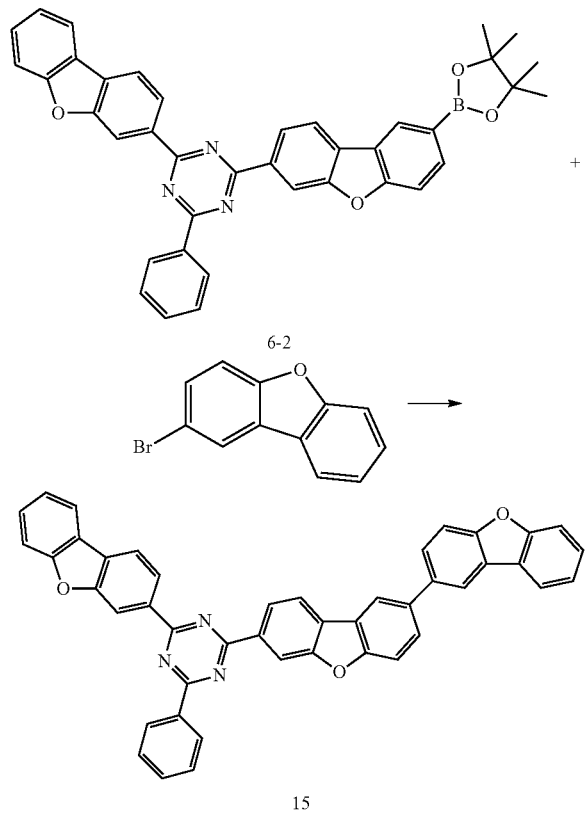

Under a nitrogen atmosphere, Intermediate 6-2 (10 g, 40.6 mmol) and 2-bromodibenzo[b,d]furan (10 g, 40.6 mmol) were added to tetrahydrofuran (200 mL) and the mixture was stirred and refluxed. Then, potassium carbonate (16.9 g, 121.9 mmol) was dissolved in water (17 mL), added thereto, sufficiently stirred, and then tetrakistriphenylphosphinopalladium (1.4 g, 1.2 mmol) was added. After the reaction for 1 hour, the reaction mixture was cooled to room temperature, the organic layer and the aqueous layer were separated, and the organic layer was distilled. This was again added to and dissolved in chloroform (425 mL) by 20 times the theoretical yield of Compound 15, and washed twice with water, the organic layer was separated, anhydrous magnesium sulfate was added thereto, stirred and filtered, and the filtrate was distilled under reduced pressure. The concentrated compound was recrystallized from chloroform and ethyl acetate to give Compound 15 (15.3 g, yield: 72%, MS: [M+H]+=524.1) as a white solid.

Example 16: Preparation of Compound 16

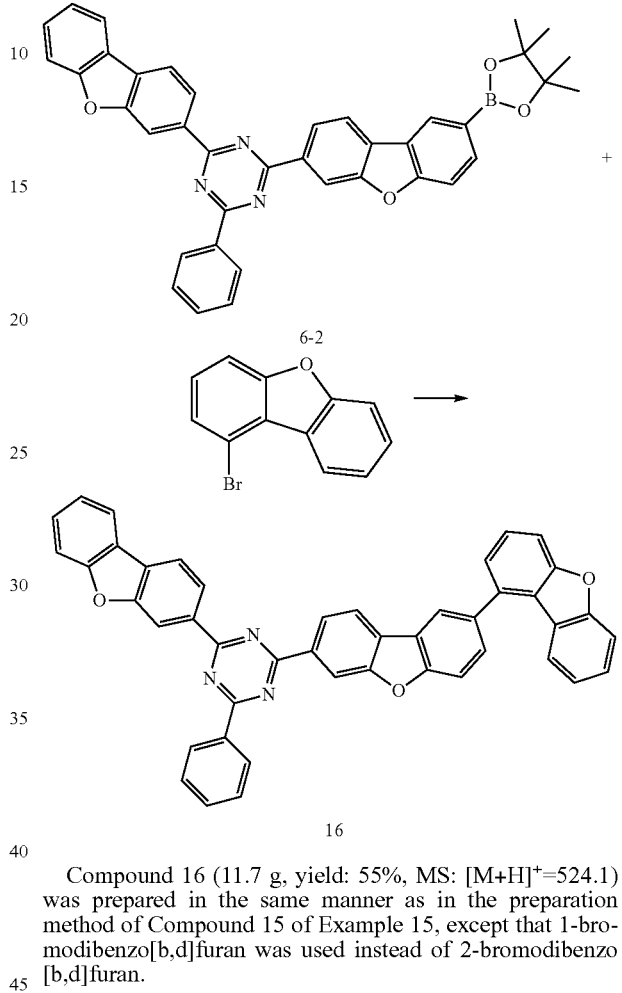

Compound 16 (11.7 g, yield: 55%, MS: [M+H]+=524.1) was prepared in the same manner as in the preparation method of Compound 15 of Example 15, except that 1-bromodibenzo[b,d]furan was used instead of 2-bromodibenzo[b,d]furan.

Experimental Example 1

A glass substrate on which ITO (indium tin oxide) was coated as a thin film to a thickness of 1,300 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, the following compound HI-1 was thermally vacuum-deposited to a thickness of 50 Å to form a hole injection layer. The following compound HT-1 was thermally vacuum-deposited on the hole injection layer to a thickness of 250 Å to form a hole transport layer, and the following compound HT-2 was vacuum-deposited on the HT-1 deposited layer to a thickness of 50 Å to form an electron blocking layer. The compound 1 prepared in the previous Example 1, the following compound YGH-1, and a phosphorescent dopant YGD-1 were co-deposited in a weight ratio of 44:44:12 on the HT-2 deposited layer to form a light emitting layer with a thickness of 400 Å. The following compound ET-1 was vacuum-deposited on the light emitting layer to a thickness of 250 Å to form an electron transport layer, and the following compound ET-2 and Li were vacuum-deposited in a weight ratio of 98:2 on the electron transport layer to form an electron injection layer with a thickness of 100 Å. Aluminum was deposited on the electron injection layer to a thickness of 1000 Å to form a cathode.

HI-1

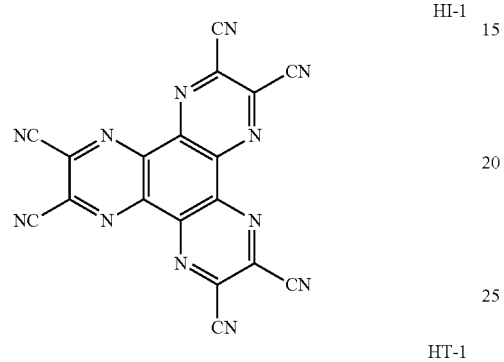

HT-1

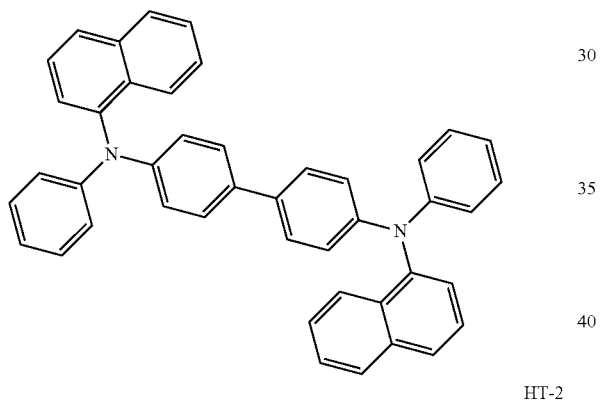

HT-2

YGH-1

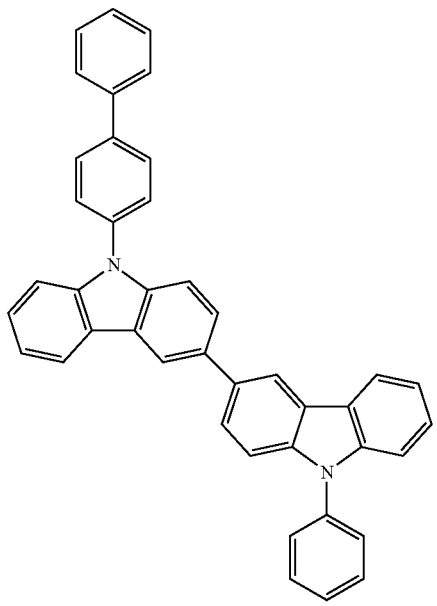

YGD-1

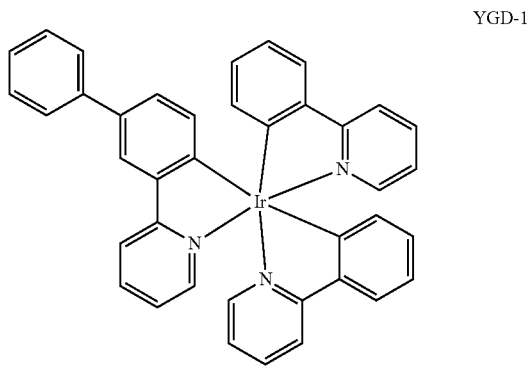

ET-1

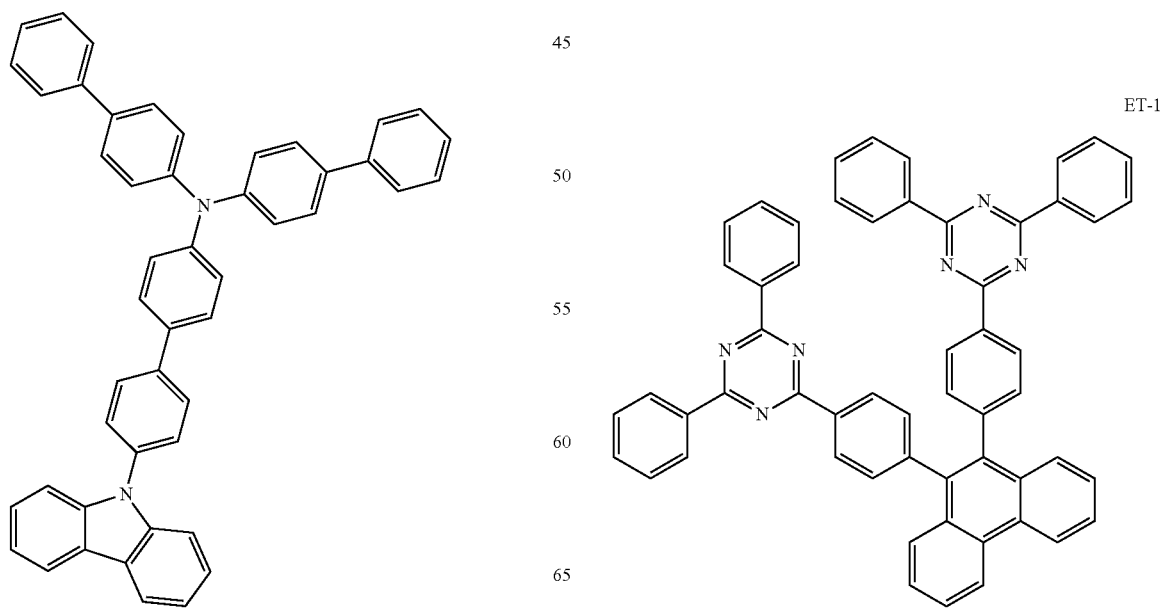

-continued

ET-2

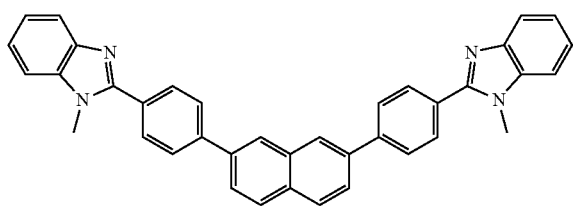

In the above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1\times10^{-7}$ to $5\times10^{-8}$ torr.

Experimental Examples 2 to 17 and Comparative Experimental Examples 1 to 5

An organic light emitting device was manufactured in the same manner as in Experimental Example 1, except that the compounds shown in Table 1 below were used instead of Compound 1 of Example 1 in Experimental Example 1. The compounds of CE1 to CE5 shown in Table 1 are as follows.

CE1

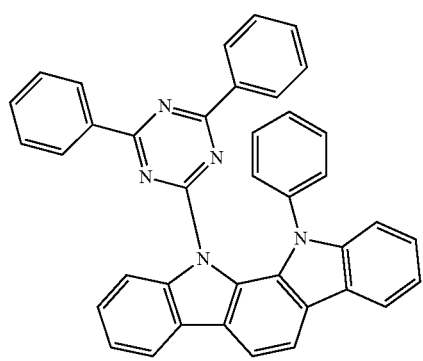

CE2

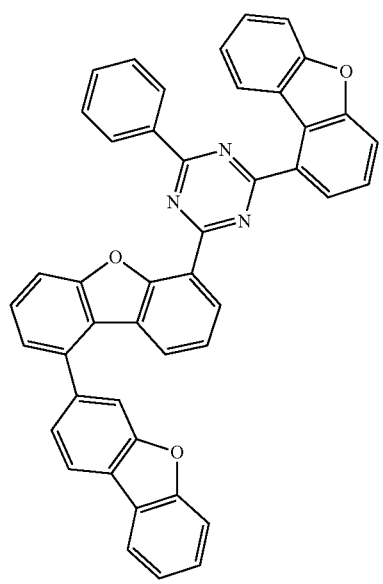

-continued

CE3

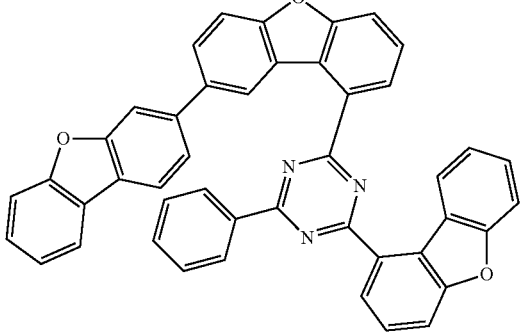

CE4

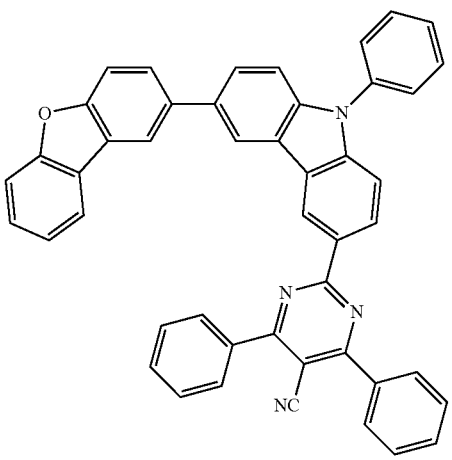

CE5

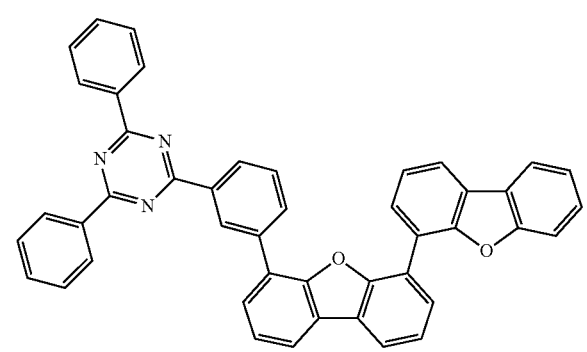

For the organic light emitting devices manufactured in Experimental Examples and Comparative Experimental Examples, the voltage and efficiency were measured at a current density of 10 mA/cm² and the lifetime was measured at a current density of 50 mA/cm². The results are shown in Table 1 below. In this case, $LT_{95}$ means the time required for the luminance to be reduced to 95% of the initial luminance.

TABLE 1

| | Compound | Voltage (V)(@10 mA/cm$^2$) | Efficiency (Cd/A)(@10 mA/cm$^2$) | Color coordinate (x, y) | Lifetime (hr)(LT$_{95}$ at 50 mA/cm$^2$) |
|---|---|---|---|---|---|
| Experimental Example 1 | Compound 1 | 3.8 | 84 | 0.45, 0.53 | 271 |
| Experimental Example 2 | Compound 2 | 3.9 | 84 | 0.46, 0.53 | 299 |
| Experimental Example 3 | Compound 3 | 3.8 | 85 | 0.46, 0.53 | 263 |
| Experimental Example 4 | Compound 4 | 3.8 | 83 | 0.46, 0.54 | 304 |
| Experimental Example 5 | Compound 5 | 4.0 | 84 | 0.46, 0.54 | 254 |
| Experimental Example 6 | Compound 6 | 3.8 | 84 | 0.46, 0.54 | 282 |
| Experimental Example 7 | Compound 7 | 3.9 | 85 | 0.46, 0.54 | 203 |
| Experimental Example 8 | Compound 8 | 4.0 | 83 | 0.46, 0.54 | 225 |
| Experimental Example 9 | Compound 9 | 3.9 | 84 | 0.46, 0.53 | 247 |
| Experimental Example 10 | Compound 10 | 4.0 | 85 | 0.46, 0.53 | 266 |
| Experimental Example 11 | Compound 11 | 3.8 | 83 | 0.46, 0.53 | 218 |
| Experimental Example 12 | Compound 12 | 3.9 | 84 | 0.46, 0.54 | 162 |
| Experimental Example 13 | Compound 13 | 3.9 | 84 | 0.46, 0.54 | 194 |
| Experimental Example 14 | Compound 14 | 3.8 | 85 | 0.46, 0.54 | 242 |
| Experimental Example 15 | Compound 15 | 4.8 | 83 | 0.46, 0.54 | 225 |
| Experimental Example 16 | Compound 16 | 3.9 | 84 | 0.46, 0.54 | 235 |
| Comparative Experimental Example 1 | CE1 | 4.0 | 79 | 0.46, 0.54 | 101 |
| Comparative Experimental Example 2 | CE2 | 4.2 | 80 | 0.46, 0.55 | 131 |
| Comparative Experimental Example 3 | CE3 | 4.1 | 79 | 0.45, 0.54 | 142 |
| Comparative Experimental Example 4 | CE4 | 4.8 | 75 | 0.42, 0.53 | 12 |
| Comparative Experimental Example 5 | CE5 | 4.2 | 83 | 0.45, 0.55 | 81 |

As shown in Table 1, it was confirmed that when the compound of the present invention was used as an organic light emitting layer material, it exhibited excellent characteristics in terms of efficiency and lifetime as compared with Comparative Experimental Examples. This confirms that triazine and dibenzofuran substituents are continuously bonded, and a dibenzofuran group and a dibenzothiophene group are substituted on the side of the triazine group, thereby increasing the electrical stability.

EXPLANATION OF SIGN

| | |
|---|---|
| 1: substrate | 2: anode |
| 3: light emitting layer | 4: cathode |
| 5: hole injection layer | 6: hole transport layer |
| 7: electron blocking layer | 8: electron transport layer |
| 9: electron injection layer | |

What is claimed is:

1. A compound of the following Chemical Formula 1:

[Chemical Formula 1]

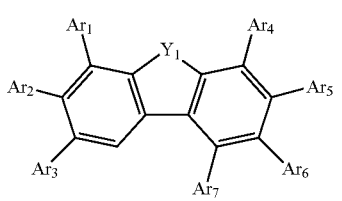

wherein, in Chemical Formula 1, $Y_1$ is O or S, one of $Ar_1$ to $Ar_3$ is of the following Chemical Formula 2, the rest being hydrogen, one of $Ar_4$ to $Ar_7$ is a substituted or unsubstituted dibenzofuran; or a substituted or unsubstituted dibenzothiophene, the rest being hydrogen, when Ar₁ is of the following Chemical Formula 2, Ar₇ is hydrogen,

[Chemical Formula 2]

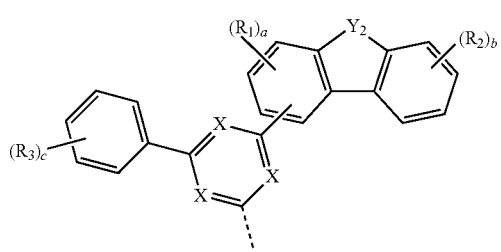

wherein, in Chemical Formula 2,
each X is independently N or CH, with the proviso that two or more of X is N,
Y₂ is O or S,
R₁ and R₂ are each independently hydrogen; deuterium; halogen; hydroxy; cyano; or nitro,
R₃ is hydrogen; deuterium; halogen; hydroxy; cyano; nitro; amino; a substituted or unsubstituted $C_{1-60}$ alkyl; a substituted or unsubstituted $C_{1-60}$ haloalkyl; a substituted or unsubstituted $C_{1-60}$ thioalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; or a substituted or unsubstituted $C_{2-60}$ alkenyl,
a is an integer from 1 to 3,
b is an integer from 1 to 4, and
c is an integer from 1 to 5.

2. The compound according to claim 1, wherein the Chemical Formula 1 is any one selected from compounds of the following Chemical Formulas 1-1 to 1-5:

[Chemical Formula 1-1]

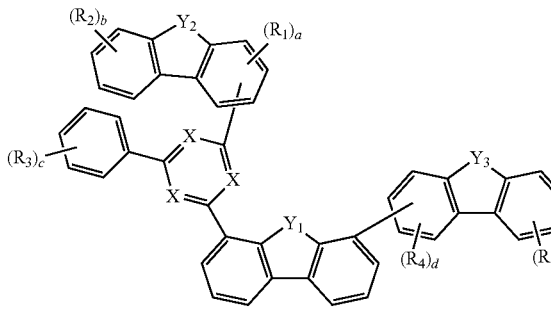

[Chemical Formula 1-2]

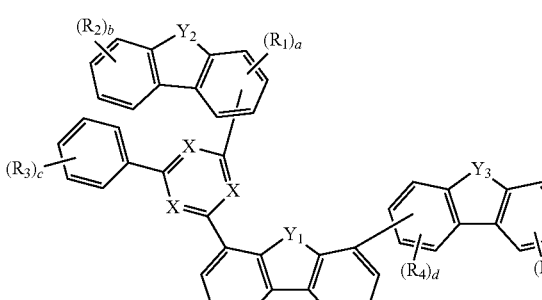

[Chemical Formula 1-3]

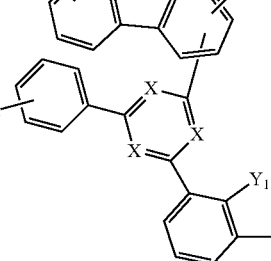

[Chemical Formula 1-4]

(additional structure)

[Chemical Formula 1-5]

(additional structure)

wherein, in Chemical Formulae 1-1 to 1-5,
Y₁, Y₂, X, R₁ to R₃, a, b and c are as defined in claim 1,
Y₃ is O or S,
R₄ and R₅ are each independently hydrogen; deuterium; halogen; hydroxy; cyano; nitro; amino; a substituted or unsubstituted $C_{1-60}$ alkyl; a substituted or unsubstituted $C_{1-60}$ haloalkyl; a substituted or unsubstituted $C_{1-60}$ thioalkyl; a substituted or unsubstituted $C_{1-60}$ alkoxy; a substituted or unsubstituted $C_{1-60}$ haloalkoxy; a substituted or unsubstituted $C_{3-60}$ cycloalkyl; or a substituted or unsubstituted $C_{2-60}$ alkenyl, a substituted or unsubstituted $C_{6-60}$ aryl; a substituted or unsubstituted $C_{6-60}$ aryloxy; or a substituted or unsubstituted $C_{2-60}$ heteroaryl containing at least one of O, N, Si and S,
d is an integer from 1 to 3, and
e is an integer from 1 to 4.

3. The compound according to claim 1, wherein every X is N.

4. The compound according to claim 1, wherein R₁ to R₃ are each independently hydrogen or deuterium.

5. The compound according to claim 1, wherein the compound of Chemical Formula 1 is selected from the group consisting of the following compounds:
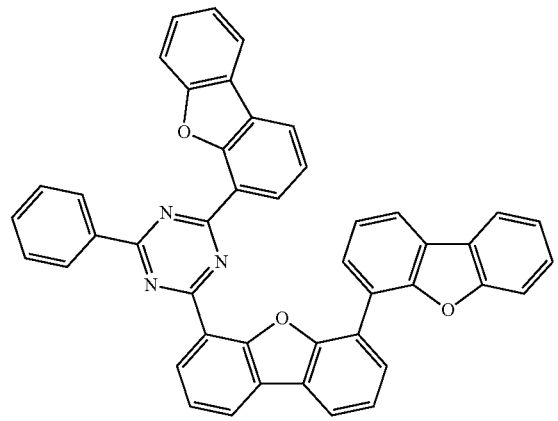
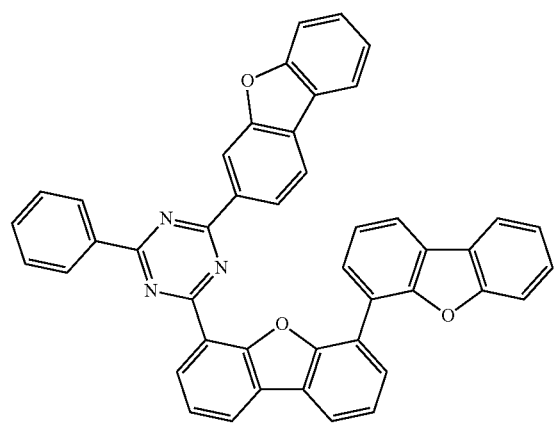
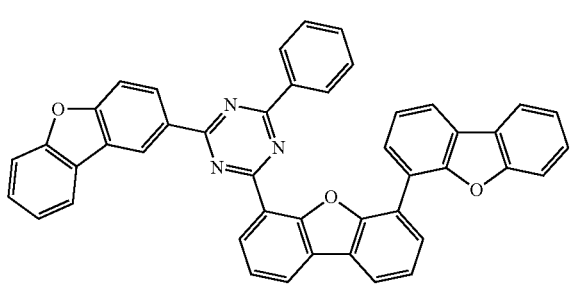
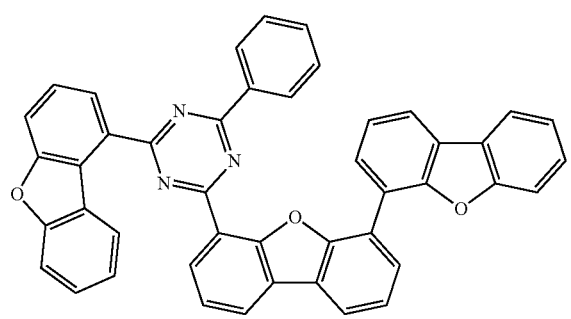
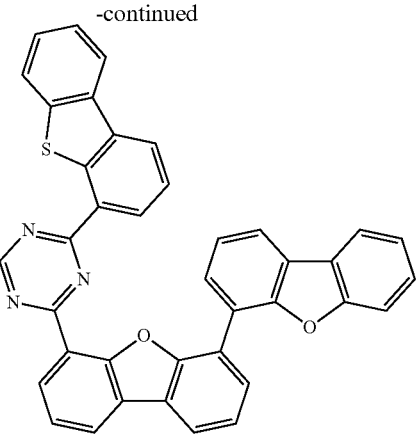
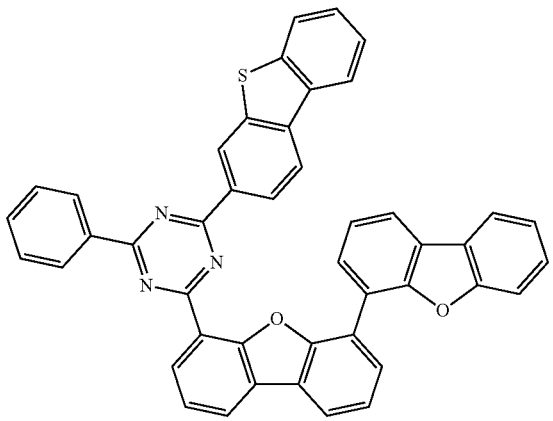
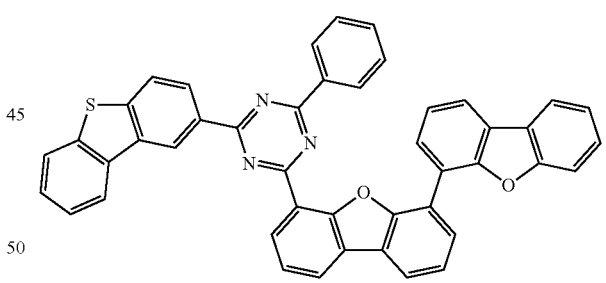
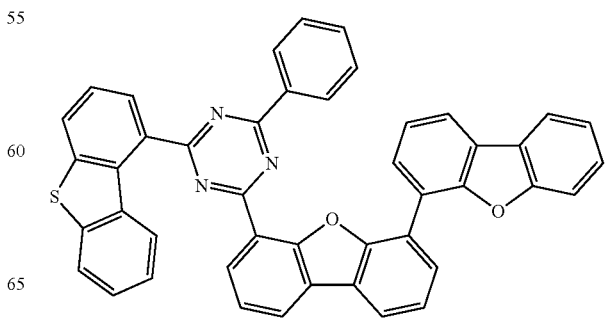

175
-continued
176
-continued
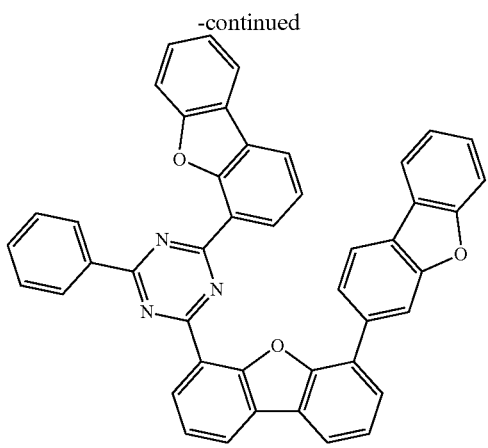
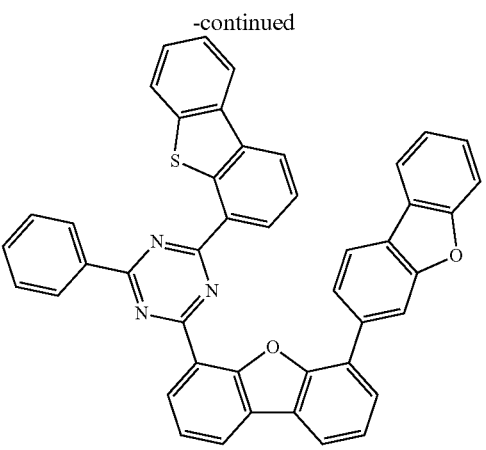
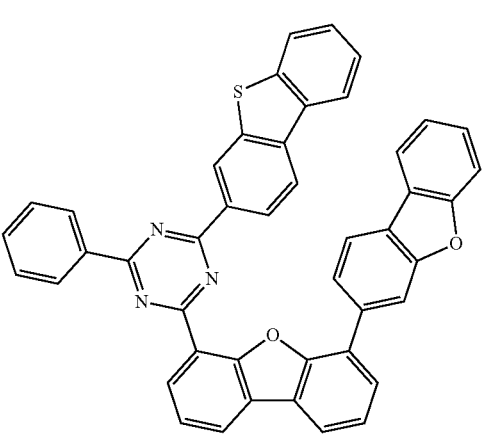
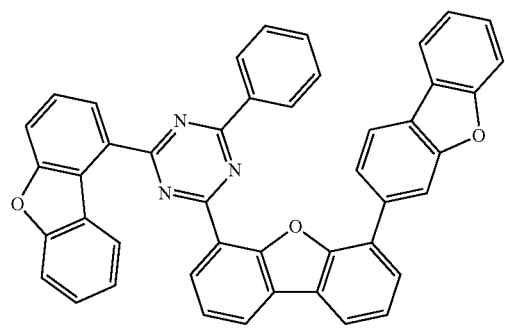
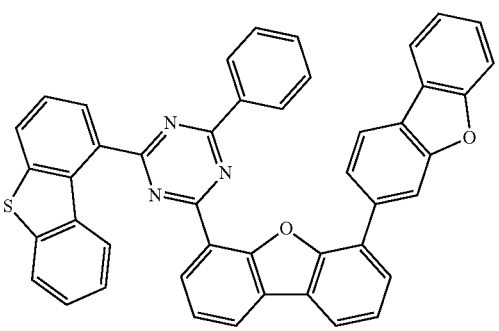

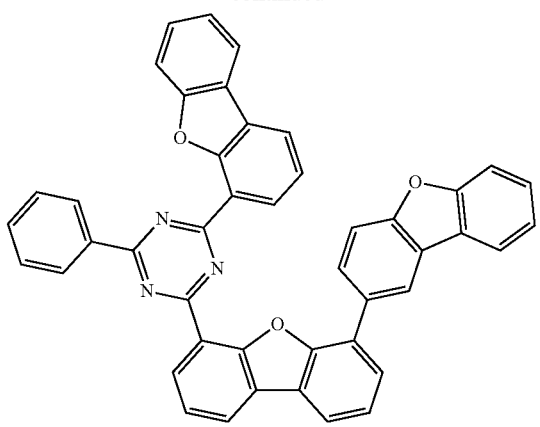
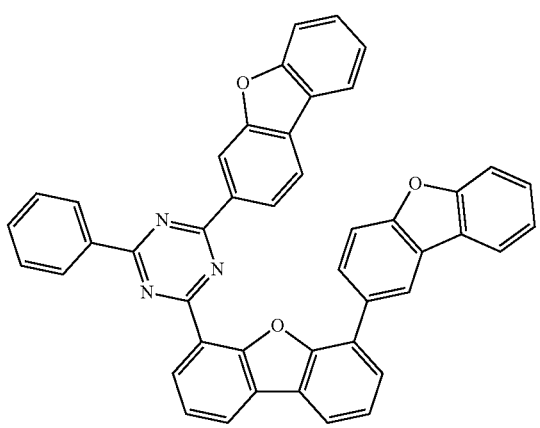
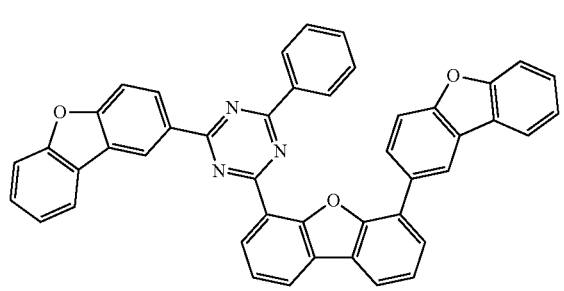
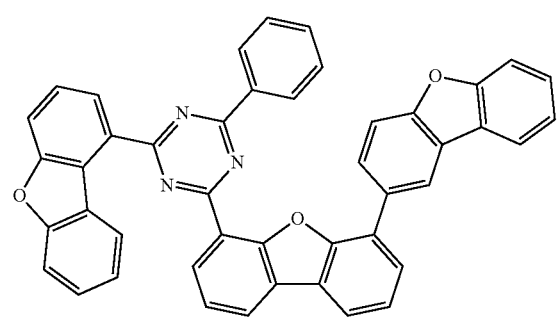
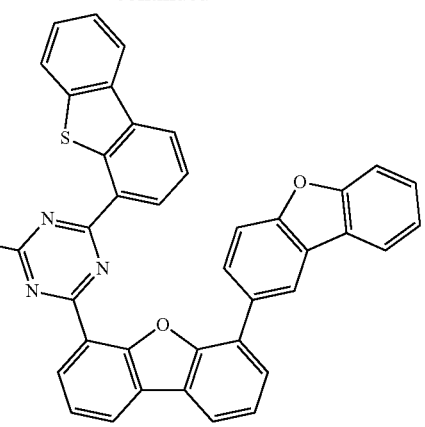
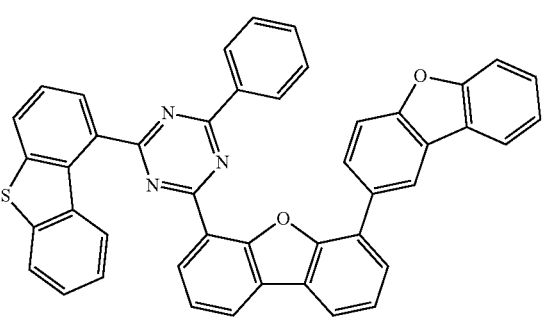

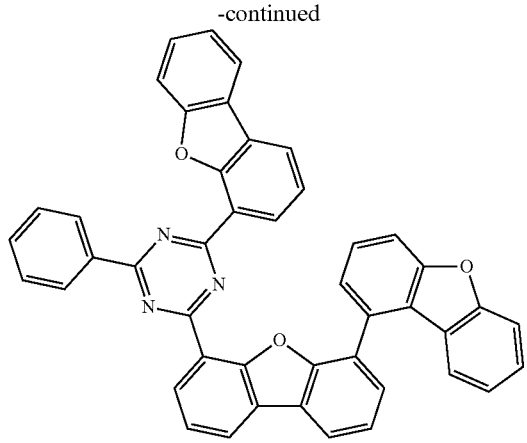
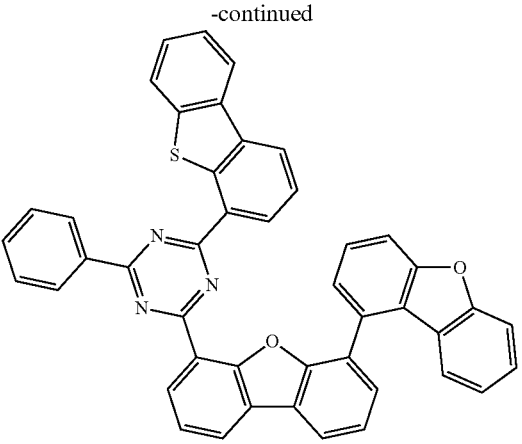

181
-continued
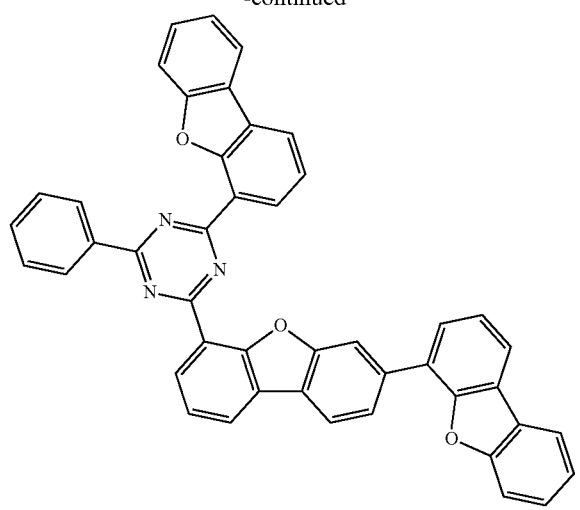
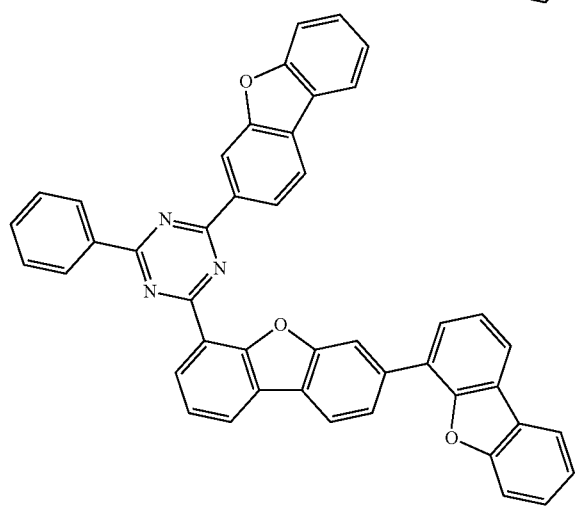
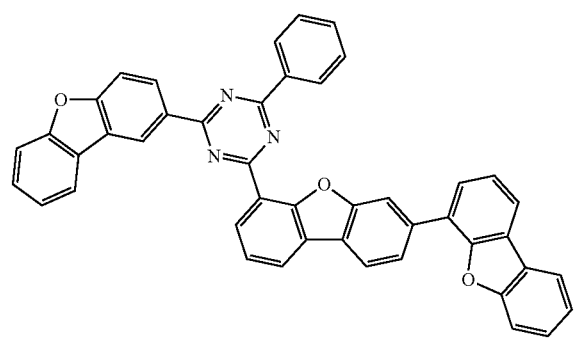
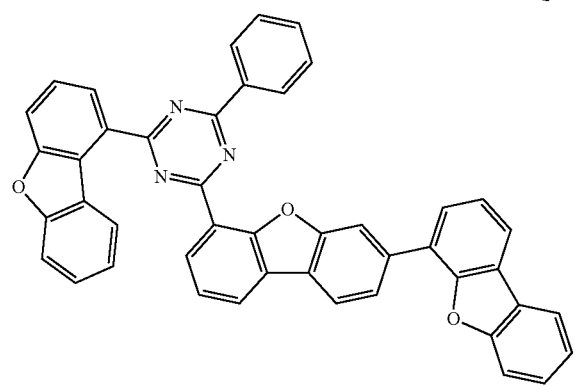
182
-continued
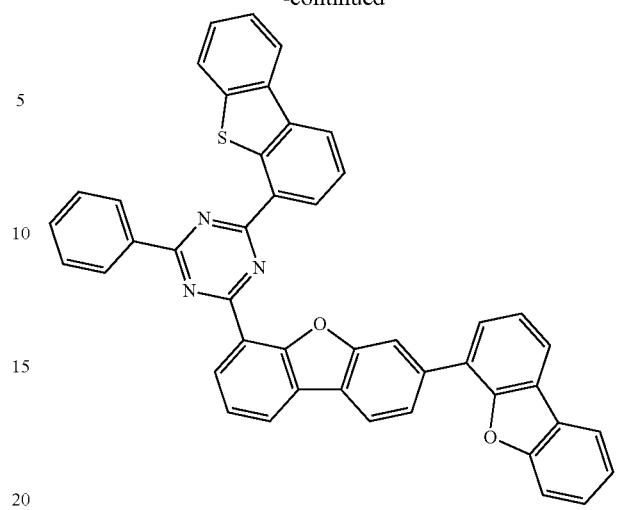
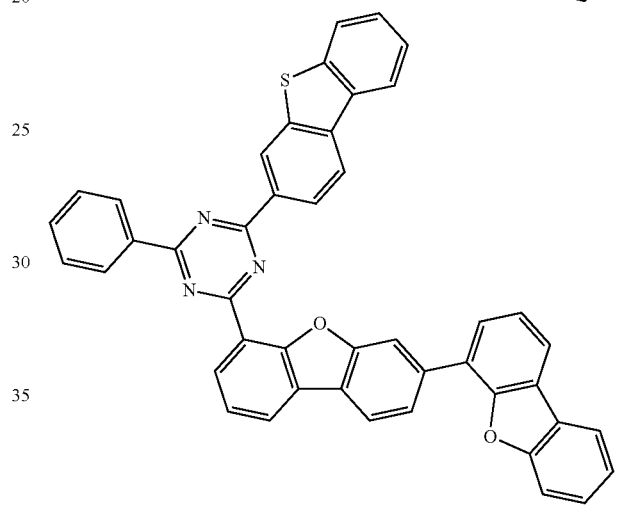
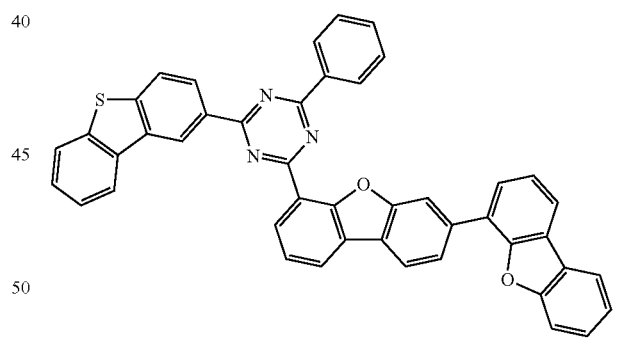
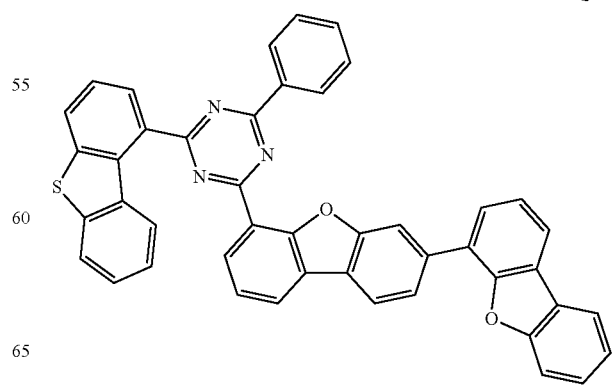

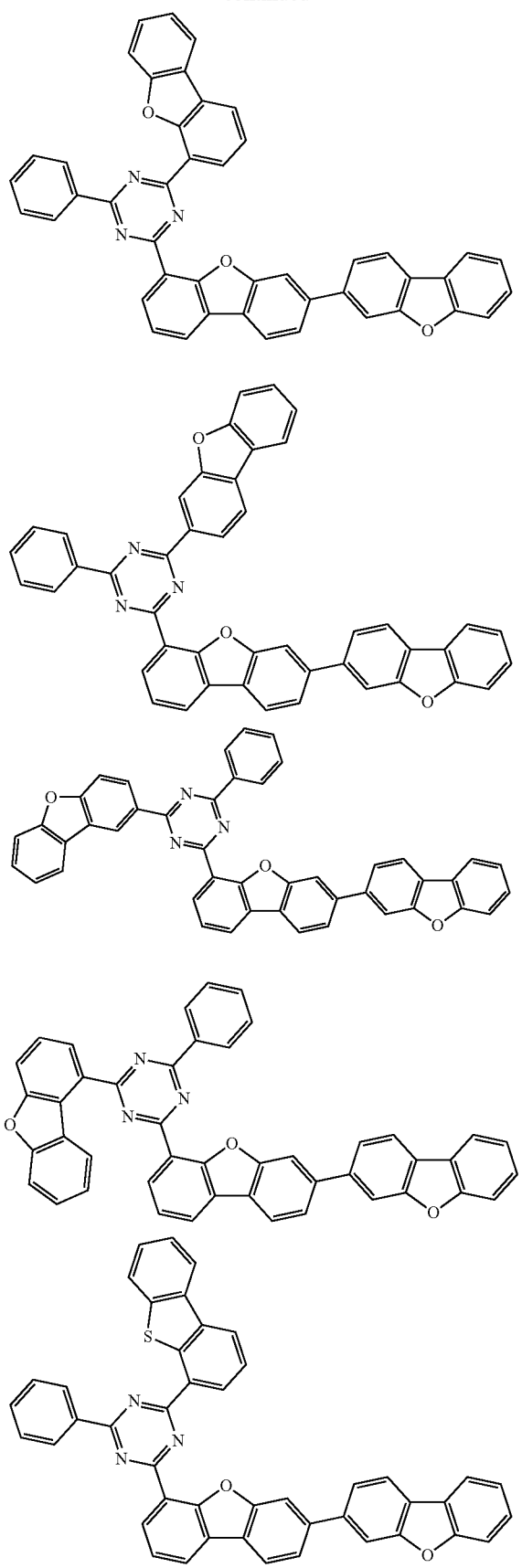
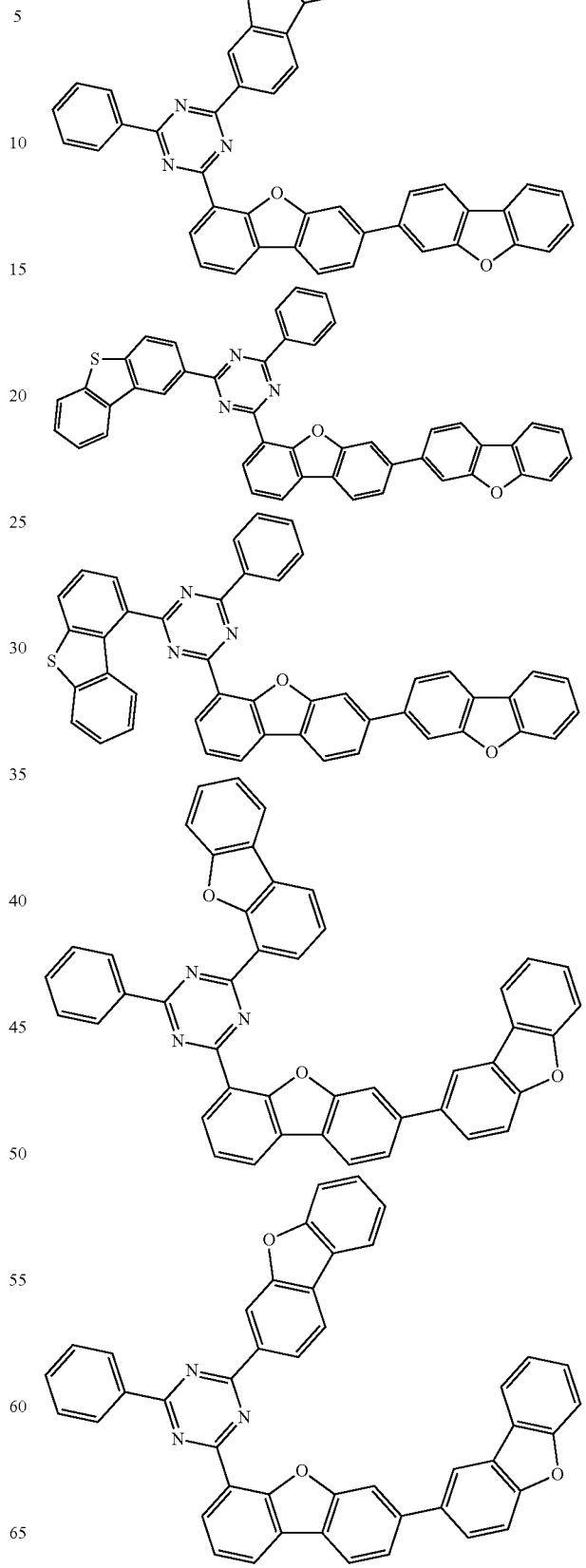

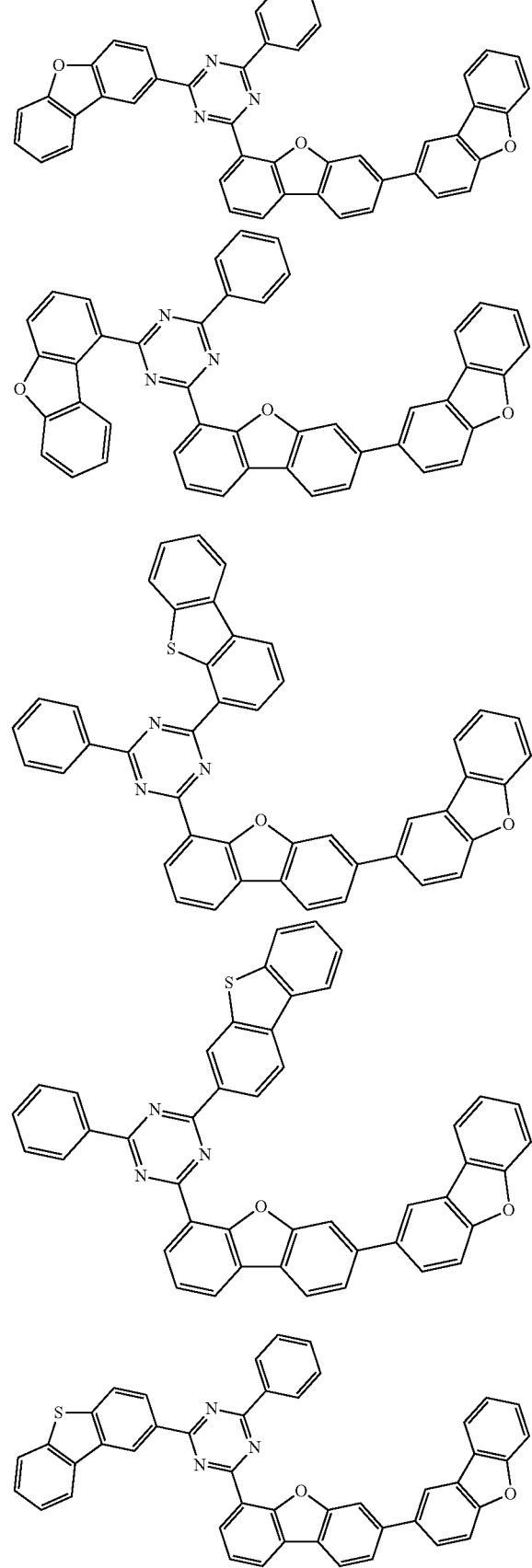
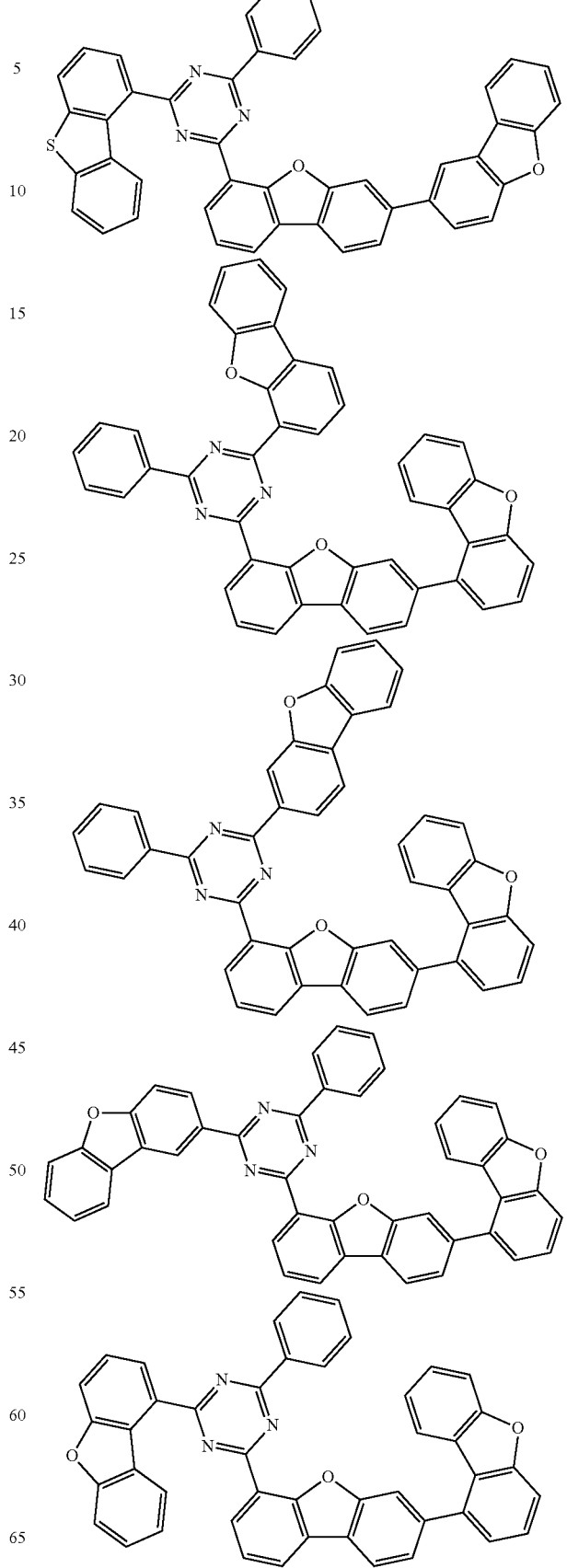

187
-continued
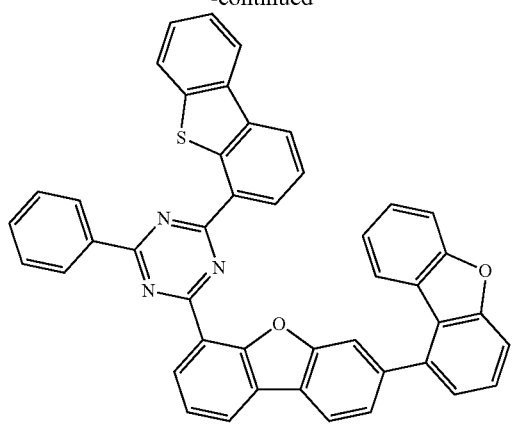
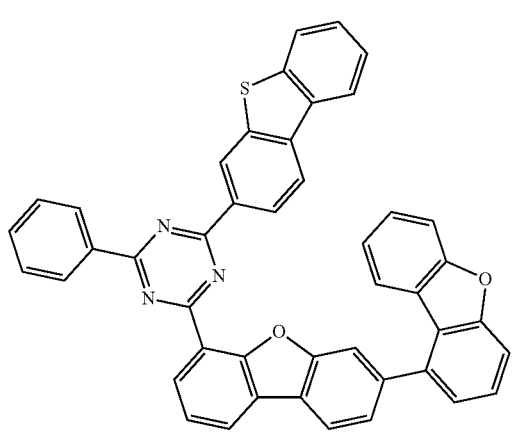
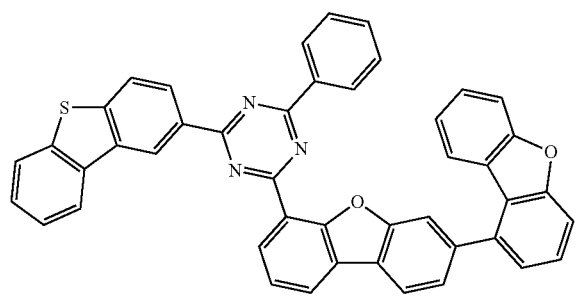
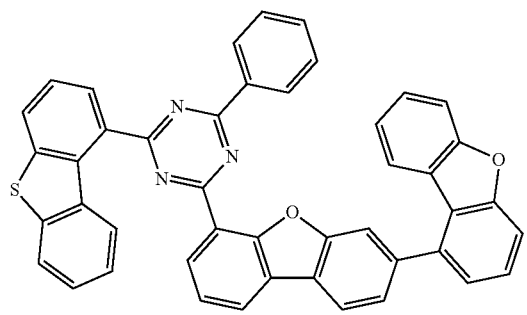
188
-continued
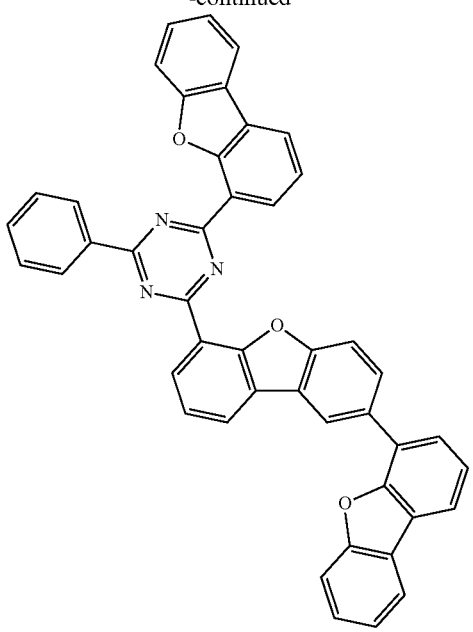
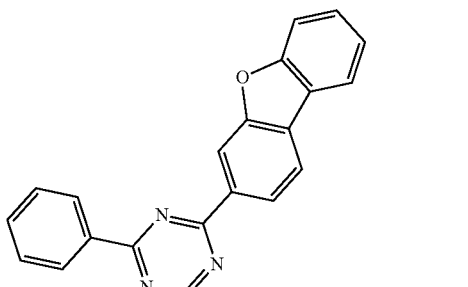

-continued
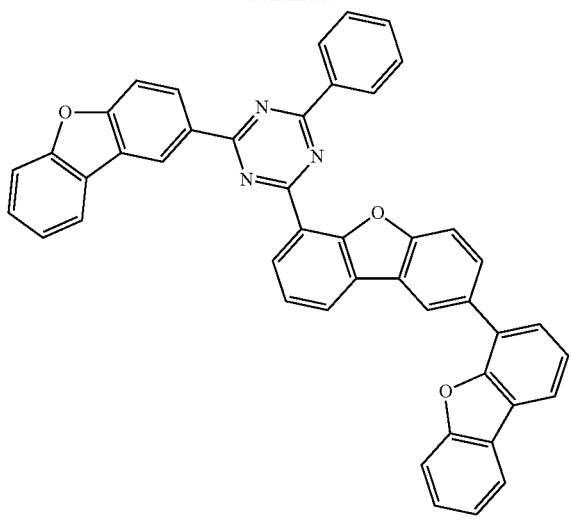
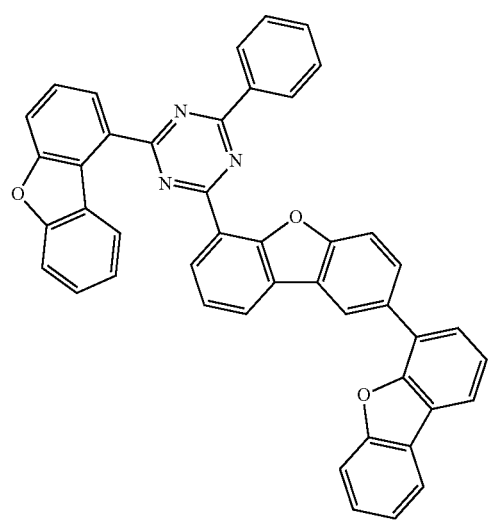
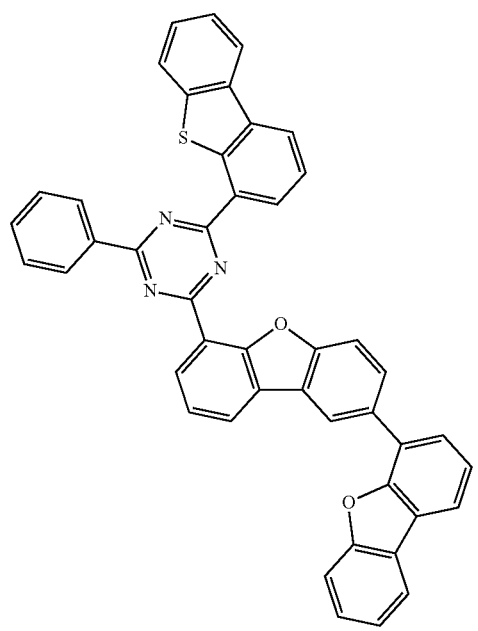
-continued
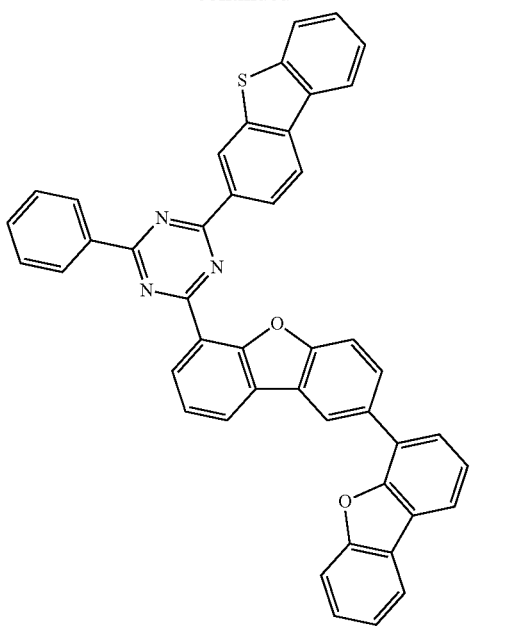
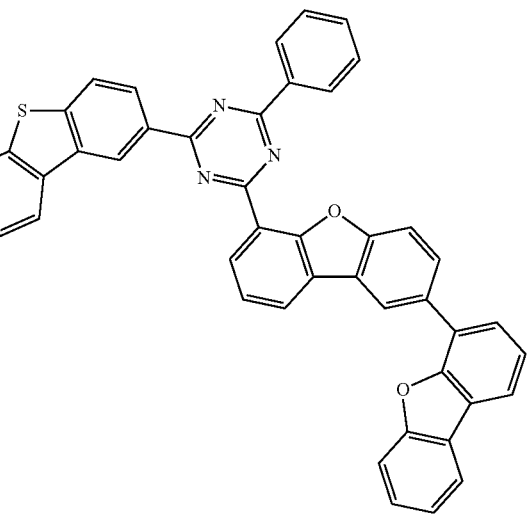
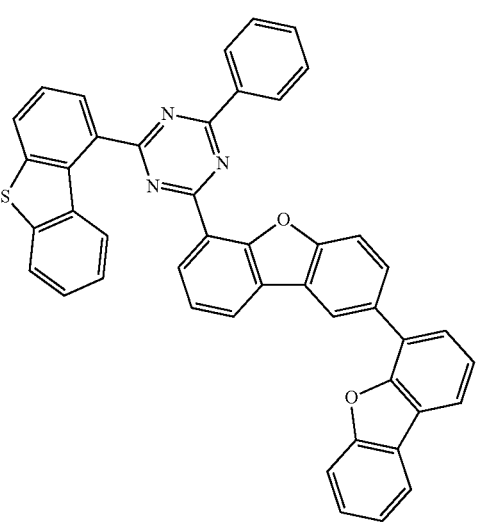

191
-continued
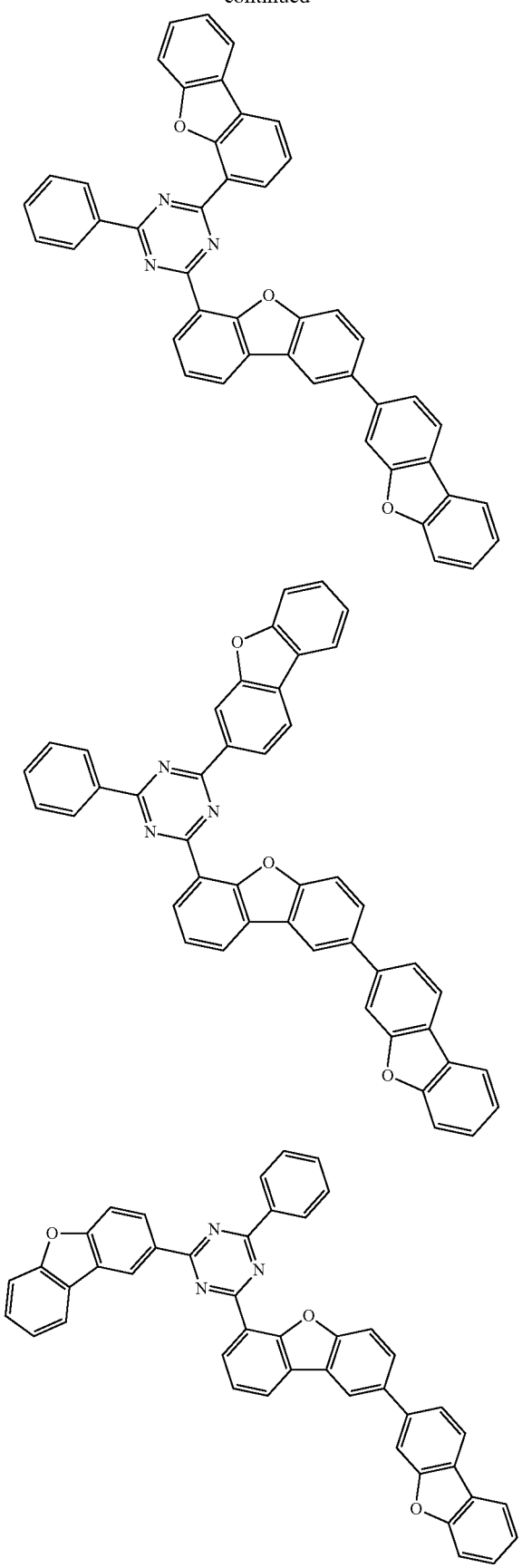
192
-continued

193
-continued
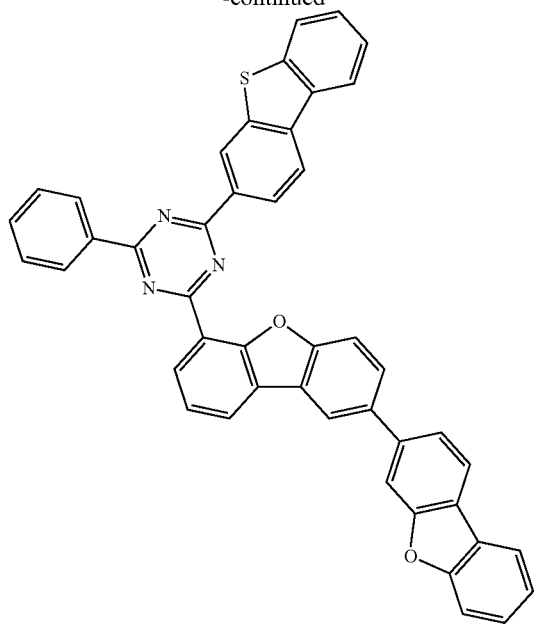
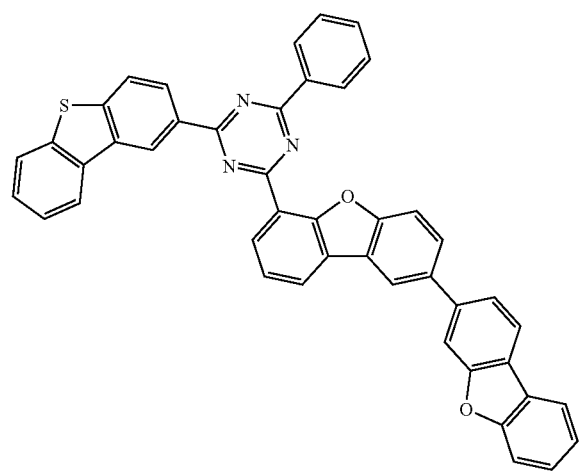
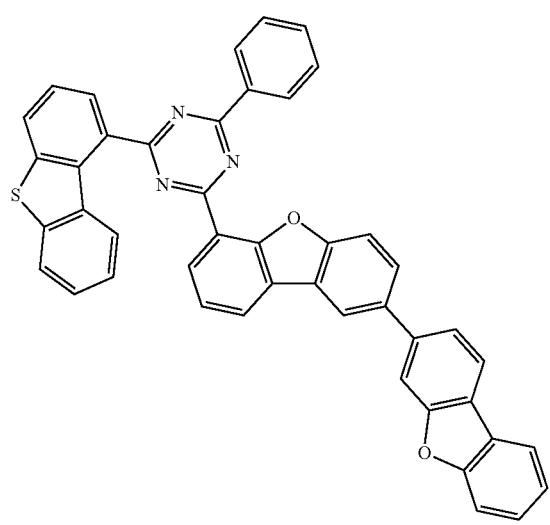
194
-continued
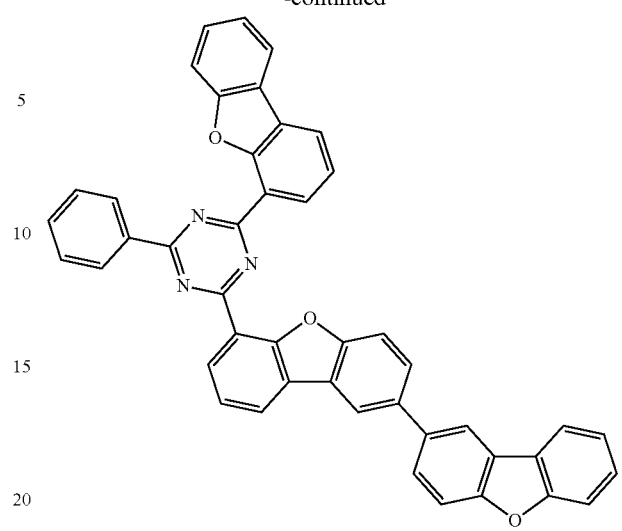
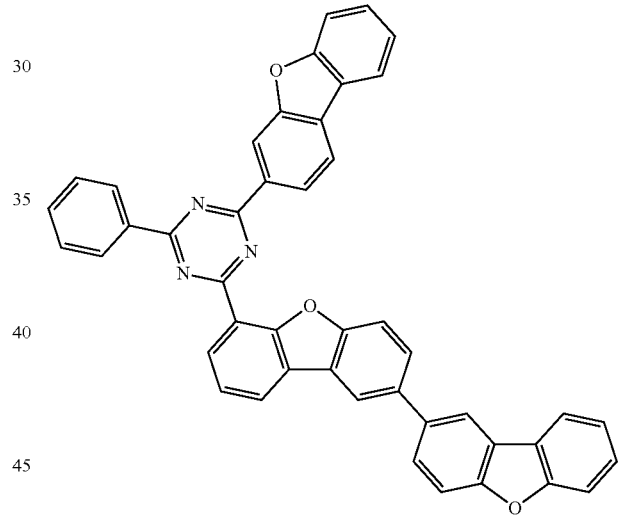
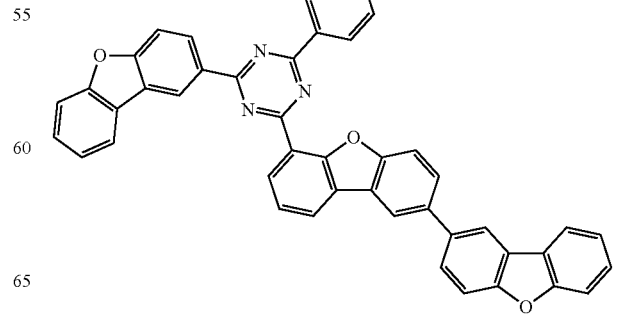

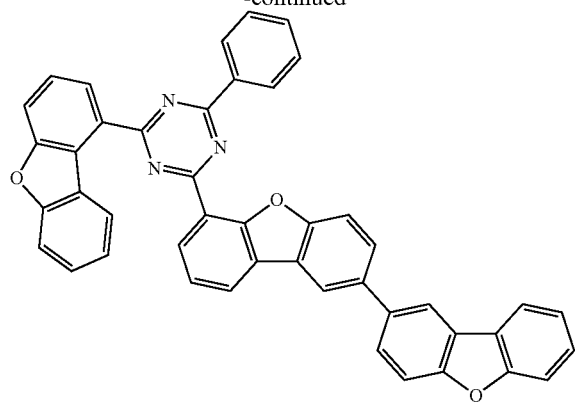
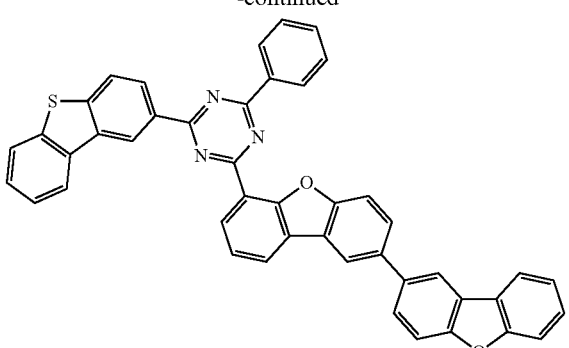
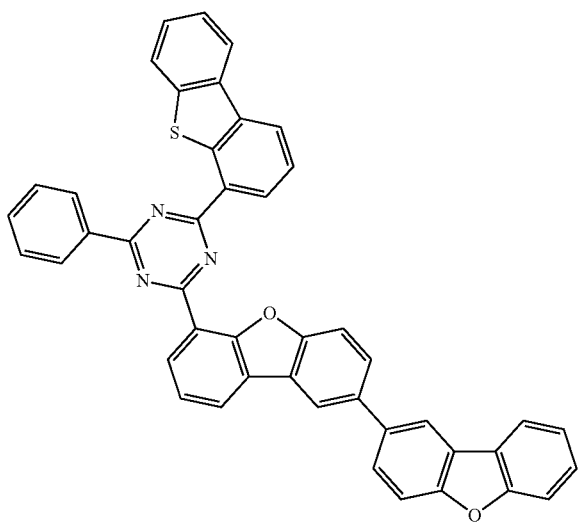
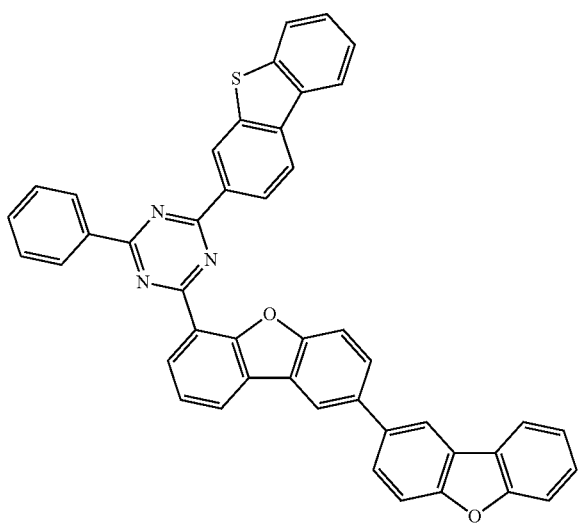
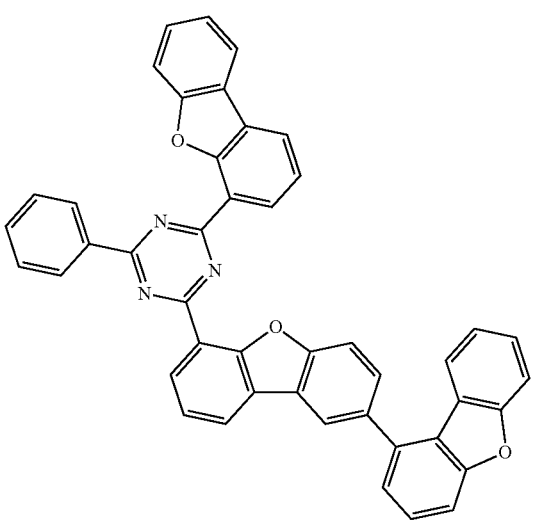

197 -continued
198 -continued
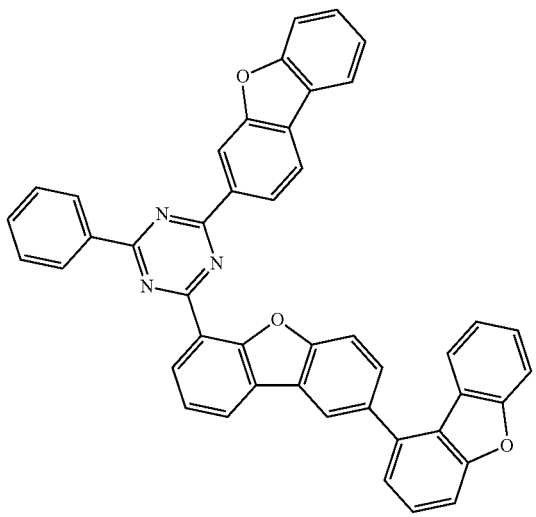
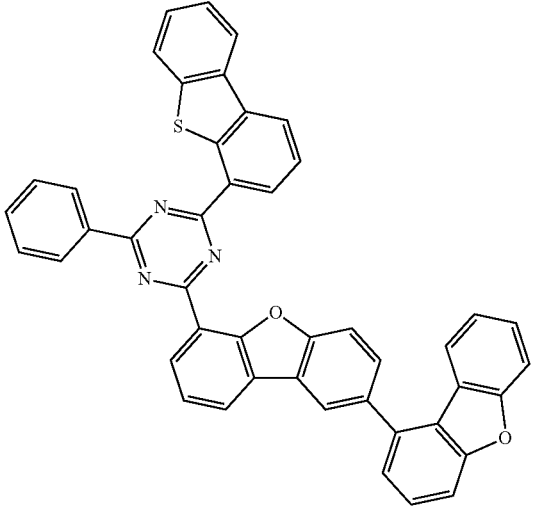
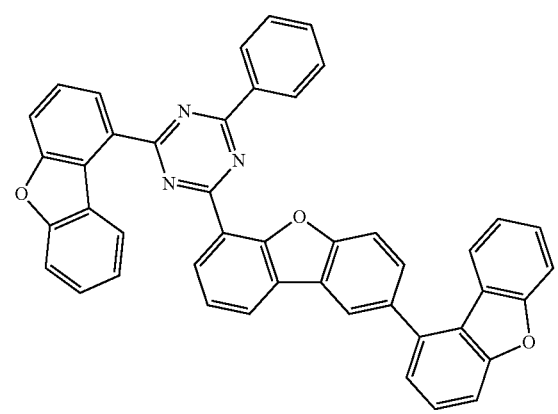

199
-continued
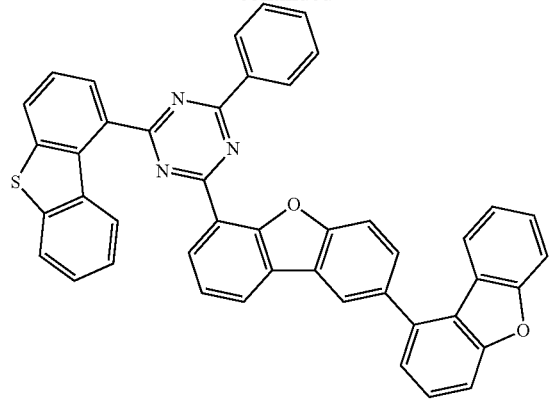
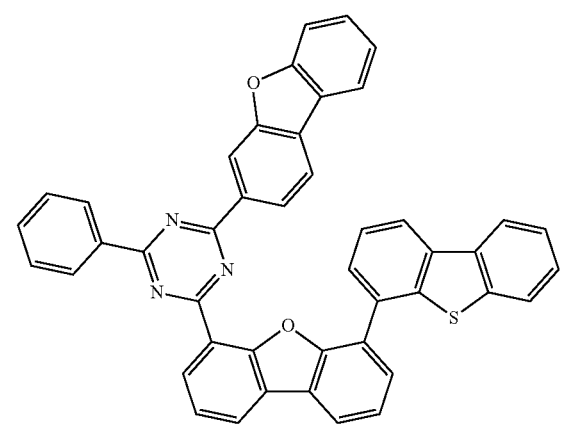
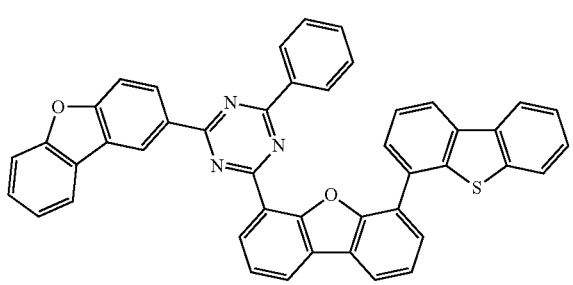
200
-continued
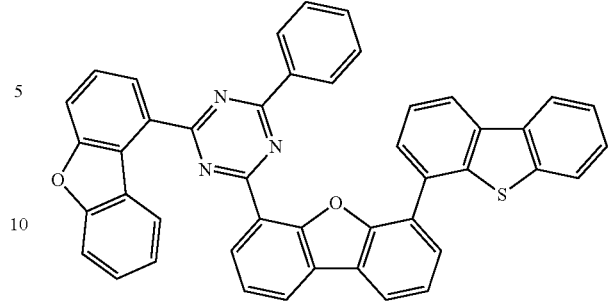
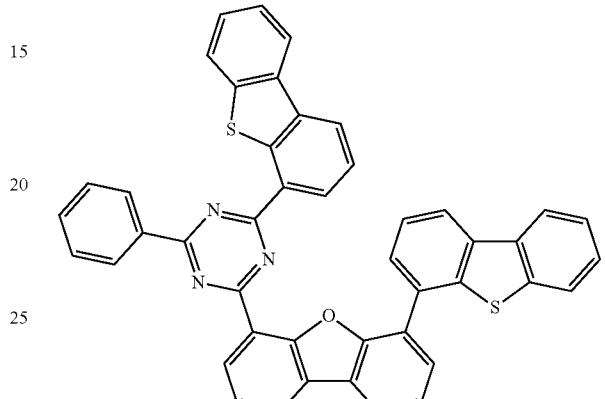
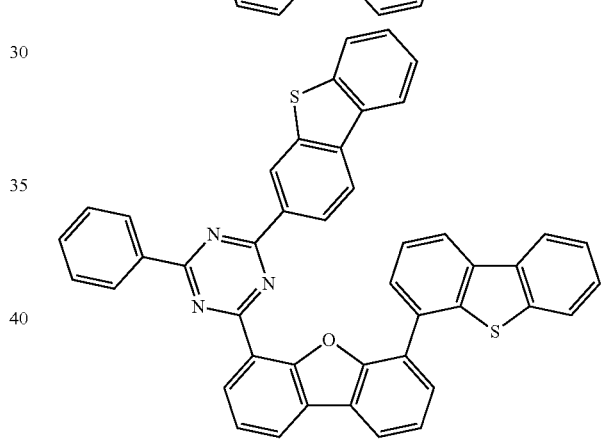
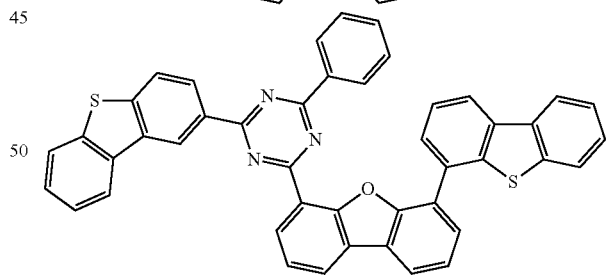
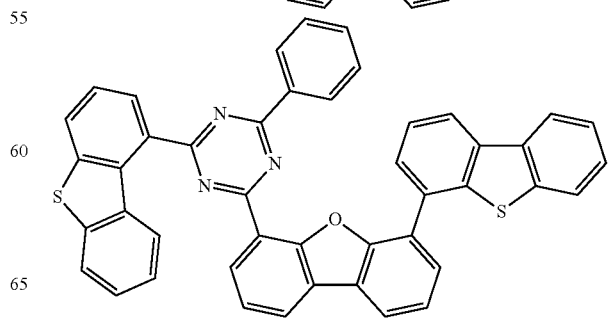

201
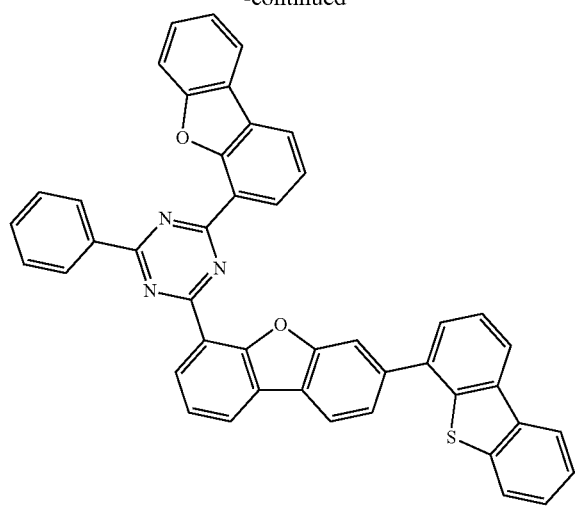
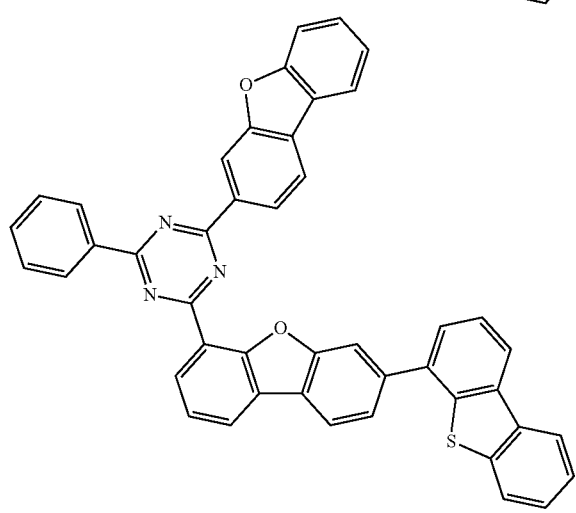
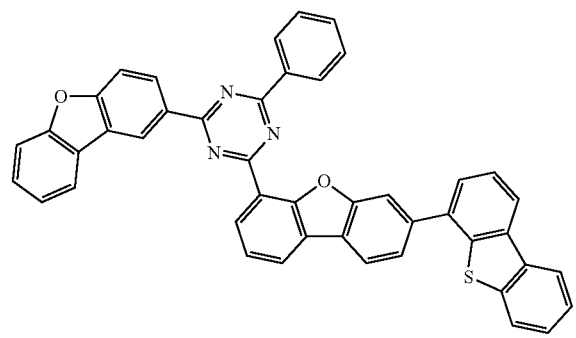
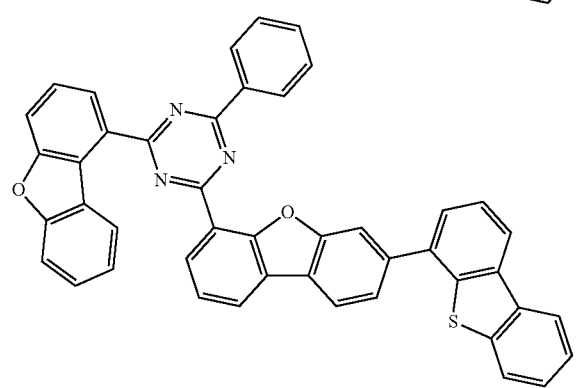
202
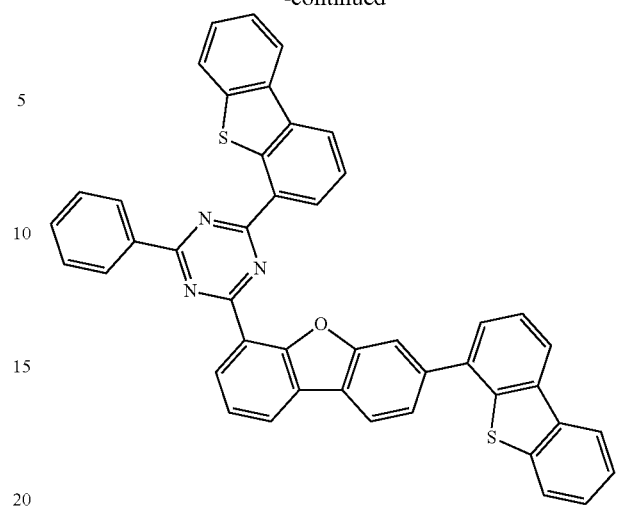
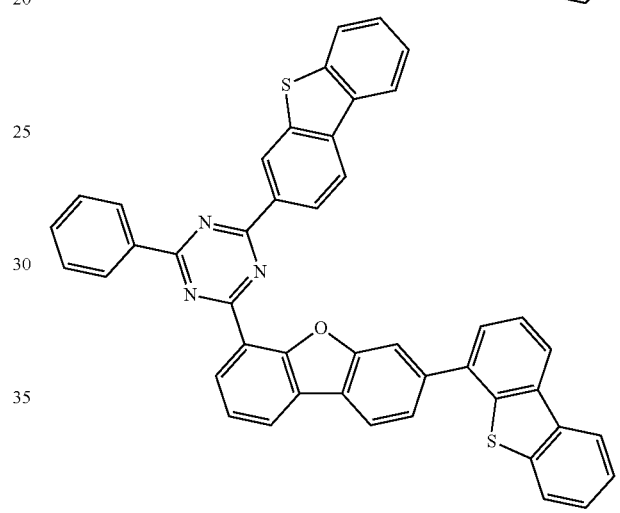
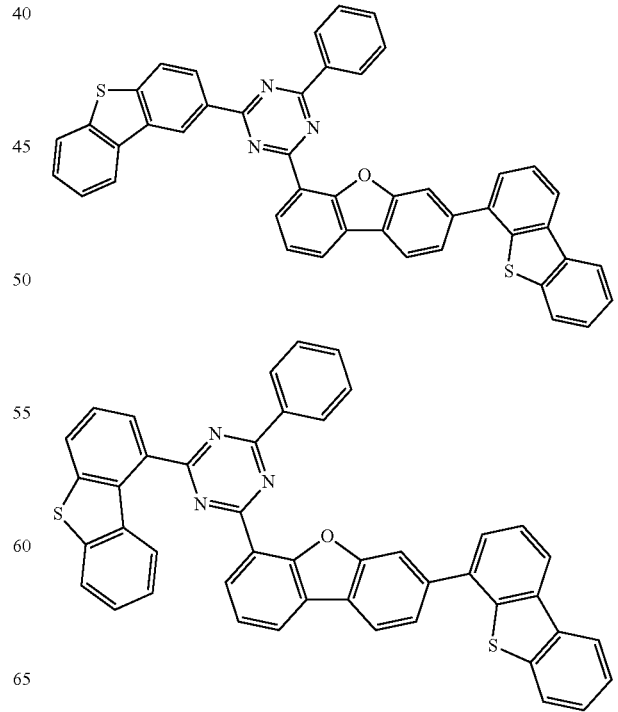

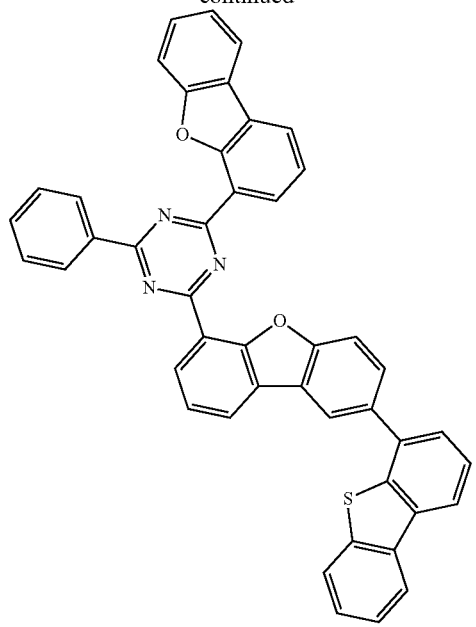
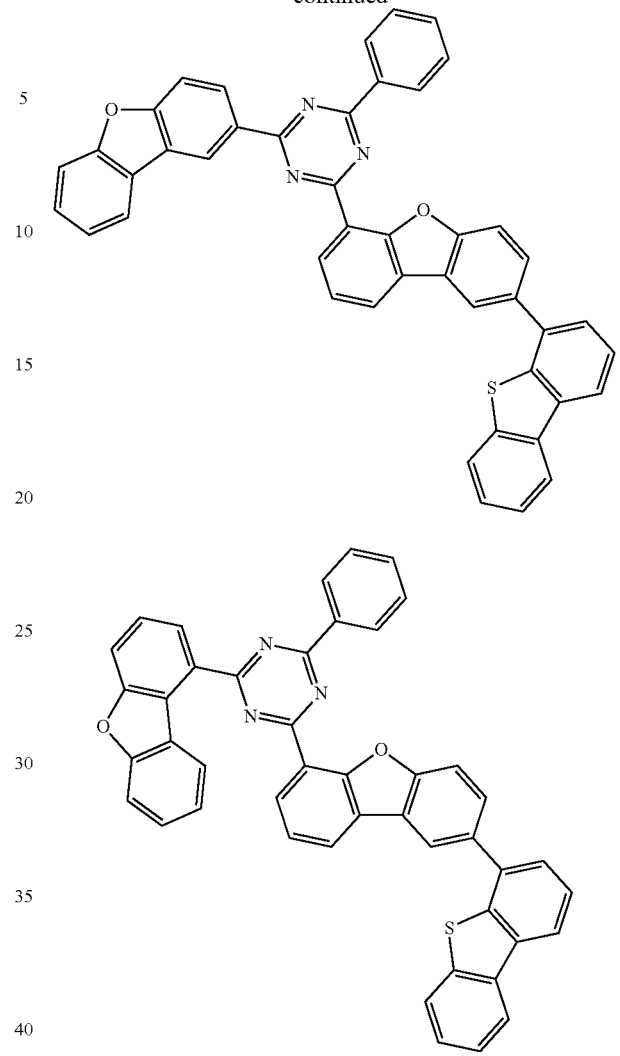
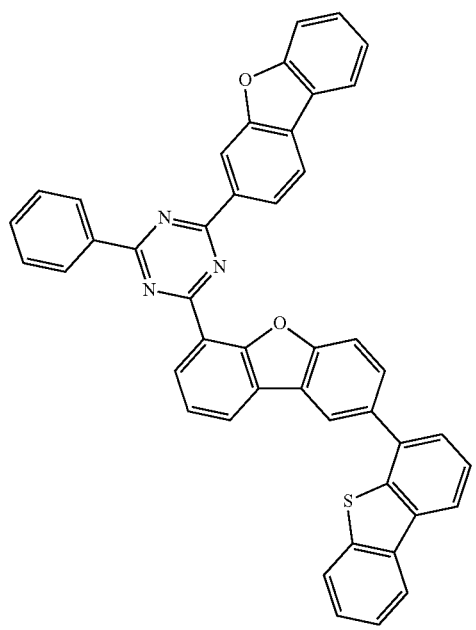
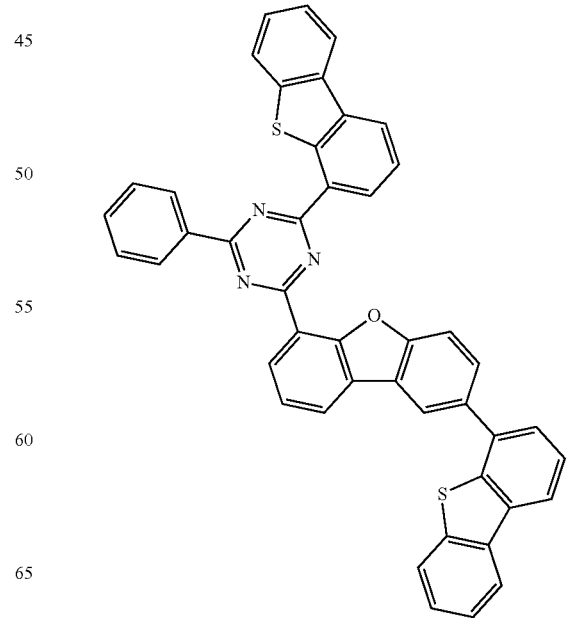

-continued
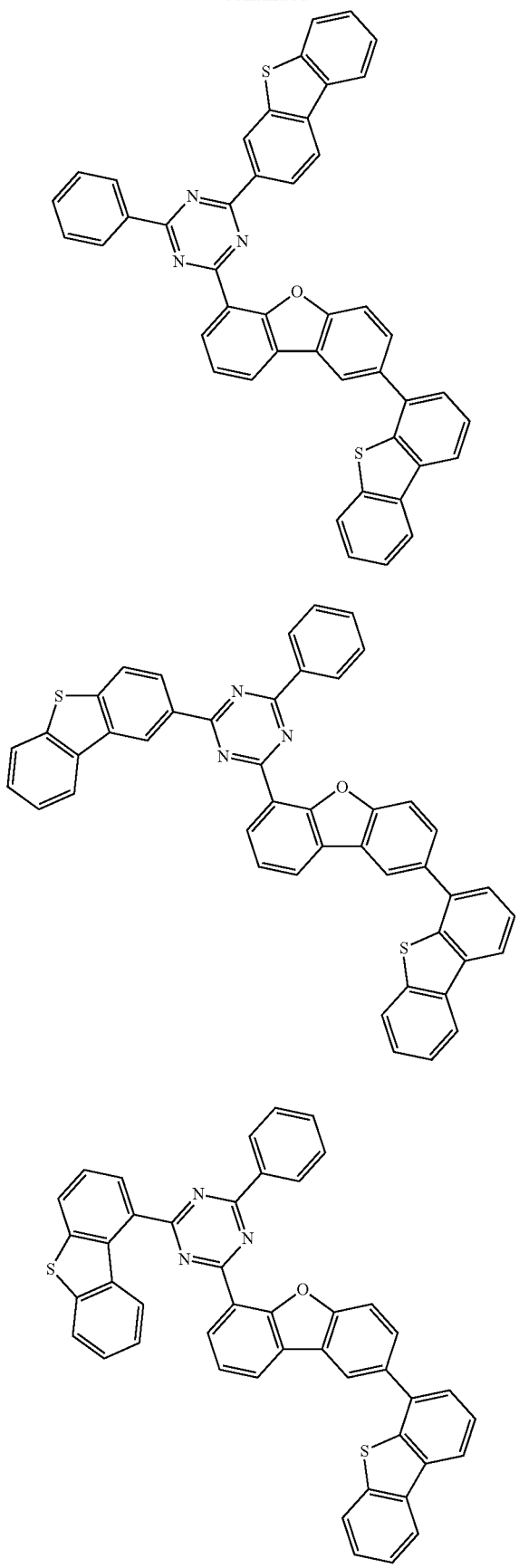
-continued
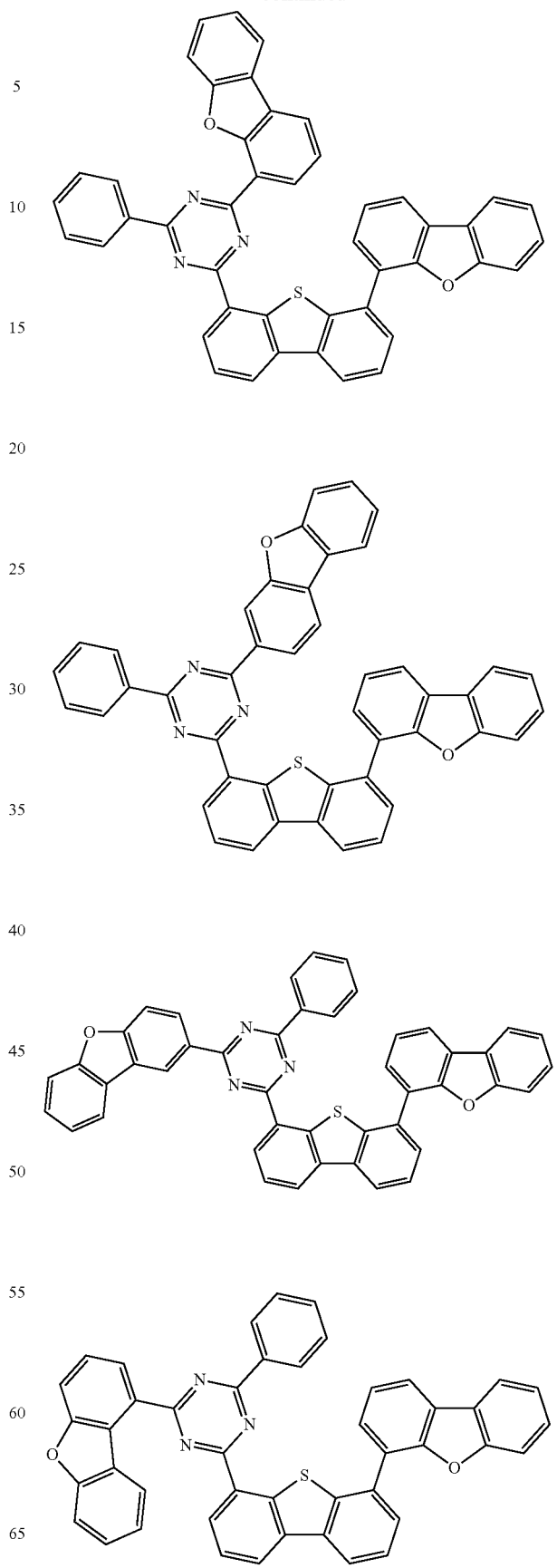

207
-continued
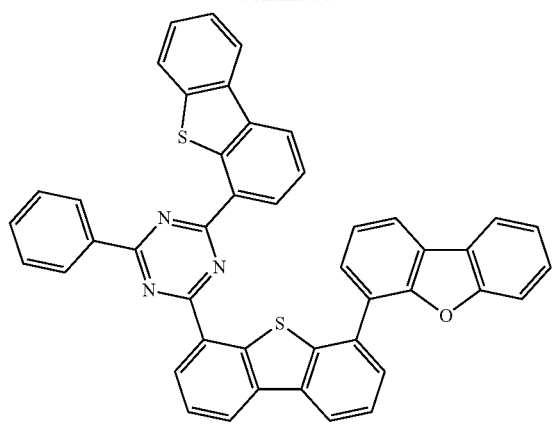
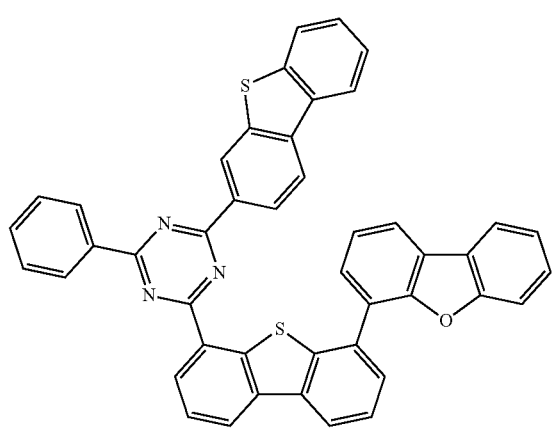
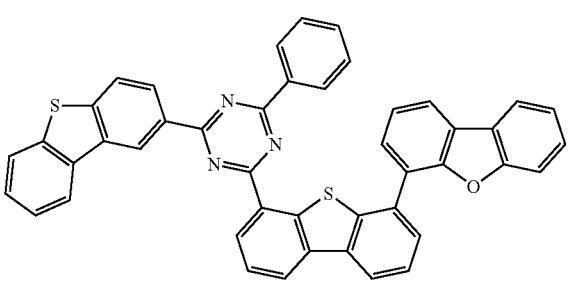
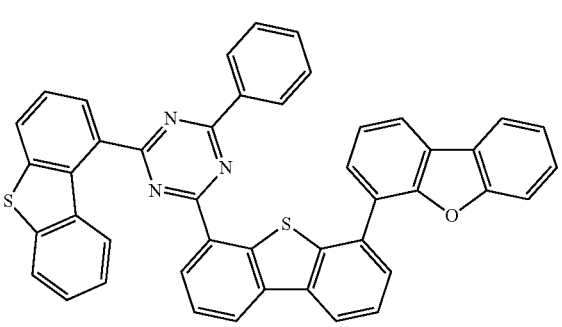
208
-continued
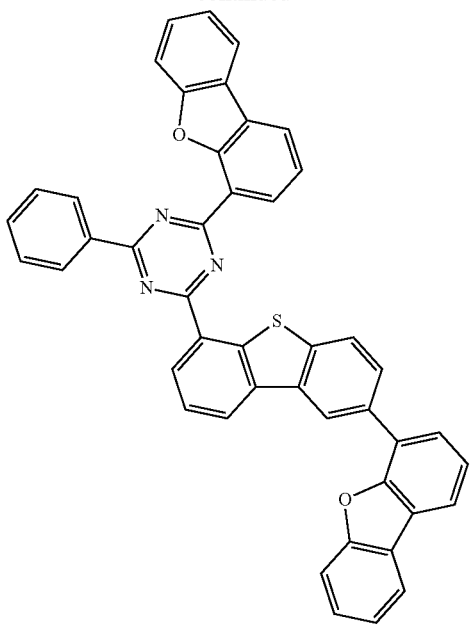
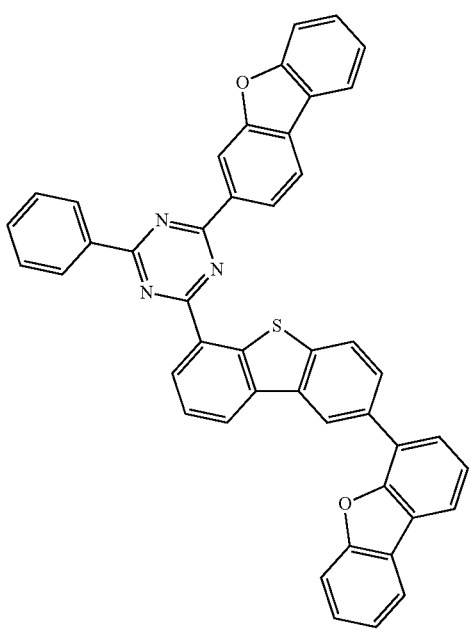

209
-continued
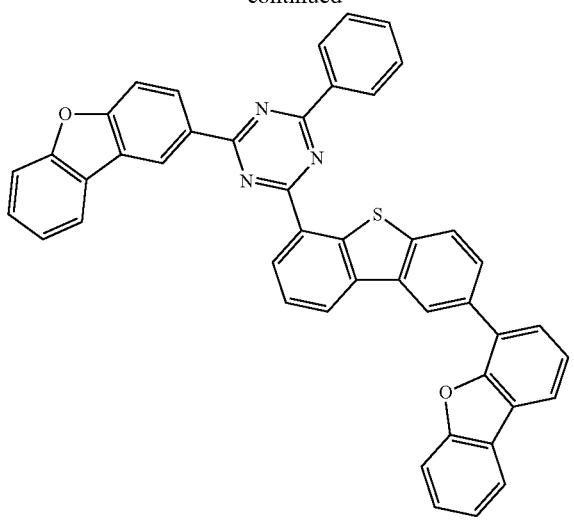
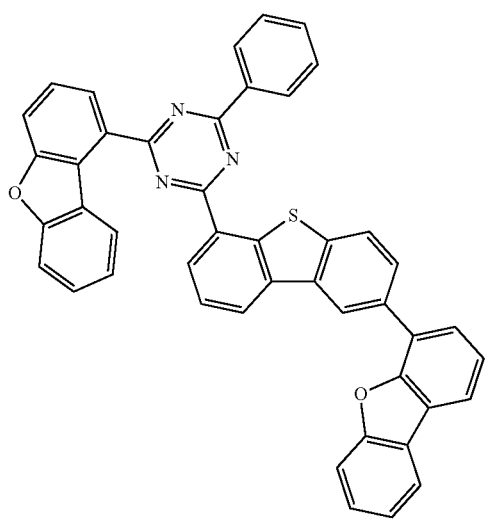
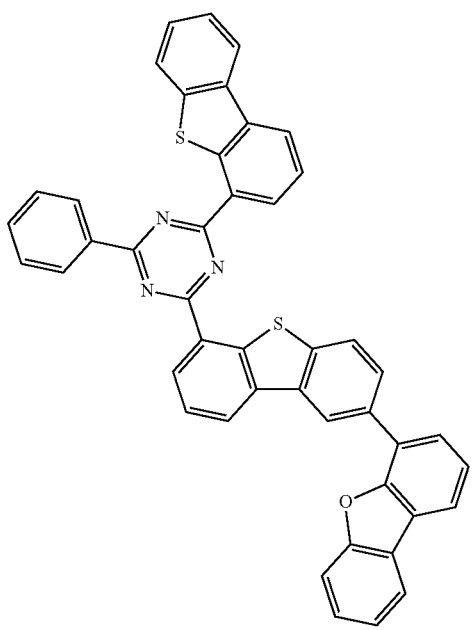
210
-continued
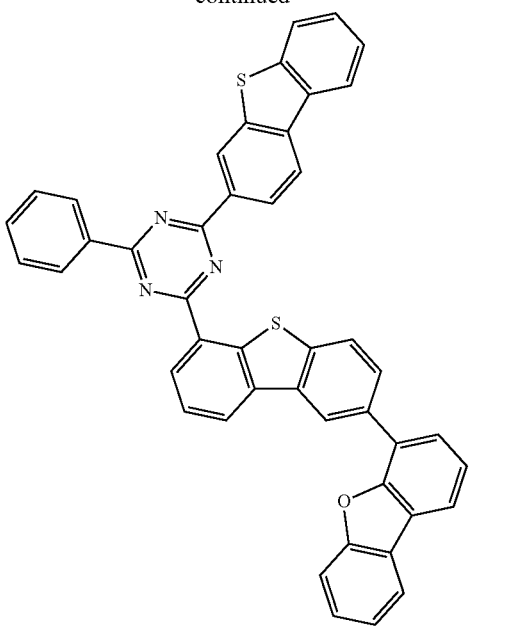
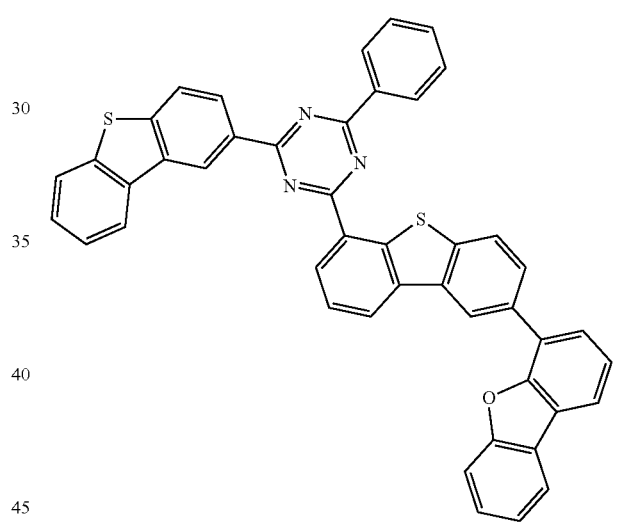
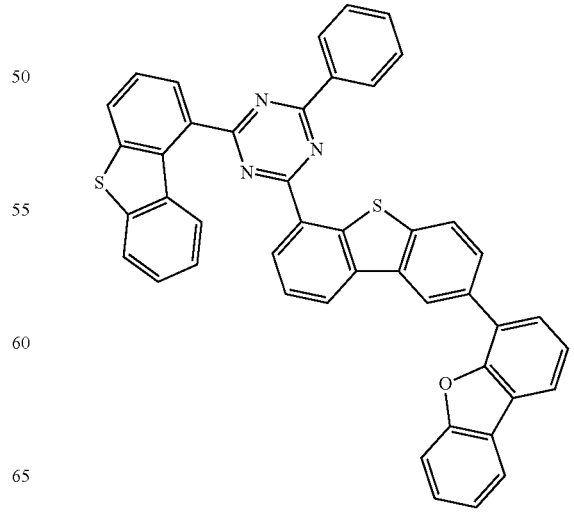

211
-continued
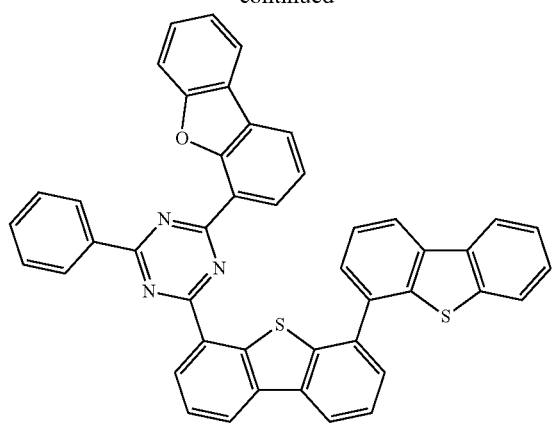
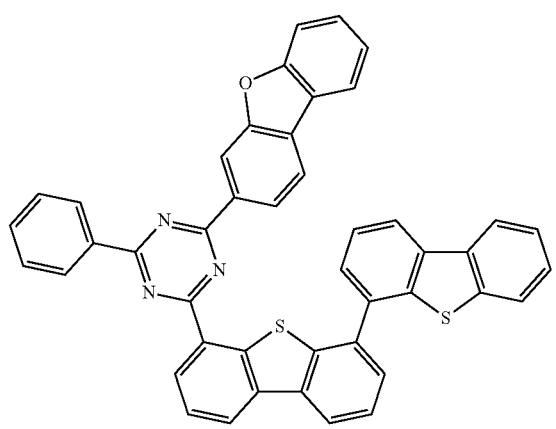
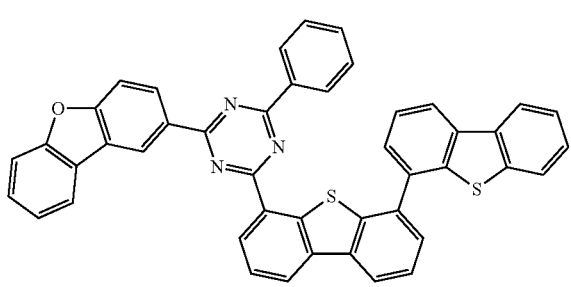
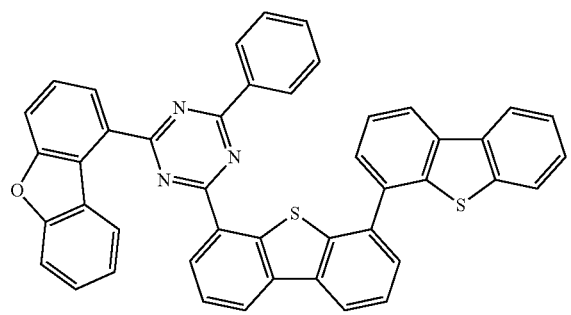
212
-continued
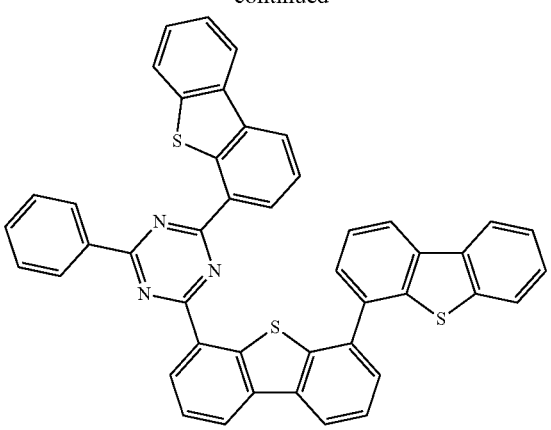
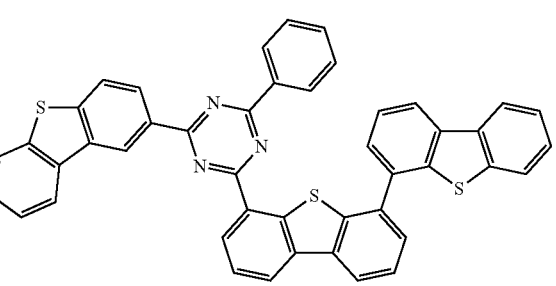
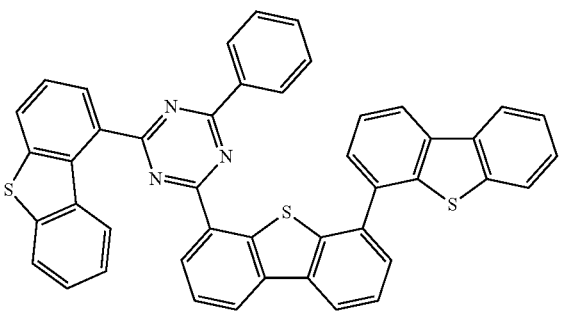

213
-continued
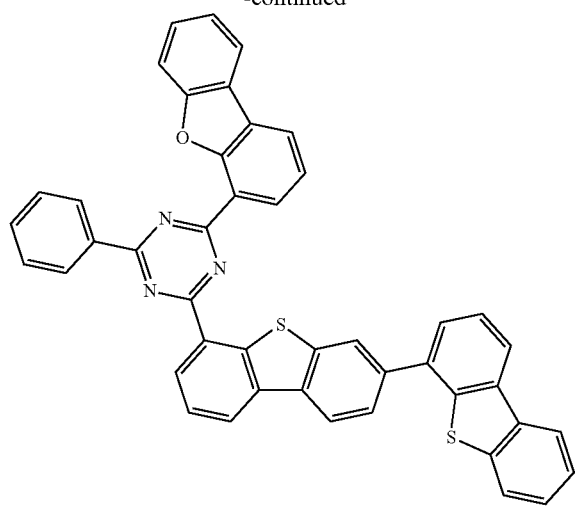
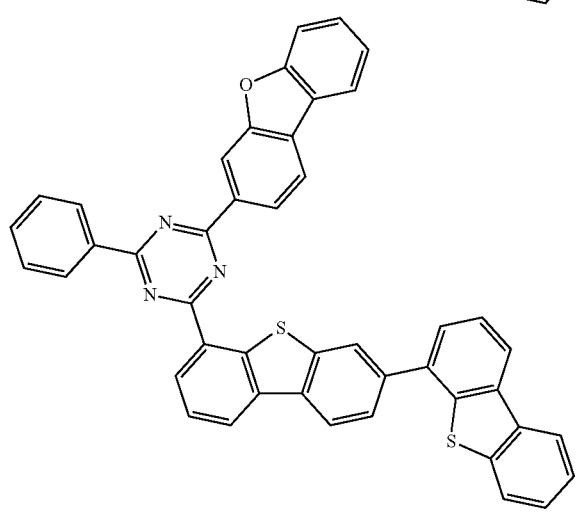
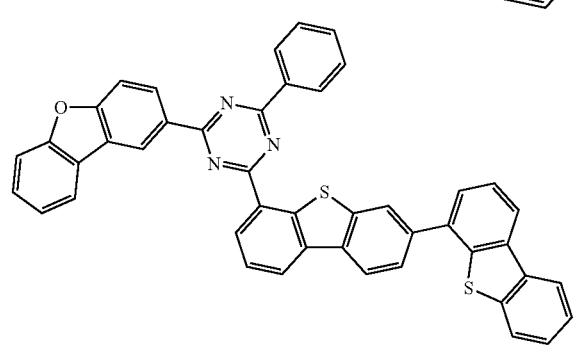
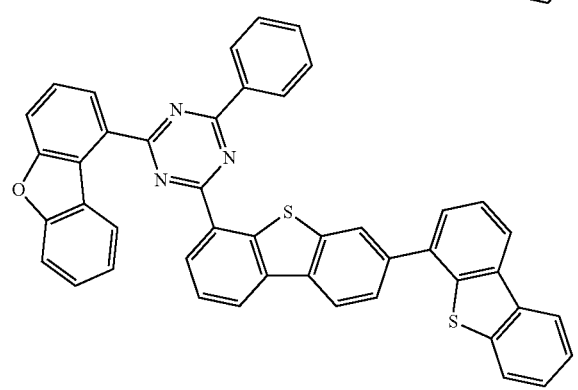
214
-continued
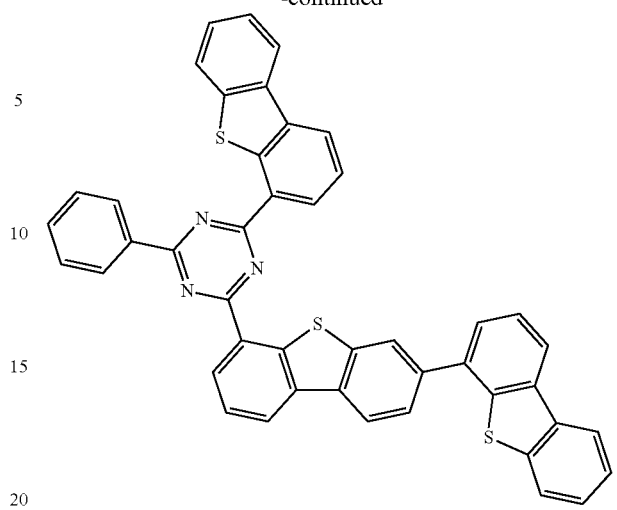
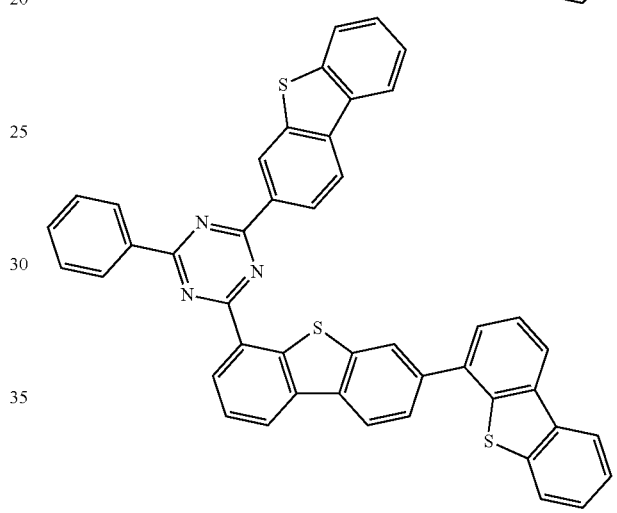
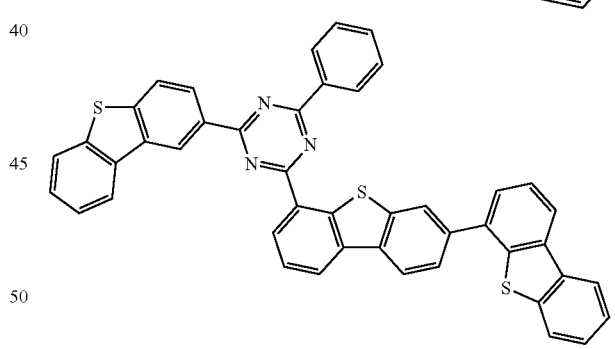
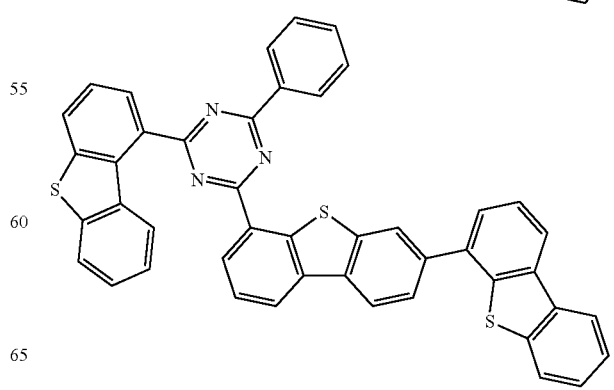

-continued
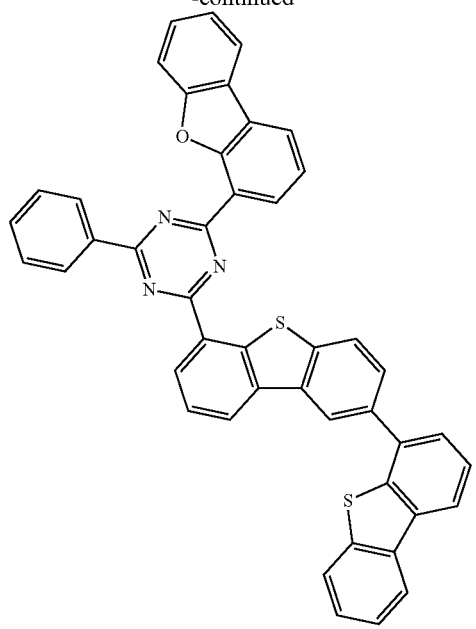
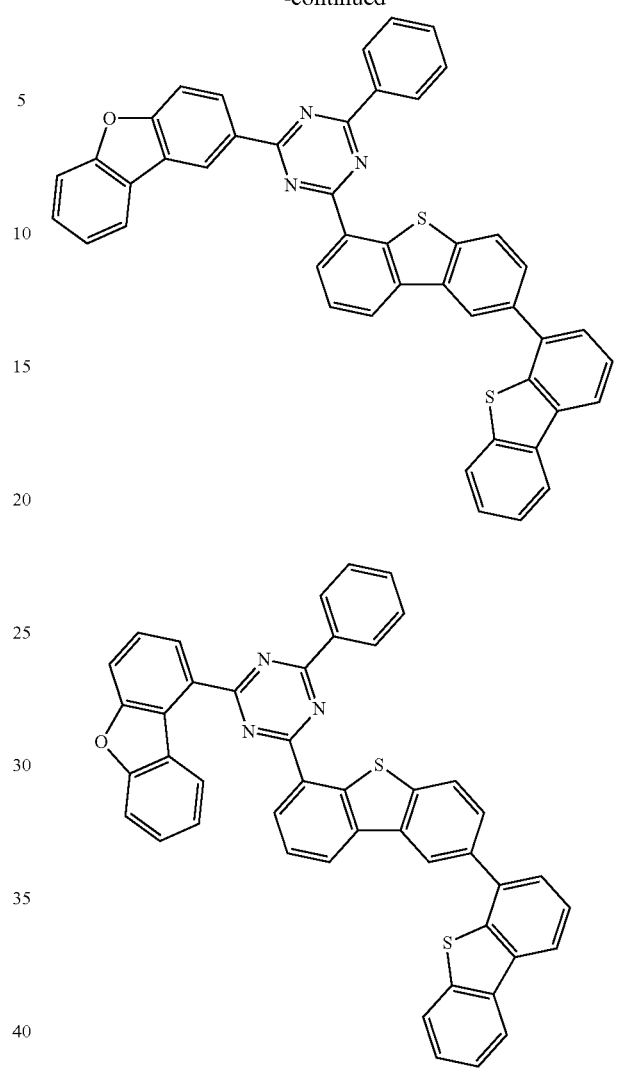
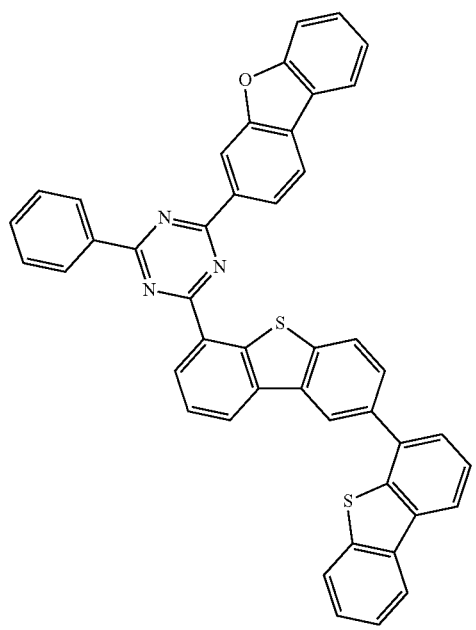
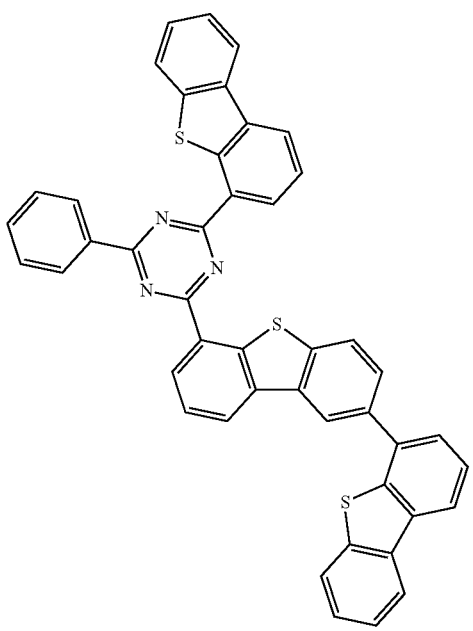

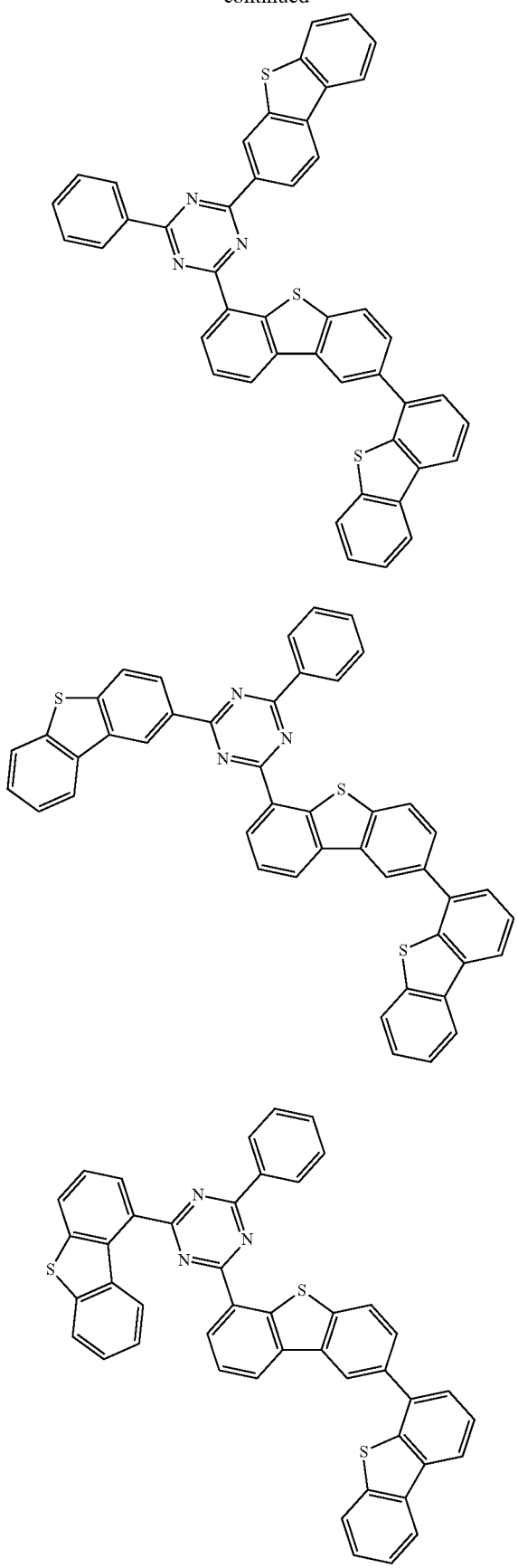
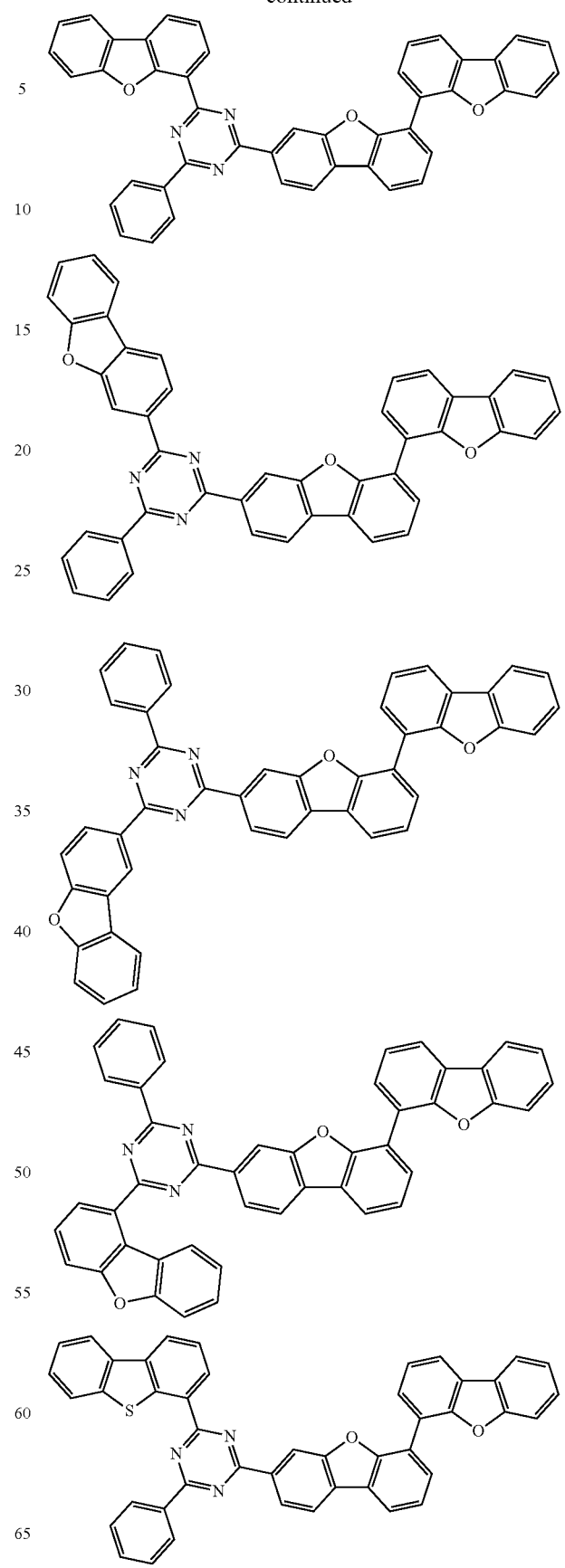

219
-continued
220
-continued
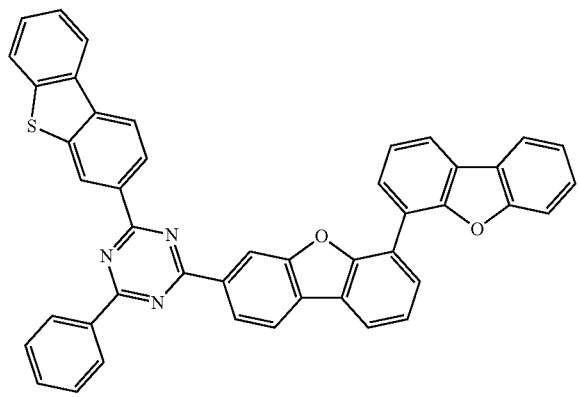
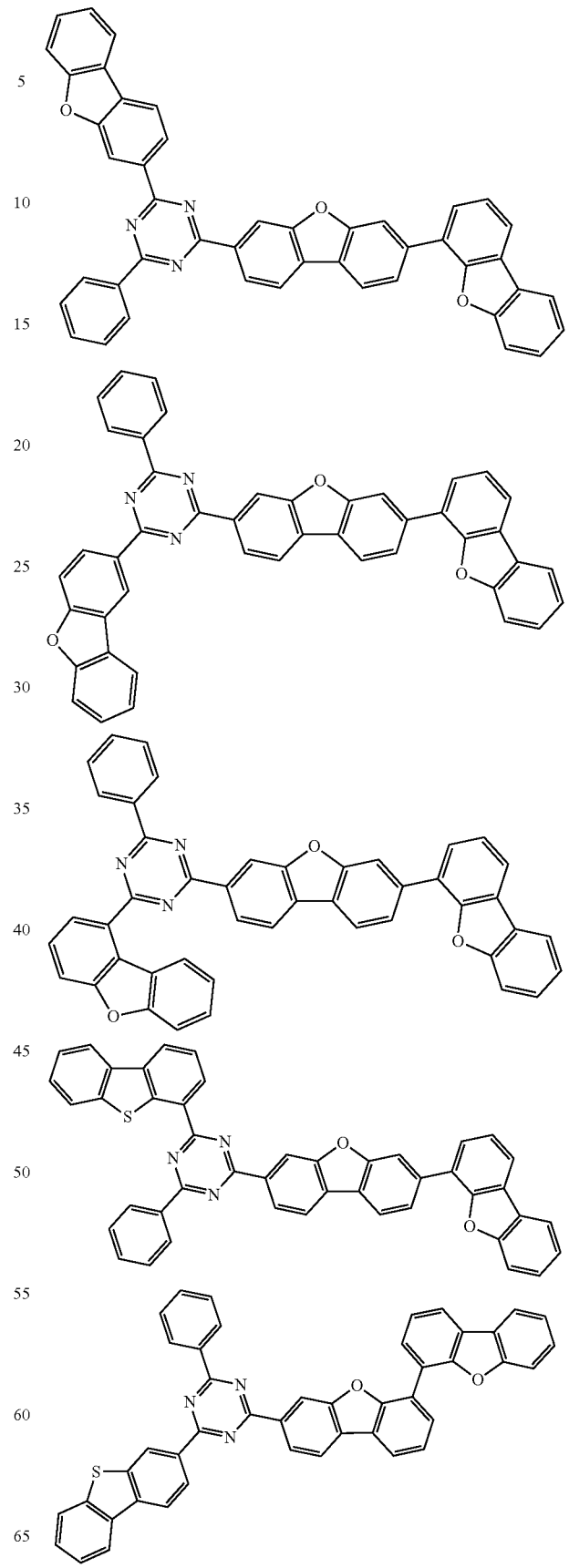

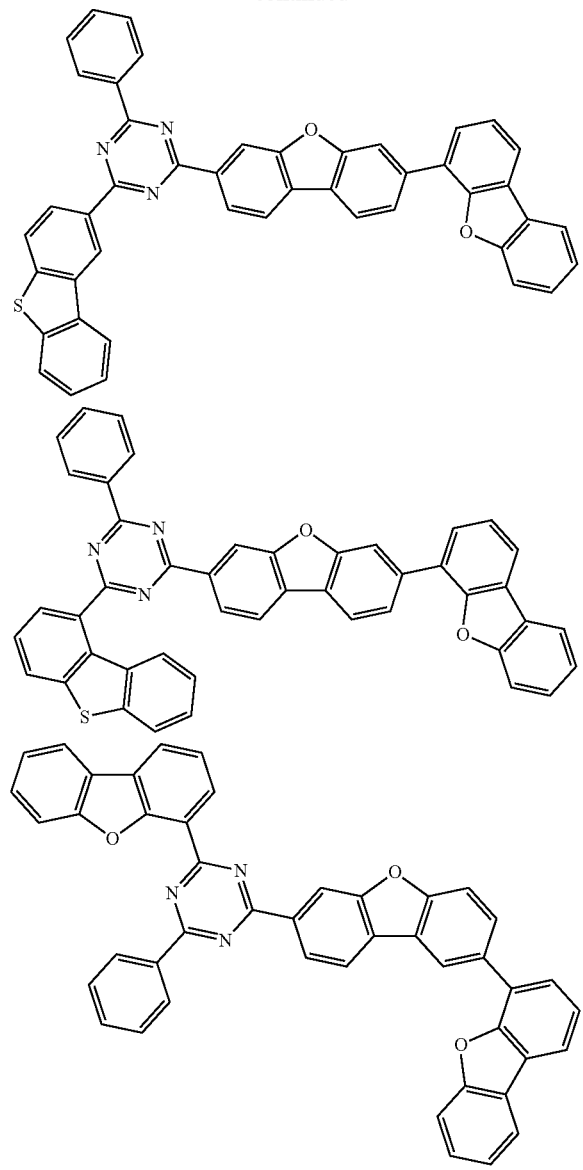
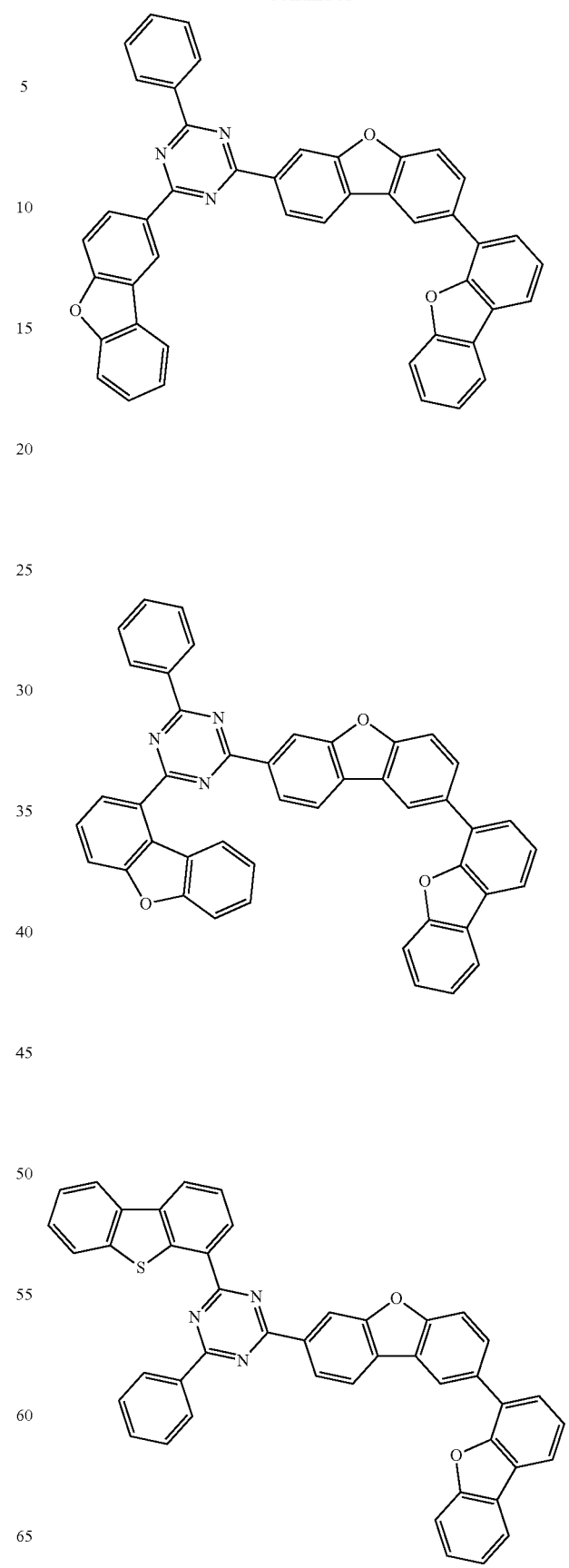

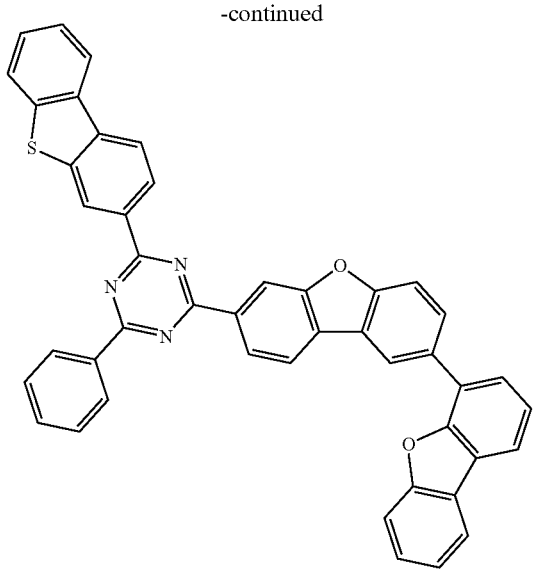
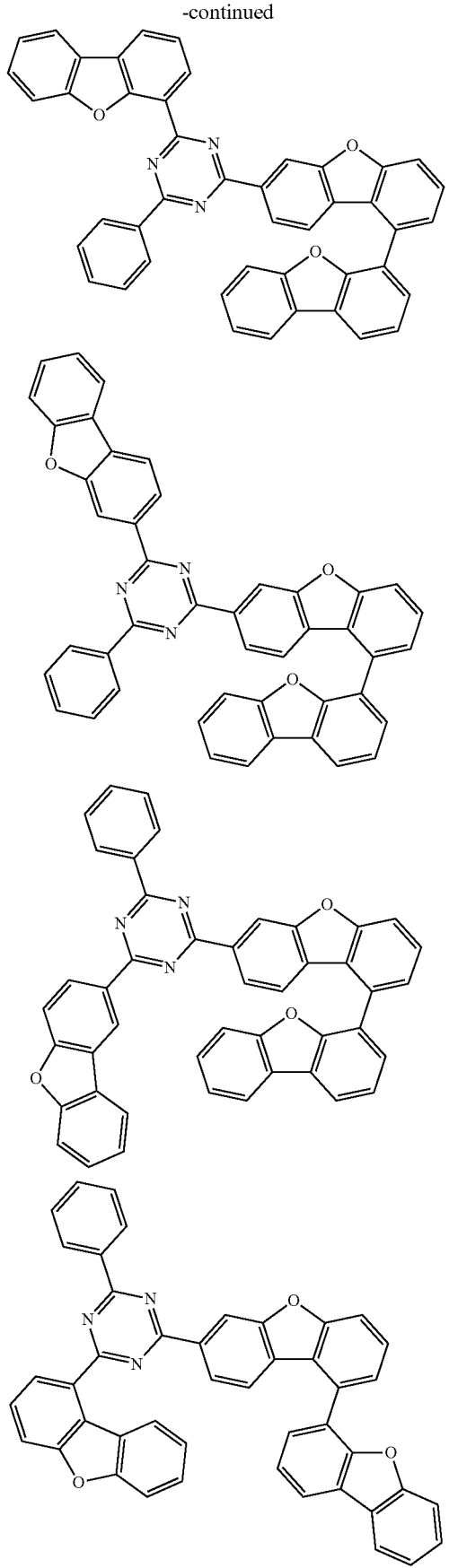

225
-continued
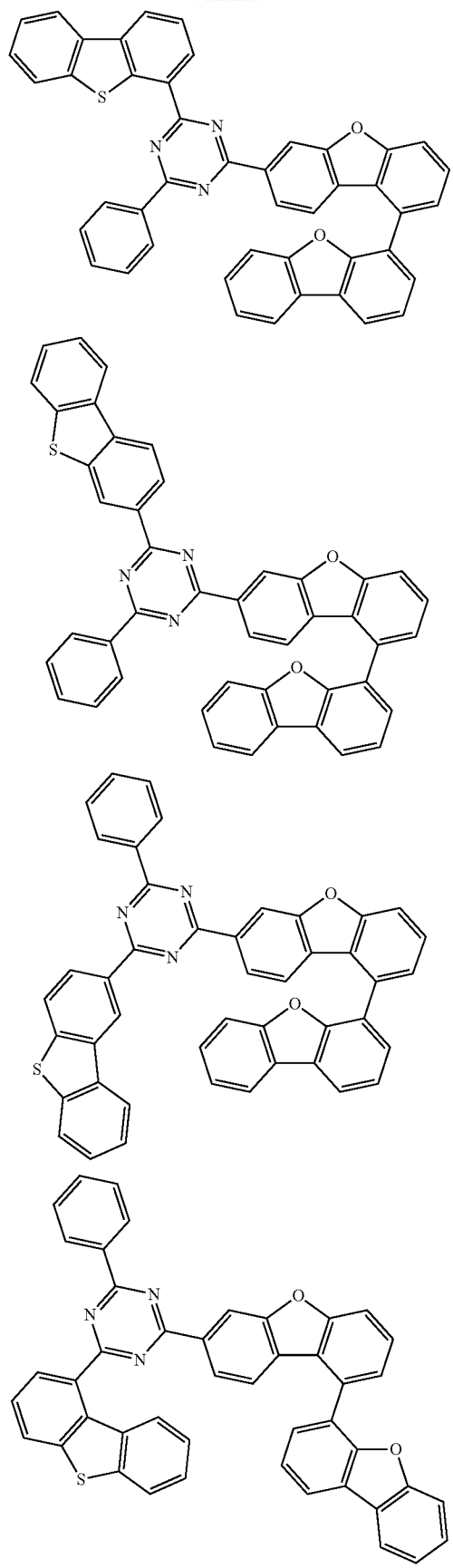
226
-continued
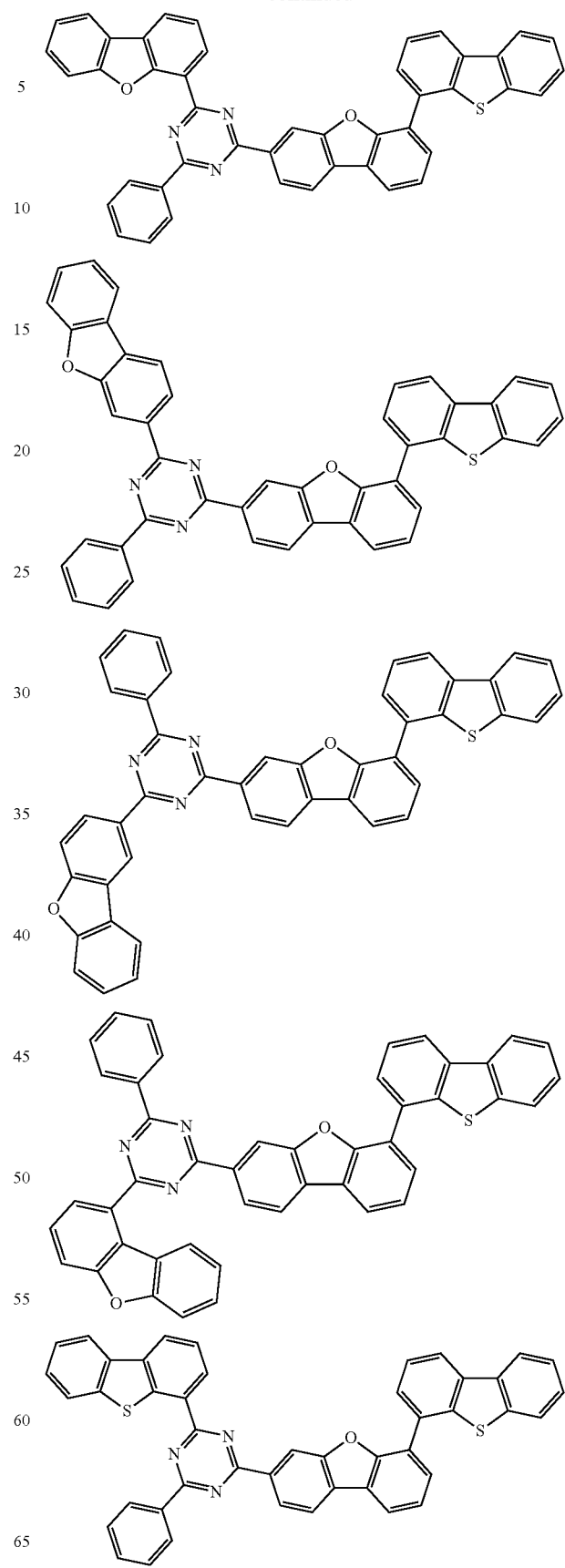

227
-continued
228
-continued
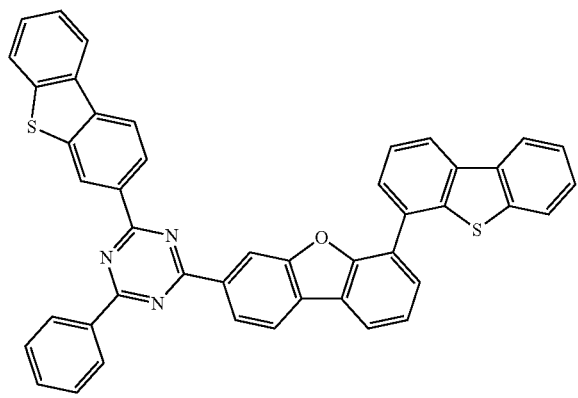
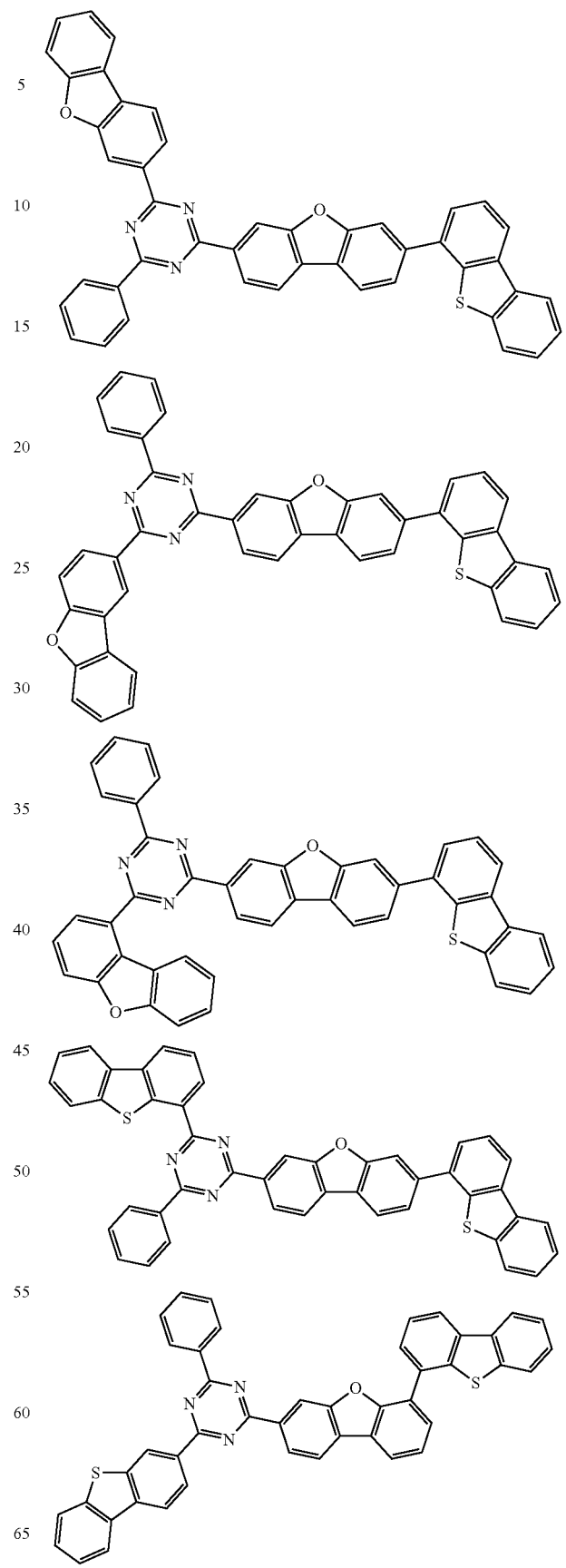

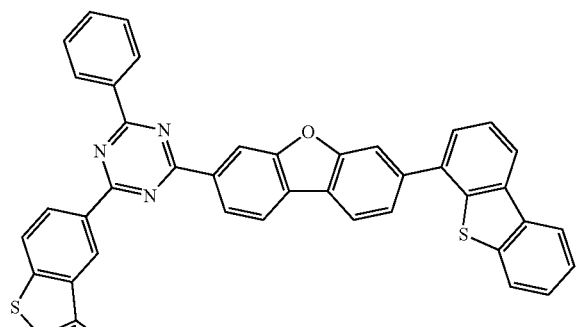
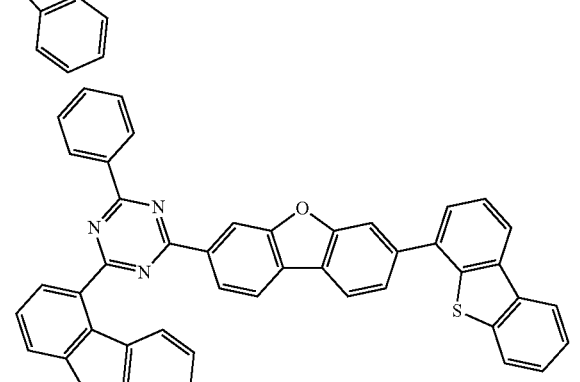
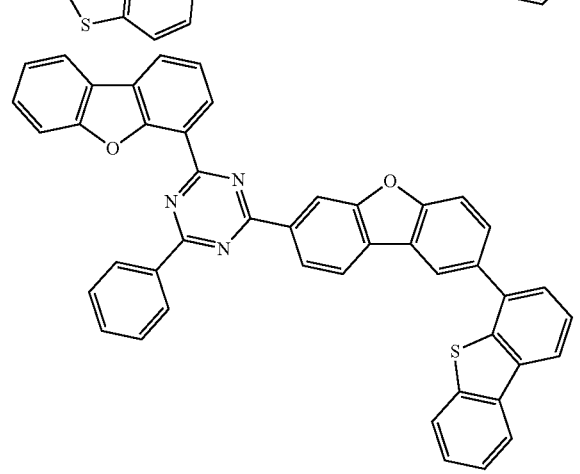
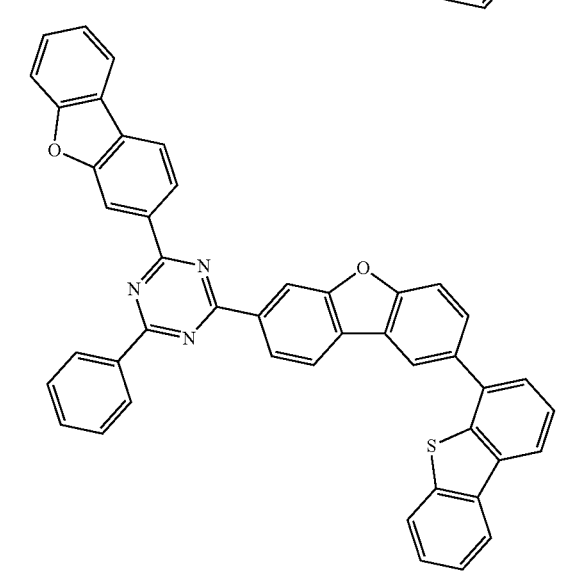
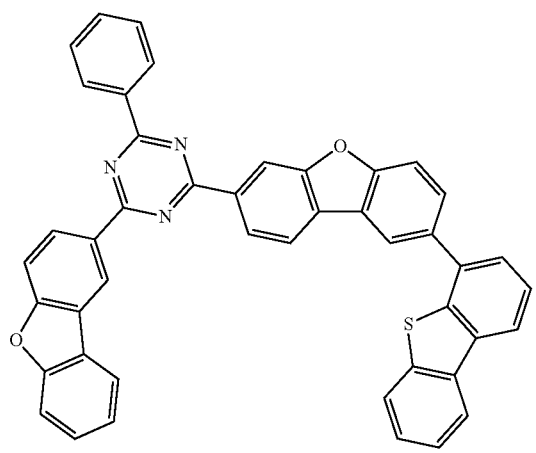
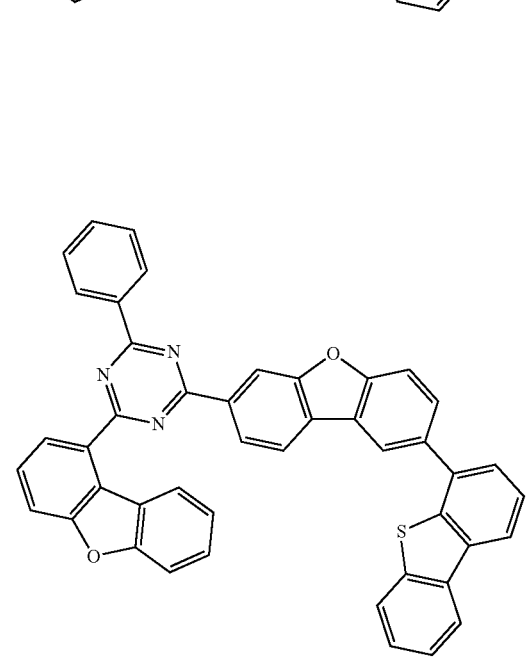
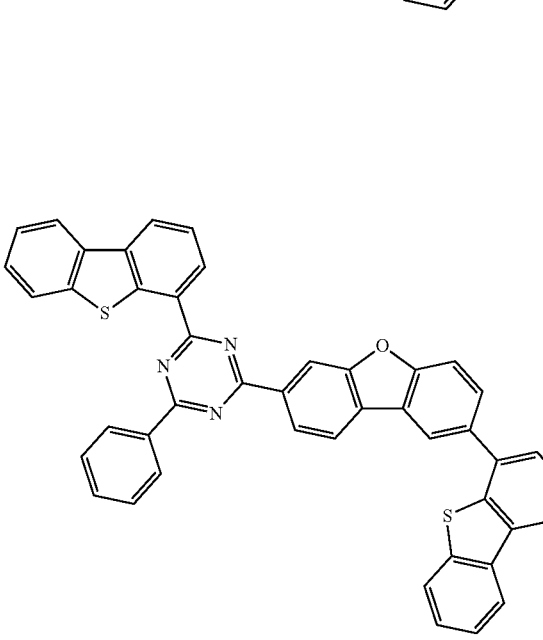

231
-continued
232
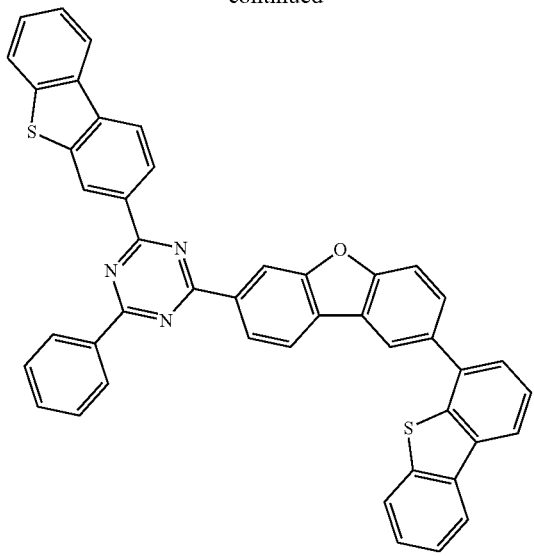
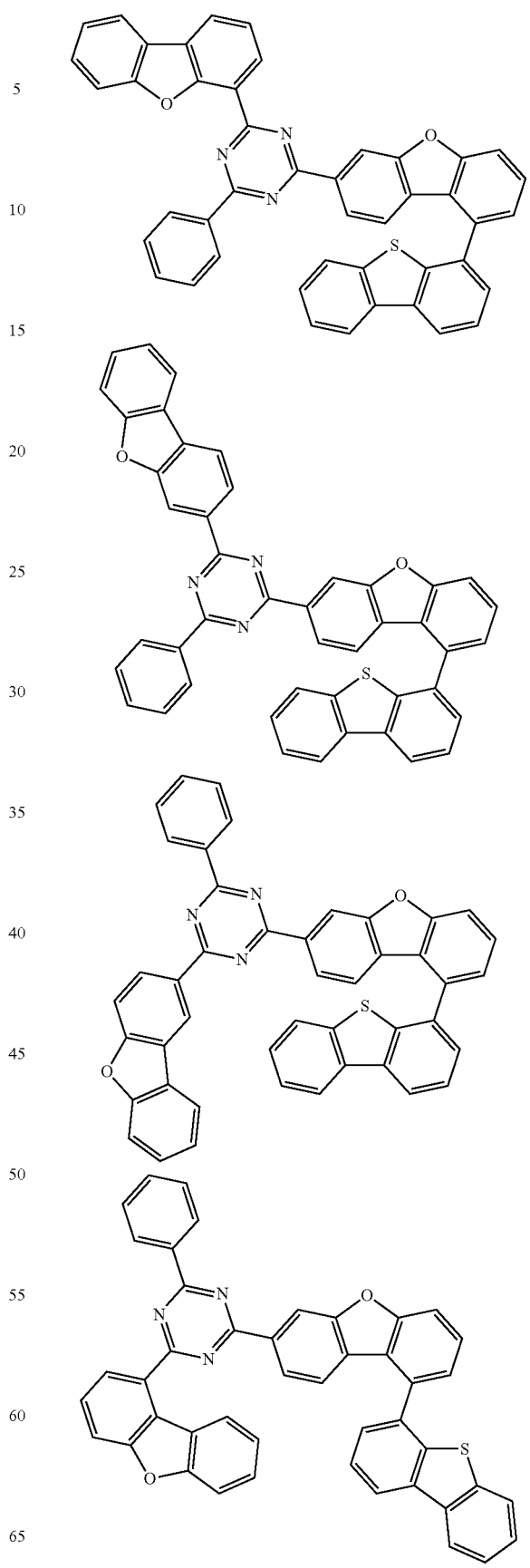

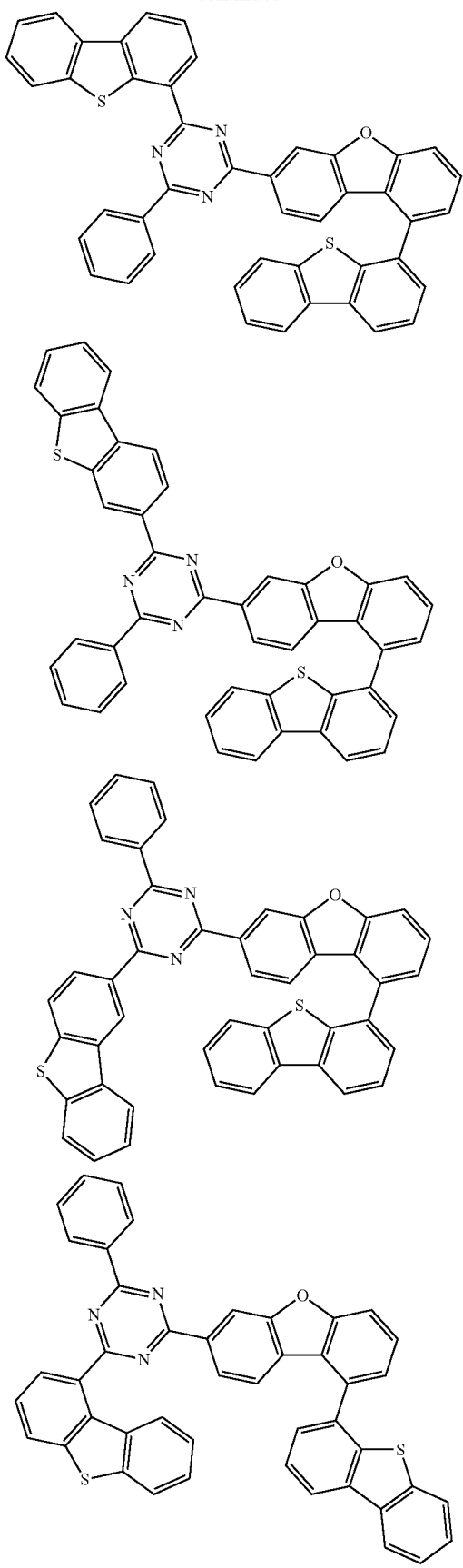
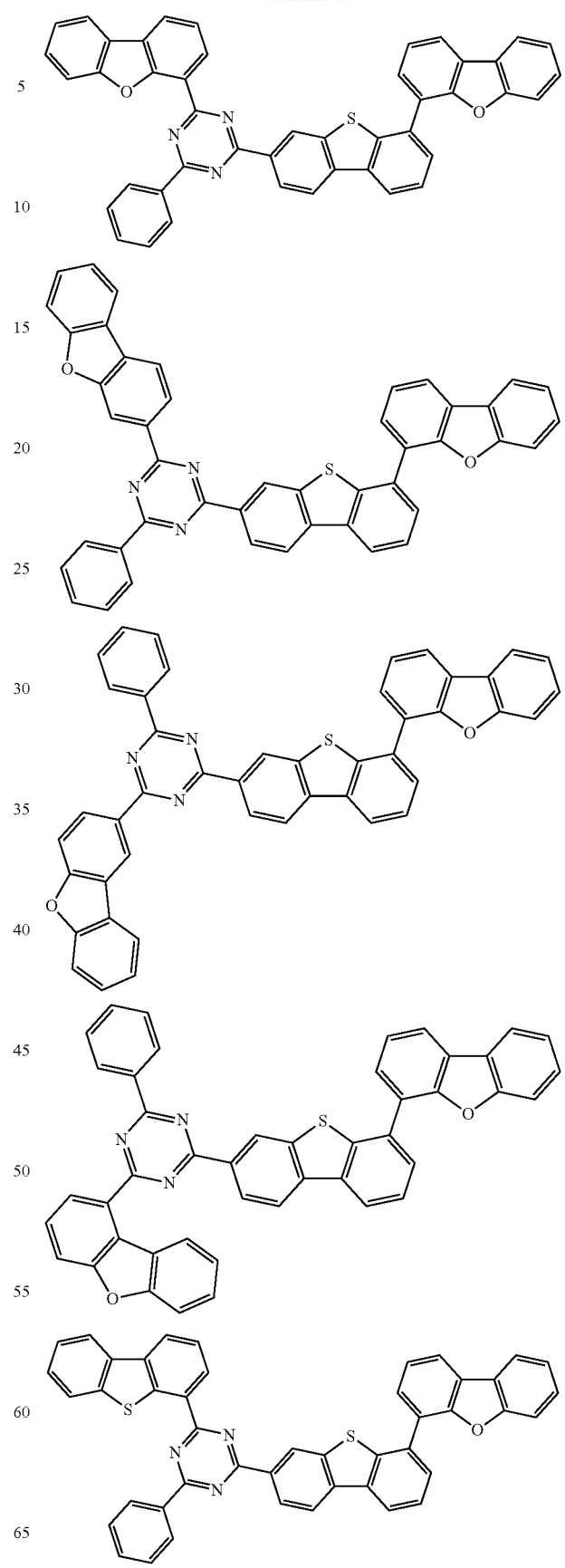

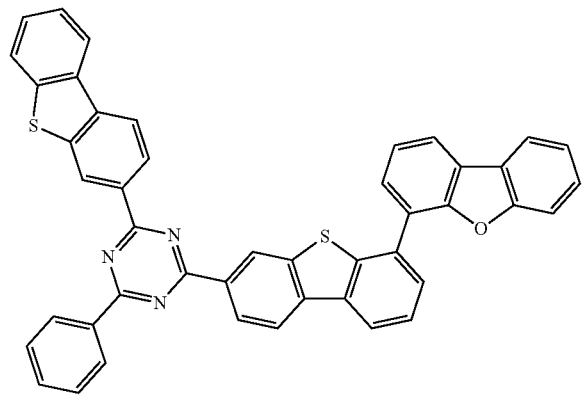
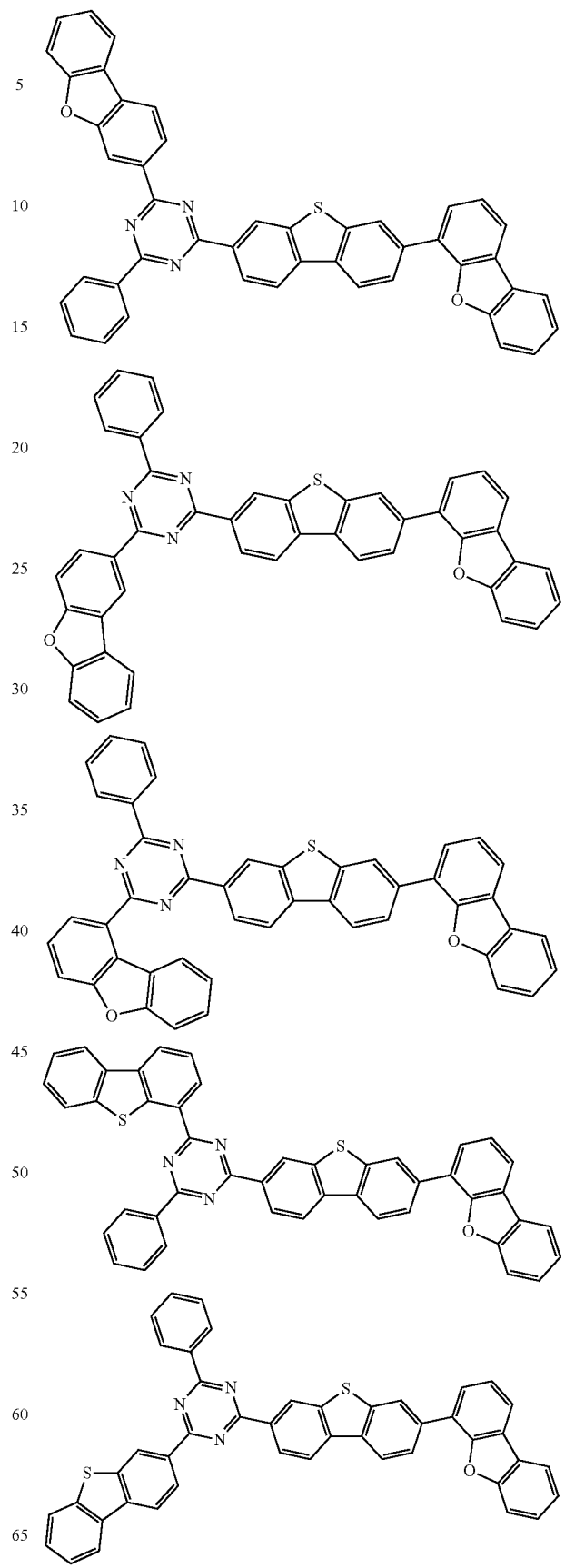

237
-continued
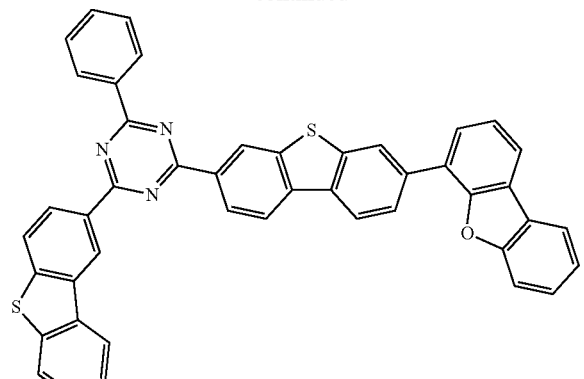
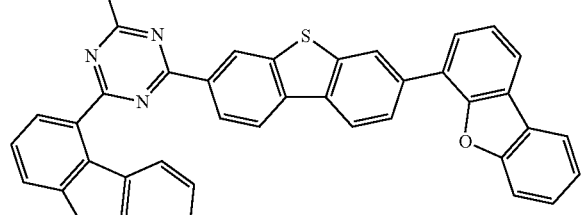
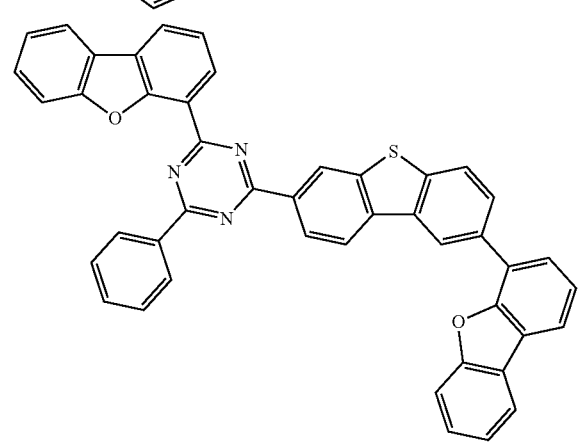
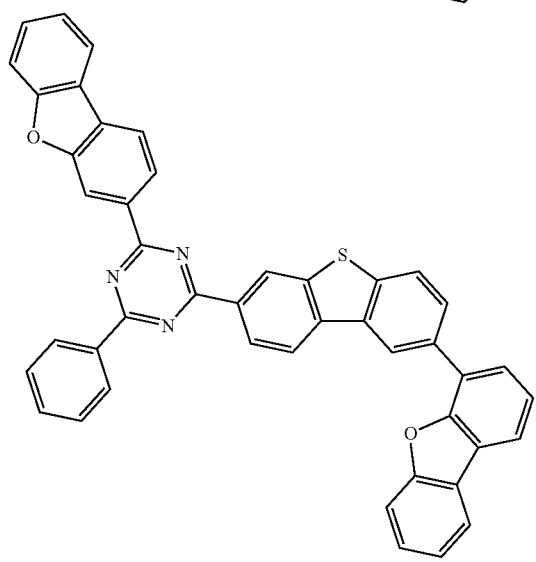
238
-continued
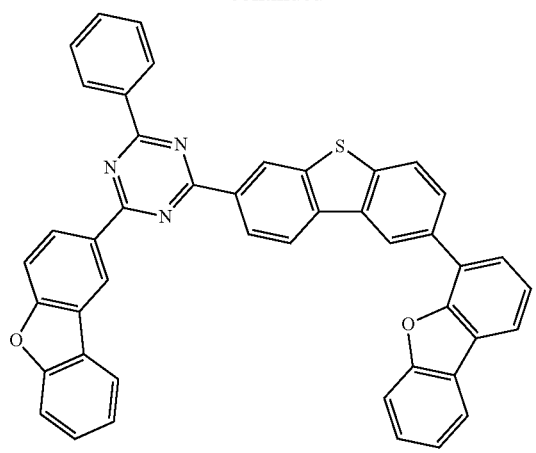
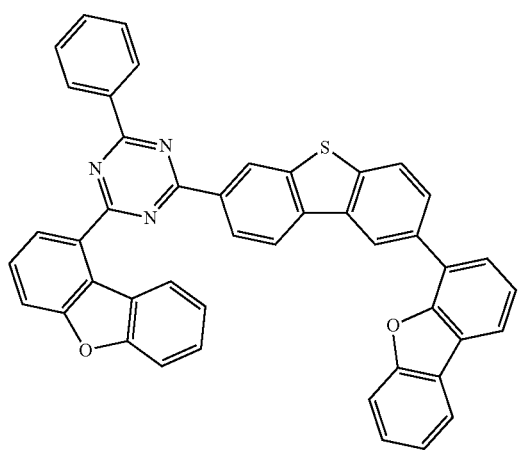
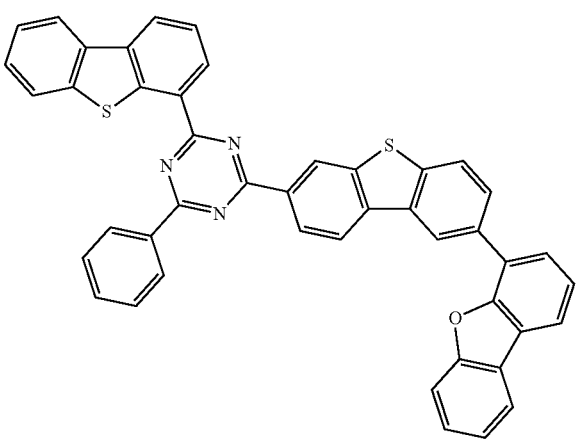

-continued
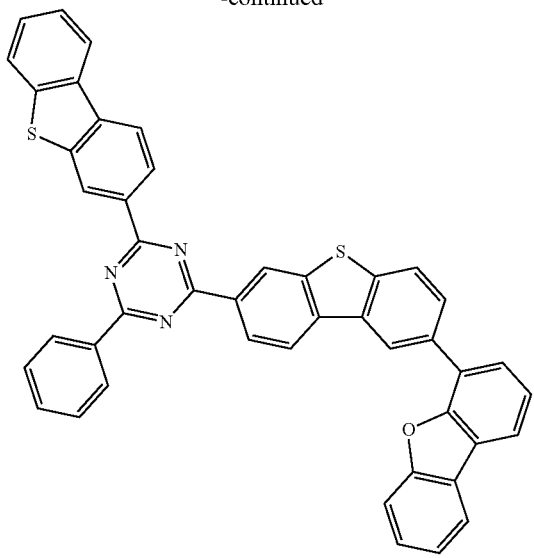
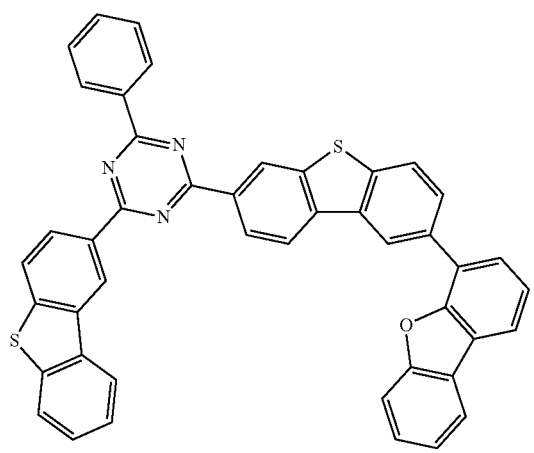
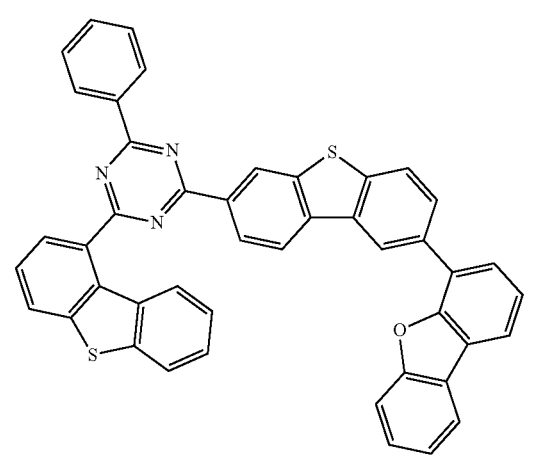
-continued
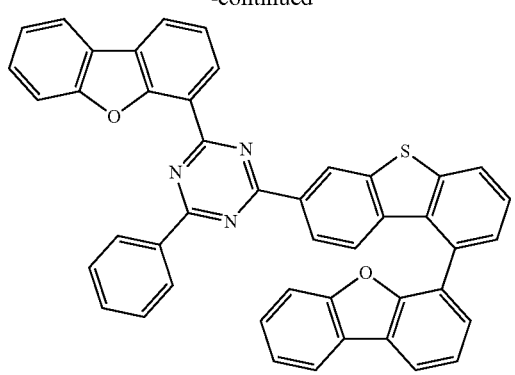
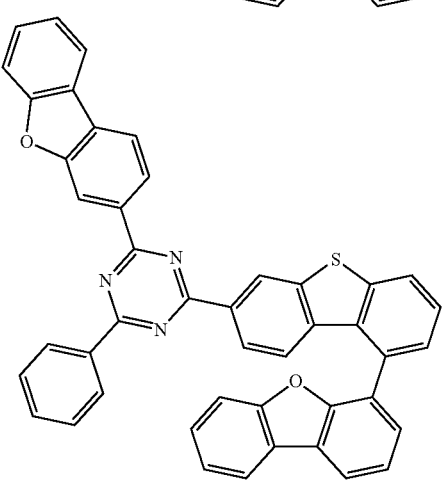

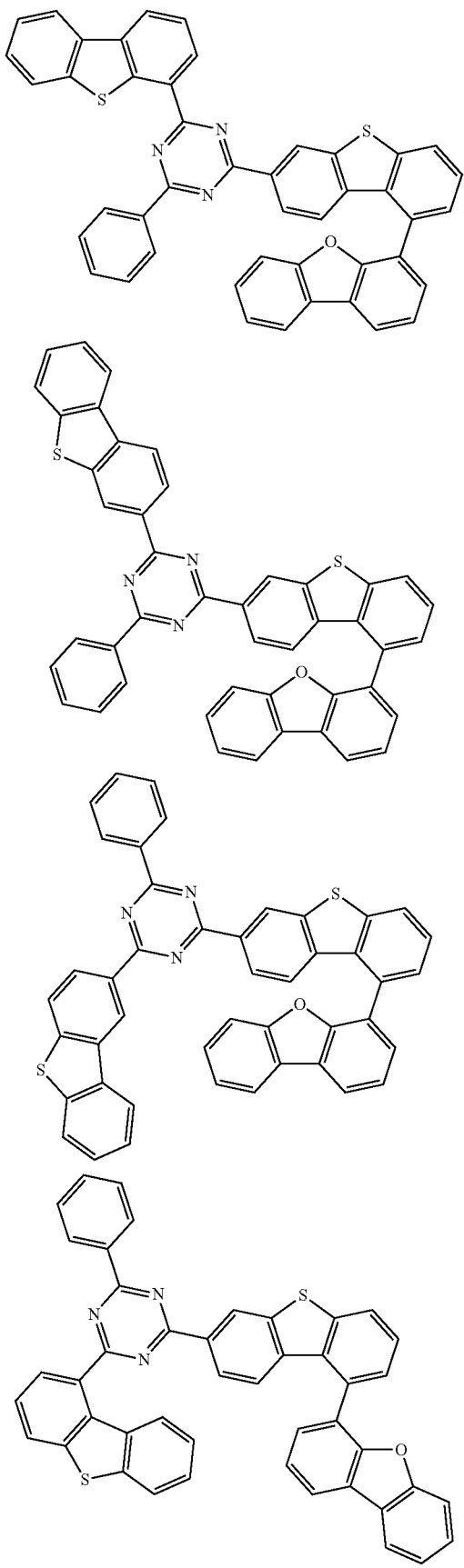
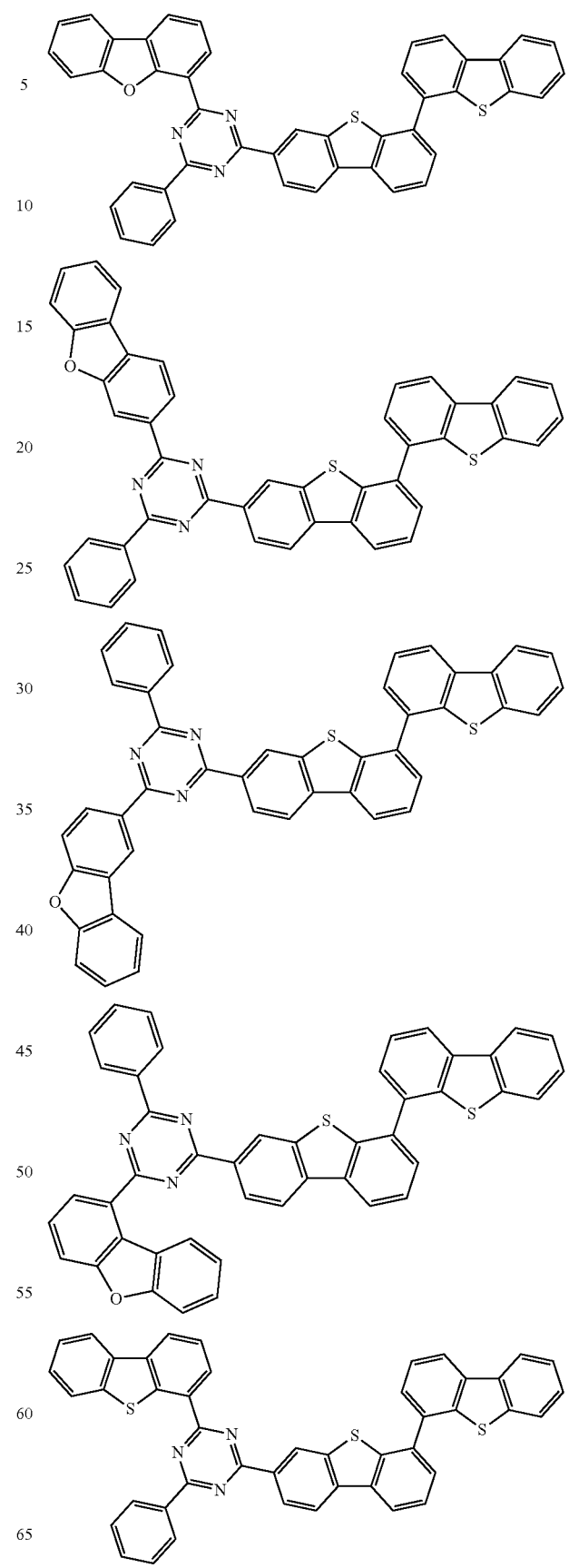

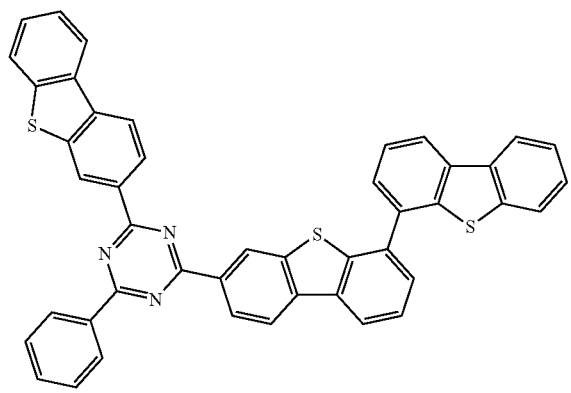
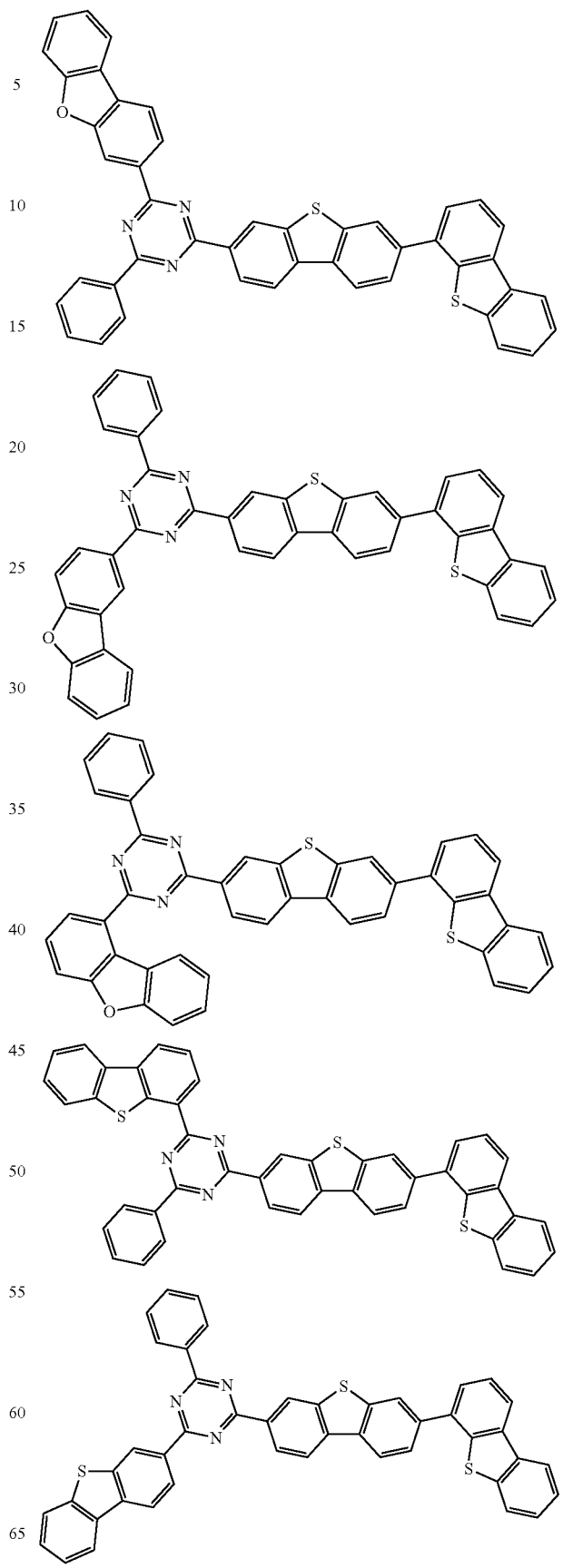

245
-continued
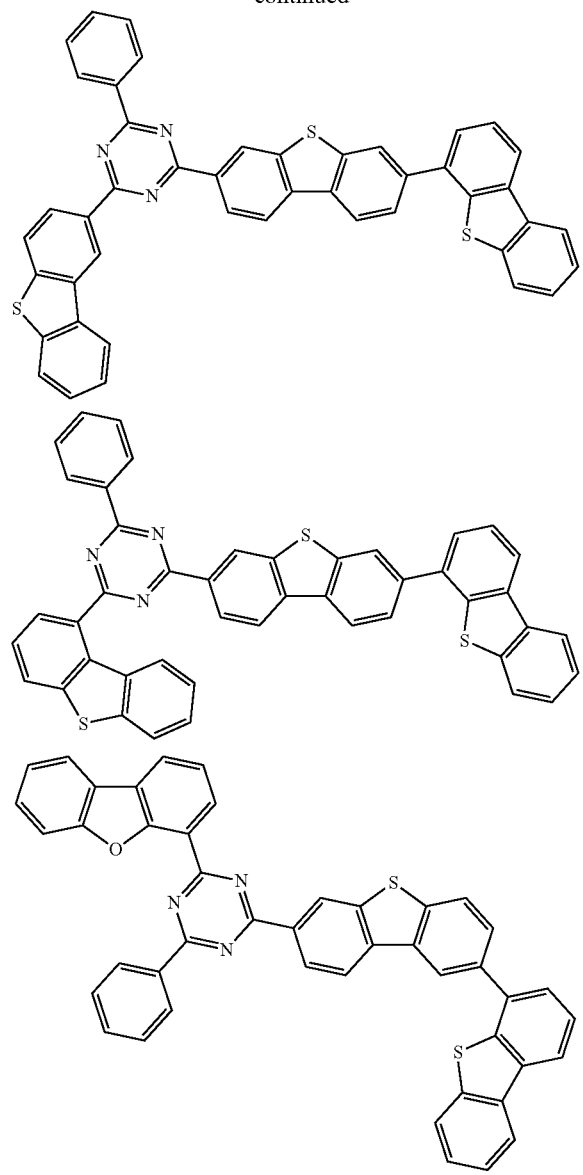
246
-continued
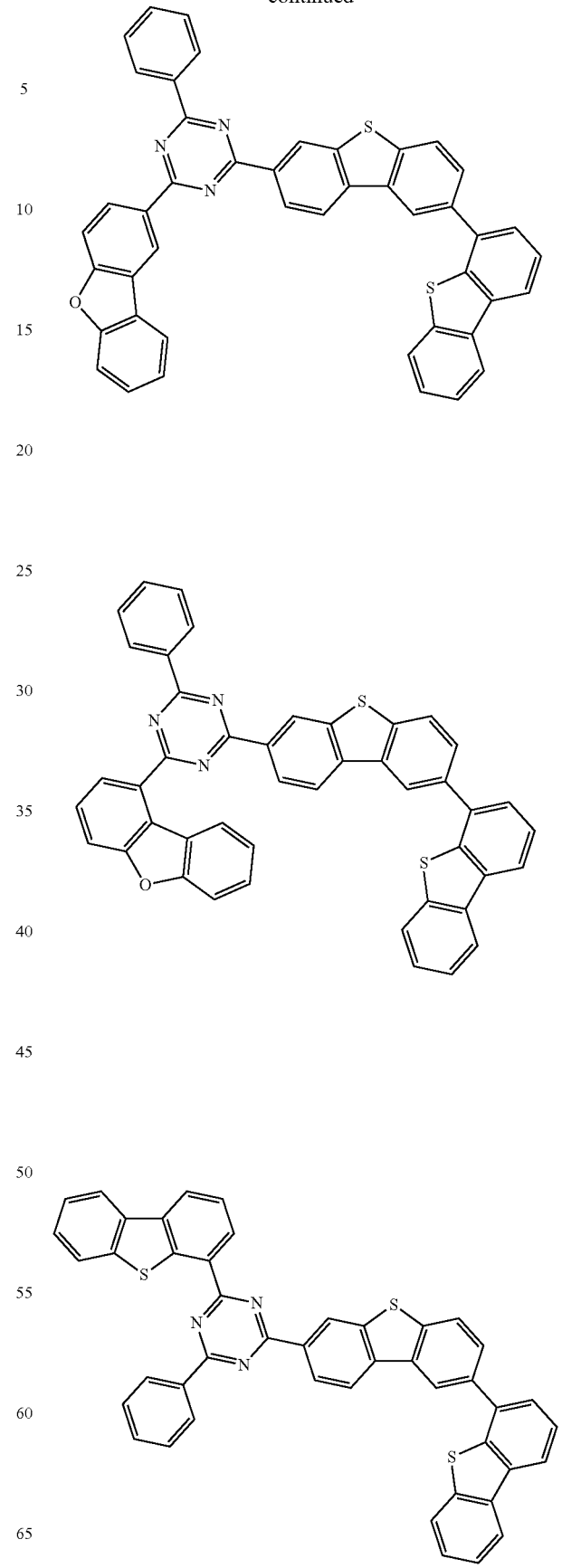

247
-continued
248
-continued
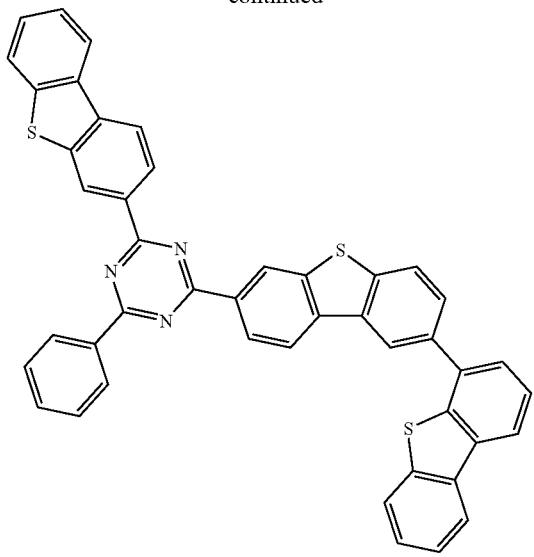
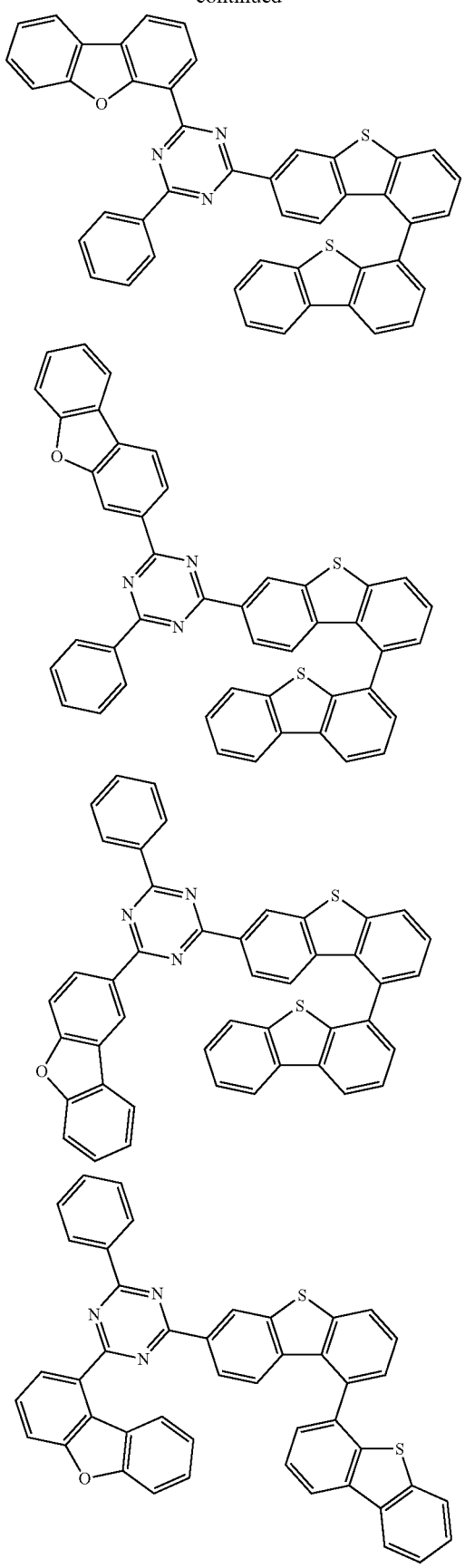

249
-continued
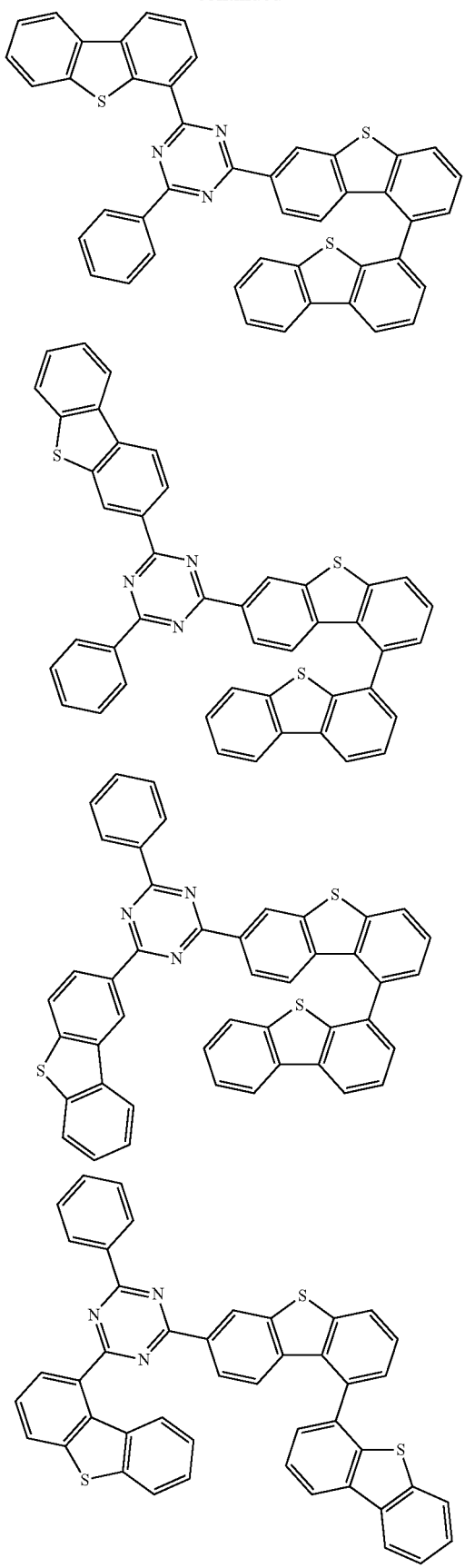
250
-continued
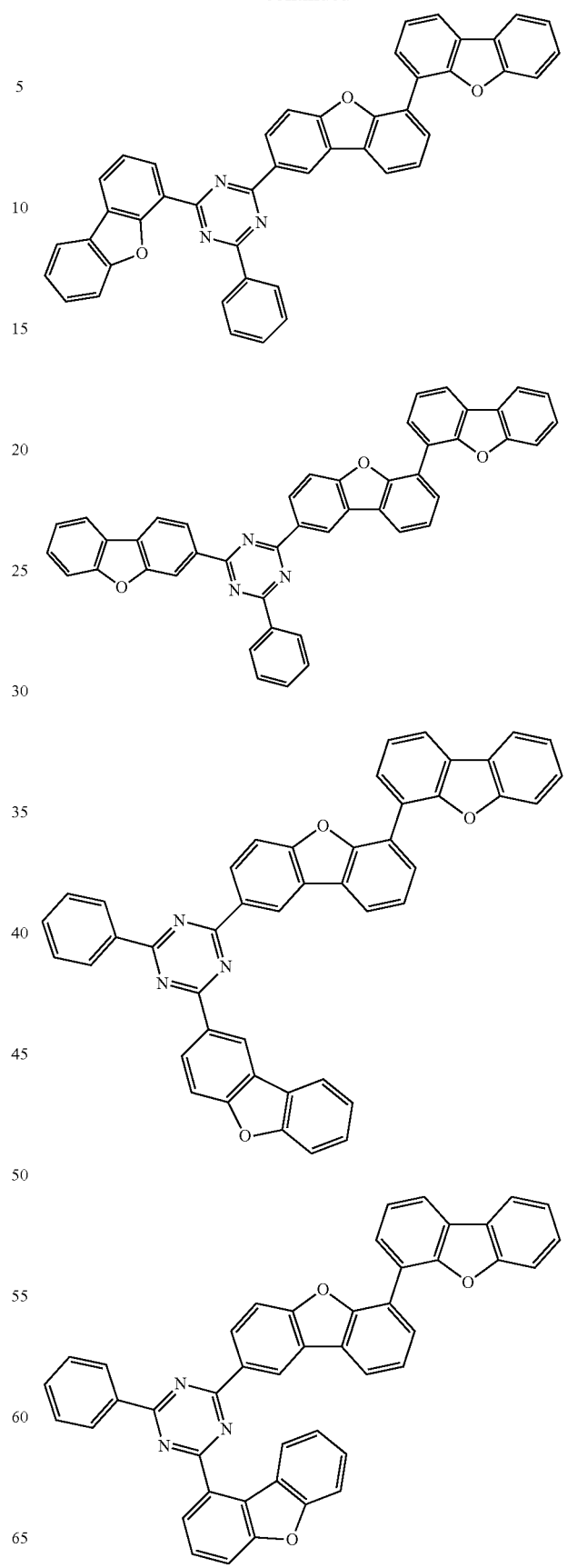

251
-continued
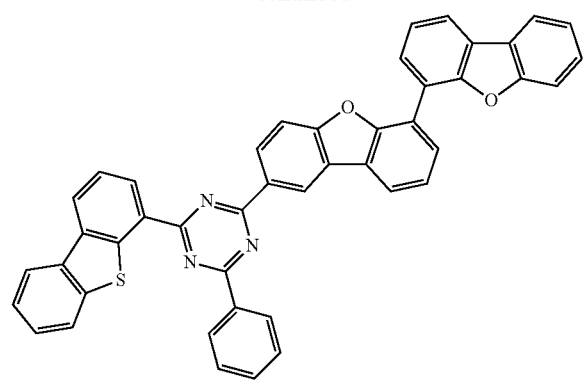
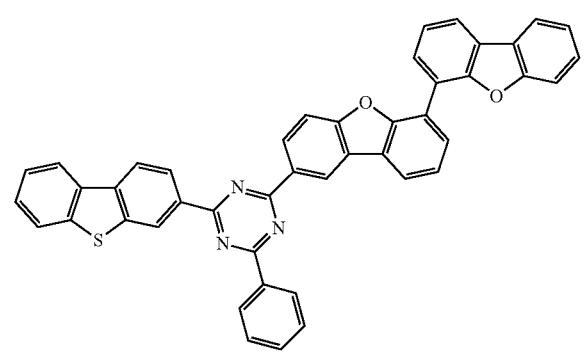
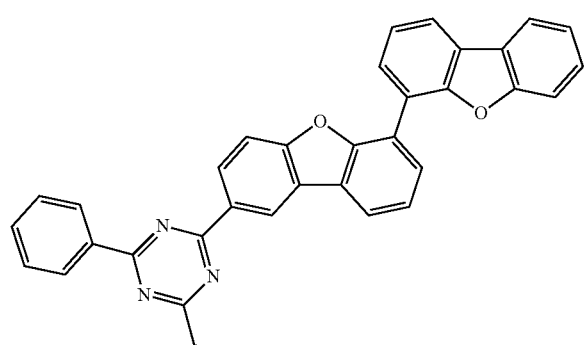
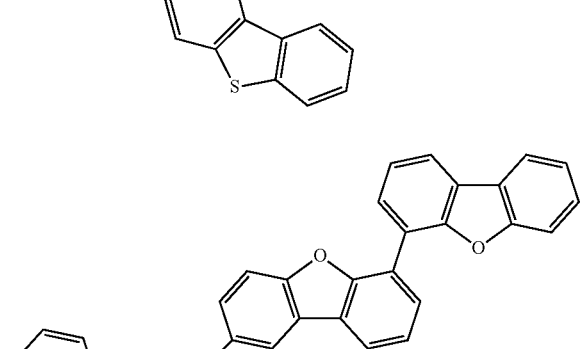
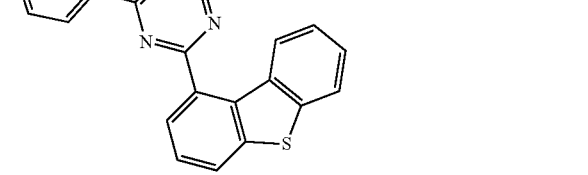
252
-continued
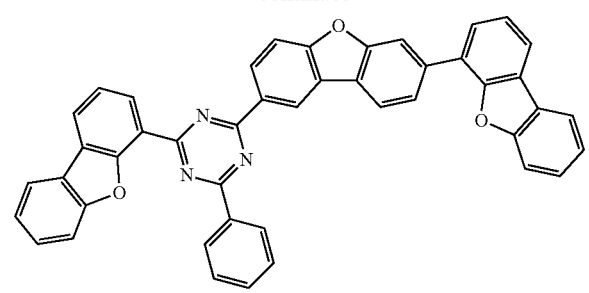
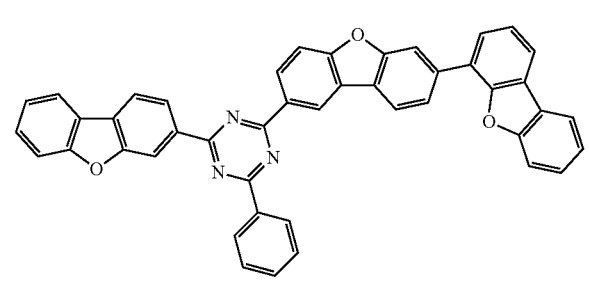
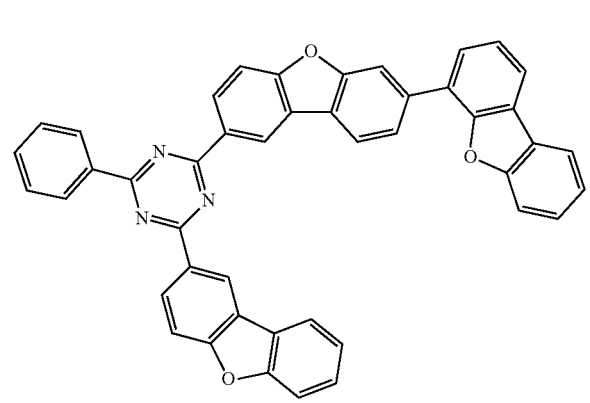
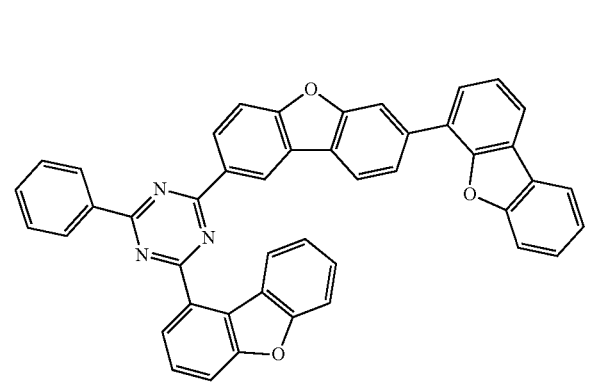
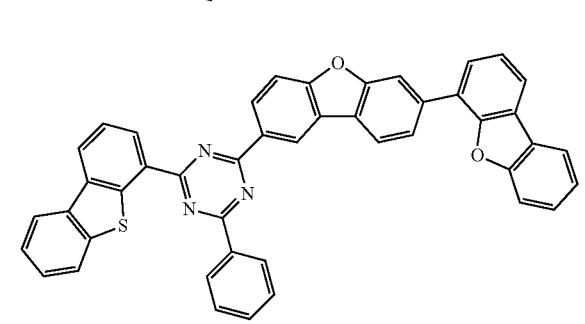

253
-continued
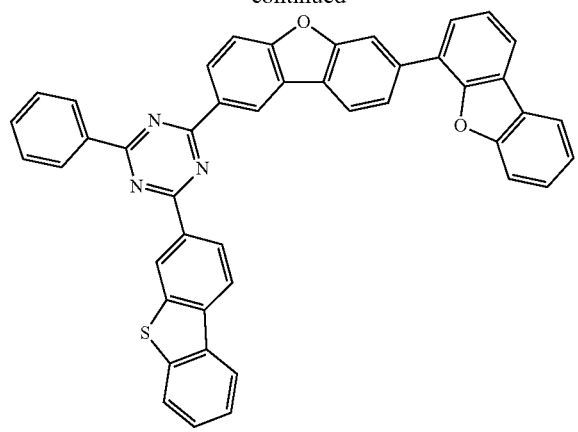
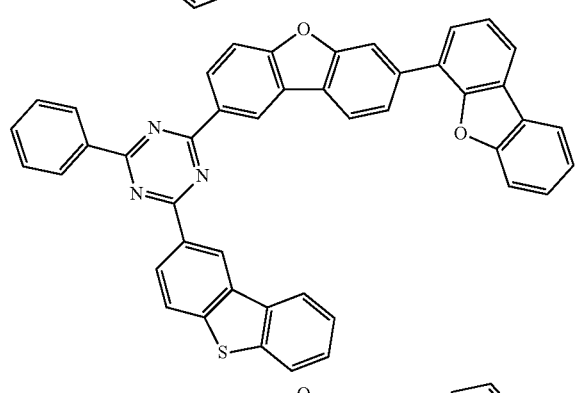
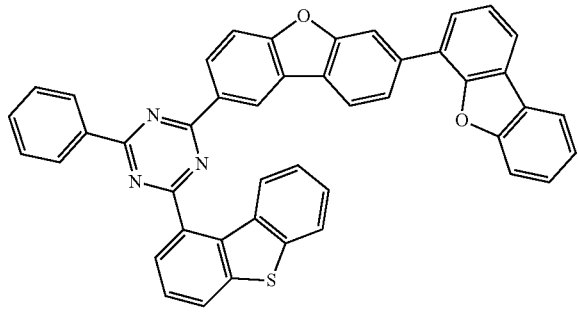
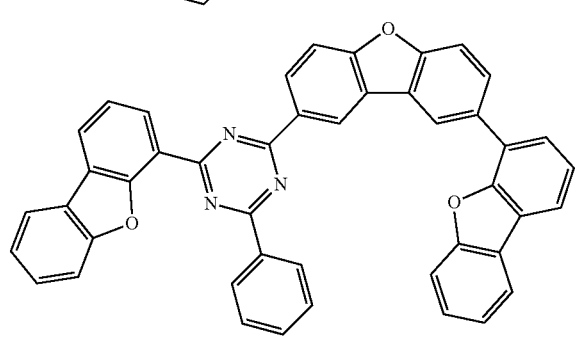
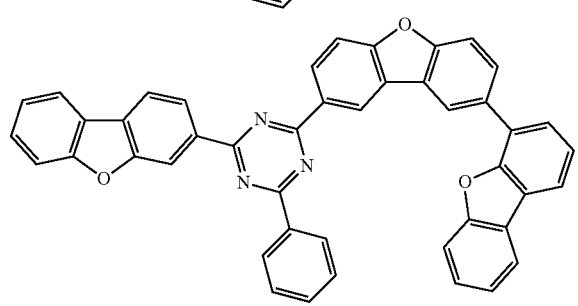
254
-continued
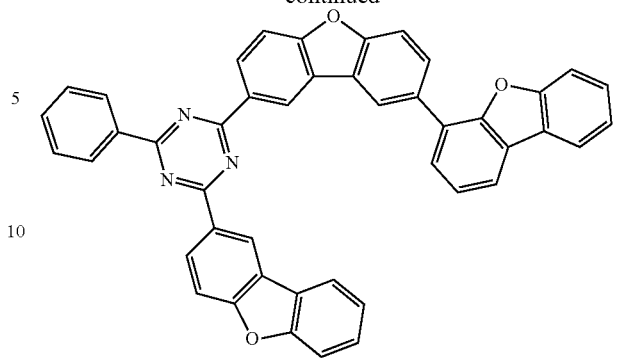
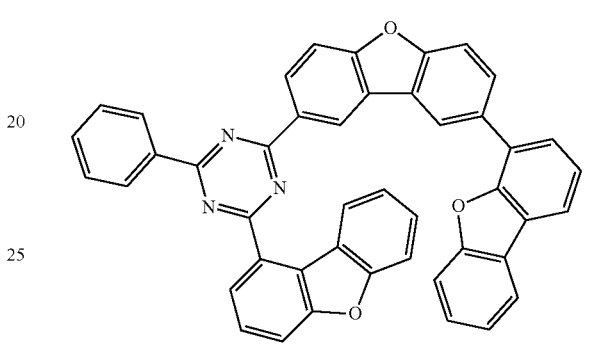
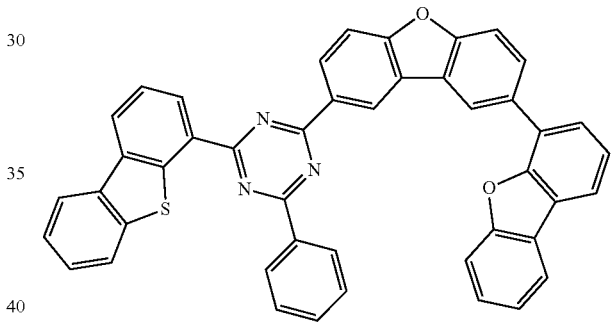
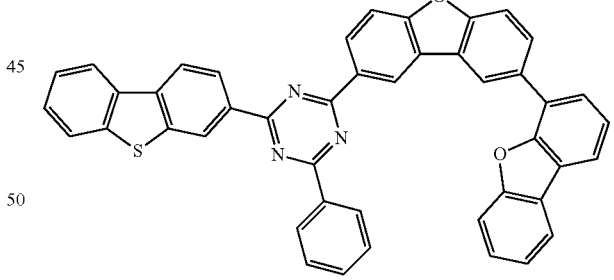
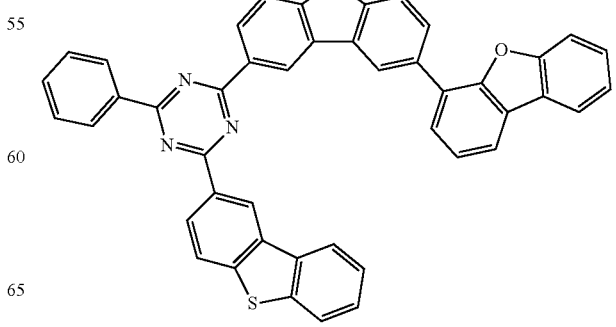

255
-continued
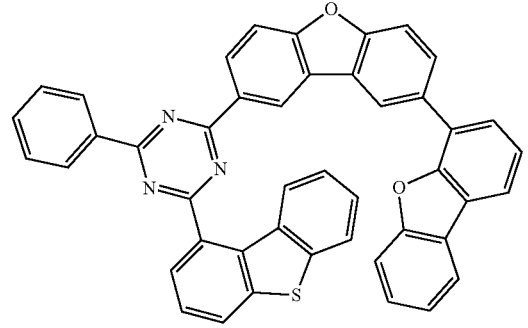
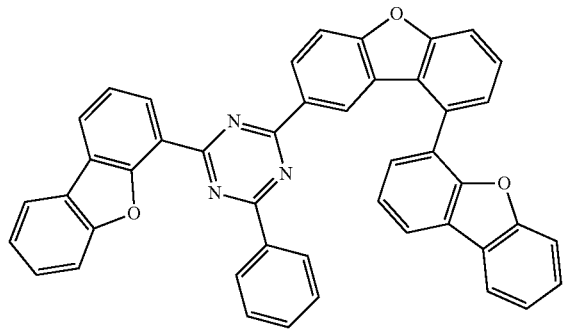
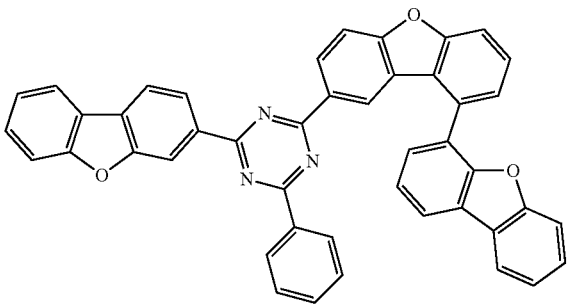
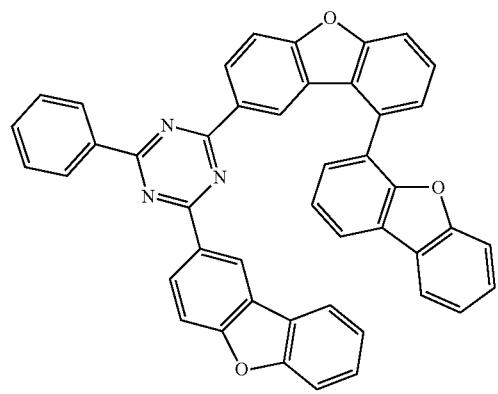
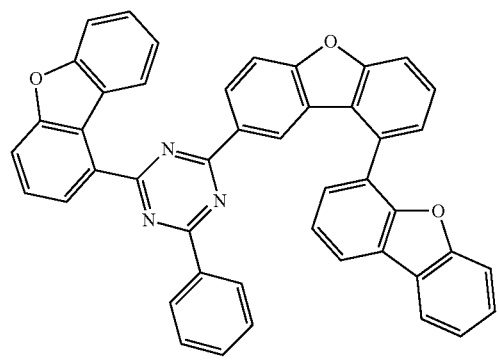
256
-continued
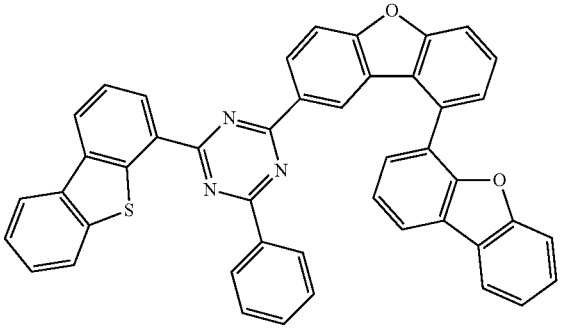
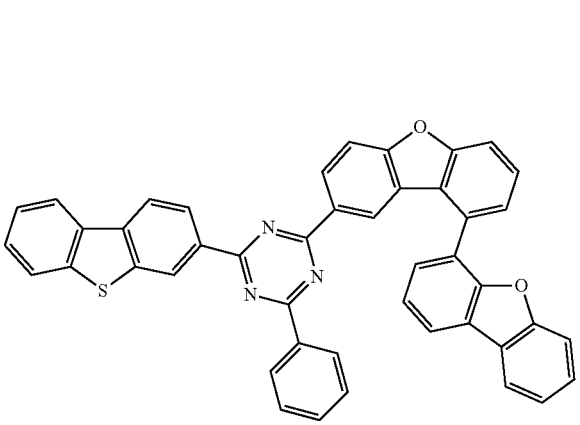
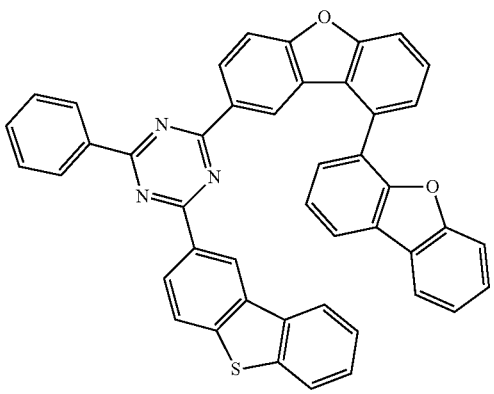
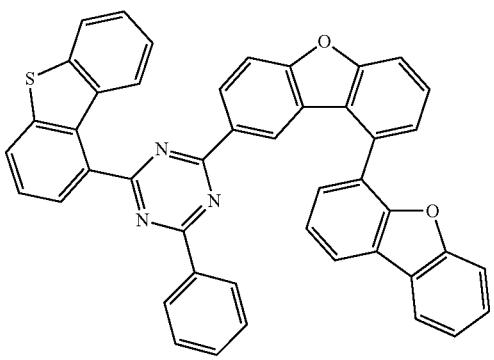

257
-continued
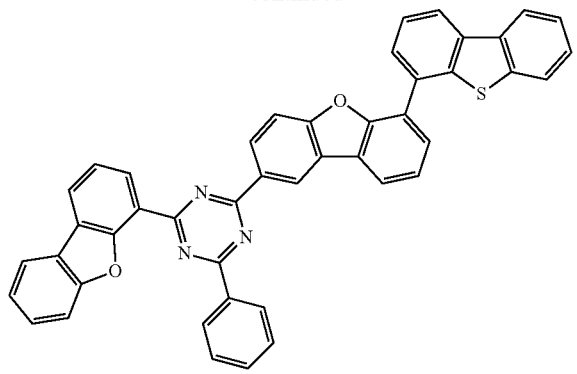
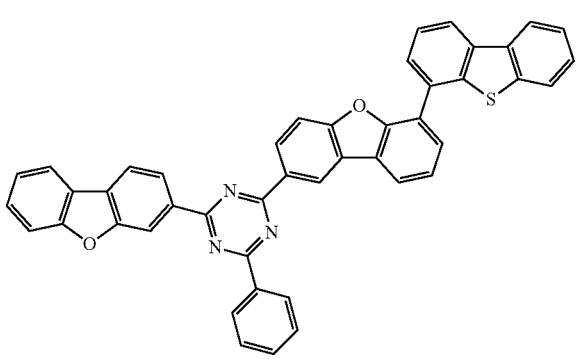
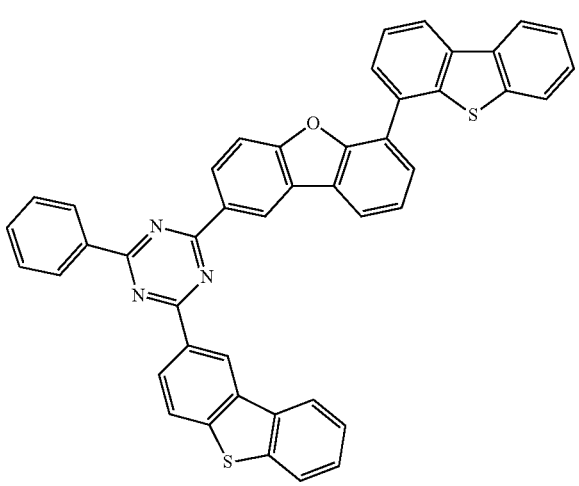
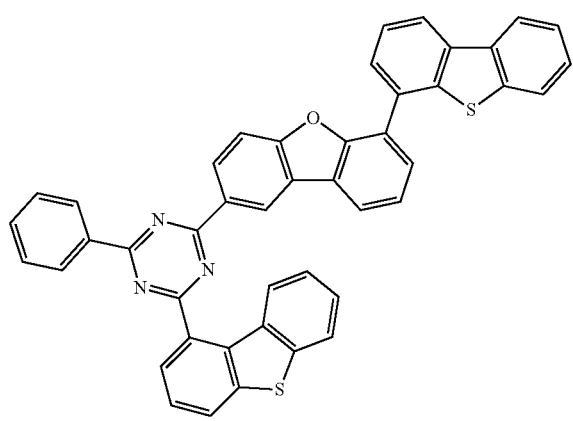
258
-continued
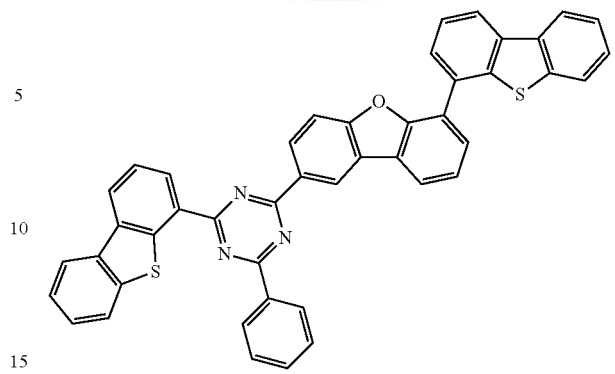
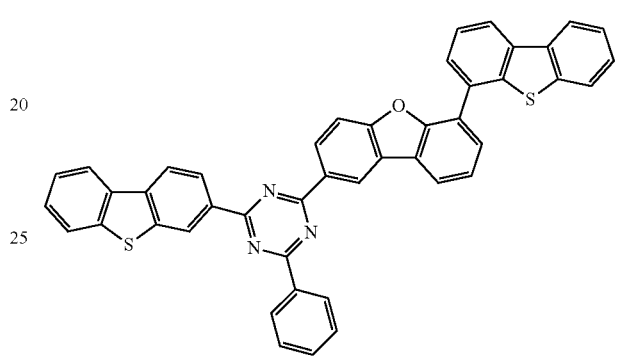
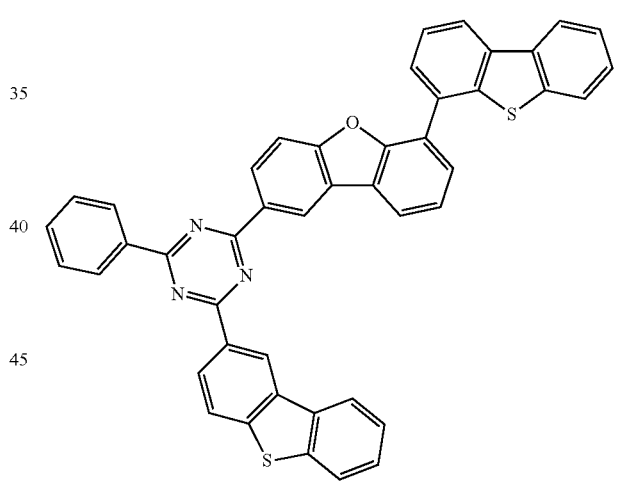
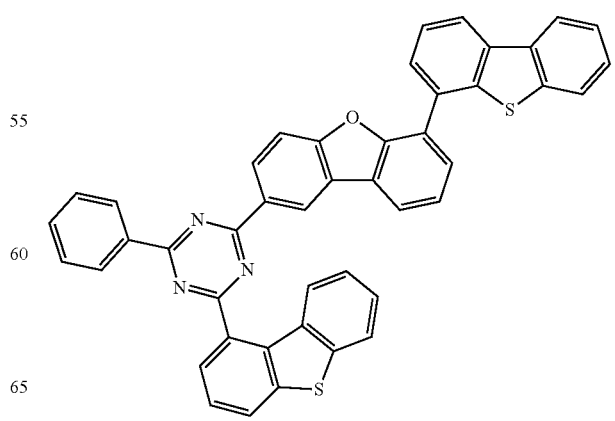

259
-continued
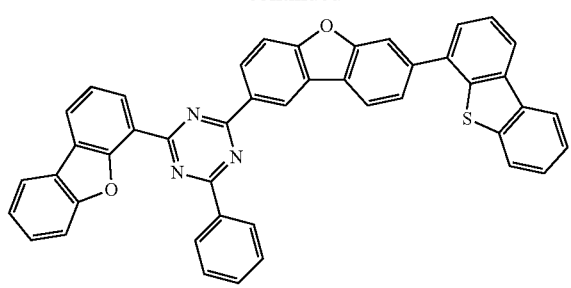
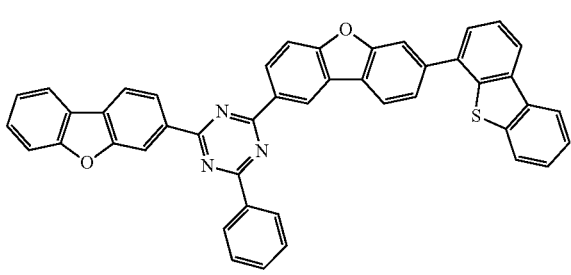
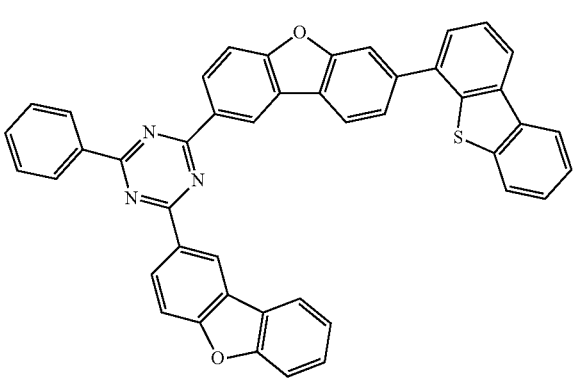
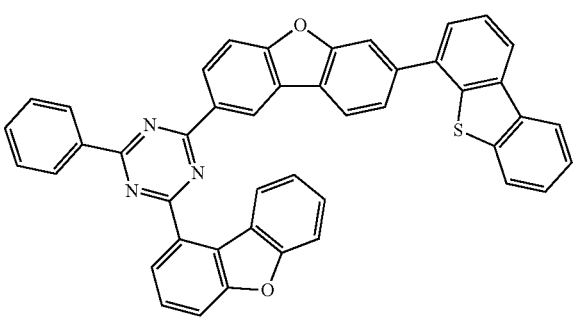
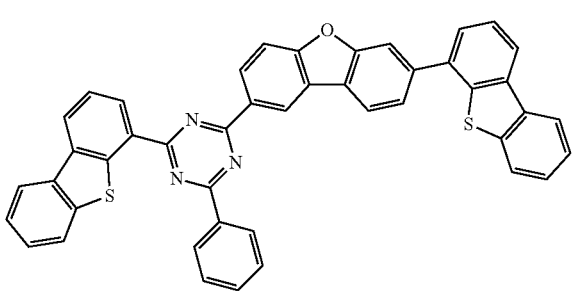
260
-continued
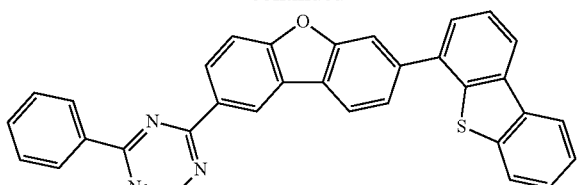
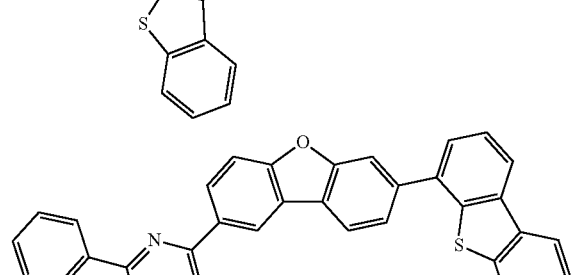
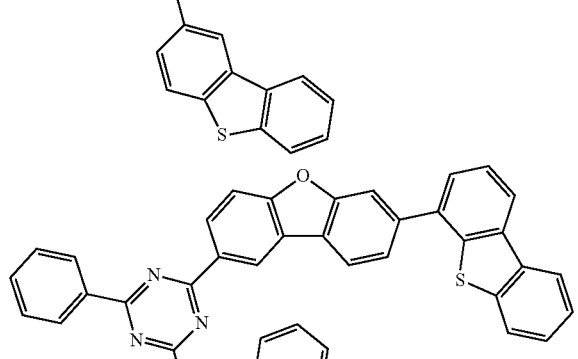
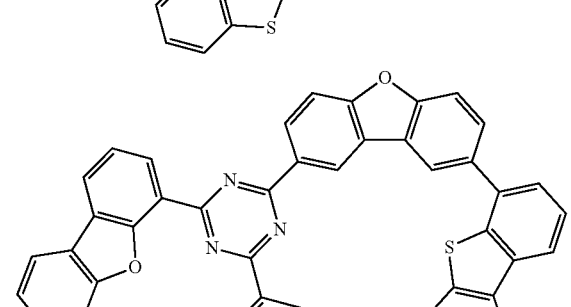
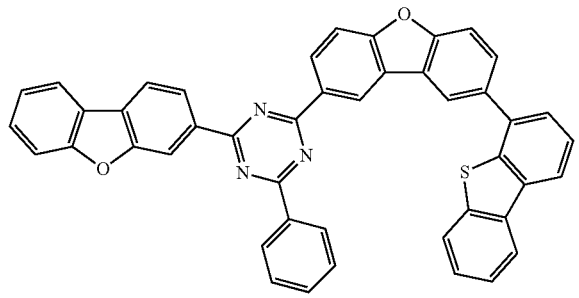

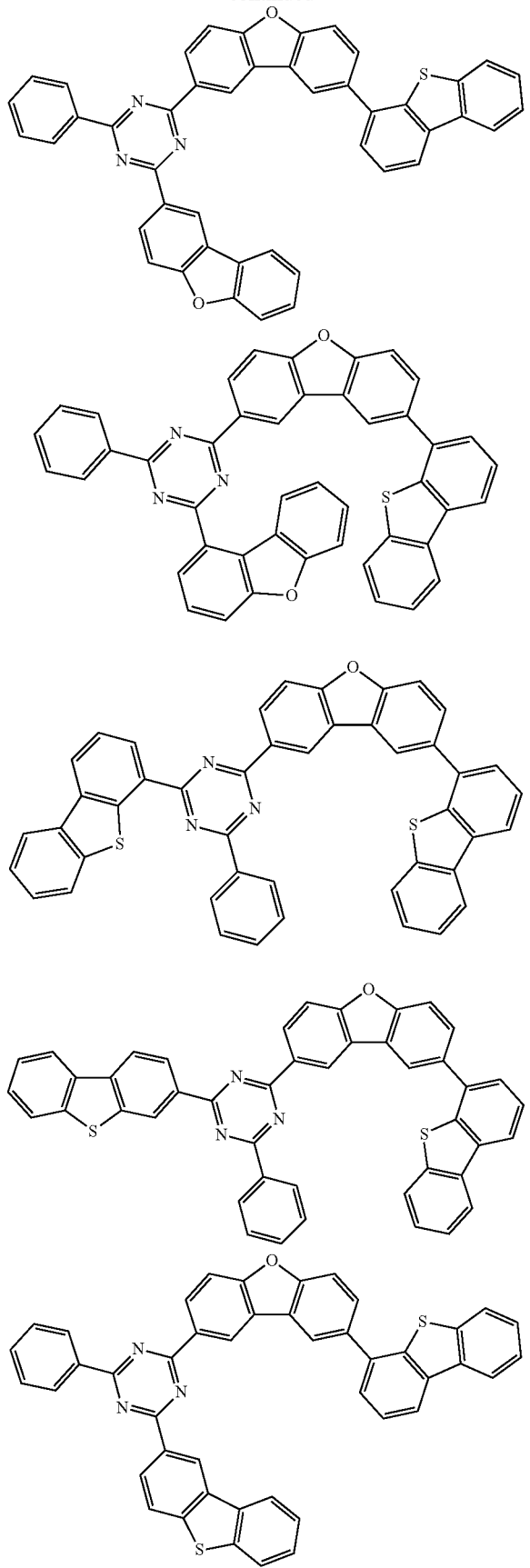
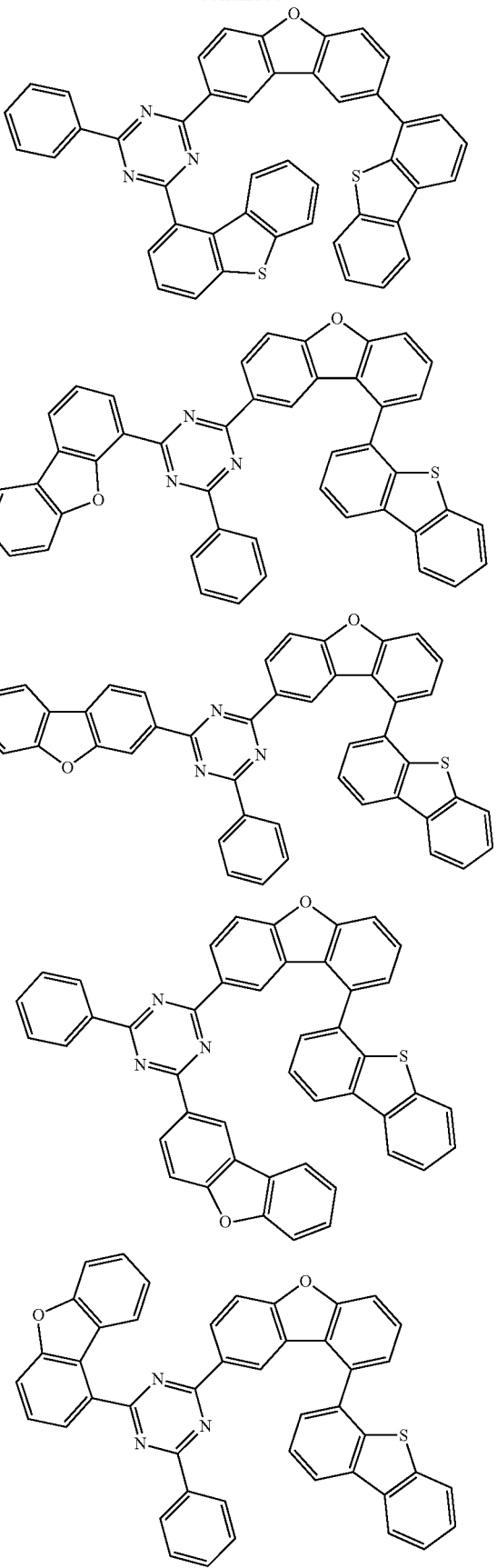

263
-continued
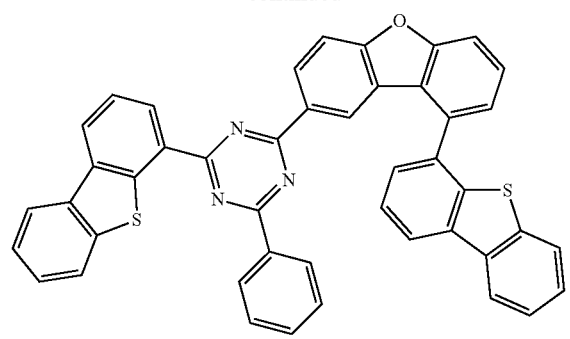
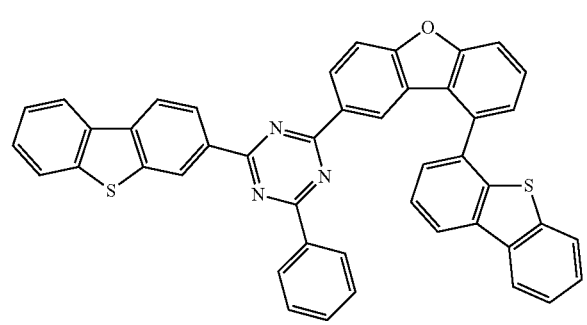
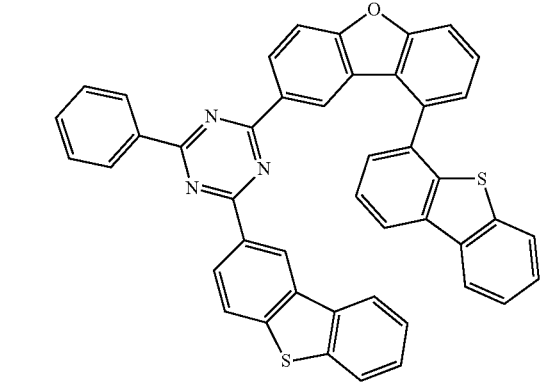
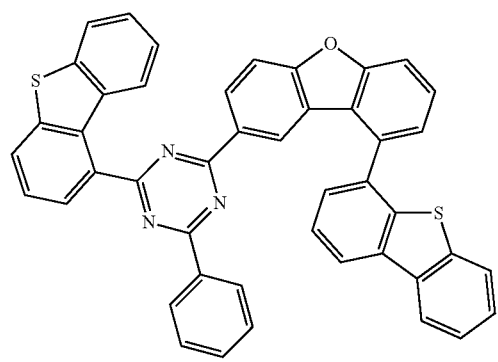
264
-continued
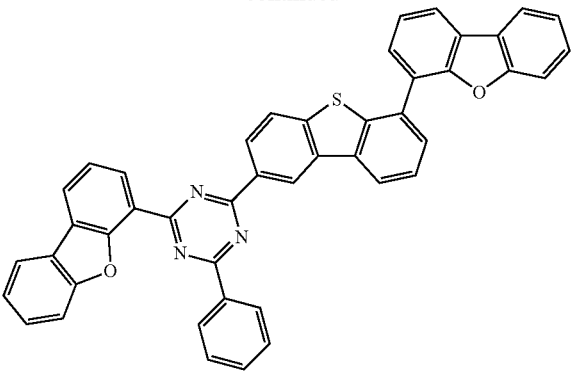

265
-continued
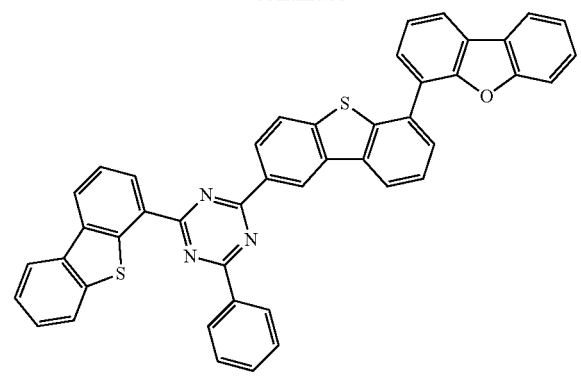
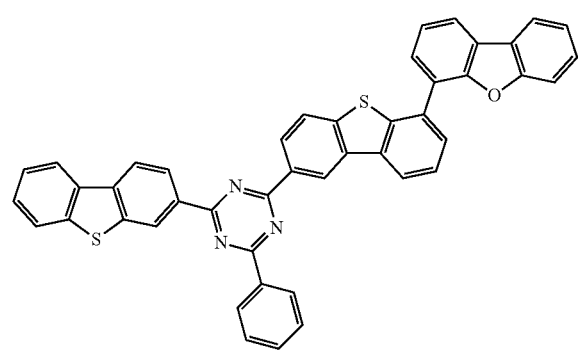
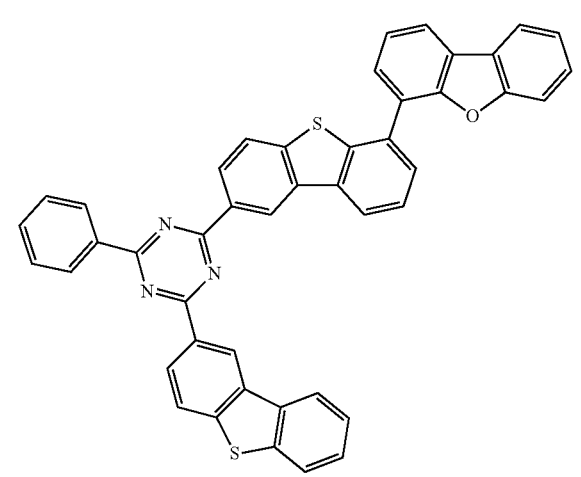
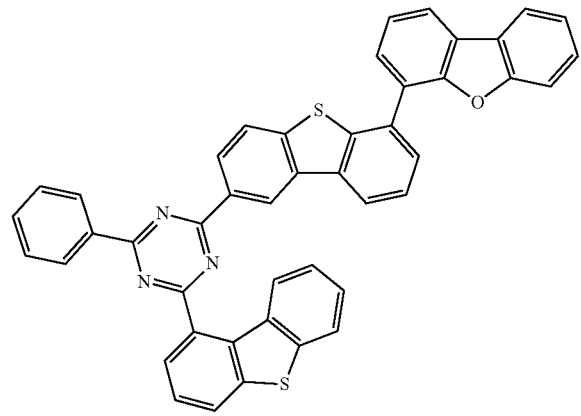
266
-continued
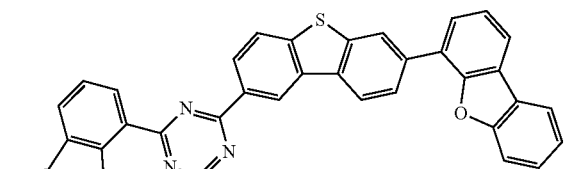
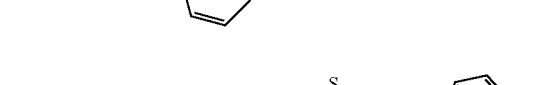
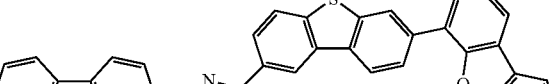
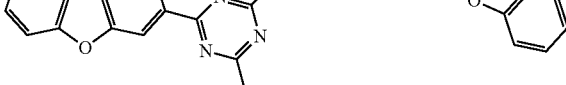

-continued
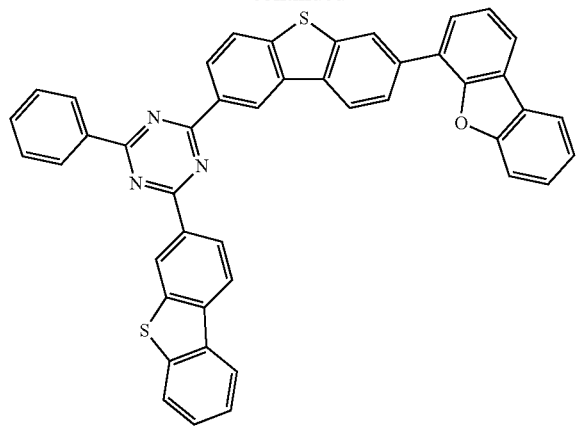
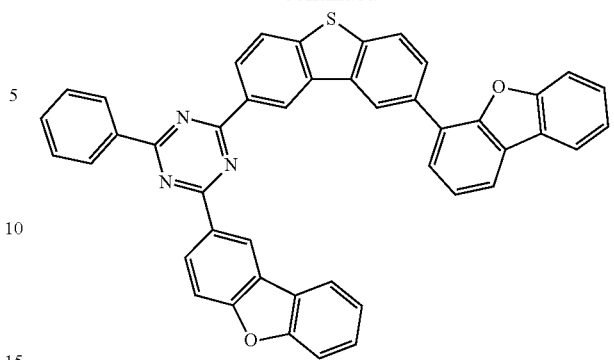
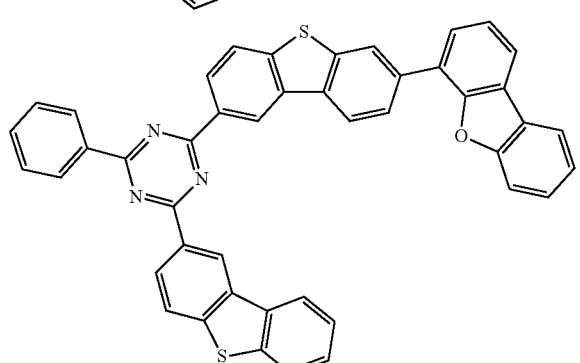
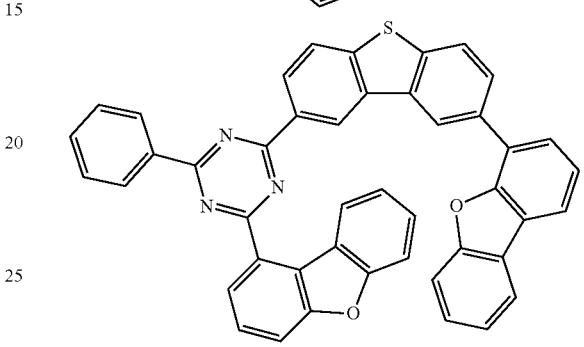
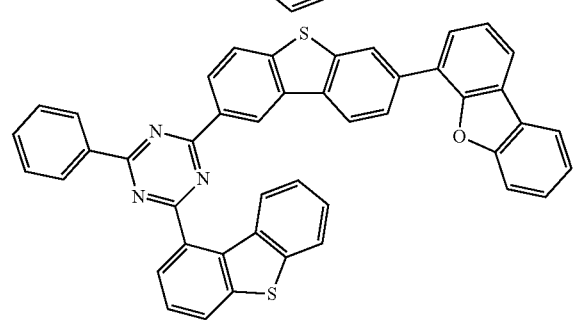
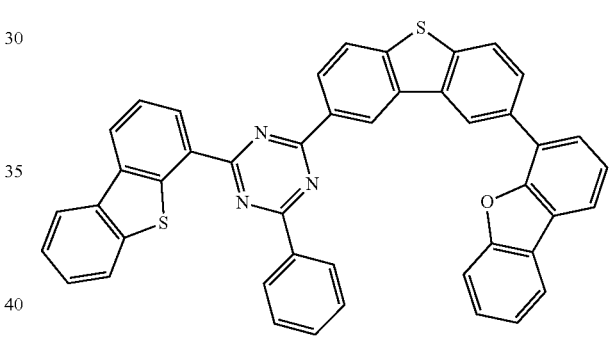
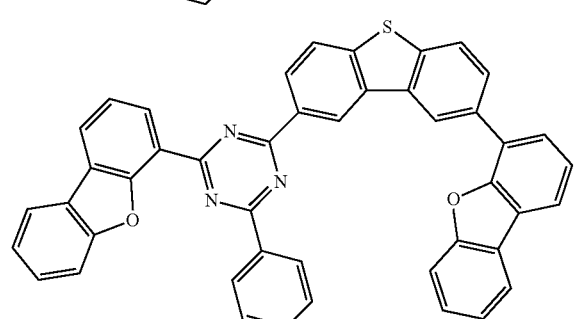
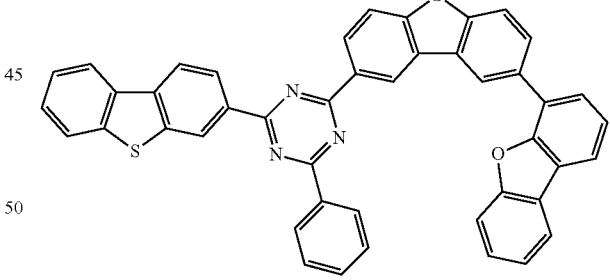
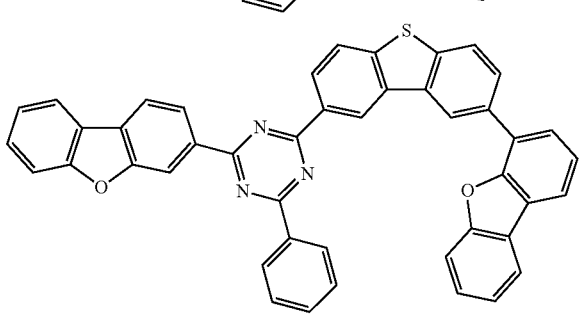
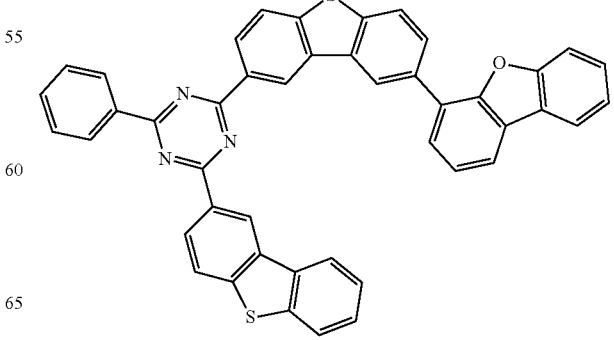

269
-continued
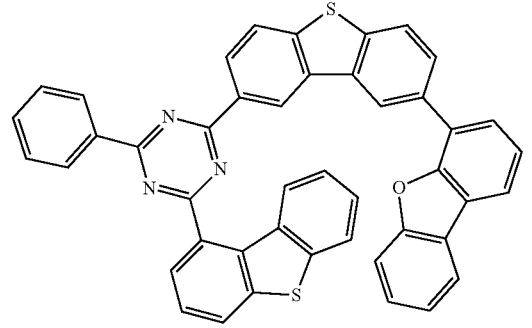
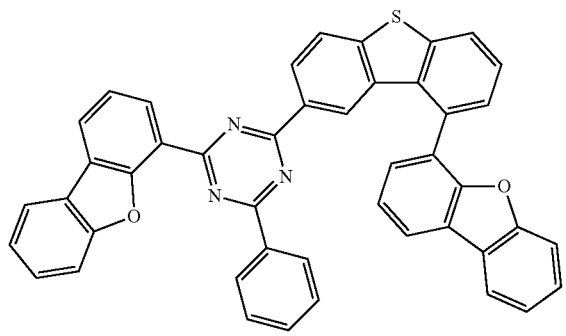
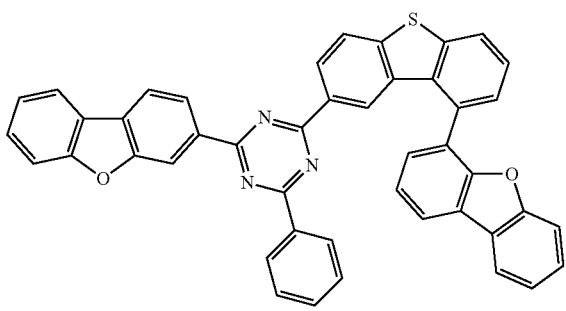
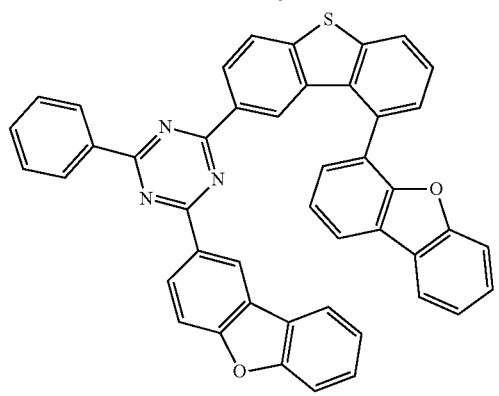
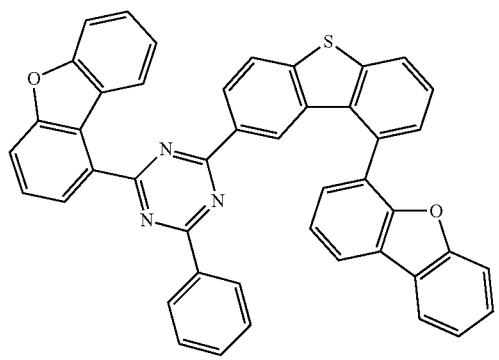
270
-continued
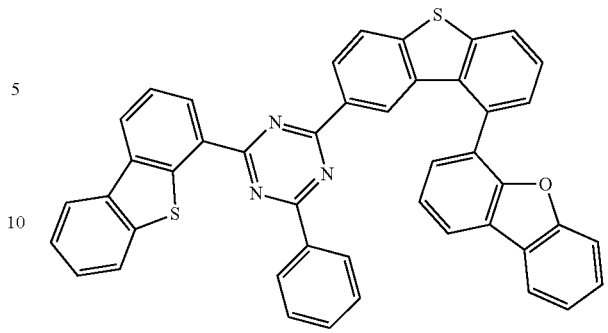
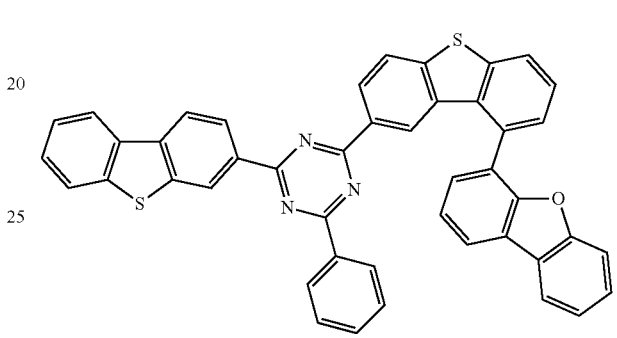
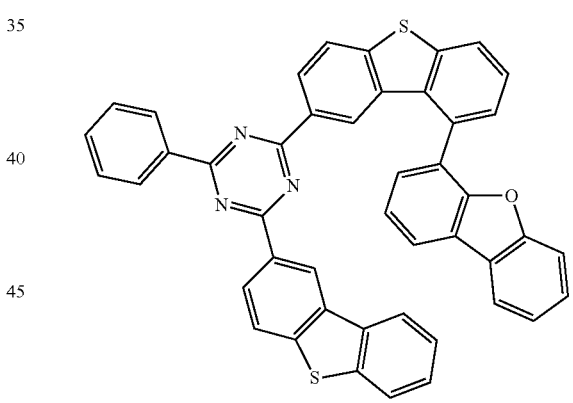
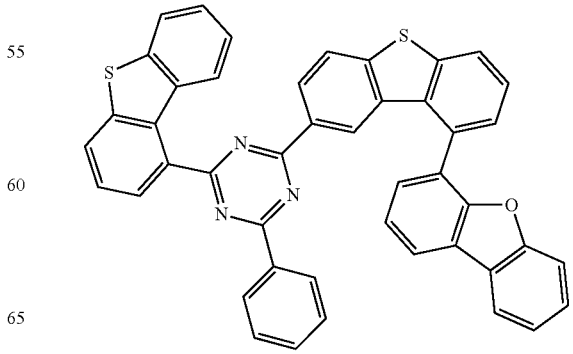

271
-continued
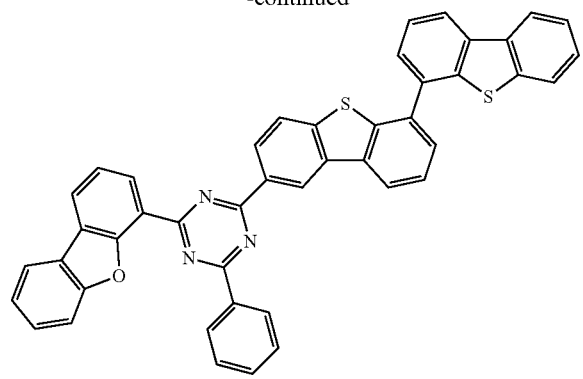
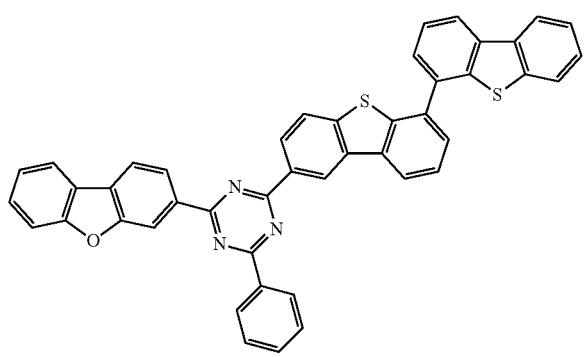
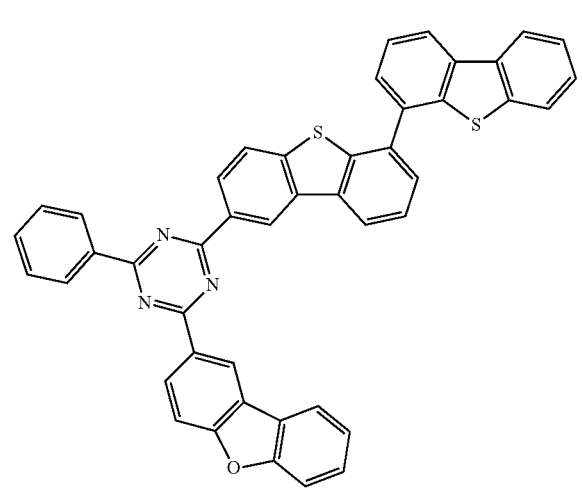
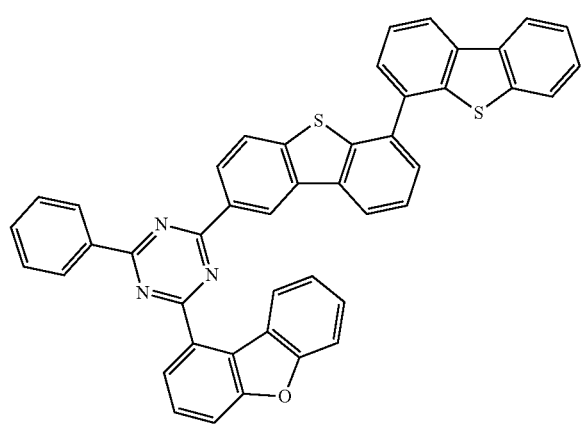
272
-continued
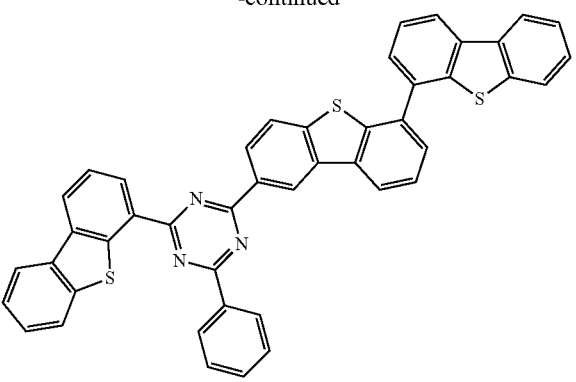
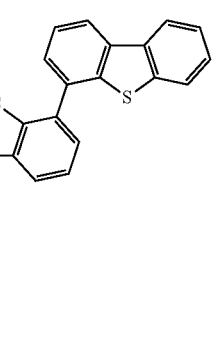
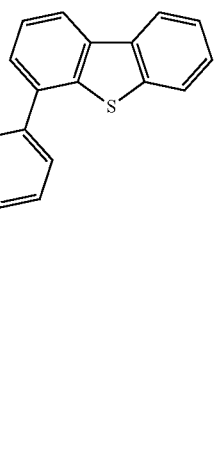
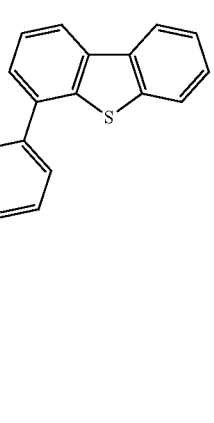

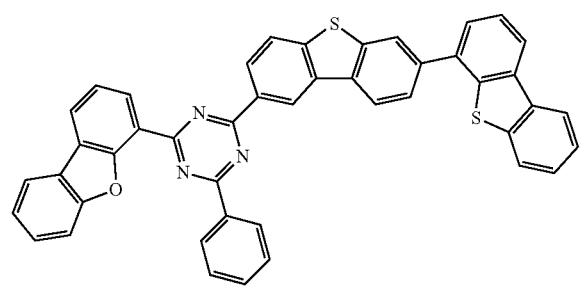
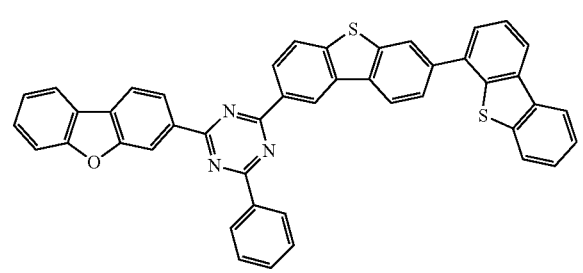
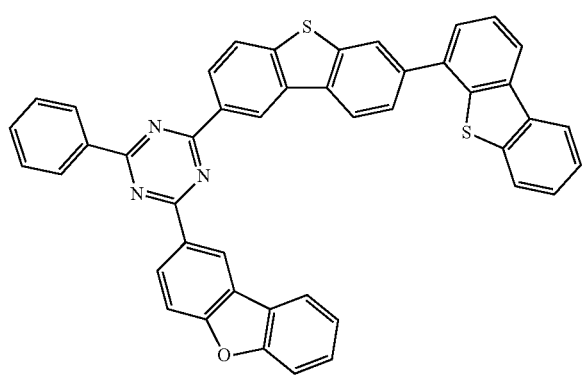
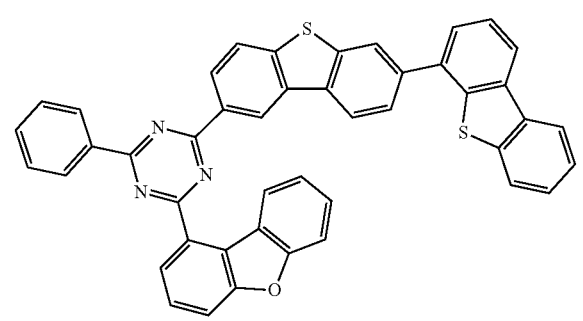
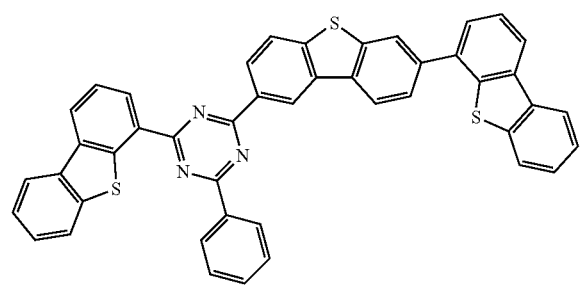
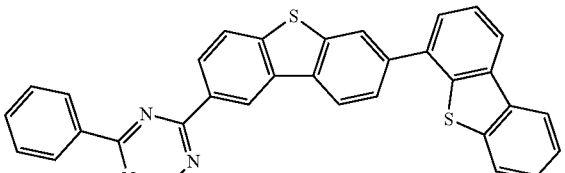
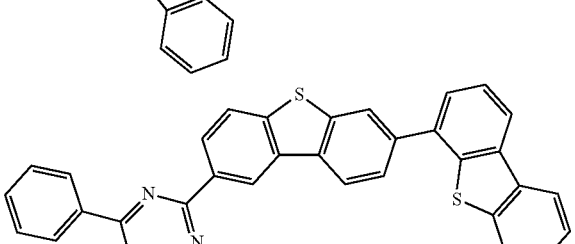
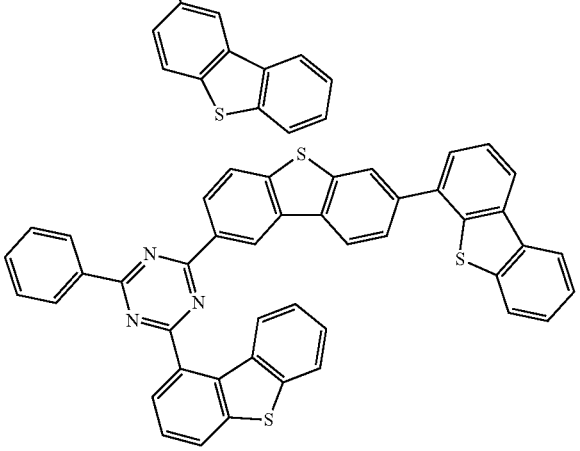
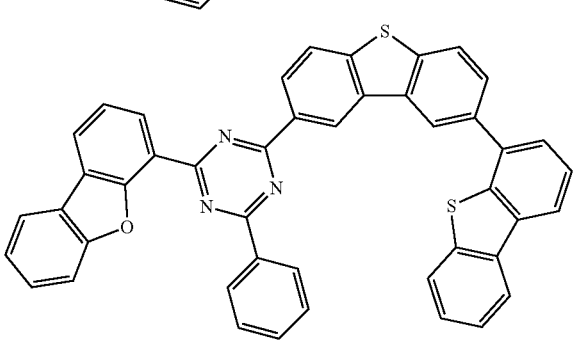
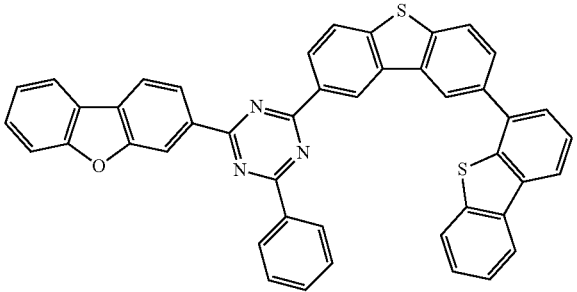

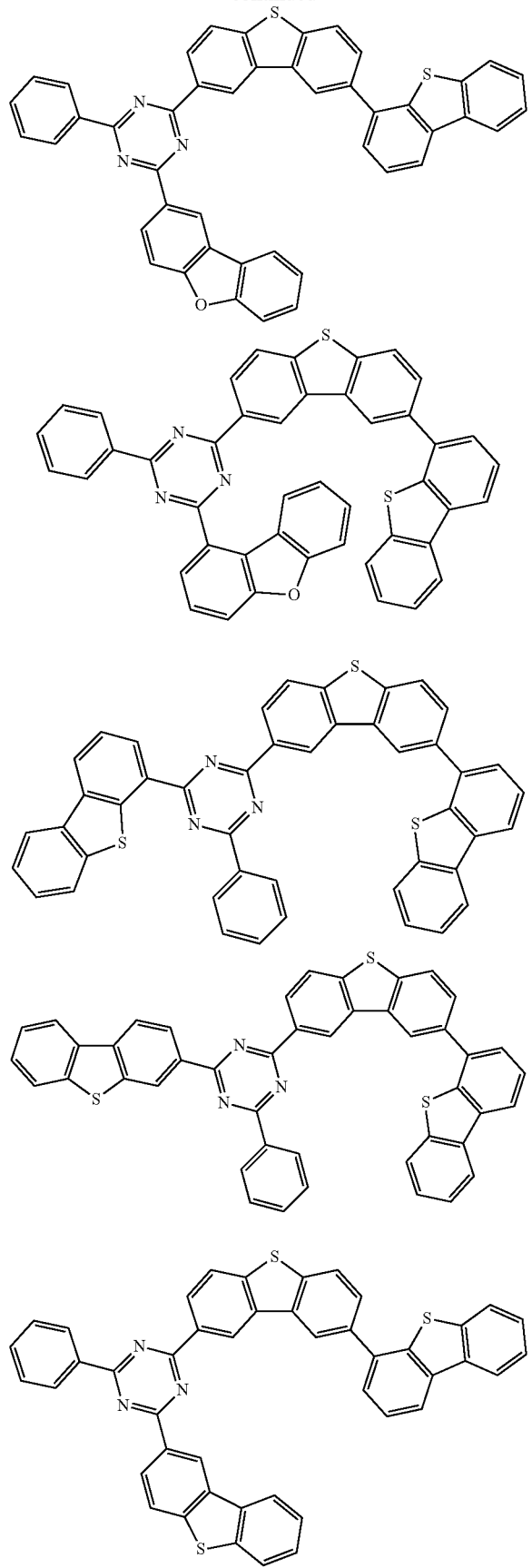
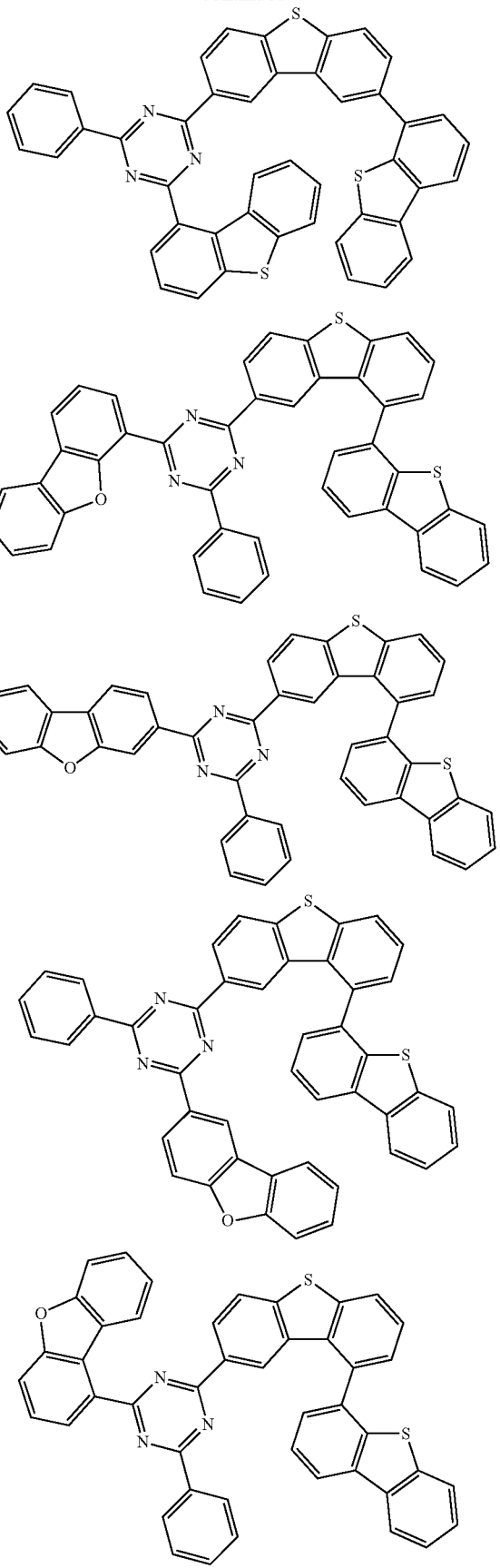

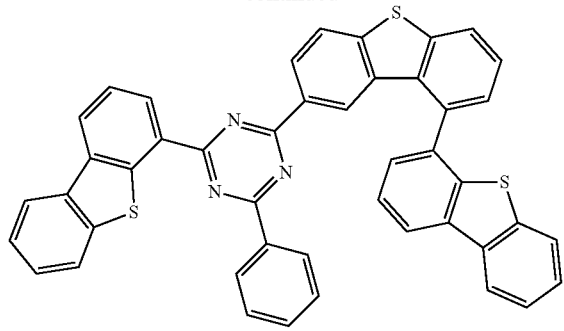
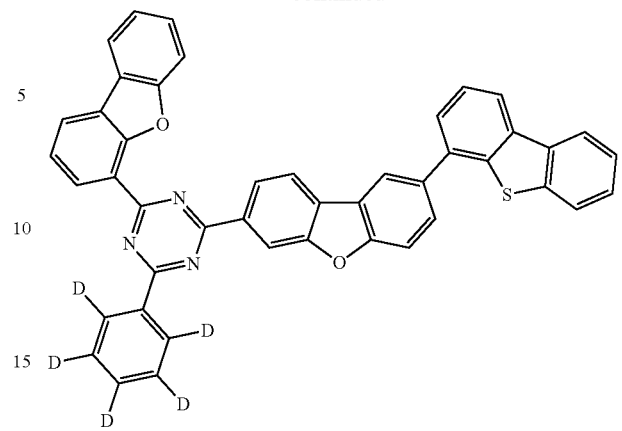
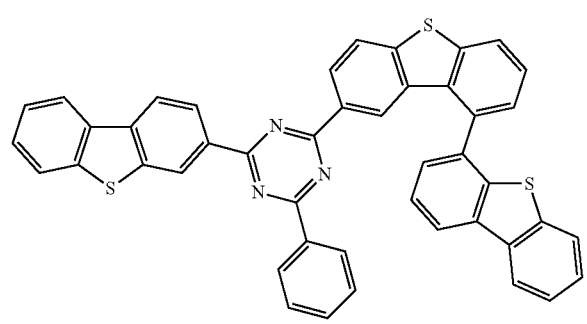
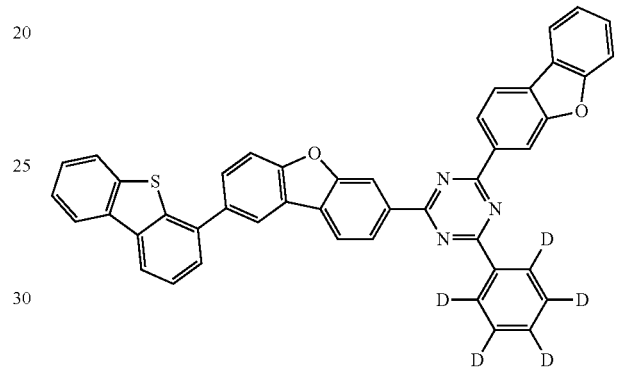
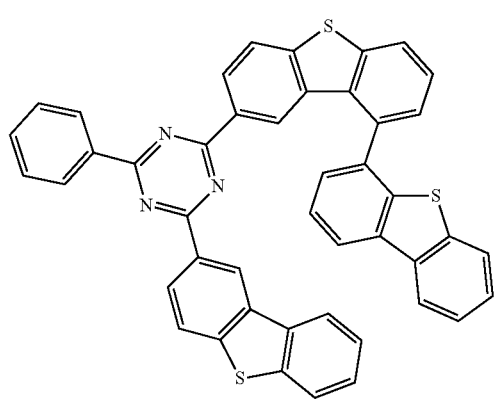
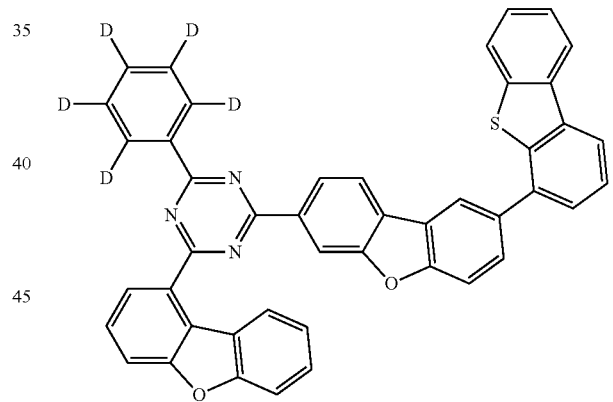
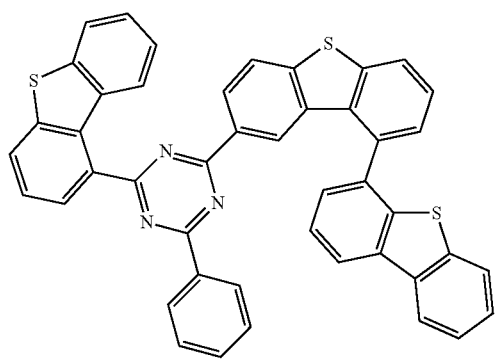
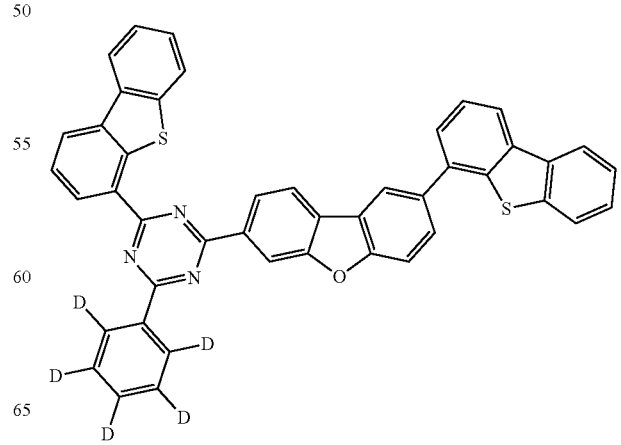

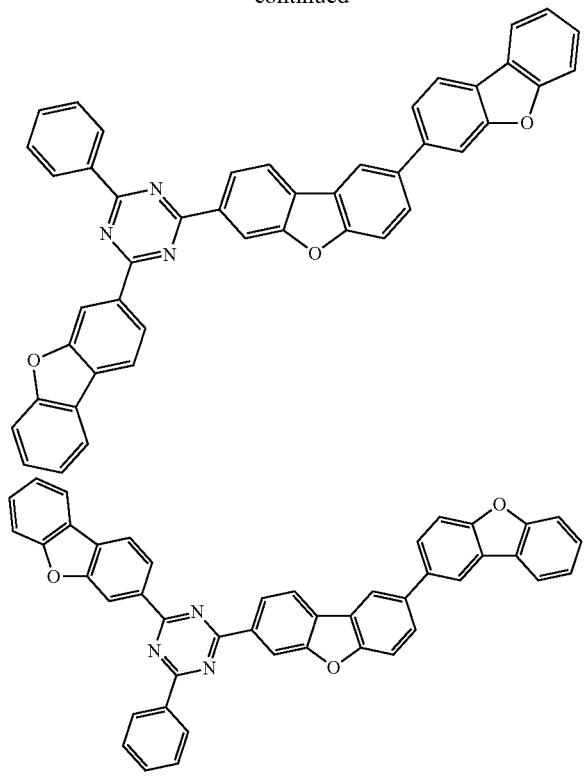

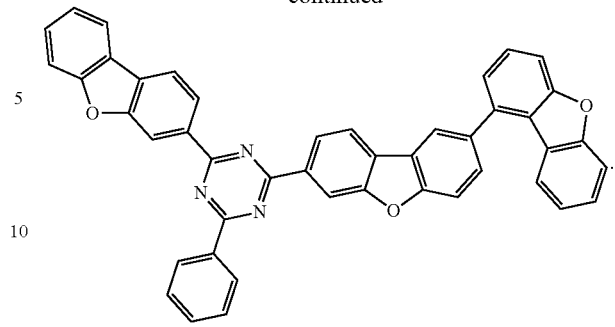

6. An organic light emitting device comprising a first electrode; a second electrode that is disposed opposite to the first electrode; and one or more organic material layers that are disposed between the first electrode and the second electrode, wherein one or more layers of the organic material layers include the compound according to claim 1.

7. The organic light emitting device according to claim 6, wherein
the organic material layer includes a light emitting layer, wherein the light emitting layer includes two or more host materials.

8. The organic light emitting device according to claim 7, wherein the two or more host materials includes the compound.

\* \* \* \* \*